US010125178B2

(12) United States Patent
Wang et al.

(10) Patent No.: US 10,125,178 B2
(45) Date of Patent: Nov. 13, 2018

(54) MODIFIED MICROORGANISMS FOR CHEMICAL PRODUCTION

(71) Applicant: Arizona Board of Regents on behalf of Arizona State University, Scottsdale, AZ (US)

(72) Inventors: Xuan Wang, Chandler, AZ (US); Reed Cartwright, Chandler, AZ (US); Christian Sievert, Tempe, AZ (US); Taylor Loeffler, Peoria, AZ (US); Lizbeth Nieves, Chandler, AZ (US); Larry Panyon, Phoenix, AZ (US); Chandler Morris, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 15/176,866

(22) Filed: Jun. 8, 2016

(65) Prior Publication Data
US 2016/0362456 A1 Dec. 15, 2016

Related U.S. Application Data

(60) Provisional application No. 62/175,127, filed on Jun. 12, 2015.

(51) Int. Cl.
*C07K 14/245* (2006.01)
*C12N 9/02* (2006.01)
*C12N 1/21* (2006.01)
*C12P 7/56* (2006.01)
*C12N 9/04* (2006.01)

(52) U.S. Cl.
CPC .......... *C07K 14/245* (2013.01); *C12N 9/0006* (2013.01); *C12Y 101/01307* (2013.01); *C12P 7/56* (2013.01)

(58) Field of Classification Search
None
See application file for complete search history.

(56) References Cited

U.S. PATENT DOCUMENTS

2015/0225745 A1   8/2015   Vroom

FOREIGN PATENT DOCUMENTS

WO        2014025747       2/2014
WO     WO 2014152434 A2 *  9/2014  ........... C07C 33/025

OTHER PUBLICATIONS

Delgado et al., Single amino acid changes in the signal receptor domain of XylR resulted in mutants that stimulate transcription in the absence of effectors, J. Biol. Chem., 1995, 270, 5144-50.*
Aiba et al., Mutations that alter the allosteric nature of cAMP receptor protein of *Escherichia coli*, EMBO J., 1985, 4, 3329-32.*
Aiba et al., Molecular cloning and nucleotide sequence of the gene for *E. coli* cAMP receptor protein, Nucleic Acid Res., 1982, 10, 1345-61.*
Zhang et al., A new logic for DNA engineering using recombination in *Escherichia coli*, Nature Genetics, 1998, 20, 123-28.*
GenBank, Accession No. AAB18546.1, 2010, www.ncbi.nlm.nih.gov.*
Sievert et al., Experimental evolution reveals an effective avenue to release catabolite repression via mutations in XylR, Proc. Natl. Acad. Sci. USA, 2017, 114, 7349-54.*
Saha, B.C. (2003). Hemicellulose bioconversion. J Ind Microbiol Biotechnol 30, 279-291.
Girio, F.M., Fonseca, C., Carvalheiro, F., Duarte, L.C., Marques, S., and Bogel-Lukasik, R. (2010). Hemicelluloses for fuel ethanol: A review. Bioresour Technol 101, 4775-4800.
Yomano, L.P., York, S.W., Shanmugam, K.T., and Ingram, L.O. (2009). Deletion of methylglyoxal synthase gene (mgsA) increased sugar co-metabolism in ethanol-producing *Escherichia coli*. Biotechnol Lett 31, 1389-1398.
Cirino, P.C., Chin, J.W., and Ingram, L.O. (2006). Engineering *Escherichia coli* for Xylitol Production From Glucose-Xylose Mixtures. Biotechnol Bioeng. 95, 1167-1176.
Grabar, T.B., Zhou, S., Shanmugam, K.T., Yomano, L.P., Ingram, L.O (2006). Methylglyoxal bypass identified as source of chiral contamination in L(+) and D(−)-lactate fermentations by recombinant *Escherichia coli*. Biotechnol Lett 28, 1527-1535.
Apel, A.R., Ouellet, M., Szmidt-Middleton, H., Keasling, J.D., Mukhopadhyay, A., "Evolved hexose transporter enhances xylose uptake and glucose/xylose co-utilization in *Saccharomyces cerevisiae*" Scientific Reports 6, Article No. 19512 (2016).
Wang, M., Yu, C., Zhao, H., "Directed evolution of xylose specific transporters to facilitate glucose-xylose co-utilization." Biotechnol Bioeng. Mar. 2016;113(3):484-91.
Ishola, M.M. Ylitervo, P. Taherzadeh, M.J., "Co-Utilization of Glucose and Xylose for Enhanced Lignocellulosic Ethanol Production with Reverse Membrane Bioreactors" Membranes, Dec. 2015; 5(4): 844-856.
Krahulec, S., Petschacher, B., Wallner, M., Longus, K., Klimacek, M., Nidetzky, B., "Fermentation of mixed glucose-xylose substrates by engineered strains of *Saccharomyces cerevisiae*: role of the coenzyme specificity of xylose reductase, and effect of glucose on xylose utilization" Microbial Cell Factories 2010 9:16.

(Continued)

Primary Examiner — Robert B Mondesi
Assistant Examiner — Todd M Epstein
(74) Attorney, Agent, or Firm — Rodney J. Fuller; Booth Udall Fuller, PLC

(57) ABSTRACT

The present invention relates to increasing xylose utilization in industrial microbe by inducing mutations in the regulator genes, crp and xylR. Thus the invention is directed to isolated nucleic acid sequences that encode mutations in the crp gene and the xylR gene and recombinant bacterium that express mutated CRP and XylR. In some embodiments, the mutation results in a point mutation at residue 142 of the CRP protein and/or at point mutation at residues 121, 182 and/or 363 of the XylR protein (based on the protein sequences in *E. coli*). The invention also includes methods of using the recombinant bacterium.

20 Claims, 8 Drawing Sheets

Specification includes a Sequence Listing.

(56) References Cited

OTHER PUBLICATIONS

Groff, D., Benkea, P.I., Battha, T.S., Bokinskya, G., Petzolda, C.J., Adams, P.D., Keasling, J.D., "Supplementation of Intracellular XylR Leads to Coutilization of Hemicellulose Sugars" Appl. Environ. Microbiol. Apr. 2012 vol. 78 No. 7 2221-2229.

Vinuselvi, P., Lee, S.K., "Engineered *Escherichia coli* capable of co-utilization of cellobiose and xylose." Enzyme Microb Technol. Jan. 5, 2012;50(1):1-4.

Gawand, P., "Metabolic Engineering for Substrate Co-utilization" Available at: https://tspace.library.utoronto.ca/bitstrearn/1807/68233/1/Gawand_Pratish_201411_PhD_thesis.pdf (Accessed Jun. 14, 2016).

Vinuselvi Parisuthama, Sang-Kyu Junga, Dougu Nama, Sung Kuk Lee, "Transcriptome-driven synthetic re-modeling of *Escherichia coli* to enhance cellobiose utilization" Chemical Engineering Science vol. 103, Nov. 15, 2013, pp. 50-57.

Hyun-Dong Shin, Jianrong Wu, Rachel Chen, "Comparative engineering of *Escherichia coli* for cellobiose utilization: Hydrolysis versus phosphorolysis" Metabolic Engineering vol. 24, Jul. 2014, pp. 9-17.

Xianzhong Chen, Li Zhou, Kangming Tian, Ashwani Kumar, Suren Singh, Bernard A. Prior, Zhengxiang Wang, "Metabolic engineering of *Escherichia coli*: A sustainable industrial platform for bio-based chemical production" Biotechnology Advances vol. 31, Issue 8, Dec. 2013, pp. 1200-1223.

Sarah Huffer, Christine M. Roche, Harvey W. Blanch, Douglas S. Clark, "*Escherichia coli* for biofuel production: bridging the gap from promise to practice" Trends in Biotechnology, vol. 30, Issue 10, Oct. 2012, pp. 538-545.

Shota Atsumi, James C Liao, "Metabolic engineering for advanced biofuels production from *Escherichia coli*" Current Opinion in Biotechnology vol. 19, Issue 5, Oct. 2008, pp. 414-419.

Nele Buschke, Rudolf Schäfer, Judith Becker, Christoph Wittmann, "Metabolic engineering of industrial platform microorganisms for biorefinery applications—Optimization of substrate spectrum and process robustness by rational and evolutive strategies" Bioresource Technology vol. 135, May 2013, pp. 544-554.

Yu-Sin Jang, Jong Myoung Park, Sol Choia, Yong Jun Choi, Do Young Seung, Jung Hee Cho, Sang Yup Lee, "Engineering of microorganisms for the production of biofuels and perspectives based on systems metabolic engineering approaches" Biotechnology Advances vol. 30, Issue 5, Sep.-Oct. 2012, pp. 989-1000.

Fuzhong Zhang, Sarah Rodriguez, Jay D Keasling, "Metabolic engineering of microbial pathways for advanced biofuels production" Current Opinion in Biotechnology vol. 22, Issue 6, Dec. 2011, pp. 775-783.

Sung Kuk Lee, Howard Chou, Timothy S Ham, Taek Soon Lee, Jay D Keasling, "Metabolic engineering of microorganisms for biofuels production: from bugs to synthetic biology to fuels" Current Opinion in Biotechnology vol. 19, Issue 6, Dec. 2008, pp. 556-563.

Jeong Wook Lee, Tae Yong Kim, Yu-Sin Jang, Sol Choi, Sang Yup Lee, "Systems metabolic engineering for chemicals and materials" Trends in Biotechnology vol. 29, Issue 8, Aug. 2011, pp. 370-378.

Jeong Wook Lee, Hyun Uk Kim, Sol Choi, Jongho Yi, Sang Yup Lee, "Microbial production of building block chemicals and polymers" Current Opinion in Biotechnology vol. 22, Issue 6, Dec. 2011, pp. 758-767.

Dokyun Na, Tae Yong Kim, Sang Yup Lee, "Construction and optimization of synthetic pathways in metabolic engineering" Current Opinion in Microbiology vol. 13, Issue 3, Jun. 2010, pp. 363-370.

Keith EJ Tyo, Kanokam Kocharin, Jens Nielsen, "Toward design-based engineering of industrial microbes" Current Opinion in Microbiology vol. 13, Issue 3, Jun. 2010, pp. 255-262.

Vikramaditya G Yadav, Gregory Stephanopoulos, "Reevaluating synthesis by biology" Current Opinion in Microbiology vol. 13, Issue 3, Jun. 2010, pp. 371-376.

Sean A. Lynch, Ryan T. Gill, "Synthetic biology: New strategies for directing design" Metabolic Engineering vol. 14, Issue 3, May 2012, pp. 205-211.

Vikramaditya G. Yadav, Marjan De Mey, Chin Giaw Lim, Parayil Kumaran Ajikumar, Gregory Stephanopoulos, "The future of metabolic engineering and synthetic biology: Towards a systematic practice" Metabolic Engineering vol. 14, Issue 3, May 2012, pp. 233-241.

Aindrila Mukhopadhyay, Alyssa M Redding, Becky J Rutherford, Jay D Keasling, "Importance of systems biology in engineering microbes for biofuel production" Current Opinion in Biotechnology vol. 19, Issue 3, Jun. 2008, pp. 228-234.

Ruilian Yao, Kazuyuki Shimizu, "Recent progress in metabolic engineering for the production of biofuels and biochemicals from renewable sources with particular emphasis on catabolite regulation and its modulation" Process Biochemistry vol. 48, Issue 9, Sep. 2013, pp. 1409-1417.

Curt R. Fischer, Daniel Klein-Marcuschamer, Gregory Stephanopoulos, "Selection and optimization of microbial hosts for biofuels production" Metabolic Engineering vol. 10, Issue 6, Nov. 2008, pp. 295-304.

Jay D. Keasling, "Synthetic biology and the development of tools for metabolic engineering" Metabolic Engineering vol. 14, Issue 3, May 2012, pp. 189-195.

Suk Min Kim, Bae Young Choi, Young Shin Ryu, Sung Hun Jung, Jung Min Park, Goo-Hee Kim, Sung Kuk Lee, "Simultaneous utilization of glucose and xylose via novel mechanisms in engineered *Escherichia coli*" Metabolic Engineering vol. 30, Jul. 2015, pp. 141-148.

Brian Pereira, Zheng-Jun Li, Marjan De Mey, Chin Giaw Lim, Haoran Zhang, Claude Hoeltgen, Gregory Stephanopoulos, "Efficient utilization of pentoses for bioproduction of the renewable two-carbon compounds ethylene glycol and glycolate" Metabolic Engineering vol. 34, Mar. 2016, pp. 80-87.

Chung-Jen Chiang, Hong Min Lee, Hong Jhih Guo, Zei Wen Wang, Li-Jen Lin, and Yun-Peng Chao, "Systematic Approach to Engineer *Escherichia coli* Pathways for Co-utilization of a Glucose-Xylose Mixture" J. Agric. Food Chem., 2013, 61 (31), pp. 7583-7590.

\* cited by examiner

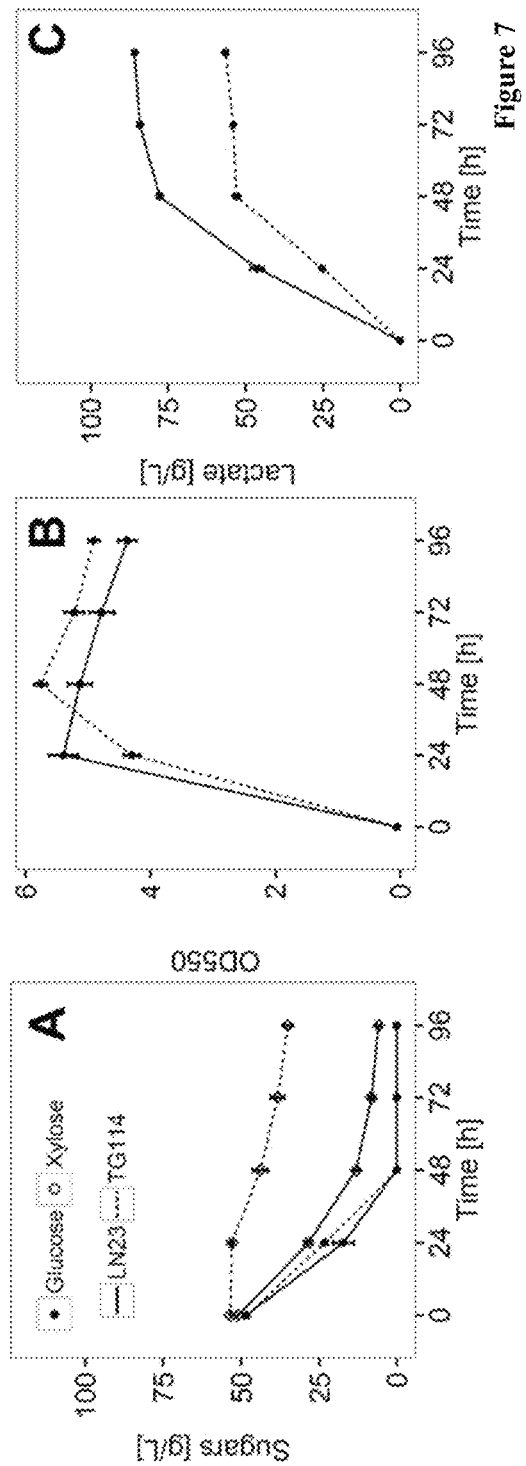
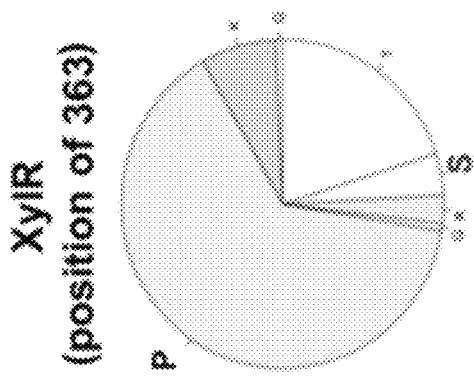
Figure 7
Figure 8

SEQUENCE LISTING

<160> NUMBER OF SEQ ID NOS: 28

<210> SEQ ID NO 1
<211> LENGTH: 192908
<212> TYPE: DNA
<213> ORGANISM: Escherichia coli

<400> SEQUENCE: 1

```
cacctgataa cataacgttg taaaaaccga atgcccagcc tttaaaaaaa cagctgggca      60
ttcggttgct tattaatcgc aataatatat tggctgtcta ttcatcgtgt tgataagata     120
tatgttatat gaatgtttat taaatgtagc gattgccttt aatgtcacga aaagggatta     180
tttgcttgct attaatttca ctgcgttctt aaacacgttt ttgtattata aatccagtca     240
tcctgcccgt agaacatcac acattatcat cctgttctcc cgcttcgttt aaatttattt     300
atcaatcaat ttgacttaag agggcggcgt gctacattaa ttaacagtaa tatgtttatg     360
taatattaag tcaactatgc aatcattaca tgggaattgt ctaattgcgt acgcaagaca     420
taaatatatt ctcaccatgg ttaatggtga atatcgctat tttaatggcg gtgacctggt     480
ttttgcggat gcaagccaaa ttcgagtaga taagtgtgtt gaaaattttg tattagtatc     540
aagggatacg ctttcattat ttctgccgat gctcaaggag gaggcattaa atcttcatgc     600
acataaaaaa atttcttcat tactcgttca tcactgtagc agagatattc ctgtttttca     660
ggaagttgcg caactatcgc agaataagaa tcttcgctat gcagaaatgc tacgtaaaag     720
agcattaatc tttgcgttgt tatctgtttt tcttgaggat gagcacttta taccgctgct     780
tttgaacgtt ttgcaaccga acatgcgaac acgagtttgt acggttatca ataataatat     840
cgcccatgag tggacactag cccgaatcgc cagcgagctg ttgatgagtc caagcctgtt     900
aaagaaaaaa ttgcgcgaag aagagacatc atattcacag ttgcttactg agtgtagaat     960
gcaacgtgct ttgcaactta ttgttataca tggcttttca attaagcgag tcgcagtgtc    1020
ctgtggatat cacagcgtgt cgtatttcat ttacgtcttt cgaaattatt atgggatgac    1080
gcccacagag tatcaggagc gatcggcgca gggattgccg aaccgtgact cggcggcaag    1140
tattgttgcg caaggaaatt tttacggcac tgaccgttct gcggaaggaa taagattata    1200
gaattttact cagacataaa aaaaacccgg catagggggac cgggaagagg atagtctgcc    1260
gtctccagac taataaaccg ttataacact ccctgttggc acgggaaact ttgtgctctc    1320
agtaagttaa atataacttt tactggaaat aagatcagcc attttttttat aaacataagc    1380
tatacgcagt gcgaaaatat attcgtgctg catttactta ttatcaatta actgttatgc    1440
aaaactactt tgtggataaa ttttggtcct accaaatctg gcagttttttt cgctaagaaa    1500
cagtctggca acatttcatt agtatactga aattgaaata atcgcagtat gaaatataag    1560
ggataatcat gactcatgtc tgctcggtga tcctcattcg tcgttcattc gatatttatc    1620
atgaacagca taaatatcg ctgcataacg agagtatcgt gctgctggag aaaaatttgg    1680
cagacgattt tgcgtttgt tcaccggata cgcgacgact ggatatcgat gagctgacag    1740
tttgccatta cttacaaaat attcgtcagc taccacgcaa tttagggtta catagcaaag    1800
accgtctatt aattaaccag tcaccccccca tgccgctggt gacggcgatt tttgatagct    1860
```

```
tcaatgaatc cggggtaaat tcaccgatac tgagcaatat gctctacctt tcctgtttat    1920
cgatgttttc tcataagaaa gaactgatcc ccttactttt caatagcatc agcactgttt    1980
caggaaaagt tgaacgcctt attagctttg atatcgccaa acgttggtat ctgcgcgata    2040
tcgcggaaag aatgtatacc agcgagagtc tcatcaaaaa aaagttgcag gatgaaaata    2100
cctgtttcag taaaatatta ctcgcttcca ggatgtcgat ggccagacga ttactcgagt    2160
tacgtcaaat tcctctgcat actattgcag aaaaatgtgg ctatagcagt acgtcgtact    2220
ttataaacac atttcgacaa tattatggtg taacgccaca tcagtttgcg caacattcgc    2280
caggtacctt ttcctgacat attttgcatt tgaatattgg tcaggatctc acacctgctt    2340
catgtgaaac tcttccctga tgatttctgc cgggctaccg gctagttctc tttcgcagtt    2400
tgccaggcgg tataggtatt ttcaggagga aaagactcgg catgtttggg attattaagc    2460
tgacaattca tacgattacg ggaatgtggg tcagtattgt gctgttcaaa ttgatgacga    2520
atggctggag tggtttctac tttcagtgct gtgtactaag cctggtattc ctgacggtta    2580
gctggttgtt gagtggtgaa tggttagcag gaaagagtaa ggctgaacct tcacgttcaa    2640
ccttactctc atttacacgt tacgcttttt taaagcgggc aaagagatgt tccactacaa    2700
cgaaaaagac cggaacgaag taaattgcca gcactgttgc ggcaaacatc ccgcccatca    2760
cgccggtacc taccgcgttt tgcgcgccag aaccggcacc atgactgata accagcggca    2820
gcacgccgag aataaaggcc agagaggtca tcaggattgg gcgtaaacgc atccgcgccg    2880
cttcgatgat tgcctctatc ggcgttttcc cttctttctg catcatctca acggcaaatt    2940
cgacaatcag gatggcgttc ttggcggaaa gcccgatggt ggtcagcaaa ccaacctgga    3000
agtagacgtc attacttaag ccgcgcagat cggtggccag taatgcgcca acgacgccta    3060
acggaacaac caacatcacc gagaacggaa ttgaccagct ctcatagagt gcggcgaggg    3120
cgaggaacac cacgaccagt gaaatggcat acagtgcagg agcctggttt gaggataacg    3180
cttcctgata cgacagtccg gtccatgagt agccgacgcc tgccggaagt ttagcgacca    3240
ggtctgccat aaatttcata gcgtcaccgg tacttttccc ggccgccgct tcacctaaaa    3300
tctccattga cgggatgccg ttgtagcgtt ccaatcgcgg tgaaccatag gtccattcgg    3360
tagacgagta ggcagaaagc ggtgccatcg tgccagaggc gttgcgtaca taccattggt    3420
tgatgttatc cggcaacata cggaacgcg tgcctgcctg acatacact tttttcaccc     3480
gccctggtt gaggaagtcg ttcacgtagc tgctgccgaa ggcggtggaa attgtctggt    3540
tgatatcaga cagcgccaca cccattgcct cagctttcgc ggcgttgacg ttcactttga    3600
acatcggcgt atcttccagg ccgttcgggc gtaccccggt gacctggtca ggcgattgcg    3660
ctgccagtga taacagctcg tttcgtgcct gggttagttt ttcgtgcccc aggttaccgt    3720
tgtccagcag ttccatatca aaacctgacg cggtacccag ttcagccacc gcgggtaagt    3780
tgaacgggaa gacgacggct ttattgatac tgcttaacgc aatcattgcc cgctgaatga    3840
tcgcggtaac cgagttttcc tcaccgacac gttcagacca cggcttgaga ctgataaacg    3900
ccaggccgtt gttttgcccc tggccgctga agccaaagcc gccaacggta aacaccgact    3960
gaacattatc tttctctttt gtaagataat aatccgtcac tgttgcagc actttcgtgg     4020
tgttaaccat ggtggcaccg gaaggtaact gcgcggtggt cataaatacc ccctgatcct    4080
cttctggtaa gaaagaggtc ggtgtacgca ggaacagcac cgccatcccg gcgcaaatca    4140
gcaggtagac caccatgtag cgaccggtac aacgcaacag cgagcgggtg ctatcggtat    4200
```

```
agtgctgagt tgattttca aacagcgtgt tgaagcgtgc gaacagggcg ttaggtttgt    4260
gaccgccttc cggcgcggct ttcgaatgg tggcgcacag ggcagggtc aggctcattg    4320 ccacaaatac tgaaagcagc atggaggaga tcagcgtgat ggagaactgg cggtagatct    4380
ccccggttgc gccgctcata aaggccatcg gcataaacac tgcggaaaga acaacagcaa    4440
taccgaccag cgcacgttgg atctgcccca tcgatttatg cgtcgcttcc ttcggtggta    4500
gcttatcttc cgcaatgaca cgctcgacgt tctccaccac cacgatggcg tcatccacca    4560
gtaaccctat cgccagcacc atcccgaaca tagttaacgt gttgatggtg aaaccgaccg    4620
ccgacaagat cgcaaacgtc ccgagaataa ccaccggtac ggcaatcgtc gggatgattg    4680
tggcacggaa attctgcaaa aacagataca tgaccaggaa gacgaggatg atagcctcaa    4740
ccagtgtttt aaaaacttcc tgaatagaaa tttcgataaa cggcgtggtg tcgtaaggat    4800
aaaccgtctt cagacttgcg gggaaatagg ctgataagcg gttcagctcc tctttgactg    4860
cccgcgaggt atccagggcg tttgctccgg tagccagttt gatggcgatc ccggcagcag    4920
gtttgccgtt atagcgcgcc acggtggaat aatcttccgc tccaagttct acgcgggcga    4980
catcacgcag cagcacttgc gaaccatctt gctgaacttt caacaggatt ttgccaaatt    5040
cttccggcgt ttgcagacgc gtctgcacaa tgatcgaggc gtttagttgc tggtctgccg    5100
cctgtggcat gccacccagt tgaccaccgg aaatctggtt gttttgcacc ttaatctggg    5160
aaataacatc ggaaggtacc agattgtatt tattgagttt ttgcgggtcc agccagatac    5220
gcatggcgta ctcggaacca aagagctgta cgctaccaac gcccgcggta cggcttagcg    5280
ggtctttgat attagacgct acatagtccg cgatatcgta ctggttgagg ctgccgttat    5340
cagaaataaa cgccgctacc atcagaatat tactgctcga cttatcaacg ctaatcccct    5400
gctgctgcac cgcttcaggt aatgaaggca tagcgagttg cagtttattt tgcacctgaa    5460
cctgtgcgat atcaggagat gtcccagtct cgaaggtcag agtgatagag gcattacccg    5520
ccgcatcact ggttgaagac atgtacatca ggccatcaag cccattcata ttttgctcaa    5580
tcacctgagt gaccgagtct tctaccgttt gcgcatcggc acctggatag gtagcgctga    5640
cggtaatggt cggtggcgca atctgcggat actgcgcaac cggtaagttc atgatcgcca    5700
gaccacctgc aagcatcata ataatggcaa gtacccaggc aaaaaccggg cgatcaataa    5760
aatagttagc catgaaagtc cccttaagcc tgcaacgtta ttgtttcgat tcggtgctgg    5820
cgttttcctg gctggaggaa attgctcgtg ctttgatacc cggacgaatg cgttgcaaac    5880
cggaaacgat cacccgatca ccagcctgca agcagaggt gacaacccac tggtcgccga    5940
tggctttgct ggcttcaatt tcgcgtagct gcacaacatc gtctttatcc agaatgagcg    6000
ccgttgcttt accctgggcg ttgtgggtga cgccttcctg cggcaccagt aatacattct    6060
ggcggctacc ttcatccact aatgccgtga cgtacatgcc aggcagcaag tcaccatttg    6120
ggttggggaa aatcgcccgt aacgtcacgg agcccgtggt ttcatccacc gtcgggtcgg    6180
agaatttcag cgtgccggtc tggctgtagc gtttaccatt ttccagattg agctgtactg    6240
gcgtactgcc ctgaacctgt ttgatttgcc cactggcgac ctcttctttc atgcgtaaga    6300
aatcctgcac cgactgcgtg agatcgacat aaatcgggtc cagacgttgt acggtaacca    6360
gcgaatctgc ctgattagcg gtaacgagtg cgccgacggt caccgacgat ttcccgctga    6420
cgcccgtaat cggcgaggtg acattcgcgt attgcagatt gatcgtcgcc tgttcaacag    6480
ccgctttggc gacggtgaca ttggcttctg cttcattcaa ctgggtgcgc gcggtgtcgt    6540
aatcctgacg gctaacgtag ttggtcttca gcaacgatgc ctggcggtta aggtgatgc    6600
```

```
gggcattgct ggcggtagag agcgctttcg ccagcgagcc tttggcggag tttagctcgg   6660
cctgtaaagg tgcaggatca atctgataca gcgaatcgcc ctggttcact ttatcgcctt   6720
cgataaagtt gcgtttaatg ataataccgc ccacctgggg acgtatctcg gcaacttcat   6780
aaggaacggt tctaccgggc aattcgctca acacattgac cgaaccgggg gagagtgtga   6840
cgacaccgac ctcaggcgtc atggcggcgg cgttttccgc cgatttgtca tcgcaggcgg   6900
tgagcatcgc gccgcagaat aacaacggta ttaacagctt tcttcttctg ttcattttag   6960
tccctgaaaa ttcttgagaa ataacggttc tttaaattgc gcgcgaggag agatatgagg   7020
gatttacaga ccagcggcat agtggggttg tcagccagta aggtgggata caggcacagt   7080
gatcgacatg gtgaggtcaa cgacaaaaaa aatgttgccg ttctgccaac agttcctgcc   7140
agcattcggg caacgaaggg ttctactggt ggatacacat accaggggaa taaagtcgtt   7200
ttagcctctc ctttagtaat caccgggggt aatgaaatca gcatctgcat ccctcgtcat   7260
gccagccatc aatttcagtt gcttatgtcc tgactaaaaa taagatgtga tacccagggt   7320
gacgatgtcg ctcatacgtc ttagtttcag cttgtacata atgttgaatt tctgaatctt   7380 taatgttttgt tgcgaaatat tgagcgtcga cgtgatattg cttttcatttt tatttttcag   7440 aatcagttgc ataattttga actgattatg tgaaaaacat aattgtgaat tcttatgggg   7500
caagtgttta ccataagtaa tctcaagaag atttttgata ctttctttgc ggctaacaaa   7560
ataaataggc gctttagctt ttagtttact gatgtgataa ggtgccaaaa caataattct   7620
ctcggcatct aatttctcca gaaatttaat cgcttcttca tcaaggatat gattgtgata   7680
ggtatcaatg ataaccttga agggtttatt gcctactttt ttgatctctg acagggaatt   7740
gatttttatc atttcgtgat tatctttcaa ctgccaaaag ccctgtaaaa gaaaagaatc   7800
tttcgtcatg agaaaaatca taacttgctc cttagccgtt atcgtttcga acatgtcatc   7860
cttttcatta tttacatcct tgtccgaatc gttgttcaat atagtaaacg cctataagaa   7920
ctttaccctt cgtgaactaa tacgtctatt aacactaatc aatacttcag atttatccat   7980
cacgcactcc atatattgat cctaagtaag attcctggtt gttatcagct tgtaaatagt   8040
aaacaaaaag ttaacgtttg cggattactg cccaagaata agttatcaat aaccagtttg   8100
tgatctctga agaatattac taaagttaaa atgtaatccg atttaaatat cgagtctcct   8160
tgtttcgact taagctggca attggattgc cagcttctt ttaacgcatt gaaattacct   8220
gagtaaataa cgcattcatg tcttcaggtt tttatatagc gtctggagac acggatattt   8280
atgcaatgta atcaacgcca gttgcaaaaa atgaacccg gattacttat ttaaccgccc   8340
atagcatcaa cgcttacgga actctttgtt cactttccca cagcacttt aaaacattaa   8400 acctgactac ggaaaaatatc agccatgata atgtttgaaa tggctaattt gccatggagt   8460
aaaaaaaatt agatgaaatt cagtaggttg aaataatcac tagcaggtaa ttatttcaat   8520
gatagtgcgc aattgatcta caacactgcg tagcggagag agtattaatc ggatcatagt   8580
cacatcaagt gactatgatc cgggtgacaa ccggggtaat tattgctgct taacgaacaa   8640
actggcgaag ctgaacaggc tggcggcgct aaatatcagt tcaattccca ccagtgtgga   8700
aaccagcgtt acagacacca tcggcgttgc accaaggaat atccaggcaa tgacgatatc   8760
cagcacacca ataacgagct gtagccagct gcctttcatt gaacgctgac gataccaact   8820
catcaggcga ataactcctg caacacagaa caaaccggca ataaatgccg caatggcaaa   8880
aatgcccagc tccggtgcgc ggatgaagaa atagccgatc aataaatagg cgactgcgac   8940
```

```
gaggaaaccg gataataccg gccagaaatt atgactgcgg ttgctgaata acccgacaat      9000
aagcgcaata cccgagcaga ttaataatgc acccactact gtgcttaaaa tatcgccaga      9060
gacgaacggg aaactgatac acagcaaccc gacgataaac agcagcacgg caataaactg      9120
gattgctctg cgatgttttt taagcatctc cagatcaaac ttcaaaattg ttgccttatc      9180
tatatataac atagaaccac cctataaaat taagaagaaa atcccctgct atcaatctat      9240
gccaaaaacg cgtctaagaa tgcagtcgat ttaataaaaa tttcctaatt gcagtatctg      9300
atgcatctgt aactcattgt attaaaataa aaatatctga ttttgatatt ttccatcaac      9360
atgacatata cagaaaacca ggttataacc tcagtgtcga aattgattcg tgacggctct      9420
ttcactttat agttgaggat attacgatga aaaagtatt aggcgttatt cttggtggtc       9480
tgcttcttct gccagttgtg agcaatgcag cggatgcgca aaaagcagct gataacaaaa      9540
aaccggtcaa ctcctggacc tgtgaagatt tcctggctgt ggacgaatcc ttccagccaa      9600
ctgcagttgg ttttgctgaa gcgctgaaca caaagataa accagaagat gcggttttag        9660
atgttcaggg tattgcaacc gtaaccccag ctatcgttca ggcttgtact caggataaac      9720
aagccaactt taaagataaa gttaaaggcg aatgggacaa aattaagaaa gatatgtaat      9780
tccgggaatg cgttacatcg tacttccttg catattgaac aggccggaat atcttcttta      9840
aaagcagcta ttcctcctgt tcatatataa tctctatatt gaatgggtta caaaatgaat      9900
atttcatctc tccgtaaagc gtttattttt atgggcgctg tagcggcttt gtcactggtg      9960
aacgcacaat ctgcgctggc agccaatgaa tccgctaaag atatgacctg ccaggaattt     10020
attgatctga atccaaaagc aatgaccccg gttgcatggt ggatgctgca tgaagaaaca     10080
gtatataaag gtggcgatac cgttactta aatgaaaccg atctcactca aattcctaaa       10140
gtgatcgaat actgtaagaa aaacccgcag aaaaatttgt ataccttcaa aaatcaagca     10200
tctaatgact tgccgaatta atgaggtaca agtaaaaagg agtagcaagt tgagccatct     10260
tgctgctcct ttttgcattt ttatatgaca gcagaattta ttatacgtct tatactcgcg     10320
gcaattgcct gtggcgctat tggcatggaa aggcaaatgc gcggcaaagg agcagggtta     10380
cgcacacatg tattaattgg catgggaagc gccctgttta tgattgtttc gaaatatggt     10440
tttgctgacg tgctgtcttt agatcacgtc ggactcgacc ccagccgtat tgctgctcag     10500
gtggtgacgg gcgtcgggtt tatcggtgca ggtaacattc tcgttcgtaa ccaaaatatt     10560
gtaggtctga cgacggcagc ggatatctgg gtgaccgccg ccataggtat ggttattggc     10620
agcggtatgt acgaactggg tatttatggt tcagtgatga ccttgttggt gctgaagtc       10680 ttccatcaat taaccttccg cctgatgaac aaaaattacc atttacagct gacattagtg     10740
aacggtaata cggtatcaat gctcgactgg tttaagcagc aaaaaataaa acggattta       10800 gtttcgttgc aggaaaatga agatcatgaa gtggtcgcca ttgatatcca gcttcatgcc     10860
acaacgtcga tagaagacct gttgcgatta ttaaaggta tggcaggggt gaaaggcgtt      10920
tcaattagct aatctgtgtg gcagcgtagc cagactcacc gtaagcctga aattcacacc     10980
agataatcaa tatgctgatg gcgtaccagc tcattgatcc gcttaagatt gaggatcatc     11040
atgatattgt gttatggca gtagaacgtt tttagcgata ttttcagttt ctccagaata       11100
tcttccgttg tcatttgatt cgcaatgcag ctcagaacct gatgttgctt gcgcgaaagt     11160
gacacagccg cttcaggcac agagcagtaa ctgccattga tgagtgcgac aaaatcaatg     11220
atagtgatag tccgcggaac aaaggtcacc ggcactttcc ccaggcagcg tttaatatta     11280
aagggggaga aaataatcac atggacaggt tttaatcgtt caatttgagt gagaaaatta     11340
```

```
gaatgaaata cattattcat taatgtatca ataatgacga aggcattctg atgcaacatt   11400
acgtcgatct cttcttcgtt ctgtatatga acgacattac ctttactcag aatgttttc   11460 atcgcggtga agaacatcgt atccctggta attataagaa acataaccga ctcctggtgc   11520
ggacattaac tttataatca gtttgccaaa ggtaattaac aggacagggc ttataataat   11580
aatagttagc ttactgtata ttaattttat gtaatacatg atgcagatgc tgagaaagca   11640
tctgcatctt tcggtggtgt tatttgacca gctcaggtgt tacctgactc accgcattgg   11700
tgtagtaagg cgcacccag cccggttccg gccagaatgc accatagccg taatcccaca   11760
ggttataggt ggtattaacc acttctctca aatgccacac ctggatgccc tgcatattca   11820
cttccaggaa gttatacggg actttattga taaagcctgg ttgttcaccc tgaatggtac   11880
cgaggatggt aacaaagtga ttacgatagt tcactggatc aaggaagccg ctttgtctgg   11940
cgagcagtcg gccctgatag ttggcttcaa tatcaggctt cgcatagcta ccaacggta   12000 atacagcgat ttctaacaac gtatccgttt tgccattgat aacgttgata accttcccac   12060
caaagcgcgc ttgttgacca acatataacc ccggctggtt atgaacagca acaaaacttt   12120
tttgaatatc aggttggtta ttgcctttga tattttgcgg aattgaacta catgcggcaa   12180
gcaaaaatga aaggctgagg atgagtgcac cttttgtcat gttcatgtta ctatccttat   12240
caacaaatat taaaaccata atagatattt ctttatagtt ttcatctgat tctgaggtga   12300
tatgcctgat agtaacgtaa acctgtctga tgtttatatc ccttctgttt agttcaattc   12360
cgttattttg gggcgtggta tgagtatcca tcgcccaata atataaccct ttgttttaaa   12420
attacataaa atctattttt attcaataat tataaagtgc taataatcaa tattatggta   12480
ttatattctg ataatgattt gataagcgaa ttcttttgcc agatggtatt tctatttcca   12540
ccccataatt tatatctttt tcattaggaa gtggcctctt taaataaggc gtgtgtgaca   12600
tttttttggg gttaagcgtc tcgtattgaa atacttagaa ctgatattca gacatttctg   12660
cccatgtttg aattttattg tatcgagaga gtgtcgcaaa ggctttaact tgcttataac   12720 attgttttg gaattcttgc tgatatgtta atatgtcatt gtatgaaaga ttggttatcc   12780
tggcctctaa aaatttaatt attgtcgaag caatttccgc ttttgctcgt aaaaagttgt   12840
cattaatggt taataatgtt gaaaataaac cttcgatttg tttgtcaaga tattgtccat   12900
ctttatataa tttgggggta gggtgttctt tatgtaaaaa atagtgtcac ctaaatttgc   12960
gtcagtgaaa tttatattaa gtagatcttc gaaataaaac cttgacaagg ttagaacgaa   13020
cccggacagg ttctgtcctg tcatattgaa atcaataaag ttggttccgg caaagacttt   13080
catcctgttt ttattttcac tgtgctcaat ataacttc gtcattttt gatacaggct   13140 ttgaatatct tttatattag ttggtaagtc agctcgttgt tcagcaataa aattagtatc   13200
tgaaaacatg gtttggacac tgaatgttat gggtattccc tcttctacgc taattttagt   13260
tatgattgcc ttgtcgggtt taggattagc gacaacaatg attcgacatt cagcactttt   13320 gttttttca tatctaatgt tattaatctg attaagtatt gattgtgtct gttgcgtaag   13380
tggtgtcgaa cttatcgttt caatgttatt aataagactt acaagttgaa ccacaacttt   13440
tgagtagtct gcatttgtat atgtggtgtt cgtgtggcat gcattaattt gttggagttg   13500
ttgttgcgct aaatcaaatt gttcagggtt gtatccttct ccagagaata tggaattaat   13560
gggttgttgt tcttcccaat tatcacaagg ccacttcggt gtgtctggcg ttttaacatt   13620
atcggtattt gttgtgcagt tataaatatc gccgtgatat gtatttatta tacctggggt   13680
```

```
aaagtcaatt gacataacat tccttattca tcatctgttt tatgctaagg tttttaaatt    13740
gaataattag aacaggaatg gattttcttc tacacacaat aaatataatg cgttatatct    13800
tcctgatata attacctttg aattcccttt catttccacc cggtaatatt tgtgtataaa    13860
aaaaaggcag tgatagtatc gtaaaggaaa acgttaacaa ctatcaaaaa gcgctcattt    13920
taaaaagtta ttatgttctc cgatagtgtg tgaaatgata ttttttgtgat gttttagatg    13980 tgtaataatg aaccaggtta aagtgtattt aaaaatgtgt tgtattagcg actgaaatct    14040
gccttttaaa aaggaggagg gtactgagac aaagagtcat tgcttctccg ataaaatgtc    14100
agagaagcat gattacgtgg ttattgtctg ttgatgactt gttgaccgag ccgtcatcat    14160
tctcaatgca ttagttaaat catttgtgat ttttaaggat tatcctgtct atgattttct    14220
acttagaagg atatggcact aactatgcat cttatagttt actgctggca tctatttaaa    14280
atagcaattg agtcaaatag cccatcaaga tagccatacc taatataacc gtcaggaatg    14340
cagctatcat cggcattctg aacattgatt taagtaatat cacttccgtc aggcttgcgc    14400
cggcactgcc gatgattaat gccattaatg ctcccagacc cattccttttt gtcatcagaa    14460 cagatgccag agggataact gcctcagccc ggatatacag cggaataccg acaacggcgc    14520
ttaatgggat ggcgaaggga ttatctgctc ctgcatgagc ggcaatccac gctgagggaa    14580
taaagccata aataaaagat cctattaata ctcctaacaa aagatatggc agtacatctt    14640
taaactgttg caacgcatct ttggtggcta gtttatggg attaatactt actacagctt    14700
tggtactgca acaggtaact acggggttct caatggcttt agccgctgga ctacaacaac    14760
tcacttttat gggcgtatat gtcgttcccg gcgaagtttt tgctagagca caacaatttg    14820
ctgatgagct tttactggca atgatatgac gttcaaaccc cagagaatcc aggataatac    14880
tggcaagaac ggagacgccg gcggcgataa tcgcgtacaa caaggtgact ttccaaccaa    14940
aggtcatcca cattagtccg acgataatgg gattaagtaa tggtgaaaca aataaaaaag    15000
tgagagtcgg accaaacccg gctttcgctg acaacaatcc acgtaacatg ggtattgtcg    15060
agcaactaca gaacggggta acggctccca acagagcagc caggagatag cctctccctt    15120
ttctggcccc catcatctgc tggattttat ggtctggcac cttttgtctt atcaggctga    15180
caccggcact aatcactata aacagcaacg aaagctcgac ggcgagaaac acaaacatct    15240
ctgcggcatc ttgcagcatc gcaagccaac tactcatacg taacctcatt ggataaatct    15300
atatttccag aataatcgaa atgaaattca gatcaagata tttctggtat tatcgaaata    15360
tcaaccagac aaaggggggtg tcatatgcag ttggaagaag ttgctaaagc gctgaaagag    15420
ctaggtcacc cgacccgttt gttcatattc aaacacctgg tcaaagcggg ggagcaaggt    15480
ttgccggtcg gtgagttgca aaagcagctt gggatacccg gctctacact cagtcaccat    15540
atttcagcac tggtatcggt agggctggtt aaacaaaacc gtgagagtcg acgctgatg    15600 tgtgtttcgc aatacgcaat gctggaagcg ataattgaat tcttacgcga ggagtgctgc    15660
gtaaatagca aaattgcctg atgcgctacg cgctacagat ttcatgccat gcacggtttt    15720
gtaggtcgga taagacgcgt tagcgtcgca tccgacataa acaaagcgca ctttaccaac    15780
tatgggcagt ggatatcgcc gctttatttc aaccgcttac ccgcttcatc aaccgcttac    15840
ccgcttcatc aaccactttc tcgccatctt ccttggagaa tgcgccttttt tgcgcatctg    15900 gcagaatttc cagcaccact tctgaagggc ggcacaggcg agttcccagc ggcgtcacca    15960
caatcggacg gttaatcaga atcgggtgct gaagcataaa gtcgattaac cgctcgtcag    16020
taaatttatc ttccgcaagg cccagttcct catacggctc gacgttttta cgcagcagcg    16080
```

```
cgcgtacggt aatccccata tcggcaatga gttttaccag ttcatcgcgc gttggtggtg   16140
tttccagata atggataatg gtcggttctg taccgctgtt gcggatcatc tccagcgtat   16200
tacgcgatgt gccgcaggcc gggttgtgat aaatggtaat gttgctcata tcagtatctc   16260
attacaaagt gaaagagaga cgaagcgcca gcgcgacgtg tgtcacaaac agcacaggca   16320
gggtcatgat aatccctgta cggaagtaat atccccagct gatagtcata ttcttctgcg   16380
aaagtacgtg cagccagagc agcgttgcca ggctaccaat cggggtaatt ttcggtccca   16440
aatcgcagcc aatcacattg cataaaccca tcgcttcttt gataacgcca gatgccgtgc   16500
tgccatcaat ggacaacgcg ccaaccagta ccgtcggcat attgttcata atagaagaga   16560
ggaaggcggt gaggaatccg gtgccgagcg tcgcggccca caggccgtta tccgccagca   16620
cgttgagtac gccagaaaga tattccgtta atccggcatt gcgcaggcca taaccacca   16680 gatacatgcc gagcgagaag atgacaatct gccagggggc accgcgcagg actttacccg   16740
tattaatcgc atgaccgcgt ttagcgacga caaataatat cagcgcgccc acagctgcaa   16800
tggcgctcac cggaatgccg agcggttcca ggacgaaaaa tcccaccagc agaagcagta   16860
aaacaaccca gccagttttg aacgtagcag gatctttgat cgcttctgcg ggagatttca   16920
gcagcgccat atcgtagttc tgcggaatat cttttgcgaaa atagagatgt aacatcacca   16980
gcgtggcaac aatcgcggcg atatccaccg gcaccatcac cgaggcgtat tcgcgaaagc   17040
cgaggccaaa gaaatcagcg gaaacgatat tcaccaggtt ggagacaata agcggcaggc   17100
tggcggtatc ggcaatgaat ccggccgcca tcacgaacgc cagcgtagtg cctttactga   17160
accctaaagc cagcagcatg gcgatgacaa tcggtgtcaa aataagcgcc gcgccatcat   17220
tggcaaacag ggcggcaacg gcagcaccga gcaggacaat ccaggtaaac agcaagcgac   17280
cacgaccatt accccagcgt gagacgtgca gcgccgccca ttcaaaaaag ccggactcat   17340
ccagcagcag gctgatgata atgacggcga taaacgcagc cgtcgcgttc cagacgatat   17400
tccacaccac cggaatatca cccggatgga ccacgcccgt aactaacgcc agtactgcgc   17460
cgagcgttgc actccagccg atgcctaaac ctttcggctg ccagataacc aatacgatgg   17520
tcaggacaaa gatagcgcct gccagtaaca taatgcctcc cggataaaac acatctgaaa   17580
attcatatgt gtttagctaa attttttaact gcaaatgttc ttactgtccc cggaacagtt   17640
ttgtcgagcc aggttgcgga caatcgcctg aaccttttcc tgttcacatc gccaggcctc   17700
atcaataatt ttcgccgccc atgctggaat atgcggtgat aagcggtaat gaacccactt   17760
accttgcttg cggtccagca atagcccgct ttcacgcagc aatgccaggt ggcgggagat   17820
cttgggctgc gactggtcga gagcagtgca gagatcgcag acgcataact ctcccagttc   17880
gctgagcagt aaaacgatgc ccagacgggt ttcatcagca agaattttga acaattggat   17940
gggtaacaga aatgacatat tgcgctcctg attgttgcag gtagtgtctc tcttcgaagc   18000
ggataagtca aaaacatata tgacttaacg aatgtgtaag tgcagaggaa ggtaataggt   18060
gtgaattttg agttggctat tcatttgaaa agaggtctga atcaggacgt aaaaaaaccg   18120
actttgcgtc ggttttttac tttccagccc tgagttggtg gctctggctg gagtgagaga   18180
gttcttatct aacagctcaa tactattagc cagtggctaa cattgcaaga attagcgatt   18240
tcttcagctg gcggaggggg cacttcggta tatatcgcaa tgacgattta tatactttca   18300
ctgggtcatc gtcatattaa gccttgtccg aatccggatg taaaaaaacc gactttgcgt   18360
cggtttttta cttcccagcc ctgagttggt ggcactggct ggagtgagaa tgccattatc   18420
```

```
taacgcatca atgctaatac catactgaaa ctattgcaag gacatgctgg tttttataacc    18480
tgaatgtact gtatgattat ccagttagct ctgaggcatt ttcactctgg taatgcgcat    18540
aaacgctttc aaagtcctgg tcagaagtac gggtggtgcc gttaactgat gctctggccg    18600
gagtgagaat gccattatct aacaataggg catgcgccgt gacaggcagt ggatgagtaa    18660
gcggatgcat tctcactcca tcgcatggag aaaacgggtg attgataaag caatcatcgt    18720
tcttggggcg ttaattgcgc tgctggaact gatccgcttt ctgcttcagc ttctgaactg    18780
atagcggaaa cgtaattaag ggctaagagc acactactct tagcccttta acatttaacg    18840
cattgtcacg aactcttctg ccgccgttgg gtgaatggcg acggtattgt cgaagtcttt    18900
tttggttgca cccatcttca gcgccaccgc gaagccctgc aacatttcgt ccataccaaa    18960
gccaatgccg tgaataccga caatcttctc ttccgatcca acgcacacca gcttcatgcg    19020
gcacggctgg cggtgagtgg tgacggcggt atacatcgcg gtgaaagagg atttatacac    19080
tttcacctga tcgtcgccat actgctcgcg cgcctgcggt tccgttaaac caacagtacc    19140
aatcggcgga tggctgaaga ccacggtcgg aatgttgctg taatccagat gctcatccgg    19200
cttgttatta aacaggcgtt cagagagacg gcgacccgct gcaactgcca ccggtgtcag    19260
ctccactgca cccgtgttat cgcccaccgc gtaaatacct tcaatattgg tgttttgata    19320
tttatcgacg acgatatagc cttttttcgtt agttttaacg ccagcggctt ccaggttgat    19380
gttgtcattg gcaggctcgc gaccaatcgc ccaaatcagg caatccaccg tttcactgcg    19440
accatcttcc agctccagcg tcaggctacc atcggcattt ttcactaccg ctttcgggat    19500
ggcgttggtg tgcagctgcg ggccttcggc gttcatcact tcgaccagcg tttcggaaat    19560
catcgggtcg aagctgcgca gcggcgcatg tttacgcaca aacagatgcg ttttcgcgcc    19620
gaggccgtta atcacgcccg ccagctcaac ggcgatgtaa cccgcgccaa caaccgccac    19680
gcgctctggc aaagcaggaa gggcgaagaa gccatcagaa tcaataccgt attccacgcc    19740
cggaatatcc gggtggctcg gacgaccgcc tgtggcgatc agaatatgat cggccgtgat    19800
ggtttcgccg tttacctcca gcgttttggc atcaacgaag cgggcaaagc ctttgattac    19860
atcaacgtta tttttaccga gcacgttttc ataggaagta tgaatacggt cgatataggc    19920
ggtacggctg gcgatcaacg tttcccagtt gaatttattg atagtggtat caaaaccata    19980
atccgggccg tacatatgga tcgcttcacg gatttgcgcc gcgtgccaca tcactttttt    20040
cggcacacag ccaacattta gcaggtgcc gcccagctct ttggcttcaa tcagcgcaca    20100
tttctggccg tacatagccg cgcggttgat ggaggcgata ccgccgctgc cgccgccgat    20160
ggcgatgtaa tcatagtgtt tagtcatgac aaagtgtcct tatcgttgat taccgcgatt    20220
gtagcgcgag acgtaatagg tgccagcaat ggctgcaatt actccggcac gatccagctt    20280
acggtggcgt gcccggtgcc tgccggaacc agtttgctgt gcagccacgg cagcacgtta    20340
ttcatctgct gttccagttt ccacggcggg ttaatcacaa tcatgccgga agcggtcatg    20400
ccacggcgat cgctgtctgg cagtaccgcc agttcaattt gcagaatttt gcgaataccg    20460
gtcgcttcca gatcgtggat catgcgctta atttgctgac gcagcaccac cggataccac    20520
agtgcgtaag taccagtggc gaaacgtttg taaccttctg ctatcccgct gaccaccgcc    20580
tgatagtcgg ttttcatttc atacggcggg tcgataagga ttaaaccacg gcgggaaacc    20640
ggcggcagtt tggccttaag ctgctggaaa ccatcggctt tttcgacgcg cgcacggctg    20700
tctttctgaa attcagaacg cagcaacggg taatcgctcg ggtgcagttc ggtcagttgc    20760
aggctgtctt gttcgcgcag tagctggcga gcaatcaatg gcgaaccggg gtagtaacgc    20820
```

```
aactgaccgc tacggttgaa gtgttttacc acattgatgt acgcctccag ttctgcgggc   20880
aaatcgtcct gctgccagat acgggcgatg ccttcgagat attcgccggt acgctcggca   20940
tgttcgctgc ctaactgata acgcccggcc cctgcgtggg tgtcgagata gagaaacggt   21000
ttatctttct ctttcagcga ctcgatgatc aggctctgaa cggtatgttt aaggacgtcg   21060
gcgtggttgc cagcgtgaaa gctgtggcga taactgagca tgggtaaagg tgttccggta   21120
agtaaaaatc ggcccgtatt cggggcgcac aaaagcttat caggacagta taccgaaaag   21180
aggccgccgc cgcgaaagcg taacgtttct cattgaaatt cactacactt aaccccatgc   21240
tacacacatt atgtaaagcg cctgttgagc gcttccttaa cctctttaac caggactgcg   21300
cgaatgacga atccgttact gactcccttt gaattgcctc cgttttctaa aattctcccg   21360
gaacatgtcg ttccagccgt gactaaggcg ctgaacgact gccgcgaaaa tgtgagcgc   21420
gtagtagcgc aaggagcacc gtacacctgg gaaaatctct gccagccgtt ggcggaagtg   21480
gacgatgtgc tggggcgtat cttctccccg gtcagccacc tgaactcggt gaaaaatagc   21540
ccggaactgc gtgaagcgta cgaacaaacc ctgccgctgc tgtcggaata cagcacctgg   21600
gtagggcaac atgaagggct gtataaagcg tatcgcgacc tgcgcgatgg cgatcattac   21660
gccacgctga acacggctca gaaaaaagcg gttgataacg cactgcgcga cttcgaactc   21720
tctggcatcg gtctgccaat agagaaacaa caacgctacg gtgagattgc cactcgtctt   21780
tccgagctgg gcaaccagta cagcaacaac gtcctcgatg cgacgatggg ctggaccaaa   21840
ctcgttaccg acgaagcgga gctggcgggg atgcctgaaa gcgcgctggc tgcggcaaaa   21900
gcccaggccg aagcgaaaga gctggaaggc tacctgctga cgctggatat cccaagctac   21960
ctgccggtaa tgacctactg cgacaaccag gccttgcgtg aagagatgta tcgcgcttac   22020
agcacccgcg cttccgatca aggcccgaac gccggtaagt gggataacag caaggtgatg   22080
gaagagatcc tcgctctgcg tcacgaactg gcgcaactgt tgggctttga aaactacgcc   22140
tttaaatccc ttgctactaa aatggcagaa aacccgcagc aggtgctgga tttcttaacc   22200
gatctggcaa aacgcgcgcg tccgcaaggc gaaaaagagc tggcacaact gcgcgccttc   22260
gccaaagcgg aatttggcgt cgatgagttg cagccgtggg atatcgcgta ctacagcgaa   22320
aaacaaaaac agcacctcta cagcatcagt gacgaacagc tgcgtccgta cttcccggaa   22380
aacaaagcgg ttaacggcct gtttgaagtg gtgaaacgta tttacggcat caccgctaaa   22440
gagcgtaaag atgttgatgt ctggcatccg gatgtacgtt tcttcgaact gtatgacgaa   22500
aataacgaac tgcgcggcag cttctacctc gatctgtatg cccgtgaaaa caagcgcggc   22560
ggggcgtgga tggatgactg cgtaggccag atgcgtaaag ctgatggttc gctgcaaaaa   22620
ccggtcgcgt atttgacttg taacttcaac cgcccggtaa atggtaaacc ggcgctgttc   22680
actcacgacg aagtgatcac cctgttccac gagttcggtc acggcctgca ccatatgctg   22740
acccgcatcg aaaccgctgc tgtttccggt atcagcggtg tgccgtggga tgcggtcgaa   22800
ctgccgagtc agtttatgga aaactggtgc tgggagccgg aggcgctggc gtttatctcc   22860
ggtcactatg aaaccggcga accgctgccg aaagagttgc tggataaaat gctggcggcg   22920
aagaactacc aggcggcgct gtttattctg cgtcagctga gttcggcct gtttgatttc   22980
cgccttcatg ctgagttccg cccggatcag ggggcaaaaa tcctcgaaac tctggcagaa   23040
atcaagaaac tggttgccgt ggtgccatct ccgtcctggg gccgtttccc gcacgctttc   23100
agccatattt tcgccggtgg ttatgcggca ggttactaca gctacctgtg ggctgacgta   23160
```

```
ctggcggcag atgctttctc gcgctttgag gaagagggca ttttcaaccg tgaaaccggg   23220
cagtcgttcc tcgacaacat tctgagccgt ggcggttcag aagagccgat ggatctgttc   23280
aaacgcttcc gtggtcgtga accgcagctg gatgcgatgc tggagcatta cggcattaag   23340
ggctgatcat tcagtgaaaa tctgcttaat tgatgaaaca ggcgccgagg acggcgcctt   23400
atctgttctg gcggcccgct gggggctgga gcacgatgaa gacaacctga tggcgctggt   23460
gttaacgccg gaacatctgg aattgcgcaa gcgtgatgag ccaaaacttg gcggcatctt   23520
tgttgatttt gttggcggag cgatggcgca ccgacgcaaa ttcggcggtg tcgcggtga   23580 ggcggtggcg aaagcggtgg gcattaaagg cgattatttg ccggatgtgg tggatgccac   23640
cgcagggctg gggcgcgatg cctttgtgct ggcttcagtc ggctgccgcg tgcggatgct   23700
ggagcgtaat ccagtcgttg ccgcattgct cgacgacggc ctggcgcgtg ttatgcgga   23760 tgcggaaatc ggcggctggt tgcaggagcg gttgcagtta attcacgcct ccagcctgac   23820
ggcgctgact gatattaccc cgcgcccgca ggtggtttat ctcgacccga tgttcccgca   23880
taagcagaaa agcgcgctag tgaaaaaaga gatgcgtgtc tttcagtcgc tggtgggacc   23940
ggatcttgat gccgatggat tactggagcc tgcacgcttg ctggcgacca aacgcgtggt   24000
ggtaaagcgc ccggactacg cgccaccgct ggcgaatgtc gccacgccaa acgcggtagt   24060
cactaaaggg cataggtttg atatttatgc aggtacgcca gtgtaaaagt aaaccagggt   24120
agcgataacg ctaccctgct ttctgcaaga ataattaatg gctttccggc gtcgcaatca   24180
tgcgtttcag ccacggcacc atcaacagca tcactactgc aacgcccagt gtgaccagac   24240
caatcttacc aaacacgttg gtatagacgg caacgtctc aagcggatcg gtaatgttgt   24300
ccggcaccgc ggtaaatgtt gccacatagc cgcccagcaa gaacgcggca gcctgcgtca   24360
ggaaccacat cccgagaata aagcccatca aatgctgcgg caccagggca gcaatcatcg   24420
ccaggccaag ggcgctaata acagttcac ctaagctctg gaataagtac accagcacga   24480
taaaccatgg cgatgtcagc ccctgggcat ccgcaaacca cattcccgca gctgcagccg   24540
tcaaaaagcc cagagagcac ataaacatgc cgagagtaaa tttcatcggc atcgagaggt   24600
ctttgccttt gttacccaga tgcgtgtaaa tgcctgccag tattgggctg gcgagtacca   24660
cccagaacgg gttaagcgcc tggaagctga ccgggttgat ggaaaaaccg agaatttcat   24720
gatgcacgtt gttgatggca agaagttca gcgatgttgg catctgggcg tagagaatgt   24780
aaaacaccac cgcttcgagc atcaggacaa aggcgacaaa catttattg cgcccggttt   24840 tatccagctt gaatgcctga cgaaagaaga tgatggtgac gacgatggag agaacaatca   24900
gcaccagatt ggcgacttct acgttgtgca tcagccatgc acatacgaag atcatcacca   24960
cgctgccaag taatacgtac aacagttttgc tgaagctcat cggcttgaag tcgggttcag   25020
aaccaatgtc tttcaccatt ccacgacagg cgatgtaaac cagtaatgcg ataattaacc   25080 ccgcccccgca caggttgtag gtgactgaat aaccgaatct atcagcgatc acaggggcca   25140
gcgataacgc tatcaacgag ccgatattga tcgacatata gaacagggtg aatgcgccat   25200
caagccgcgg atctttcggc ggatagcact tcgaaagcaa gctggctggg ttagctttaa   25260
acaggccgtt accgacagcg atagtcccca gggcgatgaa aatcaggtca ggcttaagta   25320
gcgacatgcc ggtcatgaag tagccaatcg ccagcacaag tgctccgaga acaatggtgc   25380
gtttggtccc cagcaggtgg tcgccgacat agccgccaat ggaaatgagg ccatagacca   25440
gcgcagcaaa agcaccaaaa gtgacaaaag cctgctcttg cgagaatcca agctgtttaa   25500
cgaagaaaac cgccagtacg ccctgcacgc cgtagtagcc gaatcgctcc cataactcga   25560
```

```
caaaaaagat catgaaaaat gggcgaggtt gctgcagcat ccccatgggt gttgttgtat    25620
tcatatttat taaccttcca ataccatcct gaaaagtatg aacgcgtaag ggataacgcg    25680
cgaaaaagtt tacatctgtc agagattctt aatattgatg cggtgaatag attaatacac    25740
tattacaaca gaaataacc agctgatcac actaatgatg gaaaatatga tggtgttaaa     25800
tgttgtattg gcaggagatt ttgattgcgt acgcagatcg taggccagat aaggggttta    25860
cgctgcatca ggtaacaagg cgcgccaaaa agcaaaacgc ccgcatatgc gggcgttcag    25920
gaacacgtcg tgggggatg attattcttc ttcgtcgcgc agcggaacaa tcagcatatc     25980
aacgtgaacg tgttgatca gctgacgtgc ggaagacatt agtttgctcc agaagtcctg     26040
gtggtgacca caaaccacca gatccatatc gtatttcttg attgcatcga ccagaacctg    26100
gcccaggtcg ccgctgccgc tcagggtttc agtgattggg tagcctgcat tagtggaaag    26160
ctcggtcagc gcatgatgtg tctcttcaga gatgcgtttc tgcatatcac ccagattcac    26220
atcaataagc ccggtgtata ggtcagagta gtttacatct acgtggatca gagaaacttt    26280
cgcattgtag gggcgagcca tagagactgc tttctctacc agaactttgc tttccgggga    26340
gaggtcgacc gcgatgagaa tgtgtttata agccatagtg ttactccttc cataaagttg    26400
tcgatgactg gccagctagc gtttcttgtg ccgttacgtc acccgcgtcc tgcgaactac    26460
gtgcgcgggg ctaacccagc cgtaaagatt cagtgttaag accatcctta ccttatagcg    26520
acccggatga tccgtcaatc cgccttgctt actcgttaga taaacaaatt ttcgacatga    26580
atatattgat agtggttaac cttctggaaa aaaacaacc tgatctccta cactatctat     26640
agagccgctc ggatgttggt caccacaaaa gcggtttctc caggacctgg tgttaactga    26700
ttggcagcgt atcgggagcg gtagccccgg ggtggaactc cgcgggcagg tcgccgggga    26760
ggaggtatga taagcaccgt cgcattattt tgggctttat gtgtcgtttg cattgttaac    26820
atggcgcgct atttctcatc actacgcgcg ttgttagtgg tactgcgtaa ctgcgatcca    26880
ttgctctatc aatatgttga tggagggggc tttttttacct cacatggcca acccaacaaa    26940
caggtgcgtc tcgtttggta tatctatgcc caacgttatc gcgatcatca cgatgatgag    27000
tttattcgcc gctgtgagcg ggtgcgtcgg cagtttattc tgactagcgc attgtgtggt    27060
ttggtggtgg tcagcctgat tgcattgatg atttggcatt aagcacttca gcaataataa    27120
cgcataaaaa aagcgggcca gtaaactgac ccgctcgttt tggtgcgtac gattacagga    27180
actgcaagga gagccagtac agcccgccgg aaagcagtac cgcagccgga agggtaaaca    27240
cccaggccat cagaatactg gttacggttt tacgctgtaa gccgccgcca tctaccacca    27300
tcgtccccgc gacagaagag gagagtacgt gagtagtgga aaccggcatc ccggtataac    27360
tcgccaggcc gatagacact gccgccgtca tctgggcaga catcccctga gcgtaggtca    27420
tgcctttctt accgattttc tcaccgatag tcgttgccac acggcgccag ccaatcatcg    27480
taccgatacc taacgccagc gcgaccgcca tgatgatcca caccggtgca tactcgatgg    27540
tgctaagcat gtcggacttc agtttcttca acaggcgctg atcgtcagca ctcacgccag    27600
gcatcttcac cactttgtcg atagtgtcag aaacgcacag cataatgcgg cgcatctggc    27660
tacgttgatc aagcgacagc ttgtcgtagc tttccacatc ggtggtcaac atacctttca    27720
ggcggttgag cgcgttaatg gtattcgacg gatggcagtg gaactccgca ggttgcgttg    27780
cgccagcttc cggagccggt actaactgat cagcaccggt agcctgtttg agcagcgcag    27840
gatgctgctc aaagtaagct tcgacgttgt tgatggcatc acgggtacgg gtgatttcgt    27900
```

```
agccagtggc attcatgttc accacgaagc ctgctggcgc gacgccaatc aataccaaca    27960
taaccagacc aatgcctttc tgaccatcgt tcgcgccgtg cgaaaacgcc acgccgatag    28020
cggaaaggat cagcgcgata cgcgtccaga acggcggctt tttcttgccg tctttctttt    28080
cacgctccgc tggggtcagg tggatacggg cgcgtttctt ggtgccgctc cagtagcgac    28140
gcagcaagaa aatcagaccg ccagcaaaca ccaggccgac aataggggaa acgatcagag    28200
aaccgaaaat acttaatact ttcgggatat tgagtgcatc caccactgac gtcccggtca    28260
tcaacgcatt ggttaaacca atcccgatga tcgcgccaat cagcgtatga gagctggatg    28320
caggtaaacc aaagtaccag gtacccaggt tccagataat cgccgccagc aacatagaga    28380
acaccatggc aaggccatga gacgatccca tattaagcag cagatccgtc ggcagcatat    28440
gcacaatggc ataggcaaca ctcagaccac ccagcaaaac acccaaaaag ttgaacaccg    28500
ccgccataac cacggcgagc tgagaacgca tcgcgcgggt atagataacg gttgccacgg    28560
cgttggctgt gtcatggaaa ccattgatgg cttcgtagaa cagcacaaaa gccagtgcaa    28620
gcaataataa cagcccggta tgcaaatcca ggccagcaaa caaatgtagc ataggacgtt    28680
acgccatttt gaggacatga acgcggcgca ttatcagtga ctttcgcggc gcggcaaag    28740 tgaaatatag actttttttg atttgcctcc tgtatggatt tcactcaaaa aataattatc    28800
ttatataatt caggcaaata cttcctttta gtaatattga tgctggtgcg accactgagg    28860
aatctttaca attcacgccc gttttttcta agaggagcgc aacgtggaaa ggtttgatgc    28920
cattattata ggcgctggtg cggcgggtat gttctgttct gcgctggcag gtcaggcagg    28980
acgccgggtt ctgctgatcg ataatggtaa aaaccagggg cgcaaaatcc ttatgtctgg    29040
cggtgggcgc tgcaacttta ccaacccttt a tgtcgaacca ggcgcttatc tgagccagaa    29100
tccgcatttt tgtaagtctg cactcgcgcg ttttacccag tgggatttca ttgatctggt    29160
caataaacac ggcatcgcct ggcacgagaa aacgttagga caactcttct gcgatgactc    29220
cgcgcagcag attgtcgaca tgctggtgga tgagtgcgag aagggcaatg taaccttcag    29280
attgcgtagc gaagtgctga gtgtggcgaa ggatgaaaca ggcttcacgc ttgaactgaa    29340
cggcatgact gtcggttgcg aaaagctggt catcgcgacc ggtgggctgt caatgccggg    29400
gctgggcgcg tcgccgtttg gttataagat tgccgaacaa tttggcctca acgtgctgcc    29460
gacccgcgcg ggtctggtgc cattcactct gcataaaccg ttgctcgaag agttacaggt    29520
gctggcgggc gtggcggtgc cttccgtgat taccgctgaa acggcatcg ttttccgtga    29580 gaacttactc ttcacccatc gcggcttgtc tggaccggcg gtgttgcaga tttccagcta    29640
ctggcaaccg ggtgaatttg tcagtatcaa tctgctaccg gatgtggatc tcgaaacctt    29700
cctgaatgag cagcgtaacg cacatccgaa tcagagcctg aaaaacacac tggcggttca    29760
tctaccgaag cggttggttg aacgcttaca gcaactcggg caaatcccgg atgtttcgct    29820
aaaacagctc aacgtgcgtg accaacaggc actgattagc acattgaccg actggcgcgt    29880
acaacccaac ggcactgaag gctatcgcac tgccgaagtg acgctcggcg gcgtggacac    29940
caacgaactc tcttcacgga cgatggaagc gcgcaaagtg cctgggctgt acttcatcgg    30000
cgaagtgatg gacgttaccg gctggctggg gggctataac ttccagtggg cgtggtcgag    30060
tgcgtgggct tgtgcgcagg atttgattgc agcgaagtcg tcctgacctg ttacctaaag    30120
atgaaaatta ttagagccgc attaaaaatg agctaatttt gatagtggct atcttgtgat    30180 tatttttctaa tgagcccgtg aactgaaacc ctccaggctt aatataaggt ggaaggaaag    30240
gtgattgaaa actcacccag tggccagatc tttataaaat atgaacaggt tgaaaaaaac    30300
```

```
agtaactttg ttgttttttt atccttaacc actatgcatt aatgctgcgt tatttcatga   30360
tgcctaagaa aaaccagcgt tacgcaaatg gtcaacgctg gttttatccg gtacgttgca   30420 attattttt agcagaacct gcttctaata ttgaaacgat tgagaacaac gtaaagcata    30480
ccgctcctaa accgaccaaa acccgcgaag gaataaaata tcccatgtcg gtctgcgcca   30540
tttccgcaag aaacgatgcc aggaaaaggc aaaacaggca ggtgaagacg ggaatcatcg   30600
gtattctgtt ggctaacgaa caggtacgtc tccataccag tgccagtagc cagacttttg   30660
agaatatgct gtaacagatc attccgaggc aaataagaat aatgccggga gccagtcggg   30720
cgcttgcatc ggaactgact aagacgtata tcccctgcag taccgtgatt gagccgagaa   30780
aaataaccca ataacaccac agccagtgtt ctttagttga aaacgtatta cgtgtttgat   30840
ggacaattgt ggcaacaagg ccaattagac aggcacagat tgcggttaac ccaagcaata   30900
cgtgacccgc gacataatgc ggagttatgt cagcactacg taacagcgta atagaccaaa   30960
tgaaaccgag cagggtgagt aaaacgggaa cggcaatgag gcaattaccg attaatgaag   31020
aataagcctg taccggcgtt ccatcgctct tgctccccgc tgcattttg ggaatgagca    31080 gaaagtgacc ggatgacgct gccaccgtcg atacacaggc ggcaatcata ccaacgccga   31140
aaataacatg gccggcgaca aactcgtctg ccatcacatc attgcctgct aacagtgccc   31200
aaccccatat catggtgata attgaccccg catagccaat aatggggaac aatgtattgt   31260
aaaacgtatt aacgccgcgc gtgagctgcg aaatgataat aaatgcggta gtgaataatg   31320
ccaggcatat ggccgccaga gaaatcagca catgacccgc gacgaaatac tcgctttgcc   31380
ctgaactttc cagcacaaag ccacctaacg cgatgcaaat taatcccata atcaaaggga   31440
ttaatttgaa aagccaccg atatatatgt tcactttaaa ctcctcaggt atccctgcta    31500
ataatgaaat gtgcattaat gataaatttca gcctgttaat ataacgacga gatatcatta   31560
aagacaaatg catagcataa ctatagcggg gtttactgtg ccgagtgcca ttttttaccg   31620
gttaaaaggc catgataaat aaatatttat cctaagatta attcttattc tgttgttttt   31680
tttacaatta tcttccaggg atggattgtt ttccattatt tagtaaaaga ccggatagtc   31740
tcggtgctta aaatcatcga acatataagt attattgctt tgtatcatcg taaatatgtc   31800
tttcagacat gtattgttta ttttgttact aacaagtaaa aatattacag gttatttatg   31860
aaagtatttc acaatatatt taagcacttc tcttcaaacc atcaagataa gcattcagat   31920
aaagttaaca gtcatcaaca ccatggcaag gttgataaaa cacatcgtgc aaagatagtt   31980
gaatttgata aactggataa tgattcgcaa atagataacg attttggcct gcatatcatc   32040
tatttcctgc aacatggtca ctggaaggta aatgatcgta gtcaccagat ggagaaagta   32100
tggttttata atagtgaacc ttctatagat attcaagaat ataatagatt cgccgacaat   32160
actactgata cgtttatctt tacaattata ccagacaata accatgtgtt aaaattatcg   32220
tctcccatta ccgttactgt tgagtgtaag ggcggttatt atttttattaa ttcctctgga   32280 gataaatcag atataatta taaagttgat gggctttcta tcatagcgag aaatttcttt    32340
actcttctta gtggtaattt caaacctgac tggcgttggg atgtctctaa agagacgttt   32400
actaaggaaa agtttgatag ctatgttaaa cctgtgtttt caaaaataga cttctataaa   32460
cagtgtggtg tgattaaccc acaaaatgcc aacacggctt attttggcga tacagatgga   32520
agagtaggcg ctgtactta tgcattgctc gtttcagggc atataggcat cagggaaaag    32580
ggttggagtt tattatgtga attattaaaa cacgaagaga tggcttcatc tgcatacaaa   32640
```

```
cataaaaata ataaagtgct ctacgattta ttaaatacga gagacatgat cttgaatgag   32700
ttgcatcaac atgttttttt aaaggacgat gcgataaccc cttgtatctt ccttggggat   32760
catacaggcg atagatttag tactattttt ggtgataaat atatccttac tttgctaaat   32820
tctatgcgaa atatggaggg taataaagat agccgtatta ataaaaatgt cgtcgttctg   32880
gctggaaatc atgaaatcaa ttttaatggt aactatactg cacgactagc aaatcataaa   32940
ctctctgccg gtgatacgta taacttaatt aaaacgctcg atgtttgtaa ttatgactca   33000
gaaaggcaag ttttaaccag tcatcacgga ataataagag atgaagaaaa aaaatgttat   33060
tgtctcggtg ctttgcaggt tccatttaat cagatgaaaa atcctactga tcctgaggaa   33120
ttagccaata ttttaataa aaaacataaa gaacacatgg atgatcgttt tatccatcta   33180
attagaagca atgctatagc atccacacct gtatatgaca attattttaa taacactact   33240
gctttcagac caaaacctga agatatcttc aaatgtggac agacgctcaa aaaaactaaa   33300
cagaaatatg gccattatgg attaggggta gatcagcatc aaaaaattga taattatacc   33360
atggggctaa attcctggaa gatagctcct aacgaacgtg gtgataaaaa aggtgtccca   33420
gggcttagtt gttttcaacc acattaaaac tccatgagtg ctgtggtata tcttttaat   33480 cctgccagta tttcataggt tttcttaatc gattgtagag gcatgttctg atgacgcctc   33540
tacaatcttt agggactttc tctgctatga gataagaaat ttcatattat gctttaaggc   33600
tgaatgattt gtgcaaaata taattatttt tccatcgaac atgaggtgta tgtcataaga   33660
ttaaatgtta actatgcatt cctcgcggtg aattatatga ggtaaaagat gaaaattgga   33720
actgtggcag gcactaacga cagtacaacg acaatcgcaa caaatgatat ggtgcaagag   33780
catgttacta acttcactaa agaactgttt gggtatattg caaatggtat aggtgatgat   33840
atatcaagta ttgccaggac aatgctcggt gaagttgtgg aaaaaattga tgattggcaa   33900
atagaacgtt tccaacaatc tattcgagat gacaaaatat catttaccat acaaacgaat   33960
cattcagaaa aatatagtat gctatcggac atgcgcgctc atattctacg tagggataat   34020
aattatcagt ttattgtgac aattaatagt aaaaattacg gctgctatct tgataatacc   34080
gatattaatt ggtgcagcat tgtttattta cttaataata tgacagtaaa tgatgatgct   34140
aatgatgttg cagttactga gtcgtacaaa cccgtctggg actggaaaat atcgcaattc   34200
aatgtatctg atattaaatt cgaaacaatg ataaaccccc agttcgctga cagaaccctat   34260 ttctccaatt gttcacctgt tgatcccaca agtaccagac caacctatt tggcgatacc   34320 gatggctcag tcggtgcagt tttgtacgcg cttttttgcaa cgggacattt gagaatcatg   34380
gctgaaggag aaaatttcct tagccagttg cttaatatag aagatgaagt tctcaacgta   34440
ttgctaaggg agaactttaa tgagcaactt gacactaatg ttaatacaat aatcagtatt   34500
ctgaacagaa gagatatagt tttagaaagt cttcagcctt atttagttat taataaagac   34560
gctgtgacgc catgtacgtt tcttggcgac caaaccggcg atcgatttag taatatctgt   34620
ggcgatcaat ttatcatcga tttgttaaaa cgcataatga gtatcaatga aaatgttcat   34680
gtattagctg gaaatcatga aacgaattgc aatggtaact atatgcagaa cttcacgcgt   34740
atgaaaccac ttgatgagga tacctacgct gggataaaag attatcctgt atgtttctat   34800
gaccccaaat acaaaataat ggcaaatcat catgggataa cttttgatga gcagcgaaaa   34860
cgttacatta taggaccgat aacagtctct attgatgaaa tgaccaatgc tctcgatccg   34920
gtcgaattag cggcaattat caataaaaag catcatgcta taattaatgg caaaagtttt   34980
aaaactagcc gggctatctc ttgtcgatcc tttaatcgtt attttctgt ttcgacagat   35040
```

```
tacagaccta aacttgaagc actattagca tgttcacaaa tgttaggtat aaatcaagtt   35100
gttgcacata acggaaatgg tggaagagaa cgcataggcg aaacggggac agttttaggt   35160
cttaacgccc gtgacagtaa acatgctgga agaatgttca gcatgcataa ttgccaaatt   35220
aaccctggtg cagggcctga gataaccact ccctggaagt cttaccagca tgaaaaaaac   35280
agaaatggac ttatgccttt gattagaagg cgcacaatgt tacagctctg aaccatagac   35340
aacatgaata ttaatgttac tatctggttg agactgttga taaaacgtaa aaaggaatgc   35400
tctgttcctg caactgaaca ggcgtgaaac gctatccaac aggatggata ccgttttgtc   35460
agccagtttt atagatcaca cttatgagta tgcgtgtttc atttacggcc aggaatgctg   35520
atgatgacaa cattactacc cgttttcact aagccttccc cgttggcgct caatgctctg   35580
cgcgctggtc gtatttgccg tttccttctt atcccggatg gaagaatccg ctgaacgtcg   35640
ttcggcggca gttgtaacac gcgtcgtttg cttacaggga ttatggcggg tcgattatgg   35700
ataagagtaa gcgccatctg gcgtggtggg ttgtcgggtt actggcggtg gcggctatcg   35760
tggcgtggtg gctgttgcgc ccggcaggtg tgccggaagg ctttgctgtc agcaatgggc   35820
gcattgaagc gacggaagtg gatatcgcca gcaaaattgc cgggcgtatt gacaccattc   35880
tggtgaaaga aggccagttt gttcgagaag gtgaagtgct ggcgaagatg gatactcgcg   35940
tgttgcagga acagcgactg gaagccattg cgcaaatcaa agaagcacaa agcgccgttg   36000
ctgccgcgca ggctttgctg gagcaacgcc aaagtgaaac tcgcgccgct cagtcgctgg   36060
ttaatcaacg gcaagctgaa ctggactccg tagccaaacg tcatacccgt tcccgctcgc   36120
tcgcccatcg tggggctatt tctgcgcaac agttggatga cgaccgcgcc gccgctgaga   36180
gcgcccgagc tgcgctggaa tcggcaaaag ctcaggtttc ggcttctaaa gccgctatag   36240
aagcggcacg caccaatatc attcaggcgc aaactcgcgt cgaagccgca caagccactg   36300
aacggcgcat tgccgcagat atcgatgaca gcgaactgaa agccccgcgt gacggacgcg   36360
tgcagtatcg ggttgccgag ccaggcgaag tgctggcggc aggcggtcgg gtgctgaata   36420
tggtcgatct cagcgacgtc tatatgactt tcttcctgcc aaccgaacag gcgggcacgc   36480
tgaaactggg cggtgaagcc cggctgatcc tcgatgccgc gccagatctg cgtattcctg   36540
caaccatcag ttttgtcgcc agtgtcgccc agttcacgcc aaaaaccgtc gaaaccagcg   36600
aagaacggct gaaactgatg ttccgcgtca agcgcgtat cccaccggaa ttactccagc   36660
agcatctgga atatgtcaaa accggtttac cgggcgtagc gtgggtgcgg gtgaatgaag   36720
aacttccgtg gcctgacgac ctcgtggtga ggttgccgca atgacgcatc tggaactggt   36780
tcccgtcccg cctgtcgcgc aactggcggg cgtgagccag cattatggaa aaaccgttgc   36840
gctgaacaat atcacactcg atattccggc ccgttcatg gtcgggctga ttggcccgga   36900
cggcgtcggg aagtcgagct tgttgtcgtt gatttccggt gcccgcgtca ttgaacaggg   36960
caatgtgatg gtgctgggcg gcgatatgcg cgacccgaag catcgccgcg acgtctgccc   37020
gcgcatcgcc tggatgccgc aggggctggg caaaaatctc taccacacct tatcggtgta   37080
tgaaaatgtc gattttttcg ctcgcttgtt cggtcacgat aaagcggagc gggaagtccg   37140
aattaatgag ctgctgacca gcaccgggtt agcaccgttt cgcgatcgtc cggcaggtaa   37200
actctccggc gggatgaagc aaaaactggg gctgtgctgc gcgttaatcc acgacccgga   37260
actgttgatc cttgatgagc caacaacggg ggttgacccg ctctcccgcg cccagttctg   37320
ggatctgatc gacagtattc gccagcggca gagcaatatg agcgtgctgg tcgccaccgc   37380
```

```
ctatatggaa gaggccgaac gcttcgactg gctggtagcg atgaatgccg gagaagtgct    37440
ggcaactggc agcgccgaag agctgcggca gcaaacgcaa agcgccacgc tggaagaggc    37500
gtttataaat ctgttaccgc aagcgcaacg ccaggcgcat caggcggtag tgatcccacc    37560
gtatcaacct gaaaatgcag agattgccat cgaagcgcgc gatctgacca tgcgttttgg    37620
ttccttcgtt gccgttgatc acgtcaattt ccgcattcca cgcggggaga ttttttggttt   37680
tcttggatcg aacggctgcg gtaaatccac caccatgaaa atgctcaccg gactgctgcc    37740
cgccagcgaa ggtgaggcgt ggctgtttgg gcaaccggtt gatccaaaag atatcgatac    37800
ccgccgtcgg gtgggctata tgtcgcaggc gttttcgctc tataacgaac tcaccgtgcg    37860
gcaaaacctt gagttacatg cccgtttgtt tcacatcccg gaagcggaaa ttcccgcgcg    37920
agtggctgaa atgagcgagc gttttaagct caacgacgtt gaagatgttc tgccggagtc    37980
attgccgctc ggcattcgcc agcggctttc gctggcggtg gcggtgattc atcgcccgga    38040
gatgttaatc ctcgatgaac ctacttctgg cgtcgatccg gtggcgaggg atatgttctg    38100
gcagttgatg gtcgatctct cgcgccagga caaagtaacc attttatct ccacccactt     38160
tatgaacgaa gcggaacgtt gcgaccgcat ctcactgatg cacgccggaa aagtgctcgc    38220
cagcggtaca ccgcaggaac tggttgagaa acgcggagcc gccagtctgg aagaggcatt    38280
tatcgcctat ttgcaggaag cggcaggaca gagcaacgaa gccgaagcgc cgcccgtgat    38340
acacgacacc acccacgcgc cgcgtcaggg atttagcctg cgccgtctgt ttagctacag    38400
ccgccgcgaa gcactggaac tgcgacgcga tccggtacgt tcgacgctgg cgctgatggg    38460
aacagtgatc ctgatgctga taatgggtta cggcatcagt atggatgtgg aaaacctgcg    38520
cttttgcggtg ctcgaccgcg accagaccgt cagtagccag gcgtggacgc tcaatctctc   38580
cggttcccgt tactttatcg aacagccgcc gctcaccagt tatgacgagc ttgatcgtcg    38640
gatgcgtgcg ggcgatataa cggtggcaat tgagatccct cccaatttcg ggcgcgatat    38700
cgcgcgtggt acgcctgtgg aactcggcgt ctggatcgac ggagcgatgc cgagccgtgc    38760
cgaaacggta aaaggttacg tgcaggcaat gcaccagagc tggctacagg atgtggcgag    38820
ccgacaatcc acacccgcca gccaaagcgg gctgatgaat attgagacgc gctatcgcta    38880
taacccggac gtaaaaagcc tgccagcgat tgttccggcg gtgatcccgc ttctgctgat    38940
gatgatcccg tcaatgctaa gcgcccttag cgtggtgcgg gaaaaagagc ttgggtcgat    39000
tatcaacctt tacgtgaccc ccaccacgcg tagtgaattt ttgcttggta acagttgcc    39060
atacatcgcg ctggggatgc tgaactttt cctgctctgc ggcctgtcgg tgtttgtgtt    39120
tggcgtaccg cataaaggca gtttcctgac gctcaccctg gcggcgctgc tgtatatcat    39180
cattgccacc ggaatggggc tgctgatctc caccttatg aaaagccaga ttgccgccat     39240
tttcggaacg gcgattatca cgttgatccc ggcgacacag ttttccggga tgatcgatcc    39300
ggtagcttcg ctggaagggc ctggacgttg atcggcgag gtttacccga ccagtcattt     39360
tctgactatc gcccgcggaa cgttctcgaa agcgctggat ctgactgatt tgtggcaact    39420
ttttatcccg ttgctgatag ccatcccgct ggtgatgggc ttaagtatcc tgctgctgaa    39480
aaaacaggag ggatgatgcg ccatttacgc aatatttta atctgggtat caaagagttg    39540
cgcagtctgc tcggtgataa agcgatgctg acgctgattg tcttctcgtt tacggtgtcg    39600
gtgtattcgt cagcgaccgt tacgccagga tcgttgaacc tcgcgccgat cgccattgcc    39660
gatatggatc aatcgcagtt atcgaaccgg atcgttaaca gcttctatcg cccgtggttt    39720
ttgccaccgg agatgatcac cgccgatgag atggatgccg gactggacgc cgggcgttat    39780
```

```
accttttgcga taaatattcc gcctaattt cagcgtgatg tcctcgccgg acgccagccg  39840
gatattcagg tgaacgtcga tgccacgcgc atgagccagg catttaccgg caatgggtat  39900
atccagaata ttatcaacgg tgaagtgaac agctttgtcg cgcgctaccg tgataacagc  39960
gaaccgttgg tatcgctgga aacccggatg cgctttaacc cgaaccttga tcccgcgtgg  40020
tttggcgggg tgatggcaat catcaacaac attaccatgc tggcgattgt attgaccgga  40080
tcggcgctga tccgcgagcg tgaacacggc acggtggaac acttgttggt gatgccgata  40140
acgccgtttg agatcatgat ggcaaaggtc tggtcgatgg gctggtggt gctggtggtg  40200
tcgggattat cactggtgct gatggtgaaa ggcgtgctgg tgtaccgat tgaaggctcg  40260
atcccgctgt ttatgctggg cgtggcgctc agtctgtttg ccaccacgtc aatcggcatt  40320
tttatgggga cgatagcgcg ttcaatgccg caactggggc tgctggtgat tctggtgctg  40380
ctgccgctgc aaatgctttc cggtggatcc acgccgcgcg aaagtatgcc gcagatggtg  40440
caggacatta tgctgaccat gccgacgaca cactttgtta gcctcgcgca ggccattctc  40500
taccggggtg ccggattcga atcgtctgg ccgcagttcc tgacgctgat ggcaattggc  40560
ggcgcgtttt tcaccatcgc gctgctgcga ttcaggaaga cgattgggac aatggcgtaa  40620
ggaagggaaa cttgacttca tactgtgatg tcataaagtg aagtcataag gaatgtcat  40680
gtaaacacag gtacaggctt tacgaaagaa acaaaaaaac acactggatc agctatttaa  40740
atcacccttta cctcaaggaa tcaaatggac tgatatagaa tctctggtta aagcgttagg  40800
cggagaaatt aaggaaggta gggggtcgcg ctgtaagttc atactaaata tgagcgttgc  40860
gtgtttccat cggcctcatc cgtcgccaga taccgataaa ggcgctgtag aaagcgtgcg  40920
tgactggtta ctaagtatag gggtaaaacc atgatcaaac tgaagacgcc aaactctatg  40980
gagattgccg ggcaacctgc tgttatcact tacgtgccag aactgaatgc atttcgtggc  41040
aaattcctgg gcttgtcagg ttattgtgat tttgtctctg acagcattca ggggctgcaa  41100
aaagaagggg aactttccct gcgagagtat cttgaggatt gtaaagctgc gggtattgag  41160
ccgtatgcgc gtacagaaaa gattaagacc tttacgttac gctatccaga atcgctgagt  41220
gaacgcctta ataatgcggc tgcgcagcaa caagtctctg ttaatacctta tattattgaa  41280
acactgaatg agcgtttgaa tcatttataa attttagcgg cgtacattac gcagaatatc  41340
tgcctttaca ggatctatct atgcaactga acttaattt ataaattaag ttcagttaat  41400
atcttttctt tcctcgtttc agaaataact caatcttcct tcggcaagca ctgcaaatgc  41460
ccgtgccgca cgccgcgctg ggcgataacg tcatcggcaa aatgctgcac gtcgcccata  41520
tcacctttca gcacggcgat ttccagacag tcgtcgtgat tgatatgcac atgcagcgtg  41580
gcgacggaga tcgtggtg atggtgctgg gtggagacaa tgcggctggc taagtcgcgt  41640
ttttcgtgtt catacacata ggagagcacc gcgaaacctt gcgtgccgtg ctgctgagtg  41700
gcctcctggg ccagggcgct acgcagaata tcgcggatag cttcggaacg gttgttataa  41760
ccacgacgct ggctcaggct gtccagcgtc tccagtaaat cgtcatcaag cgtgatggtg  41820
actcgttgca tttgcgttaa accttttctg tggtgcgacg gcgcacgggg aatgcgggta  41880
ataccgcgtt ttgtagcaca cgtccggcgt cagaggaaaa ggttaattta ctctcccacca  41940
cctgggtttc gacgatttgt ccgttgtcca tcaccatcac ccgctgacag aagcgttcca  42000
ccaggcgtaa gtcgtgggtg atgaacaggc aggcggtgcc aaactgttgt tgtagcttt  42060
tcagcaggcg aatgacgccc gcctgtaaca cgagatcaag gttagaaacg gcttcatcca  42120
```

```
gaatcagtag tttcggttcg accgccagcg cgcgagccag gcagacgcgc tggagctggc    42180
cgccgcttaa ctgcggtggg cgtttgtcga gaacgctgtc atcgagatcg accgccttca    42240
gcatttcgct ggcgcgcgcc agttgttcgg attttttcag tgatagcagg tggcgcatcg    42300
gttcacgcag gatctcgcgc acggttttgc gcggattcac ggcgctgatg gagtcctgaa    42360
ataccatctg aatatcgcgg cggaacgctt tacgctgggc gcgattgagt ttcgccagcg    42420
gttcgccgcg ccagctaata ttcccttgtg agggagactc taagcctacc agcagccgcg    42480
cgagggtgct ttttccgcag ccgctgcgtc ccagcagggc gacggtttcg ccgcttttca    42540
gggtcaggga acgttattc agcaccgcct gatgttgatg ttttccgcta aatccaccgt    42600
gggcatagtg atgggaaagg ccgcagacgt taagtaaggt catgatgcca gctccatacc    42660
gtagagggcg agatgagcgg aaaccaggct gcgcgtcacc gtatgtttgg gggcgttaaa    42720
cagcgtttct acatcgccct gttcgacaat tttaccttgt gacatcaccg ccacgtcatc    42780
cgccagacgc gccacaacgc ccatatcatg ggtgaccagc agcattcccg gcgcttgttt    42840
ttgcataatg ctttccagca gatcgaggat gcgcgcctgt gctaccacgt cgaggtcggt    42900
ggtcggttca tcggcgatga taaacggtga ttcacacagc accgccatcg caatcatcat    42960
gcgctgcaac atgccgccgc tcatctcgaa cgggtacagc ttcagcacgc gcgcggcgtt    43020
ttccagcccc accgcttcta tggcagcggt aagcgtagcg tcatcggcgg gtttccctaa    43080
cgccaggcag gtttcccgcg cgtgggtgtg catggtgtgc agtggattaa aggcgctgcg    43140
cgggttctgc atgatggtgg caattttgat gccgcgcagg gcgcaaggcg aaaccggttt    43200
gccatcggct aaaatttccc ccgccgtctg gcgaacgcca gcgggcaaaa tgcccagcgt    43260
cgcggcgcag gttaatgatt tcccgctgcc gctaccgccg actaacgcca gcacgcgccc    43320
gcgttgcagg gttaacgata caccgtgtac cagcggctgc gcggcctgta gcgcgatatt    43380
acgtagttca atctgttgcg gcattagtgt gcgtgctccg tcaccagatg aggatccaga    43440
tgatcgcgca gtgcgtcacc caccaggtta aaggccatca cgctgataaa cagcgccagc    43500
cccggccaga acatttgcag cggctgggtc cagatatact ggcgcgcgtc gttaatcatc    43560
acgccccatt cggcggtcgg cgcggtcaca ccgaggccaa ggaaagacat ccccgcgacg    43620
tgcagcatca tatggccgat atccagcgtt gccagcacca gcagcgaagg gatcaccgcg    43680
cctgccagat gatcgacaaa cacccgcaca tggcccgcgc cagaaagccg tgacgccagc    43740
acaaactcgc gttggcgtag tgaaatcacc aggctgcgca ccatgcgtgc ataccacgcc    43800
cagtgcgaca gggcgatggc gataattacg ttggtcagcc cggtgccgag cacgccaacc    43860
ataaagaacg acagaatcga ggtcgggaag gtcataaaca tatcggcgac gcgcatggtg    43920
gcctgatcaa cgcgcccgcc aatcaacccg gcgctgccgc caataaccag ccctaatgtc    43980
agcaccagca gcaggcaggc cattaccgaa ccgagcgaca cgcgggtcgc tgccatcagc    44040
cgcgagaaaa tatcgcgacc taagtgatcg gtgcccagcc agtgctgcgc atccggcgaa    44100
agcaggcgcg acggcaaatc aatcgcctgg gggtcatacg gcagccacca ctggctggtg    44160
agcgcaatca gcgccagcag ggcgataatg atcagcgcca ggcgtaccga ccagcgggaa    44220
gagaggaaaa agttcacgcg tgcgctcctt catgacgacg aatgcgcggg tccagcgcgg    44280
cgttgagcaa atcgacaatc aaattacaga ccacaaaaac caccaccatc atcagcgtaa    44340
agcactggat caccggatag tcacggttaa aaatcgccga caccgcatag cgcccgacgc    44400
ccggccaggc aaagatgttt tcgataatca tcgtcccgcc aatcagttcg ccgatgtgca    44460
tccccacggc ggtgatcatc ggcagcgagg cattgcgcag gatgtggcga cgttcggtct    44520
```

```
gtttgtcgtt caggccgcgc agacgcgccc aggtgacgtg acgctgaccg gcgacgtcca   44580
gcatactggc gcgcagtaaa cgcgcgttaa tcgccagcga cataaaggca atggaaaccg   44640
caggcaaaat gatgtgctgc cagccgccgt aacccatcgc gggtagccat tgcagataca   44700
ccgaaaacgc catcaccagt aaaaacgcca gccagaagtt aggcatcgac acgccaagaa   44760
acgcgatgaa acgtacggcg aaatccggca gacggtcgcg atggcgcgcc gcccagatac   44820
cgagcggtac ggaagtgagc agaattaata ccagcgccgc acctgcaagt tccagcgtgg   44880
cgggcaggaa gttcagcata tcgtccagta ccgggcgttg gctggcgaat gagataccaa   44940
agtcaagatg cagcgccttc cacaaccagg tgccgtactg gacgtacagc ggctgatcca   45000
gcccgagcat ggtgcgggta gaggccagca tctccggcgt cggcggcagg ttagataaac   45060
gcagataatc gagcgccggg tcgccggtac cgaggcgcag catcagaaaa atgatcaccg   45120
aggcggcgag caccatcggg atcagcagca gaaagcggcg taatacgtaa cgcaacatta   45180
aggtttcacc ggtttaatct gttcgaacgg aatttcagtg gcgatcggcg cgtaggggat   45240
gttacccagc tccggttttg ataccaccat cattgagatg taactgatag gcagataaac   45300
cgcctcgtca tgcagacggg tcagaatgtc gcgatacagc gcctgacgtt gcgtttcgtc   45360
atgggtcgcc agcacttcgc cgatctcttt atcaatcagc ggtttgtcgg ctaatccttg   45420
ctgtgcctgg aagtcagcgt gtgacggtac gcgcattgaa ctgaggaagg cgtgtggatc   45480
gtatggcgcg ccccaggtgc ggtggaaaat catgccaaaa cgaccgtcgc gctgacgagc   45540
atagatactg ctctcttctt cgccaatcag cgagacatct gcgccaatct ggcgcatatc   45600
agcctgaatg atttccgcca tcgatttgct taacgcatcg gtgccgatga acgacagttc   45660
aatgcgcagc ggctgaccat ttttctcgcg gatgtctttg cccgcaggca gcgtccaacc   45720 ggcttttttcc agcaacgctt tcgctttctg cggatcgtac tggcgcggtt tcaggccgag   45780
gttggcgtag ggcacagaag gggcaaacag ggtgtcggcg acctgctggg tgccatacaa   45840
cgcgttatca atcagcgatt ttttgtttac cgcgtaatta agagcttcac gtactgccag   45900
ctcattggtg ggggctttgg cggtattgag cgccagcatc acggtttcga tcggctgtga   45960
cagttgggtg tggtaagccg gattctggct aaagcgggcg aaggtatcga gcggtaataa   46020
cccttcgttt ccgtacagca ggtcgatatc gccagtttca aacgccaccg cgcgggtagt   46080
cgggtccggg atgacgttaa aggtgatctt tttaatcgct ggcttttcgc cccagtagtt   46140
ttcgttacgg acgaagacat cgtactgatt cagtttcgat tcctgcaaaa tccatggtcc   46200
ggtgccaatc ggcgctttaa ttccgttcat ggtttcatgg ttttaaact gcgagggagc   46260 gataaaacgg aaaggacggg gcagggccag ttcttgcagg aaaggatagt aggcgctttt   46320
cagggtaatt tgcagctctg ttttactgag tgctttaaca tcaacaatct ggtttgccag   46380
ctccagccag gcgtgacgtt gacggttatc gagcactgcg cggaagtttt ctgccgccgc   46440
ctcggcatcg aacggttcac cgttggagaa tttcacgtca tcacgcaggg tgaaggtcca   46500
ggttttacca tcttctgaat gagtccagct ttttgccagc cacgggatca ccgaaccgtc   46560
tgcctgatat ttcaccaatg gttcataaac catgctctgg gcgaacatct ggttaggcgt   46620
gtaaaggtgc gggtttagtg gcccgacatt caccggccag gcggtagtga tttcatctgg   46680
tgcagcggca tggacgataa aagacgcaca agccagcagc gcaaatagag tgcggcggag   46740
tgtggagagc atgataaccc caatggatta aaatagatgg cggaaataag tatgacgatt   46800
ttaagtattc gtcatactga ttacctgttc tggatcaata gatgggcagt cgggtgggcg   46860
```

```
gatcagttaa ctgaatcgat ccattgcaca ctgtcggcgg tgagcgtaaa gggggtgggg    46920
gtgcagatcg ccaggcttaa attttcaagc tgacaatggc tgactgacag cgaggagtga    46980
taggtgctgt ctacgctgac gatttgccag gcgctgccgc cacgctgttt aacgatggct    47040
tctttgcgcg tccagatgcg ccagaacatt tccagttgct gatcaggatg cacggcgtcc    47100
atctcagcgt gttccccgag gctgaatacg gcgttcgcca gccagcgcca gttggcgcgc    47160
gggcgaatca cttcgatatc gcagccgact tcgccttcat cactcaacag cagagcgata    47220
tcgtcaccgc tatggcttaa gttgaaccat agcggcgttt ccggcgcgaa tgcaggtttg    47280
ccttgttcgc catagatgat ctccggtagc ggggaaagcg tgtgcgaaag caatgcacgc    47340
cccgccagcc agcgttcgcg tcgtggacct tgcggtgctt gctcgcgtaa acccggtggc    47400
agtggagctg cgcttaaggt cgaaactttc cccagaacta tccgatacat atcagggcca    47460
acgtttaatg gaaaatgaaa gtgcgtatcg tatcacttgt cgcctcatcc cggtaaccga    47520
cttttcggtc tgcccggccc cagtaaaatc gccagtttgc tgccacctttt cgtcgttccc    47580 atccagattt tacacacgct ggttaatggc accgaaagta gcatccctac cgggccgagc    47640
agccatcccc agattaacaa tgaaagaaat accaccatgg tggacatccc caggcgatgg    47700
cccatcatcc gtggctctaa aatattgccg atgaccatat ggcaactaa aaacaatgcg    47760 ccgaccagaa tacattcgta aataccatta aacagcagca cctgaatcat tggcggtacg    47820
gcggaaatta ccgcgccgat attgggcacg tagttaagca aaaacgccag tactgcccac    47880
atcagcgcaa actgtacccc catcagctcc agcccagcc agacgatgac acctgtccat    47940
aaactgagta gcgtcttcaa tgcaagatag tgcgaaacgc ctttaagtgc gcggtgtaat    48000
cccgcgatgt gaatctgtgg attattcagc gcaaaacgca ttttgtaagg gacgtggcgc    48060
acttcaaaca gcataaaaac tacggtcatc accagcaaaa gcacgctcgc cattgccccg    48120
gaaagcccgg tcattagcgc tgtggtgaag gtaaccactt tttccgagtc catccgctgc    48180
agcattcgct ccggcgacat atgcaaatta agaaaaggca acatctcctg caatttaaaa    48240
agtttgcgcg tcagctcctt attaaacttc ggcagcatag agataaattc gttaaacgat    48300
gccgccagta cgccgaccag cgcggttagt gcgatcagca tcaccaccac tacaatcgta    48360
atggcaacgg ggcgttgtac tccccgacga ataaccagg tgacgagcgg gttgaggacg    48420
atggcaaaaa acagcgccag taacagctgc acaatgatat ctgccgctgc gtgaatgccc    48480
gcgaggatca ctaccagcga ggccagcttg agcagaatgt gcatgcccgt tttatcgggt    48540
tgaggggttt ccattgggc ttccttgtga ctttttgtat taagtgtagc gggagtcacg    48600
ccagcaatat tctgattctt actgctgatt ttcacgtcag cacatggtaa aaatgaaaca    48660
ctgttgtaaa aatgtggtga tcctcatgcc cgaacccgta gccgaacccg cgctaaacgg    48720
attgcgcctg aatttgcgca ttgtctccat tgtcatgttt aacttcgcca gctacctcac    48780
catcgggttg ccgctcgctg tattaccggg ctatgtccat gatgtgatgg gctttagcgc    48840
tttctgggca ggattggtta tcagcctgca atatttcgcc accttgctga gccgccctca    48900
tgccggacgt tatgccgatt tgctgggacc caaaaagatt gtcgtcttcg gtttatgcgg    48960 ctgcttttg agcggtctgg ggtatctgac ggcaggatta accgccagtc tgcctgtcat    49020
cagcctgtta ttactttgcc tggggcgcgt catccttggg attgggcaaa gttttgccgg    49080
aacgggatcg accctgtggg gcgttggcgt ggttggctcg ctgcatatcg gcgggtgat    49140 ttcgtggaac ggcattgtca cttacggggc gatggcgatg ggtgcgccgt taggcgtcgt    49200
gttttatcac tggggcggct tgcaggcgtt agcgttaatc attatgggcg tggcgctggt    49260
```

```
ggccattttg ttggcgatcc cgcgtccgac ggtaaaagcc agtaaaggca aaccgctgcc   49320
gtttcgcgcg gtgcttggga gcgtctggct gtacggtatg gcgctggcac tggcttccgc   49380
cggatttggc gtcatcgcca cctttatcac gctgttttat gacgctaaag gttgggacgg   49440
tgcggctttc gcgctgacgc tgtttagctg tgcgtttgtc ggtacgcgtt tgttattccc   49500
taacggcatt aaccgtatcg gtggcttaaa cgtagcgatg atttgcttta gcgttgagat   49560
aatcggcctg ctactggttg gcgtggcgac tatgccgtgg atggcgaaaa tcggcgtctt   49620
actggcgggg gccgggtttt cgctggtgtt cccggcattg ggtgtagtgg cggtaaaagc   49680
ggttccgcag caaaatcagg gggcggcgct ggcaacttac accgtattta tggatttatc   49740
gcttggcgtg actggaccac tggctgggct ggtgatgagc tgggcgggcg taccggtgat   49800
ttatctggcg gcgcgggac tggtcgcaat cgcgttatta ctgacgtggc gattaaaaaa   49860
acggcctccg gaacacgtcc ctgaggccgc ctcatcatct taaaacttac tgaataacca   49920
gcgtattaat gatgttttct gcggtggtct gcgcttttg ctgatcgtca gcgggcagcg   49980
taatttgcat ggtcagcagt tgattaccca cgttacccag aataacggaa gagtacgccg   50040 tctgccttt cgcggagata atactgtcta actgctgcat tttgtgacct ttcagctcaa   50100
tggctttatt ggttaccact tgcagctgcg gatcgcggct acgttgctga tcttccagac   50160
gcttcgccag caccgccaga tcttctttcg gatcatcgcc catgatgacg atgactgctt   50220
tctgcccggt ggcgtcggac cagacatgca tgttattggc ctgcgttccc agcttaccgc   50280
tctggtcggt catatccgct ggcagcgaga aacttaactt gccatcaagc aggttgacgg   50340
gattcccggt agcgttactt ccgcgaccg aaccctgcgc cgtagcgtta gtgtctttat   50400
catcacaggc cgcaagcccc ataaccagca ggccaattcc gacatattta accagattgc   50460
gcattgactt cttcctttcg ataaacggcc ataacggctc attcatccat cttatcacaa   50520
ctctgataac gaacctttaa ctcgcctgca aagcgttgat ttcggattta tctgccagtc   50580
ttttcaacag catattgagt aatacgccat acattggcag gaagaaaacg atactgatta   50640
acactttgaa acagtaatcg accagcgcga tttccatcca gtgttcagcc ataaaggcat   50700
ccgggctacg ccagaaggca atgaagaaaa aggccagcgt gtcactgacg ttaccgaaca   50760
gtgtggacgc tgtcggtgcc agccaccagc ggcgactctg acgcaggcgg ttaaaaacgt   50820
gcacgtcgag gatttgcccc agcgcgtagg ccatgaaact ggcggtggcg atacgggcga   50880
caaacaggtt gaagtgggcg agtgcgccga tccctgcca ggaacccata tagaatagcg   50940
acgagatgac gtaggagatt aataacgcag ggatcattac cgcgaagata atgcgtcggg   51000
ccagcggtgc gccaaaaata cgcacggtca ggtcggtagc aagaaaaata aacggaaagc   51060
taaacgcgcc ccaggtggta tggaaaccaa aaatggagac cggaagctgg accagatagt   51120
tactggaggt gatcaccagc agatgaaata cgataacca gaacaacgcc ttatagcgtt   51180
gagtttgcga gaaaacgttc atattgtacc tttttgatta accattgggg tgagggaacc   51240
caatacgtac gacacgtctg ttatcttaac ataataacgt gcttaccctt ttttcgagcc   51300
gccgcatgat actgctttac gttgacaatg caatggttaa ttttcacgca atcgttaacc   51360
tggtttgctt acggactcac agggcgtaaa ctagcgccgt ttttttaagt gatgagaaga   51420
aaatgaccga tctctttttcc agccctgacc acacactcga cgcacttggc ctgcgctgcc   51480
cggaaccggt gatgatggtg cgcaaaaccg tgcgcaatat gcagcctggc gaaactttac   51540
tgattatcgc cgacgatccg gcgacgaccc gcgatattcc tgggttttgt accttatgg   51600
```

```
aacacgaact ggttgcgaaa gagacggatg gactgcctta tcgttatttg attcgtaaag    51660
gcggttgatg gggaaagatt ggcttcgatg ccgccttttc ccctcaccct aaccctctcc    51720
ccagaggagc gaggggaccg atcgcgctca atgttgcgat cggtttgcct tatctcctgc    51780
gcaacaatct taacgcattc gctgttacca gcacggtcgc accggtatct gccagcaccg    51840
ccagccatag tccggtcatc cctagcagcg tggtgacgag gaagatccct ttcagcccca    51900
gcgcaatagt gatgttctgg cggatattgg cgtgagtggc gcgtgccagt tcaatcattt    51960
gcaccaggcc gcgcaggtgg ttatgggtta atgctgcgtc ggcggtttcc agcgccacgt    52020
ctgtgccact gcccattgca atcccaatgg cggcagcttt catcgctggc gcgtcgttaa    52080
taccatcacc gaccatcgcc aggggcgcat gttgattcag cttggtcacc gctttgactt    52140
tatcttccgg caataggccc gctttaaact ccagccccag ctcccggca attgccgccg    52200 ctgcgcgtgg attatcgccg gtgaggatca ctcctttaac ccccagcgcg ttcagttcac    52260
tgatggcagt tgctgcgtcg gcgcgcaggg tatcctgcaa tgcaatgata cccagcacgt    52320
catcattacg tactaccagc acaaccgttt gcccggcgct ttccagttca ttaatcaaac    52380
cagcaaatgc atcagcggga tgtttcccgg cagcgcaaat caatacgcgc tcaccgttaa    52440
cctgcgcttc aatgccagac ccgaccagcg cccgctgtga ttcggcggtg ggaatggcga    52500
gttcagcaac ctgtgcttcg cgtacgatgg cctgcgccag tggatgcgtc gcgccttgct    52560
cgaccgccgc cgccagtgtc agcagttcag attcactaat acccgttgcc ggatgaatcg    52620
cggtaacgcg cggtttaccg acggtcagcg taccggtttt atcaaacgcc acctgagtaa    52680
cacgacccag ctgttccagc gccgctccgc ctttaatcaa cccccacga cgcgctgccg    52740 ccgccagccc ggaggtaatc gccgcaggcg tggagataac taacgcacac gggcagccaa    52800
tcagcagcag cgtcagccct ttataaatcc actcctgcca gctggcggca aacagcagcg    52860
gtggcaccag cgtcaccagc agggcgacgg ccataatcgc tggcgtataa atacggctga    52920
aacggtcgat aaaccgctca atgggggcgc ggcgctcttc ggcttcttcg atcagtttca    52980
gaatccggtc aatggcgctg gcacccggtt ctgacagcac ttccagcgtt accagacggt    53040
ctacgctggt ggctcctgca ggaactttat cgcccgtcgc gcgctccacc ggaatggatt    53100
ctccggtcag ggcgctttca tcaaaactgg caaacggtga gagcagttta ccgtcggcag    53160
gcaaacgccc acctgcggcg acttcaatca catcgccagg ccgcaggctg ttaatcgcca    53220
cctcttcccg ctcaccgtta cgcaggcgcg tggcggtttc tggtttcagc gccattaacg    53280
cgctaacgcc ctgacgcgcg cggctggcgg cccagccttc cagtcgttca ccaatcaaaa    53340
acagcagcaa caccatcgca gcttcagccg ttgcgccaat aaacagtgca ccaatagcgg    53400
ctacgctcat taaggtttca atggcgaagt agctgccgga tttgatcagc cgtaatgcct    53460
gacgagcaat cgggtacagc ccaaccagcg tggtcgcgat aaacgccagt tgcccaaacg    53520
gatgattaaa ttgctccaga ccccagctga ttgccatcat cacgattagc gtaatcagcg    53580
gcagattctc tttcaggcgc gatgcttgtg gctcgtcggc ggcctgctca tcgcgcaggg    53640
aatagcccgc tttttgcacc gcagattcaa cctgggcacg gatgtcattg tcggcatcga    53700
ccaccagttt ttcggtggcg aacagtacct gcacctgatt cacacctgca agctggcgca    53760
cggcattttc taccttgcgc gcacaggcgg cgcagtccat gccgctgact ttccagctat    53820
agcgggtgcc ggagacgttt tcagagagcg ttggcgagct ggaacatgcg ccgtcgcagc    53880
aacagtcgtt ggcgttctgt accgtggtta gcggtttgaa cgcagcaaat tgaggggctt    53940
tcttgccgtg attgtcagga gtcgacatgg catcctccgg ttaagttttt tctcattaac    54000
```

```
cgaaggatac actctggagt cgactccaga gtcaagtttt atcagagata cagcgagcgg    54060
acgatgagga aatgaccggc aaagtagcag gccgcagcaa tcgcgttatc tgcccggaag    54120
cggcggcgat agtggctacc cagccagaca aagttactga taaacagcaa tgaagcgcca    54180
acaaacgcag agagtgccgg agcggtcgga cggaagaacc acagttcacc tgccagccac    54240
accatcacca gcgtcatgcc gataaacgtg cagataggcc aacgatactc ttccagccgc    54300
gtccagataa tcgccagtaa cagcgcgccc agaaccagca acaccagtgg cagaggccag    54360
aagaaagaga gcgtcatctg actggcgaaa tagatggtgt acagcaggtg cgagaggaaa    54420
aacgcgccga tggcgtacat cagacgttga cgtggcaaca gggttagcgc atcgcccagc    54480
agtgaggcgc acagccctgc cagcaccaga tagctaatgg cgtcgaacat cggcgcttgc    54540
caggccagta acagcaggag aagaagggtt aacggtttaa acacccagcg ttgccaggtt    54600
ggcccacgat acgatgcatc cacagatagc catgcggaaa gacagacagc gataaacgac    54660
caaagcatct tagttccttg aattcgttat ttttcgtaa gcggaatgcc tacggtcttg     54720
cttccagttt agtggcgagg gtggacggat gacaacacca taactggcag ggtatgctta    54780
tttccgcatt ttccaatgag ggataaagat gagcaaacca cctcttttct ttattgttat    54840
cattggctta attgtcgtcg ccgcatcgtt tcgttttatg caacagcgac gggaaaaagc    54900
tgataatgat atggctccgc tccagcaaaa gctggtggtg gtgagcaaca agcgggaaaa    54960
accgattaac gatcgccgtt cgcgccagca ggaagtgact ccggcaggca ccagtatgcg    55020
ctatgaggca agcttcaaac cgcaaagcgg aggaatggag cagacgtttc gcctcgacgc    55080
ccagcagtac cacgccctga cagtgggcga taaaggtacg ctgagctata aggaacgcg     55140 ctttgtcagc tttgtaggcg aacaataagg ttattttta actttaaatt tcttctgcca    55200
gaccagcagt tcaaacacgc cgaaaggaa atccgcacc ttttcggcgg tggtcatctg      55260
cgggccatct ttcggtaaag tggatttcaa tagcgccagt tgcataccat gcatcagcac    55320
ggtaaaaatc agcgccacgt taacgaaaat attcagcggg cgcgggaagg gatgcaccag    55380
attgaggatt aaaaatcccc aaacgcagag cattaacaaa cgaccaatat taatcagcat    55440
cactttctcc ttgtgcttcg cgttgataca gccgataagc cacctgaccc gccactttt     55500 cccgatgtaa tgaccagttt gccggaacag tgggcagacc gttttcgact tcgctttcga    55560
cataaatcag ggcttcgtca gccagccagc cgttatcttc cagtaaattt atcgtctctt    55620
ctaacaagcc acggcggaac ggtggatcga caaacacgat attatgcggt gtgccttttt    55680
gcgccaggaa tgacattgcg ttgctgttca ccacgcgtgc attgcctgct tttagtgtcg    55740
ccagattctt aattaactgc tgagaaactg cgcgatccat ctcaatcaac gtggccccg    55800 cagcgtagcg cgataacgct tccagcccca gcgcgccgct cccggcgaag caatccagac    55860
attgggcgtc aacaatgacc ggagccagcc agttaaacaa cgtttcgcgt acgcggtcgg    55920
tggtggggcg cagacctggg ctatcaggaa ccggagtttt acggcctcgc cactgcccgc    55980
caataatgcg gatttggccg ctgccggaat gattcggttt tttcatgata aattgctcaa    56040
tccgccagat aacacatact tgcaggcggt gatgtgaatt aagttaagtg atagactatt    56100
tcatcatttt tttagctgct atgtacatag cgttaacgct gtgccatgaa gcaacagcga    56160
ggagtgtagt cgcaaatggc gaaagaaaaa aaacgtggct ttttttcctg gctgggcttt    56220
ggtcaaaaag agcagacccc ggaaaaagag acagaagttc agaatgaaca accggttgta    56280
gaagaaatcg ttcaggcgca agagcctgtg aaggcttctg aacaagccgt cgaagagcag    56340
```

```
ccgcaggcgc atactgaagc cgaggcggaa acttttgctg ccgacgttgt ggaagtcact    56400
gaacaggttg ctgaaagtga aaaagcgcag cctgaagcgg aagtcgttgc acagccggaa    56460
ccggtcgtag aagaaacgcc ggagccagtg gctatcgagc gtgaagagct gccgttgccg    56520
gaagacgtca acgccgaaga ggtttcgcca gaagagtggc aggctgaagc ggaaaccgta    56580
gagattgtcg aagcggcgga agaagaagcg gctaaagaag aaatcaccga cgaagagctg    56640
gaagcacagg cgctggctgc cgaagcggca gaagaggcgg tgatggtggt tcctccggta    56700
gaagagcagc cggtggaaga aatcgctcag gagcaggaaa aaccgaccaa agaaggtttc    56760
ttcgcgcgcc tgaaacgcag cctgttaaaa accaaagaaa atctcggttc cggatttatc    56820
agcctgttcc gcggtaaaaa aatcgacgat gatctgtttg aggagctgga agaacagctg    56880
ttgatcgccg atgtgggcgt ggaaaccaca cgtaaaatta tcaccaatct gacgaaggc     56940 gcatcccgca agcagcttcg tgatgccgag gcgctctatg gcctgctgaa agaagagatg    57000
ggcgagattc tggcgaaagt cgatgagccg ctgaatgttg aaggtaaaac gccgttcgtg    57060
atcctgatgg tgggcgtcaa cggtgtgggt aaaaccacga cgattggtaa gctggcgcgt    57120
cagtttgagc agcagggtaa atcggtgatg ctggcggcgg gcgatacttt ccgtgcagca    57180
gcggttgaac agcttcaggt ctggggtcag cgcaacaata ttccggtgat tgcccagcat    57240
actggtgcgg attccgcctc tgttatcttc gacgccattc aggcagctaa agcgcgtaat    57300
atcgacgtcc tgattgccga taccgccgga cgtctgcaga acaaatcgca tctgatggaa    57360
gagttgaaga aaatcgtccg cgtgatgaag aaactcgacg ttgaagcgcc gcatgaagtt    57420
atgctgacta ttgatgccag caccgggcag aacgcggtaa gccaggccaa actgttccac    57480
gaagctgttg gcttaaccgg catcacgcta acgaaactgg acggcacggc gaaaggcggg    57540
gtaatttcct cggtggctga ccagtttggt atccctatcc gctacattgg tgtcggcgaa    57600
cgtattgagg atttgcgtcc gtttaaggcg gacgacttta tagaggcact ttttgcccga    57660
gaggattaac aatgattcgc tttgaacatg tcagcaaggc ttatctcggt gggagacagg    57720
cgctgcaggg cgttacgttc catatgcagc cgggtgagat ggcgtttctg accggtcatt    57780
ccggcgcagg gaaaagtacc ctcctgaagc tgatctgtgg gattgagcgg cccagcgccg    57840
ggaaaatctg gtttagcggc catgacatca cgcgtctgaa aaaccgtgaa gttccgtttc    57900
tgcgccgcca gattggcatg atttttccagg atcaccatct actgatggac cgtactgtct    57960
acgataacgt ggcgatcccg ctgattatcg ctggtgccag cggtgacgat attcgtcgcc    58020
gggtgtcggc ggcactggat aaagtcgggc tactggacaa agcgaagaac ttccctattc    58080
agctttccgg cggtgaacaa cagcgtgttg gcattgcccg cgcggtggtg aataagcccg    58140
cggtactgct ggcggacgaa ccgaccggta acctggacga cgcgttgtcg aagggattc     58200 tacgtctgtt tgaagagttt aaccgcgttg gggtaaccgt attgatggca acgcacgaca    58260
tcaacctgat ttcacggcgt tcctatcgca tgctcaccct gagcgatggt cacttgcatg    58320
gaggcgtggg ccatgaataa gcgcgatgca atcaatcata ttcggcagtt tggtgggcgt    58380
ctggatcgct tccgtaaatc ggtcggcggc tcaggcgacg gcggtcgtaa cgcaccgaaa    58440
cgcgcgaaat cctcgccaaa accggtaaat cgcaaaacca acgttttcaa cgaacaggtg    58500
cgctatgcct tccacggcgc attgcaggat ctgaaaagca aaccgttcgc cacgtttta    58560 acggtgatgg ttatcgccat ctccctgacg ctgcccagcg tctgttatat ggtgtacaaa    58620
aacgttaatc aggcggcgac gcagtattat ccgtcaccgc aaatcactgt ttacttgcaa    58680
aaaacgctgg acgatgacgc cgctgcgggc gtggtggcac agttgcaggc cgagcaaggc    58740
```

```
gtggagaaag tgaactatct ttctcgtgaa gacgcactgg gcgagttccg taactggtct    58800
ggttttggtg gtgcgctgga tatgctggaa gaaaacccgc ttccggcagt ggcggtggtg    58860
atcccgaaac tcgattttca ggggacggaa tcactcaata cgctgcgtga tcgtatcacg    58920
cagattaacg gcattgacga agtgcggatg gatgacagct ggtttgcccg tctggcggcg    58980
ttgaccgggc tggtcgggcg cgtttcggcg atgatcggcg tgttgatggt ggcggcagtg    59040
ttcctcgtca tcggcaacag cgtacgtctg agcatctttg ctcgccgtga ctccatcaac    59100
gtgcagaaac tgattggtgc gacggatggt ttcatccttc gcccgttcct gtatggtggc    59160
gcactgctgg gattttctgg cgcattgttg tcattaattt tgtcagaaat tctggtgctg    59220
cgattgtcat cggcggttgc ggaagtggca caggttttcg gaacgaagtt tgatatcaat    59280
ggtttatcgt tcgatgaatg cctgctattg ctgctggtat gctcgatgat tggctgggtg    59340
gcagcgtggc ttgccacggt acaacattta cgccacttta cgcctgaata ataaaagcgt    59400
gttatactct ttccctgcaa tgggttccgt agcagggaaa gagatcccgt tgtctcttcc    59460
cggtatttca tctctatgtc acattttgtg cgtaatttat tcacaagctt gcattgaact    59520
tgtggataaa atcacggtct gataaaacag tgaatgataa cctcgttgct cttaagctct    59580
ggcacagttg ttgctaccac tgaagcgcca gaagatatcg attgagagga tttgaatgac    59640
tgacaaaatg caaagtttag ctttagcccc agttggcaac ctggattcct acatccgggc    59700
agctaacgcg tggccgatgt tgtcggctga cgaggagcgg gcgctggctg aaaagctgca    59760
ttaccatggc gatctggaag cagctaaaac gctgatcctg tctcacctgc ggtttgttgt    59820
tcatattgct cgtaattatg cgggctatgg cctgccacag gcggatttga ttcaggaagg    59880
taacatcggc ctgatgaaag cagtgcgccg tttcaacccg gaagtgggtg tgcgcctggt    59940
ctccttcgcc gttcactgga tcaaagcaga gatccacgaa tacgttctgc gtaactggcg    60000
tatcgtcaaa gttgcgacca ccaaagcgca gcgcaaactg ttcttcaacc tgcgtaaaac    60060
caagcagcgt ctgggctggt ttaaccagga tgaagtcgaa atggtggccc gtgaactggg    60120
cgtaaccagc aaaagacgttc gtgagatgga atcacgtatg gcggcacagg acatgacctt    60180
tgacctgtct tccgacgacg attccgacag ccagccgatg gcaccggtgc tctatctgca    60240
ggataaatca tctaactttg ccgacggcat cgaagatgat aactgggaag agcaggcggc    60300
aaaccgtctg accgacgcga tgcaaggtct ggacgaacgc agccaggaca tcatccgcgc    60360
gcgctggctg gacgaagaca acaagtccac gttgcaggaa ctggctgacc gttacggtgt    60420
ttccgctgaa cgtgtgcgcc aactggaaaa gaacgcgatg aaaaaacttc gcgccgctat    60480
tgaagcgtaa tttccgctat taagcagaga accctggatg agagtccggg gttttgttt    60540 tttgggcctc tacaataatc aattcccccct ccggcaaaac gtcaatcccc acgcagattg    60600
ttaataaact gtcaaaatag ctattccaat atcataaaaa tggggtatgt tttagcagag    60660
tatgctgcta aagcacgggt agtcatgcat aaaacgaaat aaagtgctga atcacaacac    60720
cacaacacac gtaataacca aagaatgggg gattctcagg atgaacataa agggtaaagc    60780
gttactggca ggatgtatcg cgctggcatt cagcaatatg gctctggcag aagatattaa    60840
agtcgcggtc gtgggcgcaa tgtccggtcc ggttgcgcag tacggtgacc aggagtttac    60900
cggcgcagag caggcggttg cggatatcaa cgctaaaggc ggcattaaag gcaacaaact    60960
gcaaatcgta aaatatgacg atgcctgtga cccgaaacag gcggttgcgg tggcgaacaa    61020
agtcgttaac gacggcatta aatatgtgat tggtcacctc tgttcttcat caacgcagcc    61080
```

```
tgcgtctgac atctacgaag acgaaggcat tttaatgatc accccagcgg caaccgcgcc   61140
ggagctgacc gcccgtggct atcagctgat cctgcgcacc accggcctgg actccgacca   61200
ggggccgacg gcggcgaaat atattcttga gaaagtgaaa ccgcagcgta ttgctatcgt   61260
tcacgacaaa cagcaatacg gcgaaggtct ggcgcgagcg gtgcaggacg gcctgaagaa   61320
aggcaatgct aacgtggtgt tctttgatgg tatcaccgcc ggggaaaaag atttctcaac   61380
gctggtggcc cgtctgaaaa aagagaatat cgacttcgtt tactacgcg  gttatcaccc   61440
ggaaatgggg caaatcctgc gtcaggcacg cgcggcaggg ctgaaaactc agtttatggg   61500
gccggaaggt gtggctaacg tttcgctgtc taacattgcg ggcgaatcag cggaagggct   61560
gctggtgacc aagccgaaga actacgatca ggttccggcg aacaaaccca ttgttgacgc   61620
catcaaagcg aaaaaacagg atccaagtgg cgcgttcgtc tggaccaccct acgccgcgct   61680
gcaatctttg caggcgggcc tgaatcagtc tgacgatccg gctgaaatcg ccaaataccct  61740
gaaagcgaac tcggttgata ccgtgatggg gccgctgacg tgggatgaga aggcgatct   61800
gaaaggcttt gagttcggcg tatttgactg gcacgccaac ggcacggcaa ccgatgcgaa   61860
gtaacagata gataaatgaa aatgcccgat gcgctgaact gccatcgggt tttttgtgt   61920
ttgtcgaaat ggttgtagaa agattaaaca atccaggata tgcttaatgt acggtgacat   61980
accgtacata ttatacggag caggagagtt cacatgtctg ctgttaaaaa gcagcgtatc   62040
gatctgcgtt taactgacga tgacaaaagt atgattgagg aagcggcagc gatatctaat   62100
cagtccgtca gccaatttat gttgaacagc gcttcgcagc gggctgcgga agtgattgaa   62160
cagcatcggc gggtgatcct caatgaggaa tcctggacgc gggtgatgga tgcgctgagt   62220
aatccaccgt cacctggtga aaagctaaaa cgtgcggcaa aacgtcttca gggaatgtaa   62280
taatttatgg atgatctgac gatagagatt ctgaccgatg atgcagatta tgatctacag   62340
cgattcgact gcggcgagga agcgttaaat ctctttctga cgacacatct cgttcgtcaa   62400
catcgcaaca aaattctgcg agcgtatatc ctttgtcgca acactccaga acgtcaggtg   62460
ctgggatatt acacattatg cggcagttgt tttgaacgag ccgcattgcc ctcgaaatcg   62520
aaacagaaaa aaattcccta caaaaatatt cccagcgtta ctcttgggcg tctggcaatt   62580
gatcgttcat tacagggggca gggatgggga gcaacactgg ttgctcatgc catgaaagtc   62640
gtctggtcag cctctttagc ggtaggtatt cacggtcttt ttgtcgaggc gctgaataaa   62700
aaagcccata cgttttatca atcgctgggc tttatcccgt tggtcggaga aaacgaaaat   62760
gcgttatttt tcccaaccaa atccatcgaa ctgcttttca cacagagcga ttaacgcttc   62820
tcccagccgc cctgttgcgc cgtaaatccc agtgcctgca taaacgccgt catcacaccg   62880
cgatcttcca cgcctgcatc cgccatccac cagcatgaaa cgccaggatt gttacgcaaa   62940
acctcttcca gcagatattg ccccacaccg cgacggcggg tgacttcccg cacgcacagg   63000
gaatccagtg ctccctcggt gccgcttaag gtcacccgca cggccgctag caggcgctcg   63060
ttaaaacgcg cggcgtagat acggtggtta tcgtcaacct gtaaagagga aggggaatac   63120
tccggccaga tcttttgcag gtcaatccgg tcctggtcgc taaagttttc taatcgaatg   63180
atggtcagct tcatgggtaa cccgtgtaaa tcacaaaagt ggaaccagtg tagcgaaata   63240
atttaatcgg aggctttctc ttttttattt cttttggcag gtgattaatt ttttaacagc   63300
aataattaca aagttaaaac attatagaat gaaaaatacc cagcataatc ccctgaatga   63360
tagtgaatta ttccgcccctt tgtgccgtta ttttatgctg acaaaggcac ttttttctgt   63420
ttatctatca ataaattcag aatattatct gttcttaatc gactgaaaaa tagggatttt   63480
```

```
aatcactatt atcacaaaat actgcgctaa acccttaatc agacaggcaa aaacagtgca    63540
gtataaaaaa agaacagtct gatttgttaa cacataaaaa caaagcaaca caacatcacg    63600
aatggggatt tttgactatg aaacggaatg cgaaaactat catcgcaggg atgattgcac    63660
tggcaatttc acacaccgct atggctgacg atattaaagt cgccgttgtc ggcgcgatgt    63720
ccggcccgat tgcccagtgg ggcgatatgg aatttaacgg cgcgcgtcag gcgattaaag    63780
acattaatgc caaaggggga attaaaggcg ataagctggt gggcgtggaa tatgacgacg    63840
cctgcgaccc gaaacaagcc gttgcggtcg ccaacaaaat cgttaacgac ggcattaaat    63900
acgttattgg tcatctgtgt tcttcttcta cccaacctgc gtcagatatc tacgaagacg    63960
aaggtattct gatgatctcg ccgggagcga ccaacccgga gctgacccaa cgcggttatc    64020
aacacattat gcgtactgcc gggctggact cttcccaggg gcctacgcg gcaaaataca    64080 ttcttgagac ggtgaagccc cagcgcatcg ccatcattca cgacaaacaa caatatggcg    64140
aagggctggc acgttcggtg caggacgggc tgaaagctgc taacgccaat gtcgttttct    64200
tcgacggcat taccgctggc gagaaagatt tctccgcgct gatcgcccgc ctgaaaaaag    64260
aaaacatcga cttcgtttac tacgcgcggtt actacccgga aatggggcag atgctgcgcc    64320
aggcccgttc cgttggcctg aaaactcagt ttatggggcc ggaaggtgtg ggtaacgcat    64380
cattgtcgaa tattgctggc gatgctgccg aaggcatgtt ggtcactatg ccaaaacgct    64440
atgaccagga tccggcaaac cagggcatcg ttgatgcgct gaaagcagac aagaaagatc    64500
cgtccgggcc ttatgtctgg atcacctacg cggcggtgca atctctggcg actgcccttg    64560
agcgtactgg cagcgatgag ccgctggcgc tggtgaaaga tttaaaagct aacggtgcaa    64620
acaccgtgat tgggccgctg aactgggatg aaaaaggcga tcttaaggga tttgattttg    64680
gtgtcttcca gtggcacgcc gacggttcat ccacggcagc caagtgatca tcccaccgcc    64740
cgtgaaaaac gggcgggttt agaaaggtta ccttatgtct gagcagtttt tatatttctt    64800
gcagcagatg tttaacggcg tcacgctggg cagtacctac gcgctgattg ccatcggcta    64860
caccatggtt tacggcatta tcggcatgat caacttcgcc cacggcgagg tttatatgat    64920
cggcagctat gtctcattta tgatcatcgc cgcgctgatg atgatgggca ttgataccgg    64980
ctggctgctg gtggcggcgg gattcgtcgg cgcaatcgtc atcgccagcg cctacggctg    65040
gagtatcgaa cgggtagcct atcgcccggt gcgtaactct aagcgcctga ttgcgctcat    65100
ctcggcaatc ggcatgtcca tcttcctgca aaactacgtt agcctgactg aaggttcgcg    65160
tgacgtggcg ctgcccagtc tgtttaacgg tcagtgggtg gtggggcata gcgaaaaactt    65220 ctctgcctct attaccacca tgcaggcggt gatctggatt gtcaccttcc tcgccatgct    65280
ggcgctgacg gttttcattc gctattcccg tatggggcgc gcgtgtcgtg cctgcgcgga    65340
agacctgaaa atggcgagcc tgcttggcat taacaccgac cgggtgattg cgctgacctt    65400
tgtgattggc gcggcgatgg cggcggtggc aggtgtgctg ctcggtcagt tctacgcgt    65460 aattaacccc tacatcggct ttatggccgg gatgaaagcc tttaccgctg cggtgctcgg    65520
tgggattggc agcattccgg gagcgatgat tggcgggctg attctgggga ttgcggaggc    65580
gctctcttct gcctatctga gtacggaata taaggatgtg gtttcatttg ccctgctgat    65640
tctggtgctg ctggtgatgc cgaccggtat tctgggtcgc ccggaggtag agaaagtatg    65700
aaaccgatgc atattgcaat ggcgctgctc tctgccgcga tgttttttgt cctgcgggc    65760 gtctttatgg gcgtgcaact ggagctggat ggcaccaaac tggtggtcga cacggcttca    65820
```

```
gacatccgtt ggcagtgggt gtttatcggc acggcggtgg tcttttctt ccagcttttg    65880
cgaccggctt tccagaaagg gctaaaaagc gtttccggac cgaagtttat tctgcccgcg    65940
attgatggct ccacggtgaa gcagaaacta ttcctcgtgg cgctgctggt gcttgcggtg    66000
gcgtggccgt ttatggtgtc gcgtgggacg gtggatatcg ccaccctgac catgatctac    66060
attatcctcg gcctcgggct gaacgtggtt gttggtcttt ctggtctgct ggtgctgggg    66120
tacgcggct tttacgccat cggcgcttac acttttgcgc tgctcaatca ctattacggc     66180
ttgggcttct ggacttgtct gccgattgcc gggttaatgg cagcggcggc gggcttcctg    66240
ctcggctttc cggtgctgcg tctgcgcggt gattatctgg cgatcgttac cctcggcttc    66300
ggcgaaattg tgcgcatatt gctgctcaat aacaccgaaa ttaccggcgg cccgaacgga    66360
atcagtcaga tcccgaaacc gactttcttc ggccttgagt tcagccgtac cgcccgtgaa    66420
ggcggttggg acacgttcag taatttcttt ggcctgaaat acgatccctc cgatcgcgtc    66480
atcttcctgt atctggtggc gttgctgctg gtggtgctaa gctgtttgt cattaaccgc     66540
ctgctgcgga tgccgctggg gcgtgcgtgg aagcgttgc gtgaagatga gatcgcctgc     66600
cgttcgctgg gcttaagccc gcgtcgtatc aagctgaccg cttttaccat cagtgccgcg    66660
tttgccggtt ttgccggaac gctgtttgct gcgcgccagg gctttgtcag cccggaatcc    66720
ttcacctttg ctgaatcggc gtttgtactg gcgatagtgg tgctcggcg tatgggatcg     66780
cagtttgcgg tgattctggc ggcaattttg ctggtggtat cgcgcgaatt gatgcgtgat    66840
ttcaacgaat acagcatgtt aatgctcggt ggtttgatgg tgctgatgat gatctggcgt    66900
ccgcagggct gctgcccat gacgcgcccg caactgaagc tgaaaaacgg cgcagcgaaa     66960
ggagagcagg tatgagtcag ccattattat ctgtgaacgg cctgatgatg cgcttcggcg    67020
gcctgctggc ggtgaacaac gtcaatcttg aactgtaccc gcaggagatc gtctcgttaa    67080
tcggccctaa cggtgccgga aaaaccacgg ttttaactg tctgaccgga ttctacaaac     67140
ccaccggcgg caccattta ctgcgcaatc agcacctgga aggtttaccg gggcagcaaa     67200
tcgcccgcat gggcgtggtg cgcaccttcc agcatgtgcg tctgttccgt gaaatgacgg    67260
tgattgaaaa cctgctggtg gcgcagcatc aacaactgaa aaccgggctg ttctctggcc    67320
tgttgaaaac gccttctttc cgtcgcgccc agagcgaagc gctcgaccgc gccgccacct    67380
ggcttgagcg cattggtttg ctggaacacg ccaaccgtca ggcgagtaac ctggcctatg    67440
gtgaccaacg ccgtctggag attgcccgct gcatggtgac gcagccggag attttaatgc    67500
tcgacgaacc ggcggcaggt cttaacccaa aagaaaccaa agagctggat gagctgattg    67560
ccgaactgcg caatcatcac aacaccacta tcttgttgat tgaacacgat atgaagctgg    67620
tgatggggat ttcagaccga atttatgtgg tcaatcaggg gacgccactg gcaaacggta    67680
cgccggagca aatccgtaat aacccggacg tgatccgtgc ctatttaggt gaggcataag    67740
atggaaaaag tcatgttgtc ctttgacaaa gtcagcgccc actacggcaa aatccaggcg    67800
ctgcatgagg tgagcctgca tatcaatcag gcgcagattg tcaccctcat tggcgcgaac    67860
ggggcgggga aaaccacctt gctcggcacg ttatgcggcg atccgcgcgc taccagcggg    67920
cgaattgtgt ttgatgataa agacattacc gactggcaga cggcgaaaat catgcgcgaa    67980
gcggtagcga ttgtcccgga agggcgtcgc gtcttctcgc ggatgacggt ggaagagaac    68040
ctggcgatgg gcggcttttt tgccgaacgc gaccagttcc aggagcgcat aaagtgggtg    68100
tatgaactgt ttccacgtct gcatgagcgc cgtgttcagc gggcaggcac catgtccggc    68160
ggtgagcaac aaatgctggc gattggtcgc gcgctgatga gcaacccgcg tttgctgcta    68220
```

```
cttgatgagc catcgctcgg tcttgcgccg attatcatcc agcaaatttt cgacaccatc   68280
gagcagctgc gcgagcaggg gatgactatc ttcctcgtcg agcagaacgc caaccaggcg   68340
ctaaagctgg cggatcgtgg ctacgtgctg gaaaacggcc atgtggtgct ctccgatact   68400
ggtgatgcac tactggcgaa tgaagcggtg agaagtgcgt atttaggcgg gtaataacac   68460
gttgattgat aaggagtcaa aagactcctt tgagacaggt gacaaatgta aaattgcctg   68520
atgcgctgcg cttatcaggc ctactgggtg agttgcaata tattgaattt gcaagatctt   68580
gtaggccgga taaggcgttt acgccgcatc cggcatgaaa cgatgagtaa tctgtagagt   68640
ttgattcaga ccttctattt ttccgcttat ccgtgcccca tctcccattt tccctcaccc   68700
gtaccgtcac cgccttgtca tctttctgac accttactat cttacaaatg taacaaaaaa   68760 gttattttc tgtaattcga gcatgtcatg ttaccccgcg agcataaaac gcgtgaattc   68820
gcgcattcgg tacaacaaga gagataaacg atgaaccgt tacattatac agcttcagca    68880
ctggcgctcg gactggcgtt aatggggaat gcacaggcag tgacgaccat tccattctgg   68940
cattctatgg aaggggaact gggtaaagag gtggattctc tggcccaacg ttttaacgcc   69000
gaaaatccgg attacaaaat tgtaccgacc tataaaggca actacgaaca gaatttaagc   69060
gcggggattg ccgcatttcg taccggcaac gctccggcta ttttgcaggt ttatgaagtt   69120
ggcaccgcca ccatgatggc atcgaaagcc attaaaccgg tatatgacgt gtttaaagag   69180
gcggggattc aattcgatga gtcgcagttt gtgccgacgg tttccggtta ctactccgac   69240
agcaaaacgg gccacttact ctcccagcca ttcaacagct cgaccccgt tctctattac     69300 aacaaagacg ccttcaagaa agcaggatta gacccggaac aaccgccgaa aacctggcag   69360
gatctggcgg actatgccgc gaaactgaaa gcctccggta tgaagtgcgg ctacgccagc   69420
ggctggcagg gctggatcca actggaaaac tttagcgcct ggaacggtct gccgtttgcc   69480
agcaaaaaca acggctttga cggcacggac gcggtgctgg agttcaacaa gccggagcag   69540
gtgaaacaca tcgccatgct cgaggagatg aacaagaagg gcgacttcag ctacgtcggt   69600
cgtaaggatg aatccaccga gaagttctat aacggtgatt gcgcgatgac caccgcctct   69660
tccggttctc ttgccaacat tcgcgagtac gccaaattta attacggcgt aggcatgatg   69720
ccttacgacg ccgatgcgaa agatgcgcca caaaacgcca ttatcggcgg agccagcctg   69780
tgggtgatgc agggtaaaga taagaaacg tataccggtg tggcgaagtt cctcgatttc     69840
ctcgcgaagc cagaaaacgc tgccgagtgg catcagaaaa ccggttatct gccaattacc   69900
aaagcggcgt atgacctgac ccgtgagcag ggcttttacg agaaaaaccc aggtgcggat   69960
accgcgacgc gtcagatgct gaataagccg ccgttgccgt tcaccaaagg gctgcgtctg   70020
ggcaacatgc cgcagatccg cgtgattgtg gatgaagagc tggagagcgt gtggaccggt   70080
aagaagacac cacagcaggc actggatacc gccgttgagc gtggaaatca gttgctgcgc   70140
cgctttgaga atcgacgaa gtcttaatca gtgtaatgtc ggatgcgttt cgcttatctg   70200
acctggcatc gcgtgtaggc cggataagcg aagcgcatcc ggcacagttc aggaattaac   70260
cgtaatgtca tcatcccgtc cggtgttccg ctcgcgctgg ctgccttatc tgctggtcgc   70320
gccgcagctc atcatcaccg ttatctttt tatctggcct gcgggcgaag cgttgtggta    70380
ctcgctacaa agcgtcgatc cgtttggttt ctccagccag tttgtcggcc tggataactt   70440
cgtcgcgctg tttcatgaca gctactatct cgactccttc tggacgacga taaaattcag   70500 caccttttgtc accgtcagcg gtttgctggt gtcgctgttc ttcgcggcgc tggtggagta   70560
```

```
catcgtgcgc ggcagccgtt tctatcaaac cttaatgctg ctgccttacg ccgtggctcc   70620
cgccgttgcc gccgtattgt ggatcttcct gtttaacccc ggtcgcgggc tgatcaccca   70680
ttttctcgcg gagttcggct acgactggaa ccacgcgcaa acagcggtc aggcaatgtt    70740
tctggtggtg tttgcctcag tatggaagca aatcagctac aacttcctgt tcttctatgc   70800
cgcgctgcaa tccattcccc gttcgttgat cgaagccgca gccatcgacg tgcaggccc    70860
aattcgccgc ttctttaaga ttgcgctgcc gcttatcgct ccggtgagtt tcttcctgct   70920
ggtggtgaac ctggtgtatg ccttcttcga caccttcccg gtgatcgacg ccgccacgtc   70980
cggcgggccg gttcaggcca ccacgacgct gatttataag atctaccgtg aaggctttac   71040
cggactggat ctggcttcgt ctgccgcgca gtcggtggtg ttgatgttcc tcgtcatcgt   71100
gctgacggtg gtgcagttcc gctatgttga aagcaaggtg cgttaccaat gattgagaac   71160
cgtccgtggc tgacgatatt cagccatacc atgctgatcc tcgggatcgc ggtgatcctc   71220
ttcccgctgt acgtggcgtt tgtcgcggcg acgctggata acaggccgt ctatgccgcg    71280
ccgatgacgc tcatccccgg cacacatctg ctggaaaata tccacaacat ctgggttaac   71340
ggggtaggca cgaatagcgc gccgttctgg cggatgttgc ttaacagctt tgtgatggcg   71400
ttcagcatta cgctcggcaa aattaccgtc tcgatgctct cggcatttgc cattgtctgg   71460
tttcgttttc cgctacgtaa cctcttcttc tggatgattt ttatcaccct gatgctgccg   71520
gttgaagtac gtatcttccc gacggtggaa gtcatcgcca acctgaagat gctcgacagc   71580
tacgccggtt taacgctgcc gctgatggcc tcggcgaccg ccacgtttct gtttcgccag   71640
ttctttatga cgctgccgga tgaactggtg gaagcggcgc ggatcgacgg cgcgtcacca   71700
atgcgtttct tttgcgacat cgttttccg ctctccaaaa ccaatctggc ggcgctgttt    71760
gtgatcacct ttatttacgg ctggaaccag tatttgtggc cgttgttgat tattaccgat   71820
gtggatctcg gcaccaccgt ggcagggatc aaagggatga tcgctacagg cgaaggcacc   71880
actgaatgga actcagtgat ggcggcgatg ttgttaacgc ttatccctcc ggtggtgatt   71940
gttttagtga tgcagcgtgc cttcgtgcgc ggcctggtcg atagtgagaa ataagatggc   72000
aggactgaaa ttacaggcag taaccaaaag ctgggatggt aaaacccagg tcattaaacc   72060
gctgacccct gatgtggcgg atggcgaatt tatcgtgatg gtcggccgt ctggctgcgg    72120
gaaatcgacg ctgctgcgca tggttgccgg gctggagcgg gtgacagaag gcgatatctg   72180
gatcaacgac cagcgcgtga ctgaaatgga gccaaaagat cgcgggattg cgatggtgtt   72240
ccagaactac gcgctttatc cgcatatgag tgtcgaagaa acatggcgt ggggggctgaa    72300
aattcgcggc atgggcaagc agcaaattgc cgagcgcgtt aaagaagcgg cgcgcattct   72360
ggagctggac ggtctgctca aacgtcgccc gcgcgagctt tccggcggtc agcgccagcg   72420
tgtggcgatg ggccgcgcga ttgtgcgcga tccggcggtg ttcctgtttg atgagccgct   72480
ctctaacctc gatgccaagc tgcgcgtgca gatgcgtctt gaactgcaac agttgcaccg   72540
tcgcctgaaa acgacttcac tctacgttac tcacgatcag gttgaagcga tgacgctcgc   72600
ccagcgagta atggtgatga acggcggcgt tgccgaacag attggcacac cagttgaagt   72660
ctacgaaaag cccgccagcc tgtttgtagc gagttttatc ggcagtccgg cgatgaacct   72720
gctgacaggc cgcgtgaata cgaaggcac gcatttcgaa ctggacggcg gtattgagct    72780
gccgctaaac ggtggctacc gtcagtatgc cgggcgtaaa atgactctcg gcattcgccc   72840
ggaacatatt gcgctaagct cgcaggcaga aggcggcgta ccgctggtga tggacacgct   72900
ggagatcctc ggcgcagata acctggcgca cggacgctgg ggcgagcaga agctggtggt   72960
```

```
gcgactggcg catcaggagc gcccgacggc aggcagcacg ctgtggctgc atctggcgga    73020
aaatcagctg catcttttg atggtgaaac aggacaacga gtatgagtaa ctggccttat    73080
ccccgcatcg tcgctcatcg tggcggcggt aagctggccc cggaaaacac cctggcggca    73140
atcgacgtcg gggcaaaata cggtcataag atgatcgaat ttgacgcgaa gttatcgaaa    73200
gatggcgaga tcttcctgct ccatgacgac aatctcgaac gcaccagcaa cggctggggc    73260
gtcgcgggtg aactgaactg gcaggattta ctgcgcgtgg atgcgggcag ttggtacagc    73320
aaagcgttta aggtgagcc gctgccgttg ctttcgcagg tggcggaacg ctgtcgcgaa    73380
cacgggatga tggcgaatat cgaaatcaaa cccaccactg gcactggacc attaacgggc    73440
aaaatggtgg cgctggcggc acgccaactg tgggccggta tgacgccgcc gctgctgtca    73500
tcgtttgaga ttgatgcttt agaagctgca cagctggcgg caccggaact gccgcgtggt    73560
ttattgcttg atgagtggcg cgacgactgg cgcgaactga ccgcgcggct gggctgcgtc    73620
tctattcatc tcaatcataa gttgcttgat aaagcgcgag tgatgcagtt gaaagacgcc    73680
ggattacgga ttctggttta taccgtcaat aaaccccagc gcgcggcaga gttgctgcgc    73740
tggggcgtgg attgcatctg caccgatgcg attgacgtga ttggtccgaa ctttacggcc    73800
caatagtttt caacggaata tcaggctgcg gcgtgctggg ctgattcagc atgtcgccgt    73860
ttctcctctc cggcagcata tgctgctgat tcaacgaact atccggatta cggttgctgt    73920
ttaacatccc gccgttggtg ttgggcagca tttgctgccg gcgggatttt cgctcccccg    73980
gctgcgactg caacacccgc tgagaattat tgttttatctg gttttctaaa tgctgctgtt    74040
gcaactgcgt ttgcgttttc agttgctgat tcagcatccc tttttgctgg atttgctgcg    74100
tttgcatttg agtctgcatc cgctgctggc tggggatctg ataccccggc tggttagggt    74160
tgttcagagt attaatgggc tgtgcaaagc cgacaaacgg caggagtgcc gtaagaatca    74220
gaagtcgttt catcgcgtat cctcctctga agatatcctt taagtttact cgcttcccga    74280
caaaacgatg attaattcag agttatatac caggcttagc tggggttgcc ccttaatctc    74340
tggagaataa cgatgataaa accgacgttt ttacgccggg tggccattgc tgctctgctc    74400
tcaggaagtt gttttagcgc cgccgccgcg cctcctccgc cacctgtttc ttatggcgtg    74460
gaggaagatg tcttccatcc ggtacgcgcg aaacagggga tggtggcgtc tgtagatgct    74520
actgccactc aggtgggggt ggatatcctc aaggagggcg ggaatgccat tgatgccgcc    74580
gtggcagtgg ggtacgcgtt ggcggtaacg catccgcagg cggggaatct gggcggcggt    74640
ggttttatgc tgatccgcac taaggatggc aatacaaccg ctatcgattt ccgcgaaatg    74700
gcacccgcta aagcgacccg cgatatgttc ctcgatgatc agggcaaccc ggacagcaaa    74760
aaatcactca cttcgcatct ggcttccggc acaccaggta cggtcgctgg tttctcgctg    74820
gcgttggata agtacggcac tatgccgttg aacaaagtgg tgcagcccgc gttcaaactg    74880
gcacgcgatg gttttatcgt taacgatgct ttggcagacg atctcaaaac ctacggtagc    74940
gaagtgttgc cgaatcacga aaacagcaaa gctatcttct ggaaagaggg cgaaccgctg    75000
aaaaagggcg acacgctggt gcaggcgaac ctggcaaaga gcctggagat gattgctgaa    75060
aacggcccgg acgaattcta taaggcacg attgcggaac agatcgccca ggagatgcag    75120
aaaaacggtg gcttgatcac taaagaagat ttagcggcct ataaagcggt cgaacgcact    75180
ccgataagcg gcgattatcg cgggtatcag gttactccca tgccaccgcc atcctccggc    75240
gggatccata tcgtacaaat cctcaatatt ctggaaaact tcgatatgaa gaaatacggc    75300
```

```
tttggcagcg ccgatgcgat gcaaatcatg gcagaagcgg agaaatacgc ctacgccgac   75360
cgctcggaat atcttggcga cccggatttt gtcaaagtcc cgtggcaggc actgaccaat   75420
aaagcctatg ccaaatccat tgccgatcaa attgatatca acaaagcgaa gccgtccagt   75480
gagattcgcc ctggcaagct tgcgccttat gagagtaatc aaactaccca ttactctgta   75540
gtggataaag acggtaacgc ggtggcggtg acctatacgc tgaacaccac cttcggtacg   75600
ggtattgtcg cgggcgagag cggtattctg cttaataacc agatggatga tttctccgcc   75660
aaaccgggcg taccgaacgt ttacgggctg gtgggcggtg atgccaacgc cgtcgggccg   75720
aacaaacgcc cgctgtcgtc gatgtcgccg accattgtgg tgaaagacgg taaacctgg    75780 ctggttaccg gtagcccagg cggtagccgg atcatcacta cagtgctgca atggtggtg    75840 aatagcatcg attatggcat gaacgtcgcc gaagcgacca atgcgccgcg tttccaccat   75900
cagtggttgc cggacgagct gcgtgtcgaa aaagggttta gcccggatac gctcaagctg   75960
ctggaagcaa aaggtcagaa agtggcgctg aaagaggcga tgggcagtac acaaagcatt   76020
atggttgggc cggacggtga gttgtacggc gcatccgacc cgcgctcggt ggatgattta   76080 acggcgggt actaaggtta gcggccctct tcgtgggaag agggctattt tgtcagggca    76140
agccgaaggt agccttttt atttcgtaat cctgtagata ttcttccagc ggctttgccg    76200
ttcccagaga atgaatttca ccactgtctt tatcaataat aaaaggtgcg ttaccagcta   76260
agcgcgcggc ctcatctcca gtttcgagaa attctcgtgc ttcgaaacag aaataccagc   76320
cctggctaaa gcgtccatgt agagtaatga cgaccgggag atctgcatca tcaaggtaat   76380
ggttcgcttt cgcgaatgcg tcgtgataag taatcataat tataataaat attattgttg   76440
agtgttatat tattattcct gtgtgataca ttgagcaaag acgcgttcat cttcgtcaaa   76500
gatattatta aatgctggtt ttgaaaaaag ttcatcggat aagatatagt cacgaaataa   76560
gtatctgcta atattttatg atttcttttt cagaacgtcg aacgggattt tcttatttaa   76620
gatatcagaa tcttatgatt cgggtaaaat tctaaataaa tcaacatgtc attaaaatca   76680
tcatagccat tagctatttc ggctaaaata gagactacat gtcttcggtc catctcactt   76740
aaggagtgta gttccgttgt aagttttcc atagcttgca ctgctaaatt tcgaacaagg    76800
aattttctgc tggtaatctc taaaaagatg gcatggttta caatgatttt tgtttccttt   76860
tgattattat gaacaactgt ccatgatttc gtttaagaat gaagagaaat cactaaacga   76920
actgaatata ttttctgtgc caatattatc tctaatttca aaaagttac ttttaatgtc    76980 ataagtaaat attgaaatgc tatcatcccc gatcactaac cgttcttgta gatcagggtt   77040
tatgaaatca tcattatttc tataaaattc atttacggca aaaaggtttt taactgaagg   77100
ttctggaatc gagaggctaa ataatcgtaa tccattaact tcgaatccat ccattgctct   77160 taaaaagta agataatcag gttgattctt aaaaagaata ctaacttcat tacataactt    77220
ctccaggcaa ttagttgaat tagaattaaa ttctatttgg attatacttt caataaatga   77280
ttccttgagc ggtgcttcaa atggatagtc taaatcattc atcattttta ttaatttatt   77340
tatttgggtt ttagtcatca ttttgtgtgg tccataatat ttttcatggg aggataaatt   77400
gagccagata gaatggccca gggagtgatt ttgctttcac ctactaatat tcccttagct   77460
attcgtgatt gcatgttagt aaaaacttta tgatatggtt cgttttcgat taatactaaa   77520
ttttcgaaat cattagtacc accatcatct agagatagtt tatggtgaac attataattt   77580
agaggaacat tgcccttct cattcttaaa aggtcttcgg cgttgaatct tccagatgct    77640
tcggaggttt ttgcaagttt gataagaaaa ttttttctta cagttttatt aaactccttt   77700
```

```
cgtaagttag ctaagtcttt tgaaggtctc ttaatgtata ttatttctat tatgtctata    77760
ccatcaagaa gttttgttg  acctctaagt ttgcctaagt aactatttat ttctgtatat    77820
gtatcaacat tagaacgctt tgttaaaaga atagatgctg ttgctatcgc tatgcccgct    77880 gtttttcat  ttagtatttg atcatagcct tttattgcat ctccacccag tttttccgca    77940
gtatctctga atccttcaat gttcccattg tatacgccac cagcagcaag tagcctgcca    78000
atagctttgc tgtttaacgt tttgaaacga ttatttgttt ggttttttga atttggtaaa    78060
aacaaacggt tataatttc  agggagtgcc aaatagctga actcggtatt tgcgataaga    78120
tgttgacaga ggataaaattc ataactaata gttattgttt ctgtatccag ttggttttca   78180
atgatctggt gatgaatagc cgataaaaaa gcgcctctta gttgtatata ataatacttt    78240
tcccatctac caaatctatt tattcgatag aagtcaaatc ccataaataa ttgttcatta    78300
ttgttaatgg aattaataaa taatggagtg cttttatcaa ttaatttaca aaatgttata    78360
ccatggaact gtgaaccaag ccccgtatta ttaatattat ttaagagtga aatgtaaat     78420 atttcatcct catgcccgct ctgccaacga ttacctgtag actcagaagt cccacaacct    78480
gcggagatgc ttccttgttg ttctcccgtt actgtcaggt aaacaatatt actcatccct    78540
gaaaagtcct tttatggcat gctatttat  caatggcaat attatgcttg ttaattgtta    78600
tttatttact ccaggaaatt gtaggcgtat atattaaaaa ataaaatatt acactttagg    78660
aagtaattat gagttaaatc tcaatatatg tattgggcaa ataaatacct taaggaagg     78720 tatgtcgatt ttgaatgaca ccctttttcc atctcagaaa aagggcacta tcttacttca    78780
cccgcgccat ataatatgca tcgacatatt caccattacg caatgcgtac ttcttaccag    78840
tcccttcaat ttcaaagccg tattttttat agaccttaat tgccggggcg ttatcgacaa    78900
acacggttag ttcaatgcga tctacccgca accagttgtc gcacatttca atcatctctc    78960
gcatcagggc gctggcgacg ccgcggttct tccaacgaga gtcgacacag ataccaaaat    79020
cggcaacatg actgcggcgt gggcgctgtt gcacgtcaat ggtgagatgg cccacgacgt    79080
ctccatcaat acaggcgacg agttgcttga tgccggacg  atcggcgagt cgctcctgcc    79140
acatatgatc ggaaggatga ggcacctgta gtgtgttgca atacacctcc ggctgggcgt    79200
gaatctgcct gatggcctcg taatcccgtg tttctgcgtg gcgtattact atctcactca    79260 ttccttttgtc ctctttgggg taaatgtccc tttcaacatc attgactttc aaatgcgagt   79320
caaatgcatt tttttgcaaa aagtgttgga caagtgcgaa tgagaatgat tattattgtc    79380
tcgcgatcag gaagaccctc gcggagaacc tgaaagcacg acattgctca cattgcttcc    79440
agtattactt agccagccgg gtgctggctt tttttgatc  tttcgttctc aatttatcca    79500
cgggagtgct tgtgttcgtt atgcgcactc cagtaggaac cacgtccgct ttgcgctaag    79560
gtgtaaataa ccaccttaaa aaggacgaaa tcatggtcat caactgcgcc tttattggct    79620
tcggcaaaag caccacccgt taccatctgc cgtatgtact taaccgcaag gatagctggc    79680
atgtcgcgca tattttcgt  cgccatgcga agccggaaga acaggctccc atttattccc    79740
atatccattt caccagcgat ctcgacgaag tactaaacga tcccgatgtt aagctggttg    79800
ttgtctgcac ccacgcggac agccatttcg agtacgcgaa acgcgcgctg gaagccggga    79860
aaaatgtgct ggtcgaaaaa ccgttcaccc cgacgcttgc ccaggcgaag gagctgtttg    79920
cgttggcgaa aagcaaaggg ctgaccgtca cgccgtatca gaatcgtcgc tttgactcct    79980
gcttcctgac agcgaaaaaa gcgattgaaa gtggcaagtt gggagagatt gttgaagtgg    80040
```

```
aaagccattt tgactattac cgcccggtgg cagagaccaa acctgggctg ccgcaggatg    80100
gcgcgtttta tggccttggt gtgcatacga tggaccagat tatttctctg ttcggtcgcc    80160
cggatcacgt cgcttatgac atccgcagcc tgcgtaataa agccaatcct gacgacacct    80220
ttgaagcgca actgttttat ggcgacctga aagccatcgt caaaaccagc catctggtga    80280
aaatcgatta tccgaaattt atcgttcacg gtaagaaagg ttcgtttatt aaatacggta    80340
tcgaccagca ggaaaccagc ctgaaggcta atattatgcc gggcgaaccg ggattcgcag    80400
cggatgattc ggtcggtgtg ctggagtatg tcaatgacga gggcgtgacg gtcagagaag    80460
agatgaagcc ggagatgggc gattacgggc gcgtttatga tgcgttgtat caaaccatta    80520
cccacggtgc gccaaattac gtcaaggaat ctgaagttct taccaatctg␣gaaatccttg    80580 aacgcggatt tgagcaagcc tctccctcca cagtaactct cgctaagtaa gtttgatggc    80640
ccctcgaata gttcaatttt tttgaacaga ggggtcaatt ttcaccctct atcatcccag    80700
gcagatcggg tccacactaa gcccatcgaa atcattcagg gggcgaatac aaatgatcta    80760
cttacgcaaa gcaaatgaac gtggtcatgc aaatcatggc tggctggact cctggcatac    80820
tttctctttt gccaactatt acgatccgaa ctttatgggc ttctccgcgc tgcgcgtgat    80880
taacgacgac gtgattgaag cagggcaggg cttcggcact cacccgcata agatatgga    80940 aatttttgacc tacgtgctgg aaggtactgt tgagcatcag gacagcatgg gcaataaaga    81000
gcaggttccg gcgggtgagt tccagattat gagtgcgggt acgggtattc gtcactcaga    81060
gtacaaccca aacagcaccg agcgtctgca tctgtatcag atctggatca tgcctgaaga    81120
aaatggcatt acgccgcgtt atgaacagcg tcgcttcgat gccgtgcagg gcaaacagct    81180
ggtgctctcg ccggatgcgc gagatggttc gctgaaagtg catcaggata tggaactgta    81240
tcgttgggcg ttgctgaaag atgagcagtc ggtgcatcag attgccgctg aacgccgcgt    81300
ctggatccag gtggtgaaag gcaatgtcac cattaacggc gtgaaagcct cgaccagcga    81360
tggtctggca atctgggatg agcaggcaat ctccatccat gcggatagcg acagcgaagt    81420
gttactgttc gatctgccgc cggtttaaaa ctcaacggca tcttcgaagc ctgcctttt    81480 gcaggcttcc tcgctcgctc cggtcgcgtg ctgatgcacg cttccggggt tttgccgcgt    81540
cgttagcaca atgcgatgca attgatttag tgtatatcta ataattgtaa acaagcactg    81600
ttttccccgg gaaggttctg atgcgtccgt gttaaactaa gagaatctat ctcttttgta    81660
ccttcaggac gatgaaaaag aaaagacccg tacttcagga tgtggctgac cgtgtaggcg    81720
tgaccaaaat gacggtcagc cgtttttttac gcaacccgga gcaggtttcc gtcgctctac    81780
gcggcaagat tgccgccgct cttgatgaac tgggctatat tcccaatcgt gcgcccgata    81840
tcctctctaa cgccaccagc cgggcgattg gcgtcctgtt accttctctc accaaccagg    81900
ttttcgcgga agtattacgc ggaatcgaaa gcgtcaccga cgcgcacggt tatcagacca    81960
tgctggctca ctacggttat aaaccggaaa tggagcaaga acgtctcgaa tccatgctct    82020
catggaatat cgacggactg atcctcaccg aacgtaccca cacgccgcgc accttaaaga    82080
tgattgaagt ggcggggatc ccggtggtgg aactcatgga cagccagtcg ccgtgcctcg    82140
atatcgccgt cggttttgat aactttgaag cggcacgcca gatgaccacc gccattattg    82200
ctcgcgggca ttgccacatt gcctatctcg gcgcgcgtct cgacgaacgt actatcatca    82260
aacagaaggg atacgaacag gcgatgctgg atgcaggtct ggtgccgtat agcgtgatgg    82320
ttgagcaatc ttcttcttac tcttccggta ttgaactgat tcgccaggcg cggcgggaat    82380
atccgcagct ggatggcgtg ttctgtacca acgatgacct ggcggtcggc gcggcgtttg    82440
```

```
aatgtcagcg tctgggattg aaggttcctg acgatatggc gattgccggt ttccacggtc   82500
atgacattgg ccaggtgatg gagccgcggt tagcgagcgt gctgacgccg cgtgagcgga   82560
tgggcagtat tggcgctgaa cgcctgctgg cgcgtattcg tggcgaatct gtgacaccga   82620
aaatgttaga tttaggtttc accttgtcac cgggcggatc tatttaagcc tacaaatttg   82680
aagtagctca cacttataca cttaaggcac ggatggatat tgcttctgat attgtccggc   82740
tggacaatgt taccgataac agttacccgt aacatttta attcttgtat tgtggggca    82800
ccactttgag cacgactaac catgatcacc acatttacgt cttgatgggc gtatcgggca   82860
gcggcaaatc tgcggtcgcc agtgaagtgg cgcatcaact tcatgccgcg tttcttgatg   82920
gcgatttcct ccatccacgg cgcaatatcg aaaaaatggc gtctggcgaa ccgctgaatg   82980
acgacgatcg caaccgtgg ttgcaggcgc tgaacgacgc cgcgtttgct atgcagcgca    83040
ctaataaagt gtcactgatc gtctgttctg cattgaaaaa acactatcgc gacttgctgc   83100
gagaaggtaa tccgaatctc tctttcatct acctgaaagg cgattttgac gtgattgaaa   83160
gccgcctgaa agcgcgcaaa ggccatttct ttaaaaccca aatgttggtg acgcagtttg   83220
aaacgctgca ggagccgggt gcggacgaaa ctgatgtact ggtggtggat atcgatcaac   83280
cgctggaagg tgttgtggca agcaccattg aggttattaa aaaaggcaaa taagtagtga   83340
ctacattaac gcttgtttta acagcagtag ggtctgtttt actgctgctg ttttagtca    83400
tgaaggcgcg tatgcacgct ttcctggctt taatggtggt gtccatgggg gctggccttt   83460
tttccggtat gccgctcgat aaaatcgcag cgacgatgga aaaagggatg ggaggcaccc   83520
tcggcttcct ggcggtggtt gtcgccctgg gagctatgtt tggcaagatc ttacatgaaa   83580
ccggcgcagt cgatcagatt gccgtcaaaa tgctcaaatc cttcggtcac agccgcgcgc   83640
attatgccat cggccttgcg gggctggtct gtgcgctacc gctgttcttt gaagtggcga   83700
ttgttctgct gattagcgtt gctttctcaa tggcgcgcca caccggtacg aacctggtga   83760
agctggtaat cccattattc gcaggcgtgg cggccgcggc tgcgttcctg gtgcctgggc   83820
cagcgccaat gctcctcgca tcgcagatga acgccgattt tggctggatg atcctgattg   83880
gcctgtgtgc ggcaattccg ggaatgatta ttgccgggcc gctgtggggt aatttcatca   83940
gccgctacgt ggagttgcat attcctgacg acatcagcga accgcatctc ggcgaaggca   84000
aaatgccatc tttcggattc agcctgtcgc tgatcctgtt gccgctggtg ctggtggggc   84060
tgaaaaccat tgccgcgcgt tttgtgccag aaggctctac cgcttacgaa tggttcgagt   84120
ttattggtca tccgtttacc gcgattctgg ttgcttgtct ggtagcgatt tatggcctgg   84180
caatgcgtca gggcatgcca aaagacaaag tgatggagat ttgcggtcac gcgctgcaac   84240
cggcggggat cattctgctg gtgattggtg caggtggcgc gttcaaacag gtgctggttg   84300
actctggcgt aggtccggca ctgggcgaag cgttaactgg catgggcctg ccgatagcca   84360
tcacctgctt cgtgctggcc gctgcagtgc gcatcattca gggttctgcc accgtagcct   84420
gtttaacggc ggtaggactg gtgatgccgg ttattgaaca actgaactac tccggtgcgc   84480
aaatggcggc gctgtcgatt tgtatcgctg gtggttcgat tgttgtcagc cacgttaacg   84540
acgccggttt ctggttgttc ggtaaattta ccggcgcgac cgaagccgaa acgctgaaaa   84600
cctggaccat gatggaaacc atcctcggca ctgtcggtgc catcgttggg atgattgcgt   84660
tccagctgtt gagttaagtt tgttcgcccg gtagttgtga cgctaccggg ttcttttcga   84720
aaaactctcc tcgttacccc ttcatccaca ttcgaatgcc gtcgaggaac atctgggttg   84780
```

```
ccatcatcac cagaatcaat cccatcaggc gttcaagtgc gttcacccct ttctcgccca   84840
gcagacgtaa aaatagcgaa gactgtagca ggatgacaaa ggtgccgccc caggccagca   84900
gcagagcaat caccagatgc cccatctgat tcgggtactg atgagacaac aacatcagcg   84960
tggcgagaat agtcggcccg cgcgactaacg gaattgccaa cggcacgata aatggctctt   85020
cacctgccgg aagcccgctg ctatttcctg aagcgctggg gaaaatcatc ttaatggcga   85080
ttagaaacag aatgatgccg ccagaaatgg agacggtttc tgctcgcagg ctgagaaatg   85140
ccagaatttt ctcacccgca aacaggaaca ccagcatcac caggagagca ataagcaact   85200
ctcgcaccat gattgcccgc cgtcttttcg gttcagtatg tttcagtacg gacatgaaaa   85260
taggtaggtt tccgagcgga tccataatca ggatcaataa aactgctgca gaaatgattt   85320
cattcataac tcaaattccc tgataattgc cgcggacttt ctgcgtgcta acaaagcagg   85380
ataagtcgca ttactgatgg cttcgctatc attgattaat ttcacttgcg actttggctg   85440 cttttttgtat ggtgaaagat gtgccaagag gagaccggca catttataca gcacacatct   85500
ttgcaggaaa aaacgcttat gaaaaatgtt ggttttatcg gctggcgcgg tatggtcggc   85560
tccgttctca tgcaacgcat ggttgaagag cgcgacttcg acgccattcg ccctgtcttc   85620
ttttctactt ctcagcttgg ccaggctgcg ccgtcttttg gcggaaccac tggcacactt   85680
caggatgcct ttgatctgga ggcgctaaag gccctcgata tcattgtgac ctgtcagggc   85740
ggcgattata ccaacgaaat ctatccaaag cttcgtgaaa gcggatggca aggttactgg   85800
attgacgcag catcgtctct gcgcatgaaa gatgacgcca tcatcattct tgacccccgtc   85860 aatcaggacg tcattaccga cggattaaat aatggcatca ggacttttgt tggcggtaac   85920
tgtaccgtaa gcctgatgtt gatgtcgttg ggtggtttat cgccaatga tcttgttgat   85980 tgggtgtccg ttgcaaccta ccaggccgct tccggcggtg gtgcgcgaca tatgcgtgag   86040
ttattaaccc agatgggcca tctgtatggc catgtggcag atgaactcgc gaccccgtcc   86100
tctgctattc tcgatatcga acgcaaagtc acaaccttaa cccgtagcgg tgagctgccg   86160
gtggataact ttggcgtgcc gctggcgggt agcctgattc cgtggatcga caaacagctc   86220
gataacggtc agagccgcga agagtggaaa gggcaggcgg aaaccaacaa gatcctcaac   86280
acatcttccg taattccggt agatggttta tgtgtgcgtg tcggggcatt gcgctgccac   86340
agccaggcat tcactattaa attgaaaaaa gatgtgtcta ttccgaccgt ggaagaactg   86400
ctggctgcgc acaatccgtg ggcgaaagtc gttccgaacg atcgggaaat cactatgcgt   86460
gagctaaccc cagctgccgt taccggcacg ctgaccacgc cggtaggccg cctgcgtaag   86520
ctgaatatgg gaccagagtt cctgtcagcc tttaccgtgg gcgaccagct gctgtggggg   86580
gccgcggagc cgctgcgtcg gatgcttcgt caactggcgt aatctttatt cattaaatct   86640
ggggcgcgat gccgcccctg ttagtgcgta atacaggagt aagcgcagat gtttcatgat   86700
ttaccgggag ttaaatagag cattggctat tctttaaggg tggctgaata catgagtatt   86760
cacagcctta cctgaagtga ggacgacgca gagaggatgc acagagtgct gcgccgttca   86820
ggtcaaaaaa atgtcacaac cagaagtcaa aaatccaatt ggatggggtg acacaataaa   86880
acaggaagac aagcatgtcc gatcgtatcg atagagacgt gattaacgcg ctaattgcag   86940
gccattttgc ggatcctttt tccgtactgg gaatgcataa aaccaccgcg ggactggaag   87000
tccgtgccct ttacccgac gctaccgatg tgtgggtgat tgaaccgaaa accgggcgca   87060
aactcgcaaa actggagtgt ctcgactcac ggggattctt tagcggcgtc attccgcgac   87120
gtaagaattt tttccgctat cagttggctg ttgtctggca tggtcagcaa aacctgattg   87180
```

```
atgatcctta ccgttttggt ccgctaatcc aggaaatgga tgcctggcta ttatctgaag    87240
gtactcacct gcgcccgtat gaaaccttag gcgcgcatgc agatactatg gatggcgtca    87300
caggtacgcg tttctctgtc tgggctccaa acgcccgtcg ggtctcggtg gttgggcaat    87360
tcaactactg ggacggtcgc cgtcacccga tgcgcctgcg taaagagagc ggcatctggg    87420
aactgtttat ccctggggcg cataacggtc agctctataa atacgagatg attgatgcca    87480
atggcaactt gcgtctgaag tccgacccct atgccttcga agcgcaaatg cgcccggaaa    87540
ccgcgtctct tatttgcggg ctgccggaaa aggttgtaca gactgaagag cgcaaaaaag    87600
cgaatcagtt tgatgcgcca atctctattt atgaagttca cctgggttcc tggcgtcgcc    87660
acaccgacaa caatttctgg ttgagctacc gcgagctagc cgatcaactg gtgccttatg    87720
ctaaatggat gggcttttacc cacctcgaac tactgcccat taacgagcat cccttcgatg    87780
gcagttgggg ttatcagcca accggcctgt atgcaccaac ccgccgtttt ggtactcgcg    87840
acgacttccg ttatttcatt gatgccgcac acgcagctgg tctgaacgtg attctcgact    87900
gggtgccagg ccacttcccg actgatgact ttgcgcttgc cgaatttgat ggcacgaact    87960
tgtatgaaca cagcgatccg cgtgaaggct atcatcagga ctggaacacg ctgatctaca    88020
actatggtcg ccgtgaagtc agtaacttcc tcgtcggtaa cgcgctttac tggattgaac    88080
gttttggtat tgatgcgctg cgcgtcgatg cggtggcgtc aatgattat cgcgactaca    88140 gccgtaaaga gggggagtgg atcccgaacg aatttggcgg gcgcgagaat cttgaagcga    88200
ttgaattctt gcgtaatacc aaccgtattc ttggtgagca ggtttccggt gcggtgacaa    88260
tggctgagga gtctaccgat ttccctggcg tttctcgtcc gcaggatatg ggcggtctgg    88320
gcttctggta caagtggaac ctcggctgga tgcatgacac cctggactac atgaagctcg    88380
acccggttta tcgtcagtat catcacgata aactgacctt cgggattctc tacaactaca    88440
ctgaaaactt cgtcctgccg ttgtcgcatg atgaagtggt ccacggtaaa aaatcgattc    88500
tcgaccgcat gccgggcgac gcatggcaga aattcgcgaa cctgcgcgcc tactatggct    88560
ggatgtgggc attcccgggc aagaaactac tgttcatggg taacgaattt gcccagggcc    88620
gcgagtggaa ccatgacgcc agcctcgact ggcatctgtt ggaaggcggc gataactggc    88680
accacggtgt ccagcgtctg gtgcgcgatc tgaacctcac ctaccgccac cataaagcaa    88740
tgcatgaact ggattttgac ccgtacggct ttgaatggct ggtggtggat gacaaagaac    88800
gctcggtgct gatctttgtg cgtcgcgata agagggtaa cgaaatcatc gttgccagta    88860
actttacgcc ggtaccgcgt catgattatc gcttcggcat aaaccagccg ggcaaatggc    88920
gtgaaatcct caataccgat tccatgcact atcacggcag taatgcaggc aatggcggca    88980
cggtacacag cgatgagatt gccagccacg gtcgtcagca ttcactaagc ctgacgctac    89040
caccgctggc cactatctgg ctggttcggg aggcagaatg acacaactcg ccattggcaa    89100
acccgctccc ctcggcgcgc attacgacgg tcagggcgtc aacttcacac ttttctccgc    89160
tcatgccgag cgggtagaac tgtgtgtctt tgacgccaat ggccaggaac atcgctatga    89220
cttgccaggg cacagtggcg acatttggca cggttatctg ccggatgcgc gcccgggttt    89280
gcgttatggt tatcgcgttc atggcccctg gcaacccgcc gaggggcatc gctttaaccc    89340
ggcgaagttg ttgattgatc cttgcgcgcg gcaaattgac ggggagttta agataaaccc    89400
gctgctgcac gccggtcata tgaacctga ctatcgcgca aacgccgcca ttgcgccgaa    89460
atgcgtagtg gtggttgatc actatgactg ggaagatgac gccccgccgc gcacgccgtg    89520
```

```
gggcagcacc atcatttatg aagcccatgt taaaggatta acgtacttgc acccggagat    89580
cccggtcgag atccgtggca cttataaagc cctggggcat ccgtgatga tcaactattt     89640 gaaacagttg ggcattaccg cgctggaact gctgccggtg gcgcagtttg ccagtgaacc    89700
acgtctgcaa cgcatggggc taagtaacta ctggggttac aacccggtgg cgatgtttgc    89760
gctgcatccg gcgtatgcct gctcgccaga aacggcgctg catgagtttc gcgatgcaat    89820
caaagcactg cataaagcgg gtatcgaagt cattcttgat atcgtgctca accatagtgc    89880
ggaactggac ctcgacggcc cgttattctc gctgcgtggg atcgacaacc gtagctatta    89940
ttggataaga gaagacggcg attatcacaa ctggaccggt tgtggcaaca cgctcaattt    90000
gagtcatccg gcggtggtgg attatgccag cgcctgcctg cgttattggg tagaaacctg    90060
ccacgtcgat ggtttccgct tgatctggc ggcagtcatg ggccgtacgc cagagttccg     90120
tcaggatgcg ccgttgttta ccgctatcca gaactgcccg gtgctctcgc aggtgaagtt    90180
aattgctgaa ccgtgggata tcgctcctgg tggttatcag gtgggaaatt tcccgccgct    90240
gtttgccgag tggaacgatc atttccgcga tgctgcccgt cgtttctggc tacattatga    90300
tttgcctctg ggggcgtttg ccgggcgttt tgctgcctcc agcgatgttt ttaaacgtaa    90360
tggtcgtctg ccgagtgccg cgattaatct cgtcaccgcg catgacggtt ttacgcttcg    90420
cgactgcgtt tgcttcaacc ataaacacaa tgaagcaaac ggagaagaaa atcgcgacgg    90480
gaccaacaac aattacagta acaatcatgg taaagaaggg ttaggcggtt ctcttgacct    90540
ggttgaacgg cggcgcgaca gcattcacgc cctgttaaca acgttgttgc tctcccaggg    90600
tacgccgatg ttactggccg gtgacgaaca tggtcacagc cagcatggca ataacaatgc    90660
ctactgtcag gataaccaat taacctggtt ggactggtcg caggcaagca gtggtttaac    90720
cgcatttacc gccgcgttaa tccatctgcg caagcgtatt cccgctttgg tggagaatcg    90780
ctggtgggaa gaaggcgacg gcaatgtccg ttggctaaat cgatatgctc aacctttaag    90840
cacggatgag tggcaaaacg ggccgaaaca gctgcaaatt ctgctctcgg atcgcttttt    90900
gatcgcaatt aacgccacgc ttgaggtaac agagattgtt ttacctgctg gggagtggca    90960
cgccattccc ccattcgctg gagaggataa cccagtgatt acggctgtct ggcagggacc    91020
tgcacacgga ttgtgtgtgt tccagagatg ataaaaaagg agttagtcat ggttagttta    91080
gagaagaacg atcacttaat gttggcgcgc cagctgccat tgaaatctgt tgccctgata    91140
ctggcgggag gacgtggtac ccgcctgaag gatttaacca ataagcgagc aaaaccggcc    91200
gtacacttcg gcggtaagtt ccgcattata gactttgcgc tgtctaactg catcaactct    91260
gggatccgtc gtatgggcgt gatcacccag taccagtccc acactctggt gcagcacatt    91320
cagcgcggct ggtcattctt caatgaagaa atgaacgagt tgtcgatct gctgccagca     91380 cagcagagaa tgaaagggga aaactggtat cgcggcaccg cagatgcggt cacccaaaac    91440
ctcgacatta ccgccgtta taagcggaa tacgtggtga tcctggcggg cgaccatatc      91500
tacaagcaag actactcgcg tatgcttatc gatcacgtcg aaaaggcgc acgttgcacc     91560 gttgcttgta tgccagtacc gattgaagaa gcctccgcat ttggcgttat ggcggttgat    91620
gagaacgata aaattatcga attcgttgaa aaacctgcta acccaccgtc aatgccgaac    91680
gatccgagca aatctctggc gagtatgggt atctacgtct ttgacgccga ctatctgtat    91740
gaactgctgg aagaagacga tcgtgatgag aactccagcc acgactttgg caaagatttg    91800
attcccaaga tcaccgaagc cggtctgcc tatgcgcacc cgttcccgct ctcttgcgta     91860
caatccgacc cggatgccga gccgtactgg cgcgatgtgg gtacgctgga agcttactgg    91920
```

```
aaagcgaatc tcgatctggc ctctgtggtg ccggaactgg atatgtacga tcgcaattgg   91980
ccaattcgca cctacaatga atcattaccg ccagcgaaat tcgtgcagga tcgctccggt   92040
agccacggga tgacccttaa ctcactggta tccggcggtt gtgtgatctc cggttcggtg   92100
gtggtgcagt ccgttctgtt ctcgcgcgtt cgcgtgaatt cattctgcaa cattgattcc   92160
gccgtattgt taccggaagt atgggtaggt cgctcgtgcc gtctgcgccg ctgcgtcatc   92220
gatcgtgctt gtgttatccc ggaaggcatg gtgattggtg aaaacgcaga ggaagatgca   92280
cgtcgtttct atcgttcaga agaaggcatc gtgctggtaa cgcgcgaaat gctacggaag   92340
ttagggcata aacaggagcg ataatgcagg ttttacatgt atgttcagag atgttcccgc   92400
tgcttaaaac cggcggtctg gctgatgtta ttggggcatt acccgcagca caaatcgcag   92460
acggcgttga cgctcgcgta ctgttgcctg catttcccga tattcgccgt ggcgtgaccg   92520
atgcgcaggt agtatcccgt cgtgataccta tcgccggaca tatcacgctg ttgttcggtc   92580
attacaacgg ggttggcata tacctgattg acgcgccgca tctctatgat cgtccgggaa   92640
gcccgtatca cgataccaac ttatttgcct ataccgacaa cgtattgcgt tttgcgctgc   92700
tggggtgggt tggggcagaa atggccagcg ggcttgaccc attctggcgt cctgatgtgg   92760
tgcatgcgca cgactggcat gcaggccttg cgcctgcgta tctggcggcg cgcgggcgtc   92820
cggcgaagtc ggtgtttact gtgcacaacc tggcctatca aggcatgttt tatgcacatc   92880
atatgaatga catccaattg ccatggtcat tctttaatat tcatgggctg gaattcaacg   92940
gacaaatctc tttcctgaag gccggtctgt actatgccga tcacattacg gcggtcagtc   93000
caacctacgc tcgcgagatc accgaaccgc agtttgccta cggtatggaa ggtctgttgc   93060
aacagcgtca ccgtgaaggg cgtctttccg gcgtactgaa tggcgtggac gagaaaatct   93120
ggagtccaga gacggactta ctgttggcct cgcgttacac ccgcgatacg ttggaagata   93180
aagcggaaaa taagcgccag ttacaaatcg caatggggct taaggttgac gataaagtgc   93240 cgcttttttgc agtggtgagc cgtctgacca gccagaaagg tctcgacctg gtgctggaag   93300
ccttaccggg ccttctggag cagggcgggc agctggcgct actcggcgcg ggcgatccgg   93360
tgctgcagga aggtttcctt gcggcggcag cggaataccc cggccaggtg ggcgttcaga   93420
ttggctatca cgaagcattt tcgcatcgca ttatgggcgg cgcggatgtc attctggtgc   93480
ccagccgttt tgaaccgtgc ggcttaacgc aactttatgg attgaagtac ggtacgctgc   93540
cgttagtgcg gcgcaccggt gggcttgctg atacggtttc tgactgttct cttgagaacc   93600
ttgcagatgg cgtcgccagt gggtttgtct ttgaagatag taatgcctgg tcgctgttac   93660
gggctattcg acgtgctttt gtactgtggt cccgtccttc tctgtggcgg tttgtgcaac   93720
gtcaggctat ggcaatggat tttagctggc aggtcgcggc gaagtcgtac cgtgagcttt   93780
actatcgctt gaaatagttt tcaggaaacg cctatatgaa tgctccgttt acatattcat   93840
cgcccacgct tagcgtagaa gctcttaagc actctatcgc ttacaagctg atgtttacga   93900
ttggaaagga cccggtcgtc gccaataaac atgaatggct gaacgcaacg ttatttgctg   93960
tgcgcgatcg tctcgtggag cgctggttac gttcaaaccg tgcccagttg tcgcaagaaa   94020
ctcgtcaggt ttactacctg tcgatggagt ttttgattgg ccgtacgctc tccaacgcca   94080
tgttgtcgct aggaatttac gaagatgtac agggcgcact ggaagcgatg gggttaaatc   94140
tcgaagagct gattgatgaa gaaaatgacc cgggcctcgg taacggtggc ctgggacgtc   94200
tggcggcttg cttcctcgat tctctggcga cgttagggtt gccggggcgc ggttacggca   94260
```

-continued

```
tccgctatga ctacggtatg ttcaagcaga acatcgttaa cggtagccag aaagagtcgc    94320
ctgactactg gctggaatac ggtaacccgt gggaattcaa acgccacaac acgcgctata    94380
aagtccgttt tggcggccgc attcagcagg aaggtaaaaa aacgcgctgg attgaaaccg    94440
aagagattct gggagtcgct tacgatcaga taatccctgg ttacgacacc gacgcgacca    94500
acacgctgcg tttgtggagt gcgcaagcca gtagcgaaat taacctcggt aaattcaacc    94560
agggtgacta cttcgcggca gtggaagata aaaaccactc cgagaacgta tctcgcgtac    94620
tgtatccgga tgactccacc tactccgggc gtgagctgcg cctgcgtcag gaatacttct    94680
tggtttcctc gaccattcag gacattttaa gccgccatta tcagttgcat aaaacctacg    94740
ataacctggc ggataaaatc gcgattcatc tcaatgatac ccatccggta ctgtcgattc    94800
ctgagatgat gcgtctgctg atcgatgagc accaatttag ctgggacgac gcgtttgagg    94860
tgtgttgtca ggtcttctcc tacactaacc acacgctgat gagcgaggcg ctggaaacct    94920
ggccggttga tatgctgggt aaaattctgc cacgtcacct gcagatcatc tttgaaatca    94980
acgactattt cctgaaaacc ttgcaggaac agtatccgaa cgataccgat ctgctgggac    95040
gggcgtcgat cattgatgaa tccaacggtc gtcgtgtgcg tatggcctgg ctggcggttg    95100
ttgtgagcca caaagttaac ggtgtatcgg aactgcactc taatctgatg gtgcaatcgt    95160
tgtttgccga ctttgcgaaa atcttcccgg gtcgtttcac caacgtcacc aacggtgtga    95220
cgccgcgtcg ctggctagcg gtagcgaacc catcgctttc agccgtgctg gacgaacacc    95280
tgggccgtaa ctggcgcacc gaccttagcc tgcttaatga gctgcaacaa cactgtgatt    95340
tcccaatggt taatcacgct gtgcatcagg cgaagctgga gaacaaaaag cgtctggcag    95400
agtatatcgc ccagcagctg aatgtggtgg tgaatccaaa ggcgttgttc gatgtacaaa    95460
tcaaacgtat tcacgaatac aaacgtcaat tgatgaatgt gttgcatgtg attacccgct    95520
ataaccgcat caaggccgac ccggatgcga agtgggtacc gcgcgtgaat atttttggcg    95580
gtaaggcggc ttcggcctat tacatggcga agcacattat tcatttgatc aatgacgtag    95640
cgaaagtgat caacaacgat cgcagattg gcgacaagct gaaagtcgtg ttcatcccga    95700
actacagcgt tagcctggcg cagttgatca ttccggcggc cgatctgtct gaacagattt    95760
cgctggcggg gacggaagct tccggcacca gtaacatgaa gtttgcgctt aacggtgcgc    95820
ttactatcgg tacgttggac ggtgcgaatg tcgagatgct ggatcatgtc ggtgctgaca    95880
atatctttat ctttggtaac actgcggaag aagtggaaga actgcgtcgt cagggctaca    95940
aaccgcgtga atactacgag aaagatgagg agctgcatca ggtgctgacg caaatcggca    96000
gcggtgtatt cagtccggaa gatccgggtc gctatcgcga tctggttgat cgctgatca    96060
acttcggcga tcactatcag gttctggcgg attatcgcag ctatgtcgat tgtcaggata    96120
aagtcgacga actctacgag cttcaggaag agtggaccgc aaaagcgatg ctgaacattg    96180
ccaatatggg ctacttctct tctgaccgta ctatcaaaga gtacgccgat catatctggc    96240
atattgatcc ggtgagattg taatttcact aataaataga acggggccaa agggtcccgt    96300
ttttttcgcc atcatttcgg aaaagtgtcc agaagggca aggggactcg gggagtataa    96360
tttcgccatt cagaaagaat ggaaagaata atgcaaaaca gaaatggat tttgacctcg    96420
ctggtaatga cttttttcgg catccccatt ctggcgcagt ttttggcggc ggttattgcc    96480
atgctgggtg tcggacttgc cggtattatt gaagtttgta atatctttat cacgccaaca    96540
atttaccttc tgctcaacat ttttatgctg gcgctgggcg cattaatgct atttttctcg    96600
gggcgagtgt gggcggacga tagtgcacca gaaaaaagag aaatagccgt ctggcgacaa    96660
```

```
tgtctttttt tagtacccgc attattaacc ctggggtct ggataatcgc gctgcatctg    96720
gcagattatc aatttcgcca gatgggagcg ggttggttgg ctgatcttat gctcccctgg    96780
ctgggcgttt tgttagcctc attagtcggt ggtgagtact ggtggttagt cattatacct    96840
gttggcgcgc atatcagttt ttcgctggga tacggctggc cgaccagata tcctttaacg    96900
ggcacgtccg ggttacgttg ccgtaattct ctcttgttta tccttctcat gcttggtttt    96960
gtcgccggtt accaggctta tttatataaa cagcttaatc ccggcgtcgg tgtgcgtgaa    97020
aatattgata cctgggcctg gcgacccgat aaactcaata atcaactgac accactgcgt    97080
ggtaaaccgc aaattcagtt cacgcaaaac tggccgcgac ttgatggcgc aacggcggcg    97140
taccccattt atgcctctgc cttttatgca ctaagcgttt tgccggaaga ttttcacgaa    97200
tgggaatatc tggcgaactc tcgtactccc gaagcatata acaagattgt taaaggtaat    97260
gccgatatta tctttgtggc tcaaccttcc ggtgggcaga aaaaacgcgc ggaggaatcg    97320
ggcgtcactt tgatttacac gccttttgcc cgtgaagcgt tgttttcat cgtcaatgta    97380 gataacccgg ttaattccct gactgaacaa caggtgcgtg acatcttcag tggtgcaatt    97440
accaactggc gtactgttgg cggtaacgat caggagatcc agacctggca acgcccggaa    97500
gactctggta gccagacggt gatgcaatcc caggtcatga aaaatgtccg catgatctcg    97560
ccgcaggaaa cagaagtggc aagtatgatg gagggaatga ttaaagtcgt tgccgaatac    97620
cgtaatacaa acaacgcaat aggttacacc ttccgttatt acgcaacaca aatgaacgcc    97680
gataaaaata taaaactgct agcgattaac ggtattgcac cgactgccga aacattcgc     97740 aacggcaaat atccctatat cgtcgatgcc tttatggtaa cgcgggaaaa tatgacgtca    97800
gaaacacaaa aattggtgga gtggtttttta acgccgcagg ggcagagcct ggtgaagat     97860 gtaggttatg tgccgatgta taaaacgttg cattaaggcg gataataaaa atggaattag    97920
ttaatacatt atttgcaagc cttgtcggta ctgatcccctt cacaggcgtg gatattacga    97980
ttgccaactg caaatcggca tactgggatg aaggcattgt tcagcaactc attaaccagg    98040
ccctggatga agggaaaaag ttcgtcggtg ctgacggtct tgagggattg cttcgatata    98100
atgtcacatt aaatattggc ttaacgtcca gcaatgtatg gccgggattt tccctcgata    98160
ccgccaccat tagccgtctt tgtgcctgtg gtgctgactt tggatttgac ccctatatca    98220
gtgatgtacc agatgttcaa tgtgatctga acacgacaaa tgacctcacc gttcaattta    98280
cggcgatgct aaacccggat gagcgggtga tcatagcaaa gcgcccgctt aaaaaatgtg    98340
agtcctggat tgaggatatc tacatttttc aggtctttaa agatgcctgg aaatttcata    98400
acgataacag tttacgcgga tttcgtgata agcaagcgga actgaaactc tacgctcgtt    98460
attacacagt ggaaaattgc gctgaagaaa gctgtcgaga ctgcaatagt tgcattcgcc    98520
ccagcttttc cctctctcgt agtgccatta ttcgcctgaa cgtggcgaat gctcgttttg    98580
tttatcaacc gttacacgc gatcagcggg cgaggggta attatgcaac ccagcccgc     98640 catgcaggca ttaattgagc agatttatca tattttcgt cgttatccgg tgccgcagaa    98700
atttgtggtt tgttgtgaat attgcctgag tcagcaggaa caaaaggtat tacggagtac    98760
atcgttacga gcgatctcgt attccttaat caatgcatgg aatagtagcc cagggcctga    98820
tccgcaaaat agcgatgagg tccgctattt tctgccgcgt ttactggaat tgttgcaca     98880 ggggcagttt gacaatattc acgaagtatt tctctacgg cgtataaacc ttgccagtaa    98940
agaaaattgg cgtgaggatg aatggaaaat tttgcaacga tttgcctgcc agtatatgac    99000
```

```
tgattgggta tccggcgatg aagctgtcga attacagtat atgctggaaa tgttttccg     99060 tgccgatatc gctcttgcgc cattgctgga tgccattaat tcagttcccg gcttttggtc    99120
gaccgtttct cttgcctgtt tattgaacag atattgtgag gattatatca gagataacca    99180
ggacgatatc gataacgtca ttaccaccca aatcaatgcc tgggccttca acaatcaatc    99240
catcttgaaa gaacgcgcgc ggcaggcgat tgagaaccca ccaaagcagc cagaacaggg    99300
cacacagcat caggtctggg tagacgactg gataattgat gagtgtttat gcgcgatgta    99360
tgatgcatca tccgaatcac caggaaaata aaaatgatta aattccggct ttatattccc    99420
cctgtaattc tcggttttgt tatcgtgcca ttattggtat ggccgacggt tattgtctta    99480
gccgtactta tattcacgtt aacttttctg gcagaaataa tattctcctt tccgctcctg    99540
gttgtgcgta tttctcttca ggaactacaa cttgagttaa tggttgaata tgcactttt    99600 ttcagtgtaa tggctggcat cggttggcaa ttctcccgca gaacgcctcc tgaattaaaa    99660
aacagactgc attgctggct ggtcttttcg ccggtctatt tctggttaat tctctcgaat    99720
ttcattcttt atatttctcc agagaaatca gcgttgctgg aaaatatccg aaatttcttt    99780
ctgacgtttg tctggcttcc cctgaatttt tccccttttt ggccgcagcc ttggactgat    99840
tttgtcggcc cgattagtgc acagcttggt tttgcattgg gatattattg ccattggtgc    99900
agaaaaaata gaaaccagag gaagaagtgg ggcgattggg taacgtgctt aagtttggcg    99960
attttagctc aggggccgtt attcaattat ttacaatgaa tagtctaagg aatccaaata   100020
gcccggttgc acttcacaac cgggcatcat ccttacgacg ccagcgacaa cttctgctgc   100080
gtatactcca ccagccactg actcacacga gattgttgat ccgcatttag ccacatgcct   100140
tgttttgtgc gacgccacag ggcgtcgtcg gcgcggcgga cccattcgtg atccaccagg   100200
tatttcagct ccgcttcgta gaactcatga ccgaaatctt ccccgagatc gcttaccgtt   100260
cccgcattgc cgagcagcag ctcgctgttg ctgccgtaag tgcgagcgta atgacgcgcc   100320
agcgattcag tcaggaatgg atagcgacgg cgcagacgag ctgcgtaatc gtcgcggtcg   100380
ccttcaatgg caccacccgg cagcacgctc tctttcgtcc acgccgggcc aatacctga   100440 taatacggcg tcagttttc cagcgcatgt tctgccagtt ttcggtaggt ggtcagctta   100500
ccgccgaata ccgacagcag cggtgctttg ccgttttcat catggatatc aagggtgtaa   100560
tcacgggtaa tagcctgcgg cgagtcggac tcatcatcac acagcggacg cacaccggag   100620
taggtccaga cgatatcgtc acggctaagc tgtttttta agtgcgcgtt atacactttc    100680
agcagatagt tgatttcact ctcttcaatc ttcaccgctt tcggatcgcc tttatactct   100740
acgtcggtgg tgccgatgat ggaaaattcg tccatccacg ggatcacgaa cacaatacgt   100800
ttatcttcgt tttgcagaat gtaggcctgc ttctgggtat gcacacgcgg caccacaata   100860
tggctgcctt tgatcaggcg aatgccataa ggcgaaggca gatgcatccc ctcgtcgaag   100920
aactgtttca cccacgggcc ggtggcgtta accaggccgc gcgcttgcca gctatatttt   100980
ttgccggtat cgatatcttc cgcttccaca atccacaggc cgttttcgcg gcgagcagag   101040
gtggcgcgag tccgagtaag cacttcgccg cctttacgca ccaccatctg ggcgttggcg   101100
agtaccagac gggcgtcgtc tacccaacag tcagaatatt cgaatccgcg cttaatttcc   101160
ggttttaaca ctgagtttgc gccaaaacgc aaaccggttg atcccggcag gctggtgcgt   101220
ttacccagat gatcgtacat aaacagacca atgcgaatca tccacgccgg gcgcagatgc   101280
ggacgatgtg gcaggcgaaa acgcatcggg aaggcgatat gcgagccat tttcagcagc    101340 acttcacgtt cagccagcgc ctcgctgacc aggcggaatt catagtgctc aaggtagcgc   101400
```

```
aggccaccgt gaatgagttt tgaactggcg gaagaggtcg cgcaagcgag atcctgcgcc   101460
tccagcatca gcacggataa accgcgtcca gcggcgtctg ccgcgatacc agcaccattg   101520
atgccgccac ctatcacaat cagatctttg gtttccatgc tgccctcatt cactttcgtt   101580
aaagctcata aatgttcgtt atcgaacata ttagcaaaga atcgcgcttt aggtaacatt   101640
gaaaaaacat tttagagtga tatgtataac attatggcgt ttatctgccg cttcgacgta   101700
aactgtgcgg taaatttgcc cacttgtttg taaagaaaga gagacgcatg gatcagttcg   101760
aatgtattaa cgttgccgac gcgcaccaga agttgcagga aaaagaggcg gtgctggtcg   101820
atattcgcga tccacagagt ttcgctatgg ggcatgcggt gcaggctttc catttaacca   101880
acgacacgct gggcgcgttt atgcgtgata acgactttga cactccggtg atggtgatgt   101940
gttatcacgg caatagcagc aaaggcgcgg cgcagtatct gctgcaacag ggctacgatg   102000
tggtctatag cattgacggc ggctttgaag cctggcaacg tcagtttccc gcagaggtgg   102060
cgtacggcgc gtaacgcttt atactgtccc cttttgtgtg gaataagcga cagcaacgat   102120
gttgatgatt acctcttttg ctaaccccg cgtggcgcag gcgtttgttg attacatggc   102180
gacgcagggt gttatcctca cgattcaaca acataaccaa agcgatgtct ggctggcgga   102240
tgagtcccag gccgagcgcg tacgggcgga gctggcgcgt tttctcgaaa acccggcaga   102300
tccgcgttat ctggcggcca gctggcaggc aggccatacc ggcagtggcc tgcattatcg   102360
ccgttatcct ttctttgccg ccttgcgtga acgcgcaggt ccggtaacct gggtggtgat   102420
gatcgcctgc gtggtggtgt ttatcgccat gcaaattctc ggcgatcagg aagtgatgtt   102480
atggctggcc tggccattcg atccaacact gaaatttgag ttctggcgtt acttcaccca   102540
cgcgttaatg cacttctcgc tgatgcatat cctctttaac ctgctctggt ggtggtatct   102600
cggcggtgcg gtggaaaaac gcctcggtag cggtaagcta attgttatta ctctcattag   102660
cgccctgtta agcggctatg tgcagcaaaa attcagcggg ccgtggtttg gcgggctttc   102720
tggcgtggtg tatgcgctga tgggctacgt ctggctacgt ggtgaacgcg atccgcaaag   102780
tggcatttac ctgcaacgtg ggttaattat ctttgcgctg atctggattg tcgccggatg   102840
gtttgatttg tttgggatgt cgatggcgaa cggagcacac atcgccgggt tagccgtggg   102900
tttagcgatg gcttttgttg attcgctcaa tgcgcgaaaa cgaaaataat tccagggatt   102960
tataaatgaa acaaacacaa cgtcacaacg gtattatcga actggttaaa cagcagggtt   103020
atgtcagtac tgaagagctg gtagagcatt tctccgtcag cccgcagact attcgccgcg   103080
acctcaatga gctggcggag caaaacctga tcctgcgtca ccatggcggt gcggcgctgc   103140
cttccagttc ggttaacacg ccgtggcacg atcgcaaagc cacccagacc gaagaaaaag   103200
agaggattgc ccgcaaagtg gcggagcaaa tccccaacgg ctcgacactg tttatcgata   103260
tcggcaccac gccggaagcg gtggcgcacg cgctgcttaa tcacagcaat ttgcgtattg   103320
tcaccaacaa tctcaatgtt gctaacacgt tgatggtaaa agaagatttc cgcattattc   103380
tcgccggtgg cgaattacgc agccgcgatg gcgggatcat tggcgaagcg acgctcgatt   103440
ttatctccca gttccgcctt gatttcggca ttctggggat aagcggcatc gatagcgacg   103500
gctcgctgct ggagttcgat taccacgaag ttcgcaccaa gcgcgccatt attgagaact   103560
cgcgccacgt tatgctggtt gtcgatcact cgaaatttgg ccgtaacgcg atggtcaata   103620
tgggcagcat cagcatggta gatgccgtct acaccgacgc cccgccgcca gtaagcgtaa   103680
tgcaggtgct gacggaccat catattcaac tggagctgtg ctgatcctgc acggcttccc   103740
```

-continued

```
acgtcagacc aaaacgcgcc aggtatttgc gtagccgatc cgcgtcattg acgctggctt 103800
tgccctggcg cgaaacatca aaaagcaggc gtccggcagc ggaaagcgac tttgcctggc 103860
gacagagagc tatcacgtgt tccagttgca gcctgtcaaa aaggtcgatg ttttctgcct 103920
ctgcgcccag caacgccgta agcgcggagg ggcggctctc ctgccagtta tagcgcagac 103980
ggtttatctc atcttcaacc acgtccagag tgatgcgtcc gctagtggca aaggtggcca 104040
tccgcgtgac gctggcagaa agttcgcgaa agttaccgcg ccatgttgcc tgggagagg 104100
tcgcaaaagc caaccaggcg cgccgcgctt cggtgttaaa acgcacgctg tcgccagtga 104160
gtgtggcgtg gcgctccact tcataatcaa ggttcggttc aatatcttcc tggcgctggc 104220
gtagacccgg cagggtgaag gtccagagat tgatccgcgc gtacagatct tcgcgaaatt 104280
tgccttcggc aaccagctgg cgcaaatcgc gcaccgttcc ggcgataagc tgaaaatcac 104340
tgctcacctg gcgatcgctg ccaaacgggt aaaaggtttt ctcttcaatg gcttttagca 104400
gcattgcttg ttcgtctgcg cccagttcgc caatctcatc aagaaacaac attccgccgt 104460
tggcgctgcg taataaacct tcacgagatt cccgcgcccc ggtaaacgcg cctttacat 104520
gaccaaacag cgtcgacatg gcggtatcgc cgcgcagggt ggcgcagttc acttccacaa 104580
acgcgccgct aaactgatgc cgcgcctgtt ttaactcgaa gatgcgtcgc gccagaaatg 104640
acttgcccgc gccggttgga ccgttaagca gaatcggcgc gcgggatttg atcgccactt 104700
tttcgatctg ctcaatcatg cggttgaagt gggggttacg cgtggcaatg ccggacttaa 104760
gaaaatcaag cgtttgctgg cgttcctcgg caaagcggct ggcgatggcg ttataacggc 104820
ttaaatcgag atcgataatc gtcacttcac ctgcgccgcg cggctgttct tttttgcgcg 104880
gaggtgaaga ttgtatcagc cgggcgggca ggtaacgcgc ttccgccagc agaaaccagc 104940
aaatctgcgc gacgtgggtg ccggtggtga tgtgaattaa atagtcttct ttttctggct 105000
gaaactcgta accacgggcg aaatcatgca ggcaggcgta aacctcttcg aaatcccacg 105060
ggttatgcag ttcaatctca acgcccacga cttctgtttc tggcgaaacg ctggcgatat 105120
cgcgtttaag cgtttcgaat agcgagcgcg agcgggtgtc gtgcaacaat tccagccgat 105180
cgatgactaa cgattcttgc tggcataaac aaagcgtcgg acgccatttc gaccagcgct 105240
gactgccgcg tccggcataa tccagcacgg taccgacaaa gccaaaagcc actgttttac 105300
gcatcttaga tatccttata aaagacgata tttcattatc ggtgaattgg ttttgtggaa 105360
aatctccgtt tacggacgta aagatttaac ctatttaaaa acaatgaatt aaaaaattaa 105420
tctgcttatt taatttttctg gcacgacggt tgcaattatc acgacagcaa acaacgaaaa 105480
gagaaaaaca aaatgaatta cgaattactg accactgaaa atgccccggt aaaaatgtgg 105540
accaaaggcg tgccggtaga ggccgatgcg cgtcagcaac ttattaatac ggcgaagatg 105600
ccgtttattt tcaaacatat tgcggtaatg cctgatgtac acctgggtaa aggttccacc 105660
attggtagcg tgatcccgac caaagggggcg attattccgg cggcggtggg cgtggatatt 105720
ggctgtggaa tgaacgcgct gcgtaccgcg ttaacgcgg aagacctgcc tgaaaacctg 105780
gcagagctgc gtcaggcgat tgaaacggcc gtgccgcacg ggcgtaccac tggccgttgt 105840
aaacgtgata aggtgcctg ggaaaatcca cctgttaacg tcgatgctaa atgggctgag 105900
ctggaagccg gttatcagtg gttaacgcaa aaatatccgc gtttcctgaa taccaataac 105960
tataaacatc tgggaacgct gggaacgggt aaccatttta ttgaaatctg tcttgatgag 106020
tcggatcagg tgtggattat gctgcactcc ggttcacgcg gaattggtaa cgccatcggg 106080
acttacttta tcgatctggc gcaaaaagag atgcaggacc agcttgaaac gttgccgtcg 106140
```

```
cgtgatctgg cgtactttat ggaaggtacg gaatactttg atgattacct gaaagcggtg   106200
gcctgggcgc agcttttgc cagccttaac cgcgatgcaa tgatggaaaa cgtagtaaca    106260
gcgttgcaga gcgttacgca gaaaacggta agacaacagc aaacgctggc gatggaagag   106320
atcaactgtc accacaacta tgtgcaaaaa gaacagcact ttggcgaaga gatctacgtg   106380
acgcgtaaag gcgcggtgtc tgcgcgtgct ggtcaatatg gaattattcc cggttcgatg   106440
ggagcgaaaa gctttatcgt ccgtgggctg ggaaatgaag agtcgttctg ttcgtgcagc   106500
cacggtgccg gcgggtaat gagccgtact aaagcgaaaa aactgttcag cgtggaagat    106560
caaattcgtg ccaccgcgca tgtggaatgc cgtaaagatg ccgaagtgat cgacgaaatc   106620
ccgatggcgt ataaagatat tgatgcggtg atggcggcac aaagcgatct ggtggaagtt   106680
atctataccc tgcgtcaggt ggtgtgcgta aaaggataaa tgatgaaaag gatgattgcg   106740
ctggatggcg cacagggcga aggtggcggg ctgatcctgc gctcggcgct gagcctgtcg   106800
atgataaccg gccagccatt taccatcacc agcattcgtg ccgggcgagc gaaaccgggg   106860
ctgttgcgcc agcatctgac cgcggtaaaa gcggctgcgg aaatttgtag gcaacggtg    106920 gaaggcgcgg agctggggtc gcagcgtctg gtcttccggc ctggcaccgt gcgcggcggc   106980
gagtaccgct ttgctatcgg tagtgccgga agctgtacgc tggtgctgca aacggtgctg   107040
cccgcgctgt ggtttgccga tggaccttcg cgtgttgaag tgagcggagg caccgataac   107100
ccgtcggccc cgcctgcgga ttttatccgc cgggtgctgg agccgctgct ggcgaaaata   107160
ggaattcatc agcaaaccac gctgttacgt cacggttttt atcctgccgg aggcggtgtg   107220
gtggcaacgg aagtctcgcc cgtggcatcg tttaacaccct tgcaacttgg cgagcgcggg   107280
aacattgtgc agatgtgtgg agaagttcta ttagctggtg tgccgcgcca tgttgctgag   107340
cgtgaaatcg ctacactggc ggggagtttt tccctgcatg aacagaatat tcataacctg   107400
ccgcgcgacc aggggccggg taataccgtc tcgctggaag tcgaaagtga aaatatcact   107460
gaacgctttt tcgtcgtcgg tgaaaagcgc gtcagtgccg aggtggtagc cgcgcagtta   107520
gtgaaagagg tgaaacgcta cctggcaagc ccagcggcgg tggggaata tctcgccgac    107580 caactggtac tgccgatggc gctggcgggc gcggagaat ttaaggtcgc ccatccttca    107640
tgccatctgc tgaccaatat cgcggtggtg gagcgtttct tgccggtgcg gtttggtttg   107700
atagaaacag atggcgtaac gcgggtgagt attgaatgat gtaaagatgt aaaccggatc   107760
caatgcatta tccggctaaa ctcacacccc ataacccatc atcttcagca gtttctgcgc   107820
gtgctgcacg gcagcctgac ggtgggcgac gccgagtttt tggtacagat tgcggatatg   107880
cgtcttgatg gtggttgccg ccacttccag ttcgcccgca atttgttcat tgctgtaacc   107940
ggagtaaatc agccccagga cctgccattc acgttgggtc aacgggctgg tcggatcag    108000 ttctggcact tccggatgat ttagcagacg ttcaacgaaa ttctcatcga aatgggcgaa   108060
tttatgccga tgatgttgat tgatttctcg cagaatacgc tgtgcgcgat gctgttccag   108120
ttccggcagc gtattgagtt gaatcagctg gcgcagttgt tgcgccatcg cttcgccttc   108180
gatgacaaaa tggctgataa atccggtgcg attcgccagt tttaatgcgt ccagcaacac   108240
gcgctgggcg tcacttttac gtccggcctg ccagtacagt tgattaagca gcaacaggtt   108300
acggttgaga tcgctcatca accgcagact gcgggcattt tcattgagtt cttcgagaac   108360
aatttccgca ggttcaaact cgcccagcaa gatttgtgcg cgggcaatgt tgcgccattg   108420
accttgcagg aagtggttgt tcgcaaactc cggtttagcc gtatgacgca accagttggc   108480
```

```
agcggcggct ttatcgccgg tcatttgcca gtaaatcacc cggactttgt tggcgttaga   108540
gatccagtcg ctgtgatatt tgccattccc cagcaggttt tccagacggt tcagctggct   108600
acgggcgtta tctaaatcac cacgggccag cgagcattga atcaacattg ccaggcactg   108660
aagctgttgc tgtggctgat aagacgacaa gacttcaatc ccgctacgcg ccgacgcttc   108720
ggcttcatcc agccgtgccc aggcccataa cagttgtgct cggatgcgca ccagaaactc   108780
atgcatcggc agctgttcca gatgctgctc gttgatcagc tggaacgctt tttcctgtgt   108840
ttcccacgcg gtttgcagga acccttgggc aaacagaatt tcactttgct ggattaaact   108900
ccataaggcg tagtgccaga cgtcgtgctg gcgtgccatc tgttcggttt gctgcattag   108960
cgccagtgag cgggtcaatt cgcctttgca gtgcagcact tcacccagca ccgaggttgc   109020
cacaatgcgg ctatagaacc agccggcgg cagctcttcc agtgccagtt ttgccagccg   109080
ttccgcttca tccggattac catcgttaat cgccacctgg gcgcgcagag cgttaaattc   109140
tgcgtgcatg gtgccttctc tgatgtcctt gatttcatgt tcagcacggg ctagcagggt   109200
gttaacttcg ccatagcgat gttggctttg cattagccac gcctgcaata acactaactg   109260
cggattttcc agcaaactgt cccacggcag ggccttaagc gactcttcca gcagcgacag   109320
ttcgctatgg ttgaacaaac tccaggcgtg attaagcaga atatcgcgca gcatcagcgc   109380
atcgcctgcc gccagcgcat gatgaatcgc ttcgctggga aatccctggg ccatccagct   109440
ttctgcggcg gcacggtgga tttccggcag ctccgccgcc agttcccact ggcagcgctg   109500
gcgcaggaag ttgccaaaca gcgggtgata gcagaaccac tcgccggtat catccatccg   109560
ctgtaaaaac agcccctgac gctcaatctc ttcgagacgc atttgcccgt tttcttcgcc   109620
ggtcacacgg gtgatgaggg catcgttcat tgagcgcaaa atggcgcttt tcaacagaaa   109680
atggcgcgtt gcgagatcga cgttatccaa aacctcatcg accagataat ccgaaagatg   109740
gctggcattg attcccgcca ggcggcgtgc cgacttatgg gctgagtggg tattctgccg   109800
ggcggagagg gcgattagct gtagtgccgt cgcccaaccg gaaacgtcat cgcaaatccg   109860
actgctttct gcggcttcaa tcggcgatga cagacggcaa tcaaaaaact gcttcgcttc   109920
ctgatgggta aatgccagtt gctgactgcc aatttccagc agttggtcac gaacacgcag   109980
attggcaatg cccagttgcg gaaggttgcg tgacaacacc accagggtga gttttctgg    110040 ttgatggcga ataaagaagc gcattgactc gtggatcact ggattagtga tcagatgata   110100
gtcatcgatg accagataaa gtgggctatg ccattccgcc agctcaatga aaagctgggc   110160
gaagagtgac gtcaggctgg catattgccg ttttgcgcc atcgtctcac atatcgcaca    110220
gtgaccgttg gttgcctgct gcacggcggc aatgagatag ctggcgaaac gctcttgctg   110280
gttatcacct tcatccagcg agtaccagcc gatatcgttt ttgcctgccg cccactggga   110340
aatgagggtg gtcttttccgt agcccgcagg actcgtgatc agcgccagcc ggaagttgtt   110400
cgcgccggaa agtttagcca gcaggcgctc acgaaccacg gtatggtcga gtcgaaccgg   110460
acgacttagt tttgacggaa tcagcatagt taatcacttc actgtggaaa atgaggaaat   110520 attattttt ttgcgcttcg taattaatgg ttataaggtc ggccagaaac ctttctaatg    110580
caagcgatga cgttttttta tgtgtctgaa tttgcactgt gtcacaattc caaatcttta   110640
ttaacaactc acctaaaacg acgctgatcc agcgtgaata ctggtttccc ttatgttcat   110700
cagattcatt taagcaaggg tttcttcttc attcctgatg aaagtgccat ctaaaaagat   110760
gatcttaata aatctattaa gaatgagatg gagcacactg atattttac ttatgaaact     110820 gtttcactcc tttacttaat ttatagagtt accttccgct ttttgaaaat acgcaacggc   110880
```

```
catttttttgc acttagatac agattttctg cgctgtattg cattgatttg ctgctaatcc  110940
tgtggtttgc actagcttta agtggttgag atcacatttc cttgctcatc cccgcaactc  111000
ctccctgcct aatccccgc aggatgagga aggtcaacat cgagcctggc aaactagcga  111060
taacgttgtg ttgaaaatct aagaaaagtg gaactcctat gtcacaacct attttttaacg  111120 ataagcaatt tcaggaagcg ctttcacgtc agtggcagcg ttatggctta aattctgcgg  111180
ctgaaatgac tcctcgccag tggtggctag cagtgagtga agcactggcc gaaatgctgc  111240
gtgctcagcc attcgccaag ccggtggcga atcagcgaca tgttaactac atctcaatgg  111300 agttttgat tggtcgcctg acgggcaaca acctgttgaa tctcggctgg tatcaggatg  111360
tacaggattc gttgaaggct tatgacatca atctgacgga cctgctggaa gaagagatcg  111420
acccggcgct gggtaacggt ggtctgggac gtctggcggc gtgcttcctc gactcaatgg  111480
caactgtcgg tcagtctgcg acgggttacg gtctgaacta tcaatatggt ttgttccgcc  111540
agtcttttgt cgatggcaaa caggttgaag cgccggatga ctggcaccgc agtaactacc  111600
cgtggttccg ccacaacgaa gcactggatg tgcaggtagg gattggcggt aaagtgacga  111660
aagacggacg ctgggagccg gagtttacca ttaccggtca agcgtgggat ctccccgttg  111720
tcggctatcg taatggcgtg gcgcagccgc tgcgtctgtg gcaggcgacg cacgcgcatc  111780
cgtttgatct gactaaattt aacgacggtg atttcctgcg tgccgaacag cagggcatca  111840
atgcggaaaa actgaccaaa gttctctatc caaacgacaa ccatactgcc ggtaaaaagc  111900
tgcgcttgat gcagcagtac ttccagtgtg cctgttcggt agcggatatt ttgcgtcgcc  111960
atcatctggc ggggcgtaaa ctgcacgaac tggcggatta cgaagttatt cagctgaacg  112020
atacccaccc aactatcgcg attccagaac tgctgcgcgt gctgatcgat gagcaccaga  112080
tgagctggga tgacgcctgg gccattacca gcaaaacttt cgcttacacc aaccataccc  112140
tgatgccaga agcgctggaa cgctgggatg tgaaactggt gaaaggctta ctgccgcgcc  112200
atatgcagat tattaacgaa attaatactc gctttaaaac gctggtggag aaaacctggc  112260
cgggcgatga aaaagtgtgg gccaaactgg cggtggtgca cgataaacaa gtgcatatgg  112320
cgaacctgtg tgtggttggc ggtttcgcgg tgaacggtgt tgcggcgctg cactcggatc  112380
tggtggtgaa agatctgttc ccggaatatc accagctatg gccgaacaaa ttccataacg  112440
tcaccaacgg tattaccccca cgtcgctgga tcaaacagtg caaccctgca ctggcggctc  112500
tgttggataa atcactgcaa aaagagtggg ctaacgatct cgatcagctg atcaatctgg  112560
aaaaattcgc tgatgatgcg aaattccgtc agcaatatcg cgagatcaag caggcgaata  112620
aagtccgtct ggcggagttt gtgaaagttc gtaccggtat tgagatcaat ccacaggcga  112680
ttttcgatat tcagatcaaa cgtctgcatg agtacaaacg ccagcacctg aatctgctgc  112740
atattctggc gttgtacaaa gaaattcgtg aaaacccgca ggctgatcgc gtaccgcgcg  112800
tcttcctctt cggcgcgaaa gcggcaccgg gctactacct ggcgaagaat attatctttg  112860
cgatcaacaa agtggctgac gtgatcaaca acgatccact ggttggcgat aagttgaagg  112920
tggtgttcct gccggattat tgcgtttcgg cggcggaaaa actgatcccg gcggcggata  112980
tctccgaaca aatttcgact gcaggtaaag aagcttccgg taccggcaat atgaaactgg  113040
cgctcaatgg tgcgcttact gtcggtacgc tggatggtgc gaacgttgaa atcgccgaga  113100
aagtcggtga agaaaatatc tttatttttg gtcataccgt ggaacaagtg aaggctattc  113160
tggccaaagg ctacgacccg gtgaaatggc ggaagaaaga taaggtgctg gacgcagtat  113220
```

```
tgaaagagct ggaaagcggt aaatacagcg acggcgataa gcatgccttc gaccagatgc  113280
tgcacagtat cggcaaacag ggcggcgatc cgtatctggt gatggcggat ttcgcagcct  113340
atgttgaggc acaaaagcag gtggatgtgc tgtaccgcga ccaggaggcc tggactcgcg  113400
cggcgatcct caataccgcc cgctgcggta tgtttagctc ggatcgctct attcgcgatt  113460
atcaggctcg tatctggcag gcaaaacgct aaggaagctc gatggaaagc aaacgtctgg  113520
ataatgccgc gctggcggcg gggattagcc ccaattacat caatgcccac ggtaaaccgc  113580
agtcgattag cgccgaaacc aaacggcgtt tgcttgacgc gatgcatcaa cgtaccgcca  113640
cgaaagtggc ggtaacgcca gtcccgaatg tcatggttta taccagcggc aaaaaaatgc  113700
cgatggtggt ggagggcagc ggcgaatata gctggctgct gaccaccgaa gaggaacac   113760 agtacaaagg ccatgtaacg gggggcaaag cgttcaatct accgacgaag ctgccggaag  113820
gttatcacac gctgacactc acccaggacg accagcgcgc gcattgccgg gtgattgtcg  113880
ccccgaaacg ctgttacgaa ccgcaggcgt tgctgaataa acaaaagctg tggggtgcct  113940
gcgttcagct ttatacgctg cgatcggaaa aaaactgggg tattggggat tttggcgatc  114000
tcaaagcgat gctggtggat gtggcaatac gtggcgggtc gttcatcggc ctgaacccga  114060
ttcatgcgct ctatccggca aatccggaga gtgccagccc atacagcccg tcttctcgcc  114120
gttggctgaa tgtgatttat atcgacgtta acgccgttga agatttccat cttagcgaag  114180
aggctcaggc ctggtggcag ttgccgacca cgcaacagac gctgcaacag gcgcgcgatg  114240
ccgactgggt cgattactcc acggttaccg ccctaaaaat gacagcatta cgaatggcgt  114300
ggaaaggttt cgcgcaacgt gatgatgagc agatggccgc gtttcgccag tttgttgcag  114360
agcagggcga cagcctgttc tggcaggcag cctttgatgc gctacatgcc cagcaagtga  114420
aagaggacga aatgcgctgg ggctggcctg catggccaga gatgtatcag aacgtggatt  114480
caccagaagt gcgtcagttc tgcgaagaac atcgtaatga cgtcgatttt tatctctggt  114540
tgcagtggct ggcttacagc cagtttgccg cctgctggga gataagccag ggctatgaaa  114600
tgccgattgg cttgtatcgt gatctggcgg ttggcgtagc ggaaggtggg gcggaaacct  114660
ggtgtgaccg tgaactatat tgcctgaaag cgtcggttgg cgcgccgccg gatatcctcg  114720
gcccgttggg gcagaactgg ggattaccgc caatggaccc gcatatcatc accgcgcgtg  114780
cctatgaacc gttatcgag ctgttgcgtg ccaatatgca aaactgcggc gcattacgaa  114840
ttgaccatgt gatgtcgatg ctgcgtttgt ggtggatacc gtatggcgag acggcagatc  114900
agggcgcgta tgttcactat ccggtggatg atctgctctc gattctggca ctcgaaagta  114960
aacgtcatcg ctgtatggtg attggtgaag atctcggtac cgtaccggta gagattgtcg  115020
gtaagctgcg cagcagcggt gtgtactcct acaaagtgct ctatttcgaa aacgaccacg  115080
agaagacgtt ccgtgcaccg aaagcgtatc cggagcagtc gatggcggtt gcggcgacac  115140
atgacctgcc tacgctgcgc ggttactggg agagcgggga tctaacgttg gcaaaaccc   115200 tggggctgta tccggatgaa gtggtactgc gcggtctgta tcaggatcgc gaactggcga  115260
agcaagggct gctggatgca ctgcataaat atggttgtct gccaaaacgt gccgggcata  115320
aggcatcgtt gatgtcgatg acgccgacgc tgaaccgtgg tttgcagcgc tacattgccg  115380
acagtaacag tgctctgtta ggactacagc cggaagactg gctggatatg gccgaaccgg  115440
tgaatattcc tggcaccagt taccagtata aaaactggcg acgcaagctt ccgcaacgc   115500 ttgagtcgat gtttgccgat gatggcgtga acaagttgct gaaggatttg gacagacggc  115560
gcagagctgc agcgaagaag aagtagagtg cggttgatgc cggatgcgat gcatccggca  115620
```

```
gtcagtgtta tcaaatcacc atattcagca gcagacagcc taccagaccg cacaccgaga   115680
taatggtttc cagcatcgac caggatttga tggtctcgcc gatagtcagg ttaaagtact   115740
ctttgaacag ccagaagccc ggatcgttca catgagagaa aatcacacta ccggaaccca   115800
ccgcaataac catcagctcc gggctaacac ccgtcgttgc aatcagcggt gccgcgatac   115860
cacccgcagt gattgccgca acggttgcgg aacccagcgc gatacgcagt acggcagcaa   115920
tcgaccaggc catcagcagc ggagaaatgt tggtttcgtg catcatggaa gcaatgtatt   115980
tgtccacgcc gctgtctacc agcacctgct tgaacgcacc gccaccaccg atgatcaaca   116040
gcatcatcgc aatgattttg atggaagaaa ccagcgtgtc gttaatctga tccattgaac   116100
gaccacggtt cagaccaaag gtgaacatgg caatcagcac ggcaatcagc gtagccatta   116160
ccgggtcacc gaggaactcc gctaccggca ggaaagcgtg acctttcggc aggatcattt   116220
cggcaatcgc acgcatcgcc atcagtacta ccggcaccag agaggtccag acgctgacgc   116280
caaagctcgg catctcttct tcgctgaagg ttttcgcgct gtagagacct tccggaattg   116340
gcttatcgat accttttcaac acgcgagcgt aaaccggacc ggcgagaatc acggtcggga   116400
ttgccagaat agtaccgtac agcagggttt tacccatatc ggcattgaaa atggtggcaa   116460
tcgcagtcgg acccggatgc ggtggcagga agccgtgggt cacagacagt gcagctgcca   116520
ttggtacacc aacatacaac agtggaatat tcgcagaagc cgcgatggta aacaccagcg   116580
gcagcatcag cacaaagccc acttcataga acagggcaaa accaacggta aaaccggtca   116640
gtaccaccgc ccactggatg tgttttttac caaatttggc aatcagcgtg gtggcgatac   116700
gttgtgcgcc accgcagtct gccagcattt tgcccagcat tgcgccaaaa cccatgatca   116760
gggcaaggct accgagcgtc ccgccgacac cggctttgat ggagccaata actttatcca   116820
gcggcattcc ttgcattaat ccaacagcaa gcgccacgag gacgagagcg atgaagccgt   116880
tcattttgaa gcggatcatc aggagcaaca acaagattac accgatagca acaatgacta   116940
atggcatgat ttacctggcc tttcatttgt tatgggtaac gtcaatttttc tgacgacaaa   117000 ctctaattat cccaatcggg aacagagata ttgcggcacc acgactgatc cccactaaaa   117060
ctaattattg tagtcagatg tcaggagtat gtttggtacc catgtgaatg atacgggtaa   117120
catctggcgt ttgagaatca ccagagcggg gtaaatttaa attatgagag gttggtcata   117180
ttatcgcggg gaaacgaagg gagggatttg ccaaagcaat gctgtgccaa cgtctggcac   117240
atgttcaacg taggcccgaa atgacgcttt agcgtcgcat cgggcaatct acaaaagagg   117300
ggataactta gtagtaggag tgttcgccgc gctggtgttc ggtgagatcg cgcacacctt   117360
tcagctccgg gaattcgttt agcagctgct tctcgatccc ttctttcagc gtcacatcga   117420
ccatggaaca accgttacag ccgccgcaa attgcagaat ggcgtaaccg tcttcggtga   117480
tttccatcag tgaaacgcgg ccaccgtgac cagcaagctg tgggttgatc tgcgactgca   117540
gcatatactc cacgcgctcc atcagtggtg catcgtctgc cactttacgc attttggcgt   117600
taggcgcttt cagtgttagc tgagaaccca actggtcggt aacaaaatcg atctctgcat   117660
cttccaggta aggagcgctt aactcatcaa catacgcgt cagcaggtca aatttcaggg   117720
cagtgtcggt ggcttccacg gcatccggcg gacaataaga aacaccacat tcagcgttag   117780
gcgtgccagg gttaatcaca aatacgcgga tttgtgtccc ttcttcctga tttgccagca   117840
gtttggcaaa gtgcgcttgt gcagcatcgg aaatacggat catagtaatg gcctaatagt   117900
tgactatttt agttggttat aatacgccca tcatcgaggc tctacaaggt tcgacaaagg   117960
```

```
caccagacct ggacagtcgc cgcaccattg cgtaaaagca actgcgcaat ctctgcgacg   118020
gtacttccgg tggtaacgac atcatccaca atcaccatat ggcgaccttg cacgggcaat   118080
tcaagacgaa aggcattttt caggttgcgc ttgcgcagcc gggcactgag aaaatgctgg   118140
gtcgcagtgg cccgtgtacg tgtgacggct tcgctatccc attggcagtg caaccagcgt   118200
gataacggct gacacagcaa atcgctctga ttaaatcccc gacgccagtg acgccgctgc   118260
cataacggaa cgctgatgat gcgatccggc aattgcaacc cggtggtgcg acgagcgtgt   118320
aagacttcca atagtaacag acgtgacagg gcgctggcga tttcactgcg ccgggaaaat   118380
ttaagctggt ggataagcgg acttaacggc ggcgcatagt cggcaaccgt gaccagtctt   118440
tgccagggcg gcggtttttg caggcagcga ccgcagggaa gatgggagtg tgtggcgggt   118500
aatccacatt gtgggcataa cgttttatct gtgcgggtgg cgcgtgaaca gaccgaacaa   118560
atcccccaat gacctaacgc cagtggcatt cggcatagcc agcataatcc cggtactgtt   118620
agcatatgtt catccttgta agtcaaaaga gaacaatagc ggatgaataa catctggtgg   118680
cagaccaaag gtcaggggaa tgttcatctt gtgctgctgc acggatgggg actgaatgcc   118740
gaagtgtggc gttgcattga cgaggaactt agctcgcatt ttacgctgca ccttgttgac   118800
ctgcccggct tcgggcgtag ccggggattt ggtgcgctgt cacttgctga tatggccgaa   118860
gccgtgctgc aacaggcacc tgataaagcc atttggttag ctggagtct gggcgggctg   118920
gtggcaagcc aaattgtttt aacccatccc gagcgtgttc aggcgctggt caccgtggcg   118980
tcgtcacctt gttttagtgc tcgtgacgag tggccgggga taaaaccgga cgtgctggcg   119040
ggatttcagc agcaactcag tgatgatttt cagcgtacag tggagcggtt cctggcgtta   119100
caaaccatgg ggactgaaac ggcgcgccag gatgcgcggg cgttgaagaa aaccgttctg   119160
gcgttaccga tgccggaggt tgacgtgctt aatggcgggc tggaaatcct gaaaacggtc   119220
gatctccgtc agccgctgca aaacgtgtcc atgccgtttt tgcgattgta tggctatctc   119280
gacggtctgg tgccgcgcaa agtggtgccg atgctggata aactttggcc tcacagcgaa   119340
tcatatatct tcgccaaagc ggcccatgcg ccgtttattt cgcatccggt cgagttttgt   119400
cacctgctgg tggcgttgaa gcagagggtg taggcaactt ttgaaatggc gagacagaaa   119460
tttactggct cgccgcagcc aactcttctt ctgacacccc ggtaaagcgc atgatgtctg   119520
taagagggac tccggattca agcattattt tggctatatg cagggctttg gattgttccc   119580
cctcctgccg caatctttcc gcaattgtca ttaaactctc cttgtgtttc ggtgaacgtt   119640
cggcaacgcc gtcgataaaa tcgttaaaac gtaccgcgtc gccggtttgc agtatgtaat   119700
taaacagccc tttgatttgt ctgtcattag cgtatccact acttaataag caggccattt   119760
gctctaccag ccccatcagg tcgcgttgac gaatatgttt ttgaattaac tccagcagcg   119820
ccatacgtcg gtgctgcatg atttcatcat caggcatgac ggtgacatca atcagcggaa   119880
atgcggaggc ataaagctgc cttgccagtt tgggatcggc gaaacaatcc agccaacaca   119940
gcgaataggg atagggcctt tcaataccgt ggtaaaacaa caatagcacc accatcggca   120000
acgttttgta tccagcatca aggtgatttt gcattgcggc aatagcttaa cgcatcatgc   120060
gaaatgcgat cagtttgttt gaggtgcttt gatgttcaat cagacaatag atgtatcctg   120120
gtccttgttc cgttttcacc gaccacagca catcggaata gctttcacgc agatcgtcat   120180
caataaagct gctcgactcc agcttgaggg ttttcatatc acaaagcgcg tgaatgggtg   120240
ccggtaaatg aaacgcaaga aaatcacgag ccgtgtccgg ttggcgtaaa aagagtttga   120300
acagcgcatc gtgtggggtg gaactctgct ttttgctcat ggcgttcctt cacctgttgt   120360
```

```
ttgaatgccg cgactctacg cgccactcca cacctgtgta ttagcgagtt ttcatccctg   120420
cgagatgctt tcaaaggaac ttacgccgtg ctgcaagagt tgcatttta tggaaagccg    120480 cacgcaaaaa agcccggatg cagacgcata ccgggctttc caaaacaggc gatggagtaa   120540
ggttaacgca gcgcccacca ctcgcgcaga caggcttttc cttccgggca gcttttacaa   120600
ctgccagaga ggcagccgtc aggttcttcc tgaatccgca cggctttgcc catactttcc   120660
agttgttgca gcatggcgtt aatcattggc tgtggagtgt tcaatgtctg gcttatctgg   120720
gccgcttcca tacggccccg taacgccagc aaatcgcgca cctgaataag tgaagccatt   120780
aatggcaatc accggtggtg ctggctgcgc agcaactgct taccgacttg cgggttgcca   120840
gcagttcgat atccacccgg ctacgcgcgc ggcgcagcag accgataacc acgatgttaa   120900
acaggataac cgccagaatg cacaccaggc tgtaagttgg gtgctgactg tagctggcga   120960
cctgatagaa caatgttgcc agcgagtaag cgatattcag cccccacagg atggagaagc   121020
ccatccagcc acggcttgat tcacgggcga tggctcccat caccgagata catggtacat   121080
acagcaggac gaaaatcagg tagctgtaag ctgctgctgc gctaccgaat ttctgatcca   121140
tcacgcccat cgccccggta cccatttcgc cgtcgccttt gctggcttca atggggttca   121200
tcagtacgct aaggctgaag gtgtctttca ggctctgcca ggtttcatct atcgcactga   121260
acagctcttc accgaggtta aactctgccg gattgaactc ttcgtcctga atattttctg   121320
cggtgtagag ggtgttgagc gtacccacta ccacttcttt cgccatggca cctgtaaaca   121380
ggccaaccgt tgcctgccag ttatcttcat gcacgccaat tggcttgaag accggggtga   121440
tcacccggct gacggacgcc agcgccgagt cgttgatgtt atcgacgatt ttcccgctca   121500
gcgagaagct gttgaaagcg ctcaggaaaa tgctgacgat gatgatcact ttaccagcac   121560
gcagaacgaa gcctttcaga cgctgccagg tctggataat caggctttta acgtgtggta   121620
catgatagac cggcaactcc atgacaaacg gcgtcgcttc accgcgcatg atggtgtact   121680
tgagcatcag gccagtcagc accgccatca caatacccag catatacagc gagaagaccg   121740
ccagcgcacc gttctgcccg aagaaggcag ccgcgaatac tgcgaagata gccagacgcg   121800
cgccgcagga cataaacggt gccatcatga tggtcatcag acgttcacgc ggtgcatcaa   121860
gcgtacgtgc acccattacc gacggtacgt tacaaccgaa accgacgatc agcggcacaa   121920
aggatttccc cggcaagccc agcgcctgca tcagacggtc catcacaaac gccgcacgcg   121980
ccatataccc ggagtcctca aggaaggaga ggaacaggta catcatgcca atctgcggca   122040
ccagtggcag cacggtgtta atgccgccac ccaggccctg ggcgaggaag atagtcagcc   122100
agtccgggaa gtggagcgtg tagccaatcc attgaatacc atgcacaaat agcgccacgg   122160
agccgacgtc aaacagcggc tgtaacgccc gccgatgtt gatagccagc aggaacatca    122220
ggtacatcac aaagaggaaa atcggcagac cgaggaaacg gttgagcacg attttatcta   122280
ccgcagtggt gaaacggctg ggttctgccg tcagggtgtt gcttaccaca tcacagatgg   122340
cagcaatgca ctggtaacgc gcatcggcaa tgtgcagcgc cggatcgtcc atctcattac   122400
gcagacgggc gagggcggca tccagatgct gcgacgcttc accggcgtag gcgcggctgt   122460
agatatcgcc ttccagcatt tgcaggccca gccagcgacg ttgtttcagc gggatgtcgg   122520
aaggcatcac ttttgccagt gaatctgctt cgttgagtag cggctgtgcg taatgcacca   122580
gttccacatt ctcgttagct ttatagcgat caatcgccag cttgagcgct tcaataccgc   122640
gaccacgggt tgaaaccagc gggatcactg ggcagccaag acgcgccgac agagcatcaa   122700
```

```
tttcaatacg aatattttgc ttctcggcaa tgtcgagcat gttcagtgcc acgatgcagg   122760
gaatgccgag ttccagcagt tgtagcgtca ggtacaggtt acgctcaagg ttagacgcat   122820
ccaccacgtt aatcagcagg tcggcgtcgc cactcaaaat gtagtgacag gcgatttgct   122880
catcgagcga ggtctgcgat gagatggtgg tcagagaata ggtgccgggc aggtccacca   122940
gcgtgacctg atgatcggtg gtggagaatt gcccttcttt acgttcgacg gtaacgccag   123000
cccagttacc tacacgctga cgtgcgccag tgagctggtt aaataaggtt gtcttgccag   123060
aatttggatt accaattaag cctatggtta attttttcat tgttgttatc accgtattaa   123120
caggaaaccg cttccacttc taataaggcc agatcttttt tgcgtaatac caggctcaca   123180
cgacgggttt cgatatgaat ggggtcgccg agtggagcga cgcgcaccac attaaaagag   123240
gagccaggta acatgccaag agaaagcagt ttttggcgat atgccgggct gatttcatgg   123300
gaaaagccag tgattttcca cgcagtatct ggagtgtatt gcataggtgc ctacttgttt   123360
ctcattaact ggataactac ctcatggggc gtttgacagc gacatgagac cagatgattt   123420
gccaacgaag gagagattaa ataatcaaca gcacaatgat aatgagaatg gtttctatca   123480
gcaatactta aaatgtgtgc gaatgttggt ttgaataata atctgactca atgttgatgt   123540
ggctcaaggt tatatcgcag cgaaaatata attcgaatag cgaattacca ggactggcta   123600
atgtttaatt aaggtttcag ttgttaatga agtgataaat gttgccggaa tatattgtga   123660
gtttggctgt ggaataaaaa tgccggagat attctccggc acttttatgt cagacaaggc   123720
gttcgttgcc agatgcggcg tggacacctt atcgcgcagg tttagggggtc aatcagggcg   123780
tttaacgttt tttgcccatt gctgccgcca gcgcgtccat catcgcgctg ttaccggcag   123840
gctgcgcttc acgtccgcgc ggtttggctg ccgggcggtt gttttgcggg cgttcattac   123900
cgccgccgcg acgggcgttg gtttcgccag gctgctcgtc cagacgcatg gtcagggcga   123960
tacgtttacg ctgaagatcc acttccagca cttttcacctt cacaatgtcg cccgctttca   124020
ccacggtatg cggatcttct acaaacttgt tcgacaatga agagatgtga accaggccgt   124080
cctgatgcac gccgatatcg acaaacgcgc caaagttggt gacgttggtc accgcacctt   124140
cgaggatcat acccggttgc aggtcgttca ttgtctcgac gccatcggca aactgagcgg   124200
ttttaaattc cggacgcgga tcgcgacccg gttttttccag ctctttgatg atgtcagtta   124260
ctgtcggcac accgaatttt tcatcagtaa agtcagacgc tttcaggtta cgcagttcgc   124320
tgctgttacc catcagatct ttcagtgcct gctgtgttgc tgccagaatg cgttccacca   124380
ccggataggc ttccgggtgg acggtagacg cgtccagcgg gttatcacca tggttaatgc   124440
gcaagaagcc cgcgcactgc tcgaaggctt tcggcccag acggctcact ttcagcagtt   124500
gctgacggtt ctggaactga ccgttctcat cgcgccaggc cacgatgttt tgcgccatca   124560
tgcgcgtcag gcccgccacg cgggttaaca gcggaacaga agcagtgttg agatcgacgc   124620
caacggcgtt tacgcagtct tctactactg cgtccagttt gcgggccagt tgcgtctggc   124680
tgacgtcatg ctgatactga cctacgccga tagatttcgg atcgattttc accagctccg   124740
ccagcggatc ctgcaaacgg cgggcgatag acaccgcgcc acgcagcgaa acgtcgagat   124800
ccggaaactc ctgcgctgcc agctcggaag ccgagtaaac cgacgcgcca gcttcgctga   124860
cgatcacttt ctgtgcggtc actttcggga actgcttctg cacgtcgaga tagaaacgtt   124920
cagtttcgcg ggaagctgta ccgttgccga tcgccaccag ttcaacgtta tgttttttcac   124980
acaaggcagc aacggtcatc gctgcttttg cggcttgtcc ggtgtgcggg taaatggtat   125040
cggtcgctac cagtttgcca gtggcatcga ccaccgccac ttttaccccca gtacgcagac   125100
```

-continued

```
ccggatcgag gcccatcgtt gcacgcagtc cggcaggggc cgccatcagc agatcgtgca   125160
ggttacgggc aaagacgttg attgcttcat cttccgcgcg ttcgcgcacg gtacccatca   125220
gttcggtttc cagatgcatc agcaccttga tgcgccaggt ccagctcact acgcctttgc   125280
gccagctatc cgccggggca ttgttcaggc gcaggcaag gtgatccatg atgatttgct   125340
cgcaatagct ctctttgggc ggctcatcga actgcggatc ggcattcagc gaaagctgga   125400
gtacgccttc gttacgccca cggaacatcg ccagcgcgcg gtgagaaggc accgtggaca   125460
acggttcgtg atgatcgaaa tagtcgcgga attttgcccc ttcctcttct ttaccgctca   125520
ccacggttga gaccagatgc gcgttcttcc acagataatc acgcactttc gccagcagcg   125580
cggcatcttc ggcaaaacgt tccatcagga tatagcgcgc gccgtccagc gcggctttgg   125640
tatctgccac gcctttatcg gcatcaacat attgtgcagc ggcgacttct ggcgtgtgtg   125700
acggatcgct ccacagcagg tcagccaacg gctcaagccc tgcttcaatg gcgatttgcc   125760
cgcgggtgcg gcgtttaggt ttgtagggca ggtagaggtc ttcgagttcg gttttgctta   125820
gggtggcgtt gatggccttc gccagatcat cggtgagttt gccttgctcg gaaatggact   125880
tgaggatcgc ctgacgtctc tcttccagct cgcgcagata gctcagacgc gtttccagat   125940
tacgcagctg cgtgtcatcc agaccgccgg tgatttcctt acgataacgt gcgataaacg   126000
gcacggtatt cccttcgtca agcaggcgaa cggcagcgtc aacctgttcc gggcgcgcct   126060
gaatttcacc cgcaataatg cggcagaacg aatcattcat catggtttga gttcatcttt   126120
tcggatcaaa aatcagggga tagttatacg gactggctgg caaaaatgcc agccatcggc   126180
aggaggttaa gactcttcct tacggtttca cgtactcgat agcattaaca taccagctcg   126240
cttccccggc aggggtattc accaccgcca gatcgccgac ttctttttc agcaatgcgc   126300 gggccatcgg ggaatcgata gagatgtaat ctttacggcc aaaaatttca tcgtagccga   126360
caatacggaa acggtgagtc acgccatcgt cgtttcaat ctccacccac gcgccaaaaa   126420
agactttgcc ttcctgctga ggggagtaat cgacgatttt gagattttcc atgcatttag   126480
tgagatagcg cacgcgacgg tcgatttcac gcagacgctt tttattatac tgatagtcag   126540
cattttcgct gcggtcgccc agacttgcgg cccaggtcac cttttttgtg acctccgggc   126600
gttcttcacg ccagagataa ttaagctctt gtttgagttt ttcataccct tcccgggtaa   126660
ccaggggcgt tttcatctcg ttgattccct ttgtctgttt gataatgcgc acattgggta   126720
taacgtgatc atatcaacag aatcaataat gtttcgccga ataaattgta tacttaagct   126780 gctgttaat atgctttgta acaatttagg ctgaaattca taccagattt agctggtgac   126840
gaacgtgagc ttttttaaga atacacgctt acaaattgtt gcgaaccttt gggagtacaa   126900
acaatgcaag agaactacaa gattctggtg gtcgatgacg acatgcgcct gcgtgcgctg   126960
ctggaacgtt atctcaccga acaaggcttc caggttcgaa gcgtcgctaa tgcagaacag   127020
atggatcgct gctgactcg tgaatctttc catcttatgg tactggattt aatgttacct   127080
ggtgaagatg gcttgtcgat ttgccgacgt cttcgtagtc agagcaaccc gatgccgatc   127140
attatggtga cggcgaaagg ggaagaagtg gaccgtatcg taggcctgga gattggcgct   127200
gacgactaca ttccaaaacc gtttaacccg cgtgaactgc tggcccgtat tcgtgcggtg   127260
ctgcgtcgtc aggcgaacga actgccaggc gcaccgtcac aggaagaggc ggtaattgct   127320
ttcggtaagt tcaaacttaa cctcggtacg cgcgaaatgt tccgcgaaga tgagccgatg   127380
ccgctcacca gcggtgagtt tgcggtactg aaggcactgg tcagccatcc gcgtgagccg   127440
```

```
ctctcccgcg ataagctgat gaaccttgcc cgtggtcgtg aatattccgc aatggaacgc   127500
tccatcgacg tgcagatttc gcgtctgcgc cgcatggtag aagaagatcc agcgcatccg   127560
cgttacattc agaccgtttg gggcctgggc tacgtctttg taccggacgg ctctaaagca   127620
tgaggcgatt gcgcttctcg ccacgaagtt catttgcccg tacgttattg ctcatcgtca   127680
ccttgctgtt cgccagcctg gtgacgactt atctggtggt gctgaacttc gcgattttgc   127740
cgagcctcca gcagtttaat aaagtcctcg cgtacgaagt gcgtatgttg atgaccgaca   127800
aactgcaact ggaggacggc acgcagttgg ttgtgcctcc cgctttccgt cgggagatct   127860
accgtgagct ggggatctct ctctattcca acgaagctgc cgaagaagca ggtctgcgtt   127920
gggcacaaca ctatgaattc ttaagccatc agatggcaca gcaactgggc ggcccgacgg   127980
aagtgcgcgt tgaggtcaac aaaagttcgc ctgtcgtctg gctgaaaacc tggctgtcgc   128040
ccaatatctg ggtacgcgtg ccgctgaccg aaattcatca gggcgatttc tctccgctgt   128100
tccgctatac gctggcgatt atgctattgg cgataggcgg ggcgtggctg tttattcgta   128160
tccagaaccg accgttggtc gatctcgaac atgctgcttt gcaggtcggt aaagggatta   128220
ttccgccgcc gctgcgtgaa tatggcgctt cggaggtgcg ttcggttacc cgcgccttta   128280
accatatggc ggctggtgtt aagcaactgg cggatgaccg cacgctgctg atggcggggg   128340
taagtcacga cttgcgcacg ccgctgacgc gtattcgcct ggcgactgag atgatgagcg   128400
agcaggatgg ctatctggca gaatcgatca ataaagatat cgaagagtgc aacgccatca   128460
ttgagcagtt tatcgactac ctgcgcaccg gcaggagat gccgatggaa atggcggatc   128520
ttaatgcagt actcggtgag gtgattgctg ccgaaagtgg ctatgagcgg gaaattgaaa   128580
ccgcgcttta ccccggcagc attgaagtga aaatgcaccc gctgtcgatc aaacgcgcgg   128640
tggcgaatat ggtggtcaac gccgcccgtt atggcaatgg ctggatcaaa gtcagcagcg   128700
gaacggagcc gaatcgcgcc tggttccagg tggaagatga cggtccggga attgcgccgg   128760
aacaacgtaa gcacctttc cagccgtttg ttcgcggcga cagtgcacgc accattagcg   128820
gcacgggatt agggctggcg attgtgcagc gtatcgtgga taaccataac gggatgctgg   128880
agcttggcac cagcgagcgg ggcgggcttt ccattcgcgc ctggctgcct gtgccggtaa   128940
cgcgggcgca gggcacgaca aaagaagggt aaataaaacg ggaggcgaag gtgtctcccg   129000
tttttagatt gttttcaatt gattgataat gaaaggattc gcttgcaaaa gcaggagcaa   129060
ttttcgaggt gctccggtag gctgacggcg tttggtttcc cagcttttga ccaggtcata   129120
acttacccct acggcgacag caaaatcttg ctgacgtaaa cccgttgctt cacgcgatcgc  129180 ttttacatcg atctcgctaa aagtatggac gtgctctggt tcaggcgttt cttcaccctt   129240
ttcgatgcgt accatttctt ctgcgctggc aagaagatca gcaaataatt catctttcat   129300 ctgtttttcaa tgtctccgtt ggcatttcga ccatggtgga atttgtggag cttcaacatt   129360
aaagcagctt ctctgacaat agtttcaatg cctttctttg ttcttctgtt aaatcatcct   129420 gttcatttt aggataaatc aacgccagat aaattcggcc attgcgtgtt acgttgtaat   129480
aaattatccg aatgccaccc cgtttcccca ttccagaacg gttccagcga attttctaa   129540 aactgcctgt gcctgcgata atgtcaccgg cagtgggatc ttgaatgagt agttcctgaa   129600
aagcccggaa ctcatcatca ggtaacaata actggcggcg tttgctaaat ccttgtagtt   129660
caataaaggt gaacataatg catcctgcgg tctattgatt attataagtg taccgtgtac   129720
atattgatag ctaatcagat ataaaaaaac cccttatccg tttggataag gggtcaatga   129780
gatatcagct gattacagct tcggacctgc cgctaccagc gcagcacccg ctgggggtgtc   129840
```

```
agtgtattta tcgaagttgt cgataaacag tttcgccagg gtttcggctt tttcctgcca   129900
ctgttccggg gaagcgtagg tgttacgcgg atcgaggatc ttcgtgtcta cgcccggcag   129960
ttcggttggg atcgccaggt taaacatcgg cagagtgaaa gtttctgcgt tatccagcga   130020
accgttgagg atggcgtcga taatggcgcg ggtatcttta atcgagatac gtttgccagt   130080
gccgttccag ccagtgttaa ccagataagc ctgcgcgccc gccgcctgca tacgtttcac   130140
cagcacttct gcgtactgag tcgggtgcag cgacaggaac gccgcgccga agcaagcgga   130200
gaaggttggc gtcggttcgg tgatgccacg ctcagtaccg gccagtttgg cggtgaagcc   130260
agagaggaag tgatactggg tttgatcggc agtcaggcga gaaaccggcg gcaacacgcc   130320
gaaagcatca gcagtcagga agataaacctt agtcgcgtgg cccgctttgg aaaccggctt   130380
aacaatgtta tcgatgtgat agatcggata agaaacgcgg gtgttctcgg tttttgaacc   130440
atcatcaaag tcgatagtgc catcttcacg cacggtgacg ttttccagca gcgcatcgcg   130500
acggatagcg ttgtagattt caggttccgc ttctttcgac agcttgatag ttttttgcgta  130560
gcagccgcct tcgaagttaa acacgccgtc atcgtcccag ccgtgctcgt catcaccaat   130620
caggcgacgt ttcgggtcgg tggaaagggt ggttttaccg gtgccggaaa ggccgaagaa   130680
caccgcaaca tcgcctttct caccaacgtt ggcggagcag tgcatagaag cgatacctttt  130740
cagcggcagc aggtagttca tcatcgagaa catccctttc ttcatttcgc cgccgtacca   130800
ggtgccgcca atcagctgca tgcgctcggt caggttaaac gccacgaagt tttcggagtt   130860
cagaccctgt tctttccact gcgggttagt gcacttcgcg ccgttcataa cgataaagtc   130920
tggtttgaaa cctgccagct cttcatcgct cgggcgaata aacatgtttt tgacaaaatg   130980
cgcctgccag gccacttcgg tgatgaaacg gacggaaaga cgagtatccg ggttcgcacc   131040
acagaaagcg tcgacaacga acagacgttt gccggaaagc tgcctggtca ccaggccttt   131100
cagatgctgc caggtttccg gagagagagg tttgttgtcg ttttttacctt tgcctttgtc  131160
tgcccaccag aaagtatcgc gagtggtatc gtcacggacg atatacttat cttttggtga   131220
acgaccggtg aagatcccgg tatcgacggc aacggcaccc agattagtta acaccccgcg   131280
ctcataacct gtcaggctcg gatcgagctc ttcctgatac agcaggtcgt agcttgggtt   131340
gtaaacgata tcatgtacgt cactgatacc ataagcctcg agttcttgcg gggtcaaacc   131400
attgttaacg cgcatttcac tgctccttag ccaatatgta ttgcctgaat agtaaagtct   131460
ttttgggggt gttaaccgcg acaaggctca tagatttacg tatctggaga aattcatatt   131520
tgacaaaaaa ctccgtgatt cctgtcacga aacggttgct attatcgcag aaatagcatt   131580
ttaggtgtgg aaaatgttct caaaaggtta atcttggtt tatatggcgg gaatattgtg    131640
agtggaatcg cattccttaa tgaaattgat gcaaattcaa tcggtaaagt atcgattcac   131700
cacgctaact tttttgatt attttctgaa aaaagcaaaa tactactgcc cggatgcgat    131760
aattaaccca ccttttgatt ctggataacc aacatggata acgttgaact ttcaccggca   131820
acacgctggg ggatgattgc taccggatta cttcaggggc tggtttgcta cctgttgatc   131880
gcctggcttg ccggaaaaaa tcacagttgg attgtttatg gcgtgcctgc gaccgttgcg   131940
ttttcatccg ttttactctt ctccgtgatc tcttttaaac agaagcgcct tggggatgg    132000
ctggcgctgg tgtttattgc cacgctgggg atgagcggct ggctgaagtg gcaaactgat   132060
ggcatgaacc cctggagagc tgaaaaggcg ctttgggatt ttggctgcta tctgctgttg   132120
atggcaatgt tgttgctacc gtggatacaa caaagccttc gtatccgcaa tggcagtagc   132180
```

```
cgctatagct acttttacca gtcagtatgg cataacgtac ttatattact ggtgatttt   132240
ctcgccaatg gcctgacgtg gctggtgctt ctactttgga gtgagttgtt taaacttgtt  132300
ggcatcacgt ttttcaatac gctctttttt gcaaccgact ggtttatgta tcttacatta  132360
ggtctggtta ccgcactggc ggtgatcctc gcgcgtacac agtcacgttt aatcgactct  132420
attcaaaagt tgttcacgct aatcgccacg gggttgctgc cgttagtatc attgctaacc  132480
ctgatgttta tcatcaccct gccgtttacg ggcctgagcg cgatttctcg ccacatctcc  132540
gccgccgggt tgctgttaac gctggccttt ttgcaattga tcttaatggc tattgtccgc  132600
gatccgcaaa aagcgtcact tccctggacg gggccgttgc gttgcctgat taaaaccgct  132660
ttgctggttg ctccgctgta tgtgttcgtc gccgcctggg cgttatggct gcgggtcgct  132720
cagtacggct ggactgtcga ccgcttgcag ggcgtgctgg cggtgctggt gttactggtg  132780
tggtcgctgg ggtattttgt cagcatcgtc tggcgtaaag ggcaaaatcc cgttgttctt  132840
cagggcaaag tgaaccttgc ggtttcgtta ttggtgttgg tgatactggt gcttcttaat  132900
tcgccggtgc tggacagtat gcgtattagc gtgaacagtc atatggcgcg ttatcagagc  132960
ggcaaaaaca cgccagacca ggtaagtctc tatatgctcg aacagagcgg tcgctatgga  133020
cgtgcggcgc ttgagtcgct gaaaagcgat gccgggttta tgaaagaccc gaaacgcgcg  133080
cgggatctgc tgatggcgtt agatggggag caaagtcttc agaaggtggt gtcggaaaaa  133140
tcattagccg aaaatgtgtt aattgcacca ggttctggca aaccggatgc ggcattctgg  133200
tcggcattaa tcaaagaacg ctataacgtg atgacctgta ttgaaaaaga cgcctgcgta  133260
ctggtcgagc aagatctgaa tagtgatggc agggcagagc ggatcctctt tgcctttgat  133320
gatgaaagat acattgtcta tggctttgat cctgacaaga aagaatggca agagcttacg  133380
atgagtttac ttccgcgtga tataacgaaa gaaaaattac tcacagctgc gaaggatgga  133440
aaactgggaa cgaagcctaa agcgtggcgc gatcttgtag tggatggtga aaggctggat  133500
gtgaatctga atgagtgaca aagcgcatca ggtgtattag tcgtaaaatc cggcagagcc  133560
ctctctgccg gacatactca ttaatgaact tgcggatctg ccggagacgc gttgttgcgg  133620
atttcagcaa tatccatcgc attgaacaga tagtggttac cgcagtaatc acaatgcatg  133680
tcaatttcgc catcttccgc caggatgcta tcgacttctt catcaggcag cgttttcagc  133740
gcgtcggcgc aacgttcacg cgagcaggtg catttgaact ccacatcctg cggatcgtaa  133800
accgtcacct cttcttcgtg atacaaacgc cacaacactt cgtttgccgg taaggtcagc  133860
agttcttcgg ttttgatggt ttcggttagc gtcgccaggt ggtcaaagtc gtcctgctgg  133920
gcattttgcg caggcattac ctgcaacaac ataccgcctg cagccggttt gccgtctacg  133980
tcgccggtgc gaataaacag gcgcgtcggc agctgttcag aacgcataaa gtaatcttcc  134040
aggcaggccg ccagggtatc accttccaga ccaaccacgc cctgatagcg ttcgccttcg  134100
ctcggggtaa tggtgatcac cacgtaacca ttgccgacca gcgttttcag gtcggcatt   134160
tctggaattt cgccctgcac gcgcgccaca ccgcgcattt gctggttatt gttaccgtta  134220
ataaccgcca gattcatcgg accgtcgcct tgcagctgta cggtgatatc accatcaaac  134280
ttcagcgtag cggttaacag gctggtcgca accagcagtt ctgccagcac gtttttaacg  134340
ggctgcggat aatcgtgatt ctcaaggatc tgttgcaggg tttccgaaac ggttaccagt  134400
tcgccgcgca cggcaaagtt ttcaaacaga tagcgatgta attggtcatg ttgcggcata  134460
atcatctctc ttgcaggtga cagttattca ctgtcgccgt gtttaaatcg taacaggtcg  134520
cggcgctctt ttttgtccgg gcgtcggtcc gggtgcggca tggttaaggc attaagttta  134580
```

```
cgtgccagcg ccattttttc gcgtttctct acactttccg cagtctcttc atacagcaag    134640
gctgcctcgc tggcggggcg acgctgttca gtaatcgcct ttacaatcac cgtgcgttcg    134700
tcatttccct ggcgcagagt gagcgtggca ttcagctcga cgattttgct cggcttgctg    134760
cgctgcccgt tgtaatgcac cttaccgcct tcaatcattt cacgggccag cgcgcgggtt    134820
ttataaaaac gggcagccca tagccattta tccagtcgaa cctcaacagc aggttttttct    134880 ttcatggcgt ctccttcaca ttagcgaggg gatcaggcgg cggtagtcat tcagtgacgg    134940
atggcgttga tactgtttct cggcaatccc ggaatcagga ttagtcacgc cgaggcagta    135000
acgaatacca aattgcgcgg cagcatcgag aatcgcttcg ctgtcatcaa taaacagcgt    135060
tctttcagct ttcagacccg tagcttcggc caccgcatgc cataaccgct gatcctcttt    135120
cggataacca aatgtgtggg tggaaagtaa taaatcaagg tgtgcgtcca gaccggtatg    135180
ctcaagtttt accgccaggt tgtgcggatg cgcattggtg agcaaaattc gctgcttacc    135240
gctggctttc agtgcctcaa gaaacggaat ggtatcttca cgcagtacgg cacgcggtcc    135300
catctcggtg gtcatcgcac agatatccag acccagttgc tcactccagt aatcaagaca    135360
gtaccagttt agcgtatgct gtacgtcgtg atattgctgg cgcatatatt ccatcgcttc    135420
ctgtggcgta accccgtttt tcgcgcccca tgtttcaggc accagctttt gccagaaata    135480
gttatcgaag gcgaggtcga gcaatgtgcc gtccatatcc agcagaacgg tatctacgtc    135540
ctgccaggca atgttgatat gcatgaggga aatctccaga gtgaagcaat ttgcgcgaca    135600
gggtagcata acctgccgcg caaacgtgtt attcgataag gctttctgaa ggggtgatca    135660
gttgcgggtt caggcagctt tcataatagg cctgaatctc catcatgcga gtgcgatgac    135720
gctggtaacg acgccaggcc tgtacgccat tgtaaatggc gctacccagc atcgtcagta    135780
gcagcaatgt ggtgctgaga tagcgccaca ggccggaacg atccgggatc ggatgaaggc    135840
caatatgctg cgtaccattg gcgtcagtga agattttgt gacgatacct tcggcgttaa    135900
acggcgtatg catcagcatt tgtgccagtt tctggaaagc gttccactgt tcttgcggcg    135960
ggtagtcgta aagtgatgcc gaaggccagg gctgatcaac aaaatcgctg ccttcgtcgc    136020
tgacaatcag gaatccgccg ggggccggac tgtttagtga ttgtgccgct cgcgccgttt    136080
catgcgtgat aaacggcgcg gtggaggttg ccaccaggtt atccagcgat tccgcactca    136140
ccgggcgtaa taacacattc acgccatcga gcttccggc gttggcgcgt tttaccagcg    136200
cgtcccagtc tttactgttg ccgagattga ccagcgcatt tttcagtcgc acacagtcat    136260 cttttggcaga acataaatcc gctgtcttca gtacaatgtc gccaaaatca tcaagcaata    136320
ccatgccgga tttttgaatc gctgaacgta atgaggcact gacgcgagat tcatcttccg    136380
gtttagggtg cagctggcga ttaactgctt cagtcaatgc cgtcgctttg ttgaccagtt    136440
cagattctgg taatggtaat gagcgggcgt cattccagat gatctgcgag cagtcaaacg    136500
gtaaaaaagg tgaattggtt ttcgcgctcc aggttccgga agtgcgaata ttacacattc    136560
ccgtaccgct aatacgcaat gtatcgccta cccgcacgcc agcgtcagcc agttgtttta    136620
cgctggtggc ttcaatggtc tgcgcgcctt tcatccatga gagagtgaat ttcagcggca    136680
tatccagcgg gatccagaat aacagcataa acagcaccag cagcgagccc gcagcgataa    136740
tcgtactgcg cagccagtgc tgtaacggaa agtttttttac ttcatcatgc agcgaaagat    136800 atcgccctg acgcactacg tggcggtcga gatagatatc aatatcggtt tgttgaccga    136860
gatcctgagc aatgtatggc tgccagtgtg cgggatagac caggtcgata ataccgagtg    136920
```

```
aaatattgtt gatctgttcc tgatcgtttt cgccaaacaa tccccaacga cggggtgtac   136980
cgcgcagaca atgaatttct cgcaggagg attttgccgg gggcgcgaat agccccaca    137040 gacctgcgcc cagcagcagt aatgcgccgc ctgccagcca cggaacaaat acatccgggg   137100
taatcaggca gaaaaagaac atcaggaagg aggcgacgat cagcaacgct tcacgcagcc   137160
cgcgcggacg actcagcgca tattcttcat gcgtttcttt gcgaatattg agtagctcga   137220
tttgctcact ctcttccccg cgaatcgacg cctgcgtgga cggaacaggt tgcaaggcat   137280
agccgcgcgt ttcctgcatg tactcctgca gcgtatgacc gttgagtgaa ataaccagcg   137340
gcagcgaatc ggtataaatc agttcaacgg tattctcatc gttgatgtat tgttcccaga   137400 aaggggcag gtggacttct accgaatcga ggtagtaacg ccatttattc ggatcgtcgg    137460
tagagatgcc gtaacgcgtg atagcgtgtg tcagcatcat gacgttgttg ctttcggcat   137520
tcagcgccag agagatcggt gccgcgctag ctcccgttgg gccaggcacc tgtaatacct   137580
gcgtcaggct ctcaagataa ttttcaacgg cgctacgttc ttcaggtgtg agtttacgcg   137640
tttgcgcatc cgcgaaggcg ttggtccagg gcagctgacg ccgtctggat cgcacttta    137700 tcagccatcc cgcaagtagt gagcaggcca gcaaagcagc taaaaaatc acaatggtgc    137760 tcatgctttc cccatcttac ttagtctgtc aggcgtggtc agtcgcacca gacacaatac   137820
atgattctgc ggttggctat cggcaagcgt ggagtttaac ttgagcatca ttaagcacat   137880
cacagtaacc gctgatcata gcaaaccctc tgaaggcgga atatcagcaa attcctggag   137940
ttatttcaac ctattgactt ttaatttgat ttgaggacga ttatttatta agttacataa   138000
atgtaaataa catgcaattc acattgccga aagcgtgtcc gatatcgcac aataaccgct   138060
gatttcacag catagatccc acgatgagca atcattaca aaacccacc attctgaatg     138120 ttgaaactgt agcccgttcc cgactgttta ccgtcgagag cgtggatctg gagttcagca   138180
atggcgtgcg gcgtgtttat gaacgaatgc gtccaaccaa ccgggaagca gtgatgattg   138240
tgccgattgt ggacgatcac ctgatcctga tccgcgaata cgcagtggga actgaatcct   138300
acgaattagg ttttcgaaa ggattaattg atccgggtga aagcgtctac gaagccgcta    138360
accgcgagct aaaagaagag gttggatttg gtgcgaacga tctgactttt ttgaagaagc   138420
tcagcatggc accgtcttac ttttccagca aaatgaatat cgtggtcgcg caagatctct   138480
acccggaatc gctggaaggc gatgagccag agccgctacc acaggtgcgc tggccgctgg   138540
cgcatatgat ggatttgctg gaagaccctg acttcaacga agcgcgtaat gtcagcgcgc   138600
tgttcctcgt gcgcgaatgg ttgaaagggc aggggcgagt gtaaatgcgt gaagtttgcc   138660
tgatgcacaa cgcttatcag gcttatgggg ttcctgcaat atattgattt ttcacgattt   138720
tgttagccgg ataacgcgtt cacccgcatc cggcataaac aaatgcactt tgtcagccaa   138780
ctgaaaaggc gccgaagcgc cttttaatc agaacaattc ctgtgcctca ccattatcga    138840
taatggtcgt tcccacctcg tgcaccgcct gttgtgtcgg ctgcgtacct tcgatgaaat   138900
actcttcgcg gctgttgcca ccattagcta actgcccggt gctgcgatcg atattcaccg   138960
tcacaatacc cggaggcggc gtcagcggct gctccggcac accttcaaga acggctttca   139020
tataagcgtc ccatgcaggc tgggcactct tggcaccgcc ttcgtaacct gagatctgat   139080
ctttaatcgc tccggaagcc gttgtatgac cgagattacg acggtgatca tcaaagccaa   139140
tccagaccga ggtcacaacg cccggaccgt aacccgagaa ccacgcatct ttcgaactgt   139200
tagtggtacc ggttttcccg ccgatatcgc gacgctgcaa atcacgacct gcacgccagc   139260
cggtaccctg ccagcctggt tcaccaaaga tattggtgtt caaagcactc ttaatcagga   139320
```

```
atgccagcgg agtgttgatg acgtgcggtg cgtactcctg cgcgccagtc ttcgccacta    139380
acgcctgatt tgcctgctcc agctgcggca ttggtacaga acattctgc tgctcgcggg    139440 agatagcgac atcttcaaca tcgttatttt ccagcacgtt cgatttctgc gtatcaccgt    139500
aaatcaccgg aatatcgcat tccgggcagg ctactttcgg tttcgcttcg aaaatcacgc    139560
cgccctgatc gttttcaatt ttgctgataa accacgggtc caccaggaag ccaccgttcg    139620
ccatgaccgc gtagccgcgc gccacctgca ttggggtgaa ggacgctgaa cccagcgcca    139680
gcgattcggt gtggacaatg ttttgcgccg ggaagccgaa gcgttgcaga tattctgcag    139740
catagtcgac gcccatcgcc cgcattgcgc gtaccatcac cacgttttc gactgaccca    139800 gcccctgacg taagcgaatt ggaccagcat actgcggtgg tgagttcttc ggctgccagt    139860
cagaaccggc acctgcatcc cagcgagaaa ttggcacatc gttcaacata cttgccagcg    139920
tcagaccttt atccatcgcc gcggtgtaga ggaacggttt gatgttggaa cccacctgac    139980
gcagtgcctg ggtggcgcgg ttaaacttgc tctgattgaa atcaaagcca ccgaccagcg    140040
ccataacggc accgttttgc ggattgatcg acaccagcgc cgagttcact tccggcactt    140100
gtgccagcca ccatgcatcg ccaacctgac gaacccagat ttgctgaccc gtttgcagaa    140160
catcggtcac tttacgcggc gtcggtcctt gctgagtatc cgaacggtaa ggacgcgccc    140220
agcgaacgcc ttccatactc aatgcgacgg tcgacccgtc cgccagcatc gccgtcgctt    140280
gctgaggatt ggcgctggtg actgcggcag gcagcagcgg accataggtt ggcagcgcct    140340
tcagcgtatc ggtaatcttg ttgttatccc acgccgactc gcccactttc cacagcacat    140400
ttgccgggcc gcgatagccg tggcgcatgt cgtagtccag cacgttatta cgtaccgcct    140460
gctgtgcggc ctgctgcact ttgcgggtga tggtggtgta aatgcgataa ccgtcttcat    140520
aggcactttc gccataacgg ttatacatct cctggcgcac catttcgctc aggtacggcg    140580
cagagaaagc aatctccggc gcgtgatagt tagcgttaat cgcctcagtg cgtgtctgat    140640
cgaactgttg ttgggtgata taccttcat ccagcatccg cgacagtacg acgttacgcc    140700
gcgcgacggc acgatccatt gagtagagcg gattaaaggt ggaaggcgct ttcggcagcc    140760
cggcgatcac agccatttcg ttcagcgtca gttggtcgac cgttttaccg aaatagactt    140820
gtgccgcagc accgacacca taggcgcggt aaccgaggta aatcttgttc agataaagct    140880
cgaggatctc gtctttcgtc agcaactgtt caatgcgaat cgcgaggaag acttccttaa    140940
tcttacgcat cagcgtgcgt tctggactga ggaagaaatt tctcgccagc tgctgggtaa    141000
tggtactcgc cccttgtgac gcgtggccgg agaacagcgc cacacttgcc gcacggaaga    141060
tccccaccgg gtcaacgccg tgatgctcgt agaagcggct gtcttccgtc gcgataaagg    141120 cttttcaccat ctccggtggg atttgatcca acgtaaccgg aatacgacgt ttctcaccgt    141180
attgagcaat cagctcgcca tcggcgctgt aaatctgcat cggaatttgc aggcgaacat    141240
cttttaatgt cgccacatcc ggcagttgtg gctcgatgta gcggtatagg ccataaatcg    141300
agcctgctcc cagcagaatg caacagactg caaggatcaa aaaatacttt acgaacttca    141360
ctggaaattt cccatttagt ttcatttggg cagtttataa acaaacgcgc ggtagtataa    141420
aggcaagcca gacgcattga tacccgtc agagtgacgg gtgataagga gatcatcaca    141480
atggcattta agatctggca aattggttg catttacaac agcaagaagc ggtagcggtt    141540
gcgatcgtac ggggcgcaaa agaatgcttt ttgcaacgct ggtggcggtt gccgctggag    141600
aacgacatta tcaaagatgg gcggattgtt gatgcgcagc agctggctaa aacgttgtta    141660
```

```
ccttggagtc gcgaactgcc gcagcgtcat cacattatgt tggcgtttcc cgccagtcgc   141720
acattacagc ggtcatttcc gcgcccgtcg atgtcccttg gtgagcggga gcaaacggcc   141780
tggctgtcag ggacgatggc ccgcgagctg gatatggatc cggactccct gcgcttcgat   141840
tatagcgaag actcactcag ccccgcttat aacgtgactg ccgcgcaaag caaagagctg   141900
gcaacgctgc ttacgctggc agaaaggttg cgtgttcatg ttagtgcgat cacccggat   141960 gccagtgcat tacagcaatt cctgcctttt ttaccttctc atcagcaatg tctggcctgg   142020
cgtgataacg aacagtggct gtgggcgaca cgctatcgct gggggcgcaa actggcggta   142080
gggatgacta gcgcgaagga gctggcggca gcgttatccg ttgatcccga cagcgtcgcg   142140
atatgtggcg aaggcggatt tgatccctgg gaggccgttt ctgttcgtca gccgccgcta   142200
ccgccgccag gtggagactt tgccatcgcg ctgggggtgg cgcttgggaa ggcgtactga   142260
tgaacctgcc aattaatttt ttgccctggc gacagcaacg ccggaccgct tttctgcgtt   142320
tctggttgct gatgttcgtt gcgcctctgc tgctggccgt cgggataacg ctaatactgc   142380
gtctgacaag cagcgccgaa gctcgcgtag acgccgtttt gcttcagggg gaacaacaac   142440
tcgcccacag cttacagata acgaaaccac gtttgctgga gcgccaacaa attcgtgagc   142500
agcgtttgca aaggcagcgc cagcgacaat ttacccgcga ctggcaatct gcgctggaag   142560
cactggcggc tcttttacct gaacacgcct ggctgacaac gataagctgg cagcagggaa   142620
cgctggagat caaggggctt acaacaagca ttaccgcgtt aaacgcacta gaaacgtcac   142680
ttcgccagga tgcttctttt catctcaatc agcgggggc cacgcagcag gatgcgcagg   142740
gacgctggca atttgagtat cagttaacaa ggaaggttag cgatgaacat gttctttgac   142800
tggtggttcg ccacatcacc ccgcctccgc cagttttgct gggcattctg gttgctgatg   142860
ttagttacgc tcattttct gtcatcgaca caccatgaag agcgcgacgc attaattcga   142920
ctacgggcaa gtcatcacca gcagtgggcc gcactgtatc gcctggtaga caccactccc   142980
ttcagcgagg aaaaaacgct gccctttcg ccactggatt tcagttatc cggcgcgcaa   143040 ctggtttcct ggcatccatc cgcgcaggga ggcgagttgg cgttgaaaac gctgtgggaa   143100
gcagtgccgt cggcatttac acggctggca gagcgcaacg tcagcgtgag ccgttttcg   143160 ttaagcgtgg aaggtgatga tcttttgttc acgctacaac tggagacgcc gcatgagggt   143220
taaacgctgt tgttggcag gtattgcatt gtgcctttta accggtatgc gtgacccttt   143280
taaaccgccg gaagatctat gccggattag cgaacttagc cagtggcgct atcagggat   143340 ggtagggcga ggcgagcgca tcatcggtgt aataaaagac gggcaaaaga atgcgcacg   143400 ggtgcagcaa aacgatgtgc tggaaaacgg ctggacaatt ttacagctga cgccagacgt   143460
actaacgctg ggtaccggga caaactgcga accgccacaa tggttgtggc aacggcaagg   143520
agatacaaat gaagcaatgg atagccgcac tactgttgat gctgataccc ggcgtacagg   143580
cggcaaagcc gcaaaagtg acgctgatgg tggatgacgt tccggtagct caggtgttgc   143640
aggcgctggc tgaacaggag aagttgaacc tggtcgtgtc gccagacgtc agcggtacgg   143700
tgtcgttaca tctaacagat gttccctgga agcaggcact acaaactgta gtgaaaagcg   143760
ccggactgat aacgcggcag gaagacaaca ttctctcagt gcattccatt gcctggcaga   143820
ataacaatat cgcccgccag gaggcggagc aggcgcgggc gcaggcaaat ctgccgctgg   143880
aaaatcgcag tataaccctg caatacgccg acgcgggaga actggcgaaa gcggggagga   143940
agctactgag tgccaaaggg agtatgaccg tcgataaacg caccaatcgc cttttgctac   144000
gagataacaa aacggcgtta agcgcgcttg aacagtgggt agcgcaaatg gatctgccgg   144060
```

```
tcgggcaggt tgagctgtcg gcgcatattg tcaccattaa tgaaaaaagt ttgcgtgagt   144120
taggcgtgaa atggacgctg gccgatgcgc aacacgctgg tggcgttggg caagtcacca   144180
cgcttggtag cgacctctcc gtagcgacgg cgacaacgca tgtcggtttt aacattgggc   144240
gcatcaacgg acgcttgctg gatcttgagc tttccgcgct cgaacaaaaa cagcagctgg   144300
atattatcgc cagtccgcgt ctgctggcct cacatcttca gcctgccagc attaaacagg   144360
ggagcgaaat tccatatcag gtttccagcg gggaaagtgg cgcgacgtcg gtggaattta   144420
aagaggccgt cctggggatg gaggtcacgc ccacggtgtt acaaaaaggt cgcatccggc   144480
tgaaattaca catcagccag aacgttccgg ggcaggtgct acagcaggcc gatggcgaag   144540
tgctggcgat tgataagcag gagatcgaaa cgcaggtcga ggtcaaaagc ggagaaacgt   144600
tggcgctggg cggcattttt acccgtaaaa ataaatcggg tcaggatagc gtaccgttgc   144660
ttggcgacat tccctggttc gggcaattat ttcgtcatga cggaaaagaa gatgaacgac   144720
gcgagttagt ggtgtttatc acgccacgac tggtttccag tgagtaaaca gccgtaaaag   144780
cggtaatgtt tttatgctga acgtgtttca tctatttgac gcgcgcaggt atttagcata   144840
caaggagtac cgatttgaga gttggtgctc ttcgctgcct gcgttccatg atgatgattt   144900
atcattcagg cggcattttg ctgtctttt tacgctaatc ttacccggtg atttatcgcc   144960
agagcggtgg tagcaaggca gcgcgcttgc agcgaccaga tatgcagagg gatgggtgat   145020
ttattcagtt gccaaacccg ctggagtatt gagataattt tcagtctgac tctcgcaata   145080
tcttatgagg tttcagttca tgtcctgcgg cgctctctga gcaagcggg tttatcatta   145140 acgaatagtc ttagtagtac cgaaaaaatg gcagagaaac gcaatatctt tctggttggg   145200
cctatgggtg ccggaaaaag cactattggg cgccagttag ctcaacaact caatatgaa   145260 ttttacgatt ccgatcaaga gattgagaaa cgaaccggag ctgatgtggg ctgggttttc   145320
gatttagaag gcgaagaagg cttccgcgat cgcgaagaaa aggtcatcaa tgagttgacc   145380
gagaaacagg gtattgtgct ggctactggc ggcggctctg tgaaatcccg tgaaacgcgt   145440 aaccgtctt ccgctcgtgg cgttgtcgtt tatcttgaaa cgaccatcga aaagcaactt   145500
gcacgcacgc agcgtgataa aaaacgcccg ttgctgcacg ttgaaacacc gccgcgtgaa   145560
gttctggaag cgttggccaa tgaacgcaat ccgctgtatg aagagattgc cgacgtgacc   145620
attcgtactg atgatcaaag cgctaaagtg gttgcaaacc agattattca catgctgaa   145680 agcaactaat tctggcttta tatacactcg tctgcgggta cagtaattaa ggtggatgtc   145740
gcgttatgga gaggattgtc gttactctcg gggaacgtag ttacccaatt accatcgcat   145800
ctggtttgtt taatgaacca gcttcattct taccgctgaa atcgggcgag caggtcatgt   145860
tggtcaccaa cgaaaccctg gctcctctgt atctcgataa ggtccgcggc gtacttgaac   145920
aggcgggtgt taacgtcgat agcgttatcc tccctgacgg cgagcagtat aaaagcctgg   145980
ctgtactcga taccgtcttt acggcgttgt tacaaaagcc gcatggtcgc gatactacgc   146040
tggtggcgct tggcggcggc gtagtgggcg atctgaccgg cttcgcggcg gcgagttatc   146100
agcgcggtgt tcgtttcatt caagtcccga cgacgttact gtcgcaggtc gattcctccg   146160
ttggcggcaa aactgcggtc aaccatcccc tcggtaaaaa catgattggc gcgttctacc   146220
agcctgcttc agtggtggtg gatctcgact gtctgaaaac gcttccccg cgtgagttag   146280 cgtcggggct ggcagaagtc atcaaatacg gcattattct tgacggtgcg tttttaact   146340 ggctggaaga gaatctggat gcgttgttgc gtctggacgg tccggcaatg gcgtactgta   146400
```

```
ttcgccgttg ttgtgaactg aaggcagaag ttgtcgccgc cgacgagcgc gaaaccgggt    146460
tacgtgcttt actgaatctg ggacacacct ttggtcatgc cattgaagct gaaatggggt    146520
atggcaattg gttacatggt gaagcggtcg ctgcgggtat ggtgatggcg gcgcggacgt    146580
cggaacgtct cgggcagttt agttctgccg aaacgcagcg tattataacc ctgctcaagc    146640
gggctgggtt accggtcaat gggccgcgcg aaatgtccgc gcaggcgtat ttaccgcata    146700
tgctgcgtga caagaaagtc cttgcgggag agatacgctt aattcttccg ttggcaattg    146760
gtaagagtga agttcgcagc ggcgtttcgc acgagcttgt tcttaacgcc attgccgatt    146820
gtcaatcagc gtaacaacaa gaaaggtcag gccgcttatc aagcggtcta ttagcttcag    146880
gttaattgca acgtggtaag cattaacctt ttagtggggt gttaaatgga tgaattcaaa    146940
ccagaagacg agctgaaacc cgatcccagc gatcgtcgta ctggtcgttc tcgtcaatct    147000
tctgaacgtt ctgagcgtac tgaacgtggc gaaccgcaga tcaattttga tgatattgaa    147060
cttgatgaca ctgacgatcg ccgtccgact cgtgcgcaaa aagagcgcaa tgaggaaccg    147120
gaaatcgaag aagaaattga cgaatccgaa gatgaaaccg tggatgaaga gcgcgtagag    147180
cgtcgtccgc gtaagcgcaa aaaagcagcc agtaaacccg cttctcgtca gtatatgatg    147240
atgggcgtcg gcattctggt tctactgctg ttgatcatcg gtatcggttc tgcgctaaaa    147300
gccccctcga cctcttccag cgatcaaacc gcgtctggcg agaagagtat tgatcttgca    147360
ggcaatgcga ccgatcaggc gaatggggtg cagccagcgc cgggaaccac gtctgcgaa    147420 aatactcagc aggatgtttc tctgccaccg atctcttcta cgccgactca agggcaaacc    147480
ccggcggcaa cggatggtca acaacgtgtt gaagtgcagg gtgacctgaa caatgcgctg    147540
acccagccac aaaatcagca acagttgaac aatgtggcgg tcaattctac attgccgact    147600
gaaccagcaa ctgtcgcgcc agtacgcaat ggcaatgcat cgcgtgacac ggcgaaaacg    147660
caaactgctg aacgtccggc cactacgcgt ccagctcgtc agcaggcggt gattgaaccg    147720
aaaaaaccgc aagcaaccgt gaaaacggaa ccgaagccgg tagcacagac gccgaagcgt    147780
actgaaccag ctgctcctgt ggcgagcacg aaggcaccgg ctgcgacttc tgcgccagca    147840
ccaaaagaga cggcgactac ggctccagta cagacggcat ccccggcgca aaccacggca    147900
acaccagccg ctggagggaa gaccgcaggt aatgttggtt cgttgaaatc ggcaccgtcc    147960
agccattaca ctctgcagct gagcagttcc tctaactacg acaacctgaa cggttgggcg    148020
aagaaagaga atctgaaaaa ctacgttgtc tatgaaacga cgcgtaatgg tcagccgtgg    148080
tatgtcctgg tttctggcgt gtacgcttcg aaagaagagg cgaaaaaagc ggtatctaca    148140
ttgccagcag atgttcaggc caaaaacccg tgggcgaaac cgctgcgtca ggtacaggcc    148200
gatctgaagt aatcaaggtt atctcccgca atgggttatc gttgcgggag ttgcctgaag    148260
cgctggatgc tgtcggagct ttctccacag ccggagaagg tgtaattagt tagtcagcat    148320
gaagaaaaat cgcgcttttt tgaagtgggc aggggggcaag tatccctgc ttgatgatat    148380 taaacggcat ttgcccaagg gcgaatgtct ggttgagcct tttgtaggtg ccgggtcggt    148440
gtttctcaac accgactttt ctcgttatat ccttgccgat atcaatagcg acctgatcag    148500
tctctataac attgtgaaga tgcgtactga tgagtacgta caggccgcac gcgagctgtt    148560
tgttcccgaa acaaattgcg ccgaggtcta ctatcagttc cgcgaagagt tcaacaaaag    148620
ccaggatccg ttccgtcggg cggtactgtt tttatatttg aaccgctacg gttacaacgg    148680
cctgtgtcgt tacaatctgc gcggtgagtt taacgtgccg tttggccgct acaaaaaacc    148740
ctatttcccg gaagcagagt tgtatcactt cgctgaaaaa gcgcagaatg cctttttcta    148800
```

```
ttgtgagtct tacgccgata gcatggcgcg cgcagatgat gcatccgtcg tctattgcga  148860
tccgccttat gcaccgctgt ctgcgaccgc caactttacg gcgtatcaca caaacagttt  148920
tacgcttgaa caacaagcgc atctggcgga gatcgccgaa ggtctggttg agcgccatat  148980
tccagtgctg atctccaatc acgatacgat gttaacgcgt gagtggtatc agcgcgcaaa  149040
attgcatgtc gtcaaagttc gacgcagtat aagcagcaac ggcggcacac gtaaaaaggt  149100
ggacgaactg ctggctttgt acaaaccagg agtcgtttca cccgcgaaaa ataattctc  149160 aaggagaagc ggatgaaaca gtatttgatt gcccccctcaa ttctgtcggc tgattttgcc  149220
cgcctgggtg aagataccgc aaaagccctg gcagctggcg ctgatgtcgt gcattttgac  149280
gtcatggata accactatgt tcccaatctg acgattgggc caatggtgct gaaatccttg  149340
cgtaactatg gcattaccgc ccctatcgac gtacatctga tggtgaaacc cgtcgatcgc  149400
attgtgcctg atttcgctgc cgctggtgcc agcatcatta cctttcatcc agaagcctcc  149460
gagcatgttg accgcacgct gcaactgatt aaagaaaatg gctgtaaagc gggtctggta  149520
tttaacccgg cgacacctct gagctatctg gattacgtga tggataagct ggatgtgatc  149580
ctgctgatgt ccgtcaatcc tggtttcggc ggtcagtctt tcattcctca aacactggat  149640
aaactgcgcg aagtacgtcg ccgtatcgac gagtctggct ttgacattcg tctggaagtg  149700
gacggtggcg tgaaggtgaa caacattggc gaaatcgctg cggcgggcgc ggatatgttc  149760
gtcgccggtt cggcaatctt cgaccagcca gactataaaa aagtcattga tgaaatgcgc  149820
agtgaactgg caaaggtaag tcatgagtaa gtttgaagat attcgcggcg tcgcttttga  149880
tctcgacggt acgctggtgg acagtgctcc cggtcttgct gctgcggtag atatggcgct  149940
gtatgcgttg gagttacccg tcgcaggtga agaacgcgtt attacctgga ttggtaacgg  150000
cgcagatgtt ctgatggagc gtgcattggc ctgggcgcgt caggaacgtg cgactctgcg  150060
taaaacaatg ggtaaaccgt ccgttgatga cgacattccg gcagaagaac aggtacgtat  150120
tctgcgtaaa ctgttcgatc gctactatag cgaggttgcc gaagagggga cgttttgtt  150180 cccgcacgtt gccgatacgt tgggcgcgtt gcaggctaaa ggcctgccgc taggcctggt  150240
caccaacaaa ccgacgccgt tcgtcgcgcc gctgctcgaa gccttagata ttgccaaata  150300
ctttagcgtg gttatcggcg gcgatgatgt gcaaaacaaa aaaccgcatc cggacccgct  150360
gttactggtg gctgagcgga tgggaattgc cccacaacag atgctgtttg tcggcgactc  150420
acgcaatgat attcaggcgg caaaagcggc aggttgccca tcagttggct taacctacgg  150480
atataactac ggcgaggcta tcgatctcag ccagcctgat gtaatttatc agtctataaa  150540
tgaccttctg cccgcattag ggcttccgca tagcgaaaat caggaatcga aaatgactaa  150600
agcccatcgt ttttagtggc gcacagccct caggtgaatt gaccattggt aactacatgg  150660
gtgcgctgcg tcagtgggta acatgcagg atgactacca ttgcatttac tgtatcgttg  150720
accaacacgc gatcaccgtg cgccaggatg cacagaagct gcgtaaagcg acgctggata  150780
cgctggcctt gtatctggct tgtggtatcg atcctgagaa aagcaccatt tttgttcagt  150840
cccacgtacc agaacatgcg cagttaggct gggcactgaa ctgctatacc tacttcggcc  150900
aactgagccg catgacccag tttaaagata aatctgcgcg ttatgccgag aacatcaacg  150960
ctggtctgtt tgactatccg gtgctgatgg ctgcggacat cctgctgtat caaactaatc  151020
tggtaccggt gggtgaagac cagaaacagc acctggaact gagtcgcgat atcgcccagc  151080
gtttcaacgc gctgtatggc gagatcttta aggtgccgga gccgtttatt ccgaaatctg  151140
```

```
gcgcgcgcgt aatgtcgctg ctggagccga ccaagaagat gtccaagtct gacgataacc   151200
gcaataacgt tatcggcctg ctggaagatc cgaaatcggt agtgaagaaa atcaaacgcg   151260
cggtcactga ctccgacgag ccgccggtag ttcgctacga tgtgcagaac aaagcgggcg   151320
tttccaacct gctggatatc ctttctgcgg taacgggcca gagcatcccg gaactggaaa   151380
aacagttcga aggcaagatg tatggtcatc tgaaaggtga agtggctgat gccgtttccg   151440
gtatgctgac tgaattgcag gaacgctatc accgtttccg caacgatgaa gccttcctgc   151500
aacaagtgat gaaagatggc gcggaaaaag ccagcgcgca cgcttcccgt acgctaaaag   151560
cggtatacga agcgattggt tttgtggcga agccgtaatt taacattaat gccaaaaacc   151620
ggggaaaccc ggttttttta tcctcatttg caataatccg aaaaaatgtg aagcgcctcg   151680
ccgtttccac atctcacagt tgccacttat cttcatttta atgaagatat aaacattcat   151740
tttattgaaa atatattatg cgtcgaacgt ttatcaaaaa agaaggcgtc gttatcacga   151800
cgctggcccg ttatttgttg ggtgaaaaat gcggtaatag gttgaaaacc atagatgagc   151860
tggcaactga atgccgttca tccgttggcc tgaggcaggc cgcgttgaaa acgctggaat   151920
caagcggagc gatacggatt gaacgccgtg gcgcaatgg cagttatctg gtcgagatgg   151980
ataacaaagc attgctgagt catgtggata tcaacaacgt ggtatgtgcg atgcctttgc   152040
cctatacccg cttgtacgaa ggtttagcga gcggattgaa agcccagttt gatggcattc   152100 cttttttacta tgcgcatatg cgcggcgcgg atattcgcgt ggagtgttta cttaacggcg   152160
tgtatgacat ggcggtggtt tcccgactgg cggcggaaag ttatctcacg caaaagggt   152220 tttgcctcgc gctggagttg gggccgcaca cctacgttgg cgagcaccag ttgatttgcc   152280
gtaaaggcga gtccgcaaac gtgaagcgcg tggggctgga taaccgttcg gcggatcaga   152340
aaatcatgac cgatgttttt tttggcggta gtgatgtgga acgagtcgat ctctcttatc   152400
acgagagttt acaacgcatt gttaaaggcg atgtcgatgc ggtgatctgg aacgtggtgg   152460
cggaaaacga actgaccatg ctgggattag aggcgacgcc gctcacagac gatccgcgat   152520
ttttacaggc caccgaagcc gtggtcctga cgcgagccga tgattaccca atgcaacaac   152580
tgctgcgtgc cgttgtagat aaacacgccc tgctcgccca tcaacaacgc gtggtgagtg   152640
gggaacagga accgagttat taaacgaaag gcatctgata tggaaaccag actcaacctg   152700 cttttgcgagg caggcgttat tgataaggac atctgcaaag gcatgatgca ggtcgtcaac   152760
gtactggaaa cagagtgcca tctgccggtg cgcagtgagc aaggaacgat ggcgatgaca   152820
catatggcga gtgcactgat gcgcagtcgc cgtggtgaag aaatagagcc gctgataac   152880 gaattgctgg cagagctggc gcaatccagc cactggcaag ccgttgtgca attgcatcag   152940
gtgttgttga aggaattcgc actggaagtt aacccgtgtg aagaaggcta tttgctggcc   153000
aacctttatg gattatggat ggctgctaac gaagaggttt gaagctcccg acaaatccac   153060
gtcgcacaac ctaaatattc aaaaaaatga atatttaatt caaggaacag aaacgaggca   153120
acaagatgtt tgtagaagca ttgaaacgcc agaacccggc gctgatttcc gccgcactaa   153180
gtttgtggca gcagggcaag atcgccccgg acagctgggt gatcgacgtg gatcaggtac   153240
tggaaaacgg taagcgactg attgagacgc gcggctttta cggcattgaa ctgtatctga   153300
tgaccaagca gtttggccgt aacccatggc tggcggaaaa attgctggca ttaggttaca   153360
gcggcattgt ggcggtggat tacaaagagg cgcgagtcat cgccgcgct ggtttgtcgg   153420 tggcgcatca ggggcatctg gtacaaatcc cttgtcatca ggttgctgac gccgttgaac   153480
agggcaccga agtcatcacc gtgtttactc tcgacaaagc gcgggaagtt tctgcggcag   153540
```

```
cggtgaaggc cggacgtgtg cagtttgtgc tgctcaaagt ttatagcgac gatgattttc   153600
tttatccggg gcaggagagc ggttttgtac agcattcgct gcacgaggtg gttgctgaaa   153660
ttaagaaact gccggggctg catttagccg gacttaccca tttcccttgc ctgctttggg   153720
atgaggctgc cggaaaagtt ttgccgacac cgaatcttca cacgctgata caggcacggg   153780
atcaactggc gaaatctggt attgcacttg agcaactgaa cgcgccttca gcgaccagct   153840
gcacttcgct gccattgctg gcggaatacg gtgtgactca tgccgaaccc ggtcatgcgc   153900
tgacgggcac tattccggca aaccagcagg gcgatcagcc tgaacgtatc gcgatgctct   153960
ggttaagtga aatctcccat catttccgtg gcgacagcta ctgctacggc ggcggttact   154020
accgtcgtgg tcatgcgcaa catgcgctgg tgtttacgcc agaaaatcaa aagattactg   154080
aaaccaatct caaaactgtg gatgacagca gtatcgacta caccctgccg ctggcaggcg   154140
agtatccggt gagcagtgca gtggtgctct gtttccgcac gcagattttt gtcacccgta   154200
gcgatgtggt gctggtgtcc ggtattcacc gtggcgaacc gaaaatcgtt ggtcgttatg   154260
acagtcttgg aaactctctg ggggcgtaat ggcgcgattt gtggtgttag tgattgatag   154320
ctttggcgta ggggcaatga aagatgtcac gctggtgcgt ccgcaagatg cgggagcgaa   154380
tacctgtggt cacatcctga gccagttgcc gcatttgcag ctaccaacgc tggagaagct   154440
ggggctaatc aacgcattgg gttatgcgcc aggcgatatg cagccgtcag attccgcaac   154500
ctggggcgtg gcagagctgc aacatgaagg tggcgatacc tttatggggc atcaggaaat   154560
tttaggcacg cgcccgttac cgccgctgcg gatgcctttt tgcgatgtga ttgaccgtgt   154620
tgagcaggca ttagtatccg ccggttggca ggtggagcgc cgtggcgatg aactgcaatt   154680
tctgtgggtc aatcaggcgg ttgcgattgg cgataatctc gaggcggatt taggccaggt   154740
ctataacatt accgccaatc tctctgtgat ctcttttgac gacgcaatca aaattggtcg   154800
tatcgtgcgt gagcaggtac aggtcggtcg ggtcattaca tttggtggcc tgttaaccga   154860
cagtcaacgc attctcgatg ccgcagaaag caaagaaggg cgctttattg gtatcaatgc   154920
gccgcgttct ggcgcttatg acaacggttt ccaggtcgtg catatgggct atggcgtcga   154980
tgaaaaagtg caggtgccac aaaaaactgt atgaagcagg gtgccaaccg tgctggtggg   155040
taaggtggca gatatcgtca acaatcctta tggcgtgagc tggcaaaatc tggtggatag   155100
ccagcggatt atggatatca ccctcgacga atttaacacg catccgacgg cgtttatttg   155160
catcaatatc caggaaaccg acctcgctgg tcatgcagaa gacgtcgcac gttatgccga   155220
acgtttgcag gtcgttgacc gtaaccttgc ccggcttgtt gaggcgatgc agccagatga   155280
ttgcctggtc gtgatggcgg atcacggtaa cgatccgacc attggtcaca gccaccatac   155340
ccgtgaagtg gtgccagtgc tggtttatca gcaagggctg gtccacacgc aactcggtgt   155400
acgcaccacg ctttctgatg tgggggctac cgtgtgtgaa ttttccgtg cgccaccgcc   155460 acaaaatggt cgctctttc tttcctccct ccggtttgca ggagacaccc tatgagtatt   155520
gatccgacgg gttacaccct ggcccatgag catctgcata ttgatctctc cggctttaaa   155580
aacaacgtgg actgccgcct tgatcagtat gcgttcattt gccaggagat gaacgacctg   155640
atgacccggg gcgtgcgtaa tgtgattgag atgaccaacc gttacatggg gcgcaatgcg   155700
caatttatgc tcgatgtaat gcgcgagacg gggatcaacg tggtggcctg caccggttat   155760
taccaggacg cttttttccc ggagcatgtg gcgacccgca gcgtgcagga actgcgcag   155820 gagatggtcg atgaaattga acagggtatc gatggcaccg acctgaaagc cgggattatc   155880
```

-continued

```
gcggagatcg gctctagcga agggaagatt acgccgctgg aagagaaggt gtttattgcc   155940
gctgcgctgg cgcataacca gaccggacgc ccgatctcca cgcatacttc gttcagcacc   156000
atggggctgg aacaactggc tctgttgcaa gcccacggag ttgatctttc gcgcgtcacc   156060
gttggtcact gcgatctgaa agacaatctc gacaacattt tgaagatgat cgatctcggc   156120
gcgtacgtgc agttcgacac cattggtaag aacagttact acccggacga aaagcgcatt   156180
gcgatgctcc acgcgctacg tgaccgtggg ttgctgaacc gcgtcatgct gtcgatggat   156240
attacgcgcc gctcccattt aaaagccaat ggtggttatg gctatgacta tttattgacc   156300
accttattc cgcaattgcg ccagtcagga ttcagtcagg ccgatgtgga tgtgatgtta   156360
cgtgaaaatc cctctcaatt tttccaataa ggacagactc atgaaaaaga ttggcgttgc   156420
aggcttacag cgtgagcaga ttaaaaaaac cattgaagcg acggctcctg gcagttttga   156480
agttttcatt cacaacgaca tggaagcggc aatgaaagtg aaatccgggc aactggatta   156540
ctacatcggt gcgtgtaata ccggtgcggg cgcggcattg tcgattgcca tcgcggtgat   156600
tggctataac aaaagttgca ccattgccaa accaggcatt aaagcgaaag acgagcatat   156660
cgccaaaatg atcgctgaag ggaaagtggc gtttggcctt tccgttgagc acgtcgaaca   156720
cgcgattccg atgctgatta accatctgaa ataaaaggca cgactatgga tctgtatatt   156780
cagattatcg tggtggcgtg cctgacgggt atgacatcgc ttctggcgca tcgctcggcg   156840
gctgttttc atgacggcat ccgcccgatc ctgccgcaac tgattgaagg ctatatgaat   156900
cgtcgcgagg cggggagtat cgcttttggt ctgagcattg gttttgtggc ctcggtgggg   156960
atctctttta ccctgaaaac cgggctgctc aacgcatggt tactctttct tcctaccgat   157020
atcctcggcg tactggcgat aaacagcctg atggcgtttg tcttggcgc tatctggggc    157080
gtgttgatcc ttacttgcct gttgccagta aaccagctgc tgaccgcgct gccggtggat   157140
gtattaggta gcctcgggga attaagctcg ccggtggttt ctgcttttgc actgttcccg   157200
ctggtggcga ttttctacca gtttggctgg aagcaaagtc tggtcgccgc cgtgcgtgtt   157260
ctgatgaccc gtgtggtagt cgtgcgctat ttcccacatc ttaaccctga atccatcgaa   157320
atctttattg gcatggtgat gctgctgggg atcgcgataa ctcacgacct gcgtcatcgt   157380
gatgaaaatg atattgatgc cagcgggctt tcggtgtttg aagaacgcac gtcgcggatt   157440
atcaaaaact tacccatata cgccatcgtg ggagcattga ttgccgccgt tgccagcatg   157500
aagattttcg ccggcagtga agtgtcgatc ttcactctgg agaaagcgta ctccgcaggc   157560
gtaacgccgg aacaatcgca aacgctgatc aaccaggcgg cactggcaga atttatgcgc   157620
gggctgggtt ttgtaccgtt gattgccacc accgccttag caacgggtgt gtatgcagtt   157680
gcgggcttta cctttgttta tgcggtgggc tatctctcgc cgaatccgat ggttgcagcg   157740
gtattaggcg cagtggttat ttcggcggaa gtcttgctgc ttcgttcgat cggcaaatgg   157800
ctgggacgct acccgtcggt gcgtaatgcg tcggataaca tccgtaacgc catgaatatg   157860
ctgatggaag tggcgctgct ggtcggttcg attttcgcag caattaagat ggcgggttat   157920
accggattct ctatcgcggt tgccatttac ttcctcaacg aatccctggg ccgtccggta   157980
cagaaaatgg cggcaccggt cgtggcagta atgatcaccg gtattctgct gaatgttctt   158040
tactggcttg gcctgttcgt tccggcttaa ggaaggcacc tatgaagacg tttcctctgc   158100
aaagcctgac gattattgag gcgcagcaaa agcagtttgc gctggtggat agcatttgtc   158160
gccatttccc cggcagcgag tttcttactg gcggtgattt aggcttaacg ccaggactga   158220
atcaaccgcg cgttacccag cgtgtggaac aggtgctggc tgatgcattt cacgcacagg   158280
```

```
ctgcggcgct ggtgcagggc gcggggactg gcgcgattcg cgccgggctg gcggctttgc   158340
tcaaaccggg gcagcgtctt ctggtgcatg acgcgcctgt ttacccgacg acacgggtta   158400
ttattgagca gatggggctg acgcttatta ctgttgattt caatgacctg tcggcactga   158460
agcaggtcgt cgacgagcaa caaccggatg cggcgctggt gcagcatacg cgccagcagc   158520
cgcaggacag ctacgtgctg gcagatgtgc tggcaacgtt gcgcgcggca ggtgttccag   158580
cgttaaccga tgacaactat gcggtgatga aggtggcgcg aatcggctgt gaatgcggcg   158640
cgaatgtctc gacatttttcc tgcttcaagc tatttgggcc agagggtgtt ggtgcagtgg   158700
tcggcgatgt tgatgttatc aaccgtattc gcgccacgct ttactccggc ggtagccaga   158760
tccagggcgc acaggcgctg gaagtattgc gtggtctggt gtttgcgcca gtgatgcacg   158820
cggtgcagga aggggtatct gaacggttgc tggctttgct taacggtggt gcggtgccgg   158880
aagtgaaaag cgcggtgatt gctaatgcgc agtcgaaggt gttgattgtc gagtttcatc   158940
agccgattgc cgccagagtg ctggaagagg cgcaaaagcg cggtgccttg ccttacccgg   159000
tgggtgcaga gtcgaaatat gaaatcccgc cgctcttttta tcgccttttcc ggaacgtttc   159060 gccaggcgaa tccacaatca gaacattgtg cgattcgcat taacccgaat cgcagcggtg   159120
aagagacggt gctgcggatt ttgcgtgaga gtattgccag tatttaatgc tggatagcac   159180
cgtcaagcta aattccgtac tgaacggtcc cctcgcccct atggggagag ggttagggtg   159240
aggggaacgc acgggatgta aaattcaacg cgccagcatc gccggatgcg atgctggcgc   159300
atcttatccg gcctacggtt aatgtctttt attatcaata gttaaggtga tgcgattggc   159360
gcggcagaag agttcggaga cgtgcaccgg tttgtcattc tgatcaaagg cgattttgct   159420
gatgcgaaac aacggttcgc ccagttcgca tttcagccat tttgcctgcg ggcgggtggc   159480
ggcaaagata tcgatggtct tttttgtcgct gaccactcgc gtgtcaaaac gctcctgaaa   159540
taactgatag gtggagcttc cttcgacgta aatctcatca aagtcaggat aacgcgacag   159600
cgggatccat gaactatcaa taaacagcgg ctctttatcg agatacatca cccggcagag   159660
atggaacact tcgctgtttc cggggatgtt cagcttttcg caaaacggcg cggcgctgac   159720
ccgttcctgt tcgatcactt tctctttcgt cgccttgcct tgtgagacgc caaaatcggt   159780
aaaaccactg acagtaagca gggcgttttc aactttctgg cttttgtacaa aggtgccttt   159840 tccctgccag cggatcagta cgccgtctgc cactaagtcg ctgatggctt tgcgaatggt   159900
aatgcggctg acgttatatt gtgtacaaag ctcgttttcg gtagggatct gttgcccggc   159960
ctggtaaacc ccctgcgcga tatcatccag cagtcgctgg cggacggtag cgtagaggag   160020
ttgatgagag tagcggtccg tagctgacat aatcgaccct gaaataaaga atgaattact   160080
cggattatag ggtcgttttc cggcaagtaa cagcacgttg gcgtgaagat gctcacgcca   160140
acgttatacc taccaggcac cgtggtactg aatggttttc gccgcgcacg ccgttccctg   160200
cgccatcgcc tgcggtaatg tcatccccgc agaccagccg caaaggaatc cggcaatgaa   160260
cgaatctccg gcacccatgg tgtcgataac cgtcaccggt tcaggagcct gacgccagaa   160320
ctgcgcgcca tcccaggcaa tgctgccgtt ttcacccagc gtgacaatca ccacgcctgc   160380
gccacgggca acaatcgctt tcatcttcag acgcagcgtt tcgtcttctt gcggtgcgga   160440
ggcaaaggca aaatcgagat gcggcaccag tgtctgccag agcgggctgt cccacttgtc   160500
ggagaagtcg aaagcggtaa gtttgcccgc agcgtgcagc tgtgggaatg cgtcttccgc   160560
atgtccccag attgccgcgt gcacaatgtc atactgcgcc agccaggcgt aatcctcttc   160620
```

```
actcagggca aagtcggcca tcacgccttc ggtgtagtcg ccaaaaacgc gatcattgtc    160680
gtgcagttcc acctgagttt gtgcggtaac gccgtgtttc gtatggacat ggctgatatc    160740
gacgcccatg cgggcgagat cctgcttcag ctttgtgccg tagtcatcgt cacccaccca    160800
ggtaatgcat cccggctgta tgccgtagcg agtgcagtac accgccacat tgaccgcatt    160860
accgccagaa aacgctttat tcagttgcgg gtagatatcg acgcagttat cgccgattgt    160920
cgccagggtt ttcatctctc atcctccggc agcagcgcgc gaaagcgttc cagcgcctgg    160980
cgggcataga gtctgggctc gttcatatac atcgtcacca gttccaccgt gcagtaaccg    161040
tcatagcccc ggtcgataat atcgcgcatc agctcccgca gcggcatttt gccttcgccg    161100
ggaatgtaat gtgtgtcact ggccccgtcg ctgtcgacaa tatgcagatg acgcaattta    161160
tcacccagtt tgtcgaaata actcatcacc ggttccgcct ggacatacgg cgcgcaaatg    161220
tcgaccatgc tgaacaggcg cggcgaaggc accagccgca gcgcatgaag cacatcatta    161280
gcattacaca cgacgttcga ttcatacggc gttaacggtt cgaggatcag atccatgccg    161340
atgttttccg cgtactcaca cagttcgctt aggttctctg ccagccgtcc ccagataaca    161400
ttaggtggcg tgagatagcc cgcgtgggcc gcggaaatca gcgtataacc cgcgttcatc    161460
tcttttgcca tatccatcgc cagcttgatc atgtcgaggc tttcgcgacg catatgttca    161520
tcgcccagca tcatgttata cggatagccg ttggtttctg gcgtatagcc gataatcggc    161580
atctgatacg tctgcgccag cgccttgatt tgtttgatgc cgcccgcttt taagtccggc    161640
gcgaacgcgt gcgggcgacc gccccaaatt tcgatgccgt cgtaacccag ctcgcttgca    161700
tcacgaaatg cgtgttcaat aggcagccgc tggtggccgc aggtaaacat acctgttttc    161760
atcgggtaac tccttgcgta aattcggccc gttgccgggc cgggagaggg attaatattc    161820
caccagacca ccgtaatagc ggcgttcatc cgggttgtga tctttgtaaa tagacaggta    161880
gtagcagagc cactccattg gcacgaacat caggaacggt gccagccacg ggtgcagccc    161940
ttgcgaaatt tcgcgtaat cgatgacgat cacgttgtca gtacgctgtt taacaaagtt    162000
aatggcgcgt tcggtggtgt ggcgactttc atcattgccg agcaggaaca ggaacggaac    162060
gcccggttcg acaatctcca gcgggccatg gcggaactct ccgctctcaa tcacgcagcc    162120
gtgcgtccag gtaaattcca tcagcgttac aatgccttct ttgtaaccca gcggacgcag    162180
cggacccgca gcaacggtat aaatcatcgg ccactggctg gccagttcac caagctggcg    162240 gccttttctct tcccaggtgc gtaccagatg accgagcgca ttcggcaact gcttgagatc    162300 gttttttgatc ttgccgattt ccgcgttcgg cgcgaggcgg gtgatcatct ccagcaccac    162360
gctgtagcag agcagcaggt gaatttccca gatacagtcg gcctgataat caatgctaaa    162420
ttccgccgcc gaggtaatcg ggctgtccgc gcgtttggtg aacgccgcag tgagtgcgcc    162480
gcaggcccgg cccagctcca gcgctttgat tacctcttcc gttttaccgt agtcagaaac    162540
gccaatcacc gcgcaacgat cgtcgaggcg atacggggtg ttatcgcaga actcccagcc    162600
ggaaatggcg tagacctgaa gatcggaaaa gcgatccgcc agatgtttcg ccgtttgcgc    162660
cgcgttgagt ggcgagccgc aggcaacgaa ataaatacga tcaatgtcgc gcttcaccat    162720
ctcttccacg atggcgtgca ccagcggaac gtcatggctg agaacttttt ccacttcctg    162780
aaccatattt tcggtgacca gaaagtccac ggtgctttta tcaatatcca acattttatt    162840
ttctccagat aacattacga caaagcgttg agctggcggc tacgcttcgt ccagaaggcg    162900
taagcaggca gaccagtagc aataacgatg acggcgcaga taaggccggg aatcggtgcc    162960
cagacaaagg ttgaggcgac cagaatgagg cttgacgcaa tggcgagggt ggtcatcagc    163020
```

```
ccgaaagccg gagtacgcca cagcggtttg taatcgtcgc gtttacgaca ccagatgatg   163080
gagccgaagg tgagggtatt tttgaaacac atcaccaggg tgaaataacc cagcaggctg   163140
gtgagatcgg aaacgaagat gaagaagatc cccagcgccc cttgcaggat gatggagaca   163200
tccggcgtgt tgtatttcgg atgcacatgg ccgaagcatt taaagaacag gttgtctttc   163260
gccatcgcgt attccagccg cggctggtac atcacgcagc tggaaagcga accaagaatg   163320
acgatcatcg ccgtgatggc aacaaagatc cagcggtgc tgccgagtgc ggggatccag    163380
gtcagggcgt cggaaatcgg cgtttcagaa ttggcgagtt tgtcgaaggg catcaggccg   163440
gaaatcacca gcgccagcag ggtgtagagc accagaacca gcagacagga accaatcagc   163500
gctcgtggca tggtttttcc ggggttttta atttcgccgg tcatataaca gatagaggcc   163560
atgccggtat acgaccaact ggtggcagag atccccgcca gcagcgccat aaagctgccc   163620
gttgcgccaa tcgcagtggt ggtaggggcg gcaaaattct ccgctttaaa ccagaagatc   163680
ccaaggccaa tgacgatagt gaacgggata attttggcga tggtaattag cgtctgaaac   163740
gctgcgccgc cttcaacgga gcgcaggtgt agcaacataa aggcgataat taatccggcg   163800
gcgataaatt taccgagcaa cggatcgata ggcgttaaaa agccaagatt gctgacaatc   163860
gccagcgcca taatcgacaa tgacggcgca tcgttggccc agaagctggc ccagccggag   163920
aggaaagcca gcggtcggct tccggcattt ttcagataaa cataatctgc gccatttttcc  163980 ggataagcgg tggatagttc cgcatagacg cacatttgcg ggatcacaat taacccgcca   164040
atgacaaacg cgagcaccgt aagccacggc gtgcccgctg cttttgccac ttcacccaca   164100
gatacaaaaa taccggagcc gacggttgtc ccgacggcga ttgcaagaac ggcccaaaat   164160
ccgagcttgc gttggagttc ctggcttccc atagcgatac cttttcttg tccaatacgt    164220 tgtagggag agtttgcagt catttaaaag gtaacatgac aatgcatgat gaatataaca    164280
acatatgatg ttatgtaatg tggaggaaga tcacaaaatt tcgcacagga tcgcgctgtg   164340
gctaatggat gtagttatca aattgaattt aaagtgaaaa tatttttacg ggcggggca    164400 agaaggacat agaaacaaat acgccctcgg aaaatccaga gggcgtcggg caattaaacc   164460
ggtgttagcc gatttctgtc agagacttac tgtgcagtag gaccgcaacc gccaatgatt   164520
ttagaaatag aaattgccgg gtgcagcagg tagtcgtaag agcagttctt atcacggttt   164580
tcaatatgac cagtacatgc agttaacgta gccagtactg cacctaccag tgcaacttta   164640
ataaatttgt tcatttacat tccctatgta ttatatatta attatattc attgattgta    164700 tgaatataag cagactgctc gttaagaacg atacaggaat atttaattgg cgtcagtgag   164760
cgaatgactt aattttgtaa gtcgctgtaa cggtgaatat aacccattag cagataaatat  164820 ttattaaggg gctatgtttt atttgctgaa tatataaaaa gagtcattaa gaaggccaga   164880
attctctggc ccgggttaaa ttaatggttg gagaaccagt tcagtttatc gcgcaggcca   164940
acaacccgac caataataat tagcgatgga ctgttcattt gctgagcaag ttcaccgagt   165000
tgcgtgagcg taccgtcaat cacgcgctgc gtgactgccg taccgttttc gacaattgcc   165060
accggcattt cgcctggcat tccgtgttca atcagctttt gctgaatagt cgcggcctga   165120
ttcaacccca tatagaacac cagcgtcgt tttttctgccg ccaggttttc ccagtccagc    165180
tcgccaccag tttttaagtg tccggtaatt aagcgcacgc tctgggcata atcgcgatgc   165240
gtgagcggaa tacccgaata ggcagagcaa ccagaagctg cggtaatacc cggaaccacc   165300
gagaacggaa tacccgcgtt gcacagtgtt tccagctctt cgccaccacg gccaaaaata   165360
```

```
aacggatcgc cacctttcag ccgcaccacg cgtttgcctt tttgcgcttc ccgcagcagg   165420
atctggttaa tctcttcctg gggtacgcag tggtatcccg cgcgtttgcc gacgaaaaca   165480
cggtccgcat cgcggcgtac cagattcata atatcgtcag aaaccagacg gtcgtagacc   165540
accacatctg cctgctgaat tgttgcagt cctttcagtg tcagcagccc ggcatcgccc    165600
ggacctgcac caaccagcac cacttcaccg cgatggtcga gcggttcgtt gattaactgt   165660
tcggtcgttt cagtaatggc tttctgatcg ttgtttgcca gcgactgcgc caggcggtcg   165720
ttaacgaaca atttctccca gaaacggcga cgttcaccca ttgttgcgaa ctgttgtttc   165780
actcgaccgc gtaattgccc ggcgtatttc gctacctggc ccagatgtaa cggcagcagt   165840
gattcaagtt tttcgcgcaa caggcgtgcc agaaccggag aggtgccgcc agaggagacc   165900
gctaccatga gcggtgagcg gtcaataatc gacggcataa taagctggc ggctttcggc    165960 gcatcgacca cgttacagaa gatgcgacga gcttcagcgg cttcgctgac gcgctggtta   166020
agcgcgtcat catccgtcgc tgcaatcgcc agccagcagg tgtcgagaag gctttcatca   166080
aatgcccctt cgacgagggt taacatgcct gcatctgccc atgcggtgaa ctgtggaata   166140
aacgctaatg cattcaccgt taagcgagcg cctgcgtcta acagcaacct tgctttgcgt   166200
tccgcgacat caccaccgcc gacaatcaga cagtcgcgat cgcgtaattg gcaaaatata   166260
ggcaaatgat ccacgtaaaa acccttagt aattaaccgg cagccgtttc agtttgatta     166320
aatttgtccg caaccggacg attcgctttc ggcgtagcat accaataacc caatcccatg   166380
aatacggcac ctgataaagt attacccagc gtcacccaca gcaggttatg accaataccc   166440
gccagcgtgt aggcttcgct gtggttgccg aaccaggaga gcgcgaacag cgtcatgtta   166500
gcgatagagt gctcgtagcc agacgcgata aatgccagca gacaccacca gatagcgata   166560
aatttcgccg cccttcagt gcgcagcgcc atccagattg ccaggcaaac cagccagtta    166620
cacaatgcac ctttgaagaa cagtaccatt gccggtgcag tggttttagc cagcgcgacg   166680
gagtgaacga tgctggtatc taccggcagc aggctaccgc cgcccagct atagagcatg    166740 gcaacgaaga cggaaccgac caggttaccc agccaggttt gcggcaggat tgcccacatt   166800
tgcccgtggc tgatgctgcc cgcttttacc ccaaaggtga ggaacatggt gtgtccggtg   166860
aacagttcag aaccggcgat aatcaccagc gttaaggcga taccaaaggt cgcgcccatc   166920
accagcggac gtacggacgg gtcgagcaaa ttaccgagcg tgaaaatcaa gatgatccca   166980
agacccacat acgcgcccgc catggcggag ctgacccaaa agccgagcgg gttatttgcc   167040
gacaggcgtg caatgcgcgc agcgttagcc gcacacttat taatagtgtc tgtaaacatt   167100
tgattatcct ttaaaaata aaacaaaaa aataaaacaa aaagtttaaa aaatgtcctg     167160
caatataccg aaggtcatta caggaccatg caaaaagggg aggcattgcg cctcccgtta   167220
aaacattaac cgcgcagctg caccacgccg tctttcactc gtgcttcgta atgtttgacg   167280
gaaaactgtt cgtcttccat gcacaagcca tcacttaagc gaaaacgctg ttttttcagc   167340
gggctggcga cccacagctc gccctggtgt tccgcaatca gcccgcgtga cagcacgctg   167400
gactcgaaga acgggtcgat gttgctgatc gcaaacacct gatcgctgtg atacgggcgg   167460
aaaattgcta cctgctcgtc acctaacagc gcgcagacgc cggtttcagg caggatgtca   167520
tcgattttgc agatgtcttt ccactggctc atgcgttgtc ctccaccaga gttaccggga   167580
tacgttcata cggcgttgcc ggacggtgct gttcgcgctc tggcaccatc tgtacgttcg   167640
ggtcacgctt gtcgctgttg atgaagtgtt tgaagcgagt ctgcgcggac ggtgtattga   167700
ccgtttcagt ccactcacac actaccgctt cacgcaggcg cgccatctct tcttccagat   167760
```

```
gtgcgttcag ccccagtttg tcgtcaatga tcaccgcttt cagataatcg atgccgcctt   167820
cgaggttttc taaccacggc gcggtacgcg tcagtttgtc ggcggtacgg atgtagaaca   167880
tcatgaagcg gtcgagatat ttgatcagcg tttcgcgatc gatatccgct gccagcagat   167940
ccgcatgacg cggtttcatg ccgccgttac cgcaaacata caggttccag ccttttttcag  168000 tggcgataat acccacgtct ttaccctgag cttctgaaca ttcacgggta cagccggaga   168060 caccgaacatt cattttgtgc ggcgtacgga tgcctttgta gcggttttcc agttccacgc   168120
cgaggccgac gctgtcgcca acgccgtagc ggcaccaggt gctacccacg caggttttcg   168180
ccatacgtag tgctttcgca taggcatgac cggtttcgaa gccagcttca atcagctgac   168240
gccagatctc cggcagatcg tctttctgtg cgccaaacat cgccaggcgc tgagagccgg   168300
tgattttggt gtagagatta aattcacgcg cgatacgacc cactgccatc agtccttccg   168360
gggtgatttc accgcccgga gagcgcggga tcaccgagta ggttccgtct ttctggatgt   168420
tagcgaggaa gttgtcgtta gaatcctgca gcggagtatg ttccggcttc agaatgtatt   168480
cgttccagca ggaggccagc agcgaaccga cggttggttt acaaacttca caaccgtagc   168540
ctttgccgtg tttcgccagc agttcttcga aggttttaat gccttcaacg cggatcaaat   168600
ggaacagttc ctgacgcgaa taagcaaagt gttcgcacag gttgttgtta acttcgatgc   168660
cctgtttcgc cagttccgcg ttcagtacct gagtgaccag cgggatacag ccaccgcagc   168720
cagtacccgc tttggtttca gctttcagcg ccgcaacggt gtggcagcct tgttgatgg    168780 cagcaatcag atcacctttg gtgacgtcga agcaggagca gatttgcgcg ctgtccggca   168840
gtttatcaac accgatagac ggcttgccgc taccagagtg tgctggcagg atcagggaat   168900
ccgggttttc cggcagttcg atagcgttca gcaccagttg cagcaggtta ccgtagtcgc   168960
tggtatcgcc caccagtacc gcaccgagca gggttttgtt gtcttcgctg acaatcaggc   169020
gtttgtagat ctctttactt tcgtcgaggt aaacgtagct acgtgcgcca ggcgtgcgac   169080
cgtgcgcatc accaataccg cctacgtcta cgcccagcag tttcagcttg cgctaaggt    169140 cagcaccttc aaaggcgttt tcgctaccga gaatatggtc aacggcgacc tgcgccattt   169200
tgtagcctgg tgctaccaga ccaaatacac ggttgttcca gcttgcgcat tcaccgatgg   169260
cgtagatatc cggatcggaa gtctggcagg aatcattaat gacaataccc ccacgcggag   169320
caacgtccag accacactgg gttgccagct tatcgcgcgg acggataccg gtagagaaga   169380
cgataaagtc gacttccagt tcgctgccgt cggcaaaacg catggtttta cgcgcttcga   169440
caccttcctg cacaatctca agggtgtttt tgctggtgtg aacgcgcacg cccatacttt   169500
cgattttgcg acgcagctgc tcgccaccca tctgatcaag ctgttccgcc atcagcatag   169560
gggcaaattc gataacgtgg gtttcaatac ctaagttttt cagcgcgcca gcggcttcca   169620
gacctaacag gccgccacca acaacggcac gcgcgcttgct gcgacgggcg caggattcaa   169680
tggcgttgag gtcttcaatg gtgcgataga caaagcagtc ctgagtatca gaaccttga    169740 ttggcgggat ccacgggtag gaaccggttg ccatgatcag cttgtcataa aaaacggtac   169800
gtccggcgct ggagtgaatc accttctcct gacggttgat ggtgatagcg cgttccgcga   169860
ccagaacttt gatgccgtgt ttctcgtaga agccttcgcg caccagcgac agctcttcgg   169920
cggtgtggtg agagaagtaa gacgagaggt gtacgcggtc ataagcgatg cgcggttctt   169980
cacagaaaac ggtaatatca aagttggccg catcagattt atcaagaaga tcttcgataa   170040
agcgatggcc gaccataccg ttaccgataa ttgcgagtct gactttgctc attttttgcct 170100
```

```
cgatttcttt tctattaccg cctaccttaa cgattcagca accccgctta ttgatgtaaa    170160
tcaaattcac ctttatatac tccttaaggg gtatattgct gatttgtata aatttttctta   170220 agtcacggaa ttgtctgata tttcatgttt gtgcaaaaaa tagacaaaat gaacgggttt    170280
atagaaatag atgcacgtag cggggggaaga gaggaaaagg ccggacgacg atagtgccgt   170340
ccggcattag caattaatga gaggtcaggg tgttatgctg acggtgacgg ctgacgaaac    170400
ctaacaggaa gcacatcaca aagacgacag cgtacagacc gtttgctgta agcagtgccg    170460
cctgcggacc gctatgttca acaatcgggc cggtaaccac aaaggtcaac atagtaccga    170520
tggttccgca ggtcaggaca aagttaacca gttttggcga cggtactttg gtctgctgtg    170580
aacccagggt gatgatggtg gtatagatcg cgctggagaa gaagcccaga gcgagaattg    170640
accacgccat atgtgctggt gttccggtgt taaagacgta catcagaatc gcagccagac    170700
cagccagtac ggtcagaatg cgttgcaaat caaagaagcg aagaataaag ctgaacgccc    170760
acatgccgac catgtatgac atccagaagt tactcaccag cgtgcccgcg tcgttcaggc    170820
tcatgcccag gcctttggca tactcaggca cccaggagat aaaacctaac tgaccgagga    170880
tgtagcacag cgccacaaca gagagaaaca gtacgccgat cccccacttt tctttctcta    170940
ccggagcatc cgttttttggc gcatgtttgc ccagcgccgg gaactcacag ccgaaggtca    171000
gaataaaaat agcgacatac accagcccga tgcaggcata aacccagtac cactcaatgc    171060
tgcgcgccag tagaaacgcg gcgatcattg ggaaaatcat cccagccata ctgaagaagg    171120
agtcggtaaa taacaggcgg gaaccgcgct gacgcccttc atacatttgt gttaccagga    171180
atgtaccaat cgacatggtg atgccgctga ccaccccgag aatgaacatc gccgccgaga    171240
acagcgccag gctgtggctg aacatcaaac cggcaaccgc cagcaccatc aggagaaagc    171300
caaaacgtaa ctgcgttttc aacgggacga tttccatcag ccaggcgttg aggaagatag    171360
agattaaaat gccggcgttg aggaaggtga aggtgttact catactggaa acaggcagat    171420
tgaaataatc ggcgatattt cccatccaca tcccggtgac aataaccaac gcaccagtca    171480
gtgcgtagga gagaaagcta atccatgtga gcttgatgcg attgctgtta gtcatgattg    171540
gcctgcgttc aaaaataaaa tggcatagcg ggatatgccg cgagcgggcg attttaggtg    171600
attttgtgat ctgtttaaat gttttattgc aatcggttgc taaattgcat tttaagaggt    171660
gattttgatc acggaataaa aagtgatcgt caggttacat atatttcaga tacgtaaaat    171720
taggtaaagg gatggccttg ttcttgaagg ctatttagaa tctcttcact tgctttttttt   171780 ctgctctgtt tgttaaggaa atctcatgtt caaatcgacc ctggcggcga tggctgctgt    171840
tttcgctctt tctgctcttt ctcccgcagc aatggcagcg aaaggggacc cgcacgtatt    171900
gttgacaacc tcagctggta acatcgaact ggagctggat aaacaaaaag cgccagtgtc    171960
tgtgcaaaac tttgtcgatt atgtgaacag cggttttttat aacaacacta cctttcaccg   172020
cgtcattcct ggctttatga ttcagggcgg cggtttcacc gagcagatgc agcagaaaaa    172080
accaaacccg ccaatcaaaa atgaagccga taacggcctg cgcaacacgc gtggtaccat    172140
cgcgatggcg cgtaccgctg acaaagacag cgccaccagc cagttcttta tcaacgttgc    172200
cgataacgcc ttccttgacc atggtcagcg tgatttcggt tacgcggtat ttggtaaagt    172260
ggtgaaaggc atggacgtgg ccgataagat ttcccaggtg ccgactcatg acgttggtcc    172320
gtaccagaat gtgccgtcaa aaccggtagt tatcctttcc gctaaagtcc tgccgtaatg    172380
atttctcgcg cgggcaatct tgcccgcgct tctgctctcc cggcgtaacc cggatttgcc    172440
gcttatactt gtggcaaatg gacacgttca gggaggcatc aagtgaagaa actcaccgat    172500
```

```
aagcaaaagt cccgtctctg ggagcttcag cgtaatcgta atttccaggc cagtcgccgt 172560
cttgaaggcg tcgagatgcc tttagtcact cttactgccg cagaggcttt agcgcgcctt 172620
gaagagctga ggaggcacta tgagcgataa attcggcgaa gggcgcgatc cgtatcttta 172680
tcctggcctt gatatcatgc gtaaccggct gaacatccac cagcagcagc ggctggaaca 172740
ggccgcttac gaaatgacgg cgctgcgtgc tgcgaccatt gagcttggtc cgctggtgcg 172800
cggtttaccg catttgcgca ctatccatcg ccagctgtat caggatattt tcgactgggc 172860
ggggcaactg cgtgaagttg atatttatca gggtgatacg ccgttctgcc actttgctta 172920
tatcgaaaaa gagggcaatg ccctgatgca ggatctggag gaagaaggtt atctggttgg 172980
cctggagaaa gcgaagttcg tcgagcggct ggcgcattac tattgtgaaa tcaacgtgct 173040
gcatcccttc cgggtgggaa gtggtctggc acagcggatc ttcttcgagc aactggcgat 173100
tcatgccgga tatcaactga gctggcaggg tatcgaaaaa gaggcctgga atcaggcaaa 173160
tcagagtggg gcaatggggg atctcaccgc actgcagatg atatttagca aagtggtaag 173220
cgaagccggg gaatctgagt aaaatagcgc ggttctttg taccggagcc gccatgatcc 173280
tgcttataga taactacgat tcttttacct ggaacctcta ccagtacttt tgtgaactgg 173340
gggcggatgt gctggttaag cgcaacgatg cgttgacgct ggcggatatc gacgccctta 173400
aaccacaaaa aattgtcatc tcacctggcc cctgtacgcc agatgaagcc gggatctccc 173460
ttgacgttat tcgccactat gccgggcgct tgccgattct tggcgtctgc ctcggtcatc 173520
aggcaatggc gcaggcattt ggcggtaaag ttgtgcgcgc cgcaaaggtc atgcacggca 173580
aaacctcgcc gattacacat aacggtgagg gcgtatttcg ggggctggca aatccactta 173640
ccgtgacacg ctaccattcg ctggtggtgg aacctgactc attaccagcg tgctttgacg 173700
tgacggcctg gagcgaaacc cgcgagatta tgggggattcg ccatcgccag tgggatctgg 173760
aaggtgtgca gttccatcca gaaagtattc ttagcgaaca aggacatcaa ctgctggcta 173820
atttcctgca tcgctgattt ctgattgcca tttagtgatt ttttatgcat attttgtgat 173880
tataatttca caattattta tgcgtaacag ggtgatcatg agatggcaat tgaacaaaca 173940
gcaattacac gcgcgacttt cgatgaagtg atcctgccga tttatgctcc ggcagagttc 174000
attccggtaa aagtcaggg cagccgaatc tgggatcagc aaggcaagga gtatgtcgat 174060
ttcgcgggtg gcattgcagt tacggcgttg gccattgcc atcctgcgct ggtgaacgcg 174120
ttaaaaaccc agggcgaaac tctgtggcat atcagtaacg ttttcaccaa tgaaccggcg 174180
ctgcgtcttg ggcgcaaact gattgaggcg acgtttgccg aacgcgtggt gtttatgaac 174240
tccggcacgg aagctaacga aaccgccttt aaactggcac gccattacgc ctgtgtgcgt 174300
catagtccgt tcaaaaccaa aattattgcc ttccataacg cttttcatgg tcgctcgctg 174360
tttaccgtct cggtgggcgg gcagccaaaa tattccgacg gctttgggcc aaaaccggca 174420
gacatcatcc acgttccttt taacgatctc cacgcagtga aagcggtgat ggatgatcac 174480
acctgtgcgg tggtggttga gccgatccag ggcgagggcg gtgtgacggc agcgacgcca 174540
gagttttttgc agggcttgcg cgagctgtgc gatcaacatc aggcattatt ggtgtttgat 174600
gaagtacagt gcgggatggg gcggaccggc gatttgtttg cttacatgca ctacggcgtg 174660
acgccggata ttctgaccct ctgcgaaagcg ttaggcggcg gcttcccgat tagcgccatg 174720
ctgaccacgg cagaaattgc ttctgcattt catcctggtt ctcacggttc cacctacggc 174780
ggtaatcctc tgtcctgtgc agtagcgggc gcggcgtttg atatcatcaa taccctgaa 174840
```

```
gtgctggaag gcattcaggc gaaacgccag cgttttgttg accatctgca gaagatcgat   174900
cagcagtacg atgtgtttag cgatattcgc ggtatggggc tgttgattgg cgcggagctt   174960
aagccacagt tcaaaggtcg ggcgcgtgat ttcctgtatg cgggcgcagg ggctggcgta   175020
atggtgctga atgccggacc ggatgtgatg cgttttgcac cgtcgctggt ggtggaagat   175080
gcggatatcg atgaagggat gcaacgtttc gcccacgcgg tggcgaaggt ggttggggcg   175140
taaatacgaa gcatcaggca aaagatgtcg gatgcggcgt gaatgcctta tccgatggtt   175200
tagcctgcat tacgccttcg aatcccgcaa cttgcgactc agccaaatcc cgtgatgcgg   175260
tcgctgacgc catgccatcg acgaaatggt gtgcatggtg ttcagatgac caataacccg   175320
ctgtaaatgc tgctccagcg tacctgccgc gccttcgtgc ggctgcatct ccggcgcatc   175380
catgatattg gcatcgccag aactacccgg ttcgtcatac tccagtcgct gctgacaacg   175440
ctgaatggcg atttcacaag actgtaaata ctcttgtgcc agttcaggtg gcaatgcccg   175500
gtgttcccgc gccagcgtgg tcatggcatt aatatgctca acaataaact ggctgtgcgt   175560
tacccacagt ttcatatctg ccagataatg gctgttaaac gccggttcct gcatcgcctg   175620
attcaatgag ttatacagag tgttatgtgc ctgatttacc cgcattcgct gccaggccag   175680
tggcgtaggt tgcggatcct cgctaagaat caagcgaatc gcttcctgat aggcttctaa   175740
agcgtcatgg gcgttttac gcaataaccc gctctgccac tgcggccaca gccagacagt   175800
accgccgaaa gcaattaaac aaccaataat ggtatcgata agacgcggaa ggatgtattg   175860
ctcgccgttc aaccacaata gttgcagggt atacactgcg gtaatagtaa aaccgaccgt   175920
cgcccagccg tagttttttgc gcaatatcag gtagctggcg agggtggtaa tcagcatcaa   175980
cgtcagggtg taaccttcgg gaattttaaa gtgcagcgcc acgcccgcaa tgattaaccc   176040
gaccacggtt cccacggagc gattcacaat cctcagacgg gttgcgccat agccattttg   176100
tgtcaccagc aataccgtca tcaggatcca gtacgacttc ggcagatgca gcgcggtgcc   176160
catcaggctg gcaacgctta acatcacact gagtcgtccg gcattgcgta gcgccggaga   176220
ctttagtgac agataacttt tcagcgccgg aagtaatggc attcgccgct gtttatcggc   176280
cagtaagtca cgggcataga gcggtttttg ggtgcgcagc acgcgggcga tgcggctgaa   176340
atgccagtag cagaattgcc caaccggatt atccggatgc tggcgggcga ttttttccag   176400
tgcgccaatt tgcttttcca tcgtaaaacg cgttggcagg cgatggtaaa gaatgtcatc   176460
agccagcacg cgcaggcgag cggcgacggt ttgcgcattc cagcggataa cttcttccgc   176520
atggctacgc tcgaccagct tttgcacctc ttccggctga tgcaaactga ccgaaatatg   176580
ttcctgtaaa tccagcgcct cctggaaaat acgcagcatc cgcttgtagt cagtattatt   176640
ttgcgcggaa agcatatgca tttgctgata gcactgggta attagatcga ccgcttttg   176700 ctggcgcacc agcagcggcg gcagcgcttt ttcagggtcg gtgtgctggg taagcaggct   176760
gtatttggct tcacaataat ctgccagttc acggtacagc agacttagtg actcgcgcag   176820
cggttgttcg cgccagatcc agaaccaaaa ccagttaaac aatccgtacc agagagtgcc   176880
caacgcatag atgagcaacg gttcccagac cggcatgtat cccgccagac tgagggtaaa   176940
aatggctgcc agcagcgatg cgggaagcaa ttttgcgtgc aatggcccca actcagcagt   177000
gacgccaagt accagcgtta atccggtcag caaaaagggc aggggaacat cttttgccag   177060
tagcagctgt gtcagtaagc tacaggtggc aaacagcgac gcaccaatga ttaagcgttt   177120
gaaaaaacgt ttatgaggcg tatcaaggcc tgcaatattg caacaggcag gaacgagaga   177180
gaagagcaga ccgaatcgta attcgccaag cattaaccca acggccacgg gcaaacatag   177240
```

-continued

```
caccagcgtt tgtcgaagtg catagttgat atcggggtga taaatcagtc tgcgccacat 177300
cgggggaaac aaaatggcgc gctaccaggt aacgcgccac tccgacggga ttaacgagtg 177360
ccgtaaacga cgatggtttt accgtgtgcg gagatcaggt tctgatcttc cagcatcttc 177420
agaatgcgtc ccacgvtttc acgagaacag ccgacaatct gaccgatttc ctgacgggta 177480
attttgattt gcataccgtc cgggtgagtc atagcatctg gttgttttgc caggttcagc 177540
agagtctgtg caatgcggcc cgtcacgtcg aggaacgcca ggttgcccac tttctctgaa 177600
gtgacttgca gacgacgcgc catctgtgca gacagacgca tcagaatgtc cgggtttacc 177660
tgaatcaatt ggcgaaattt tttgtacgaa atttcagcca cttcacaggc ggttttcgca 177720
cgtacccatg cgctacgttc ctggccctct tcaaacaggc ccagttcgcc aataaaatca 177780
ccctgattca gataggagag gatcatttct ttaccctctt cgtctttgat cagcactgcc 177840
acagagcctt taacgatgta gtacagcgtt tccgcttttt caccctggtg aataagcgtg 177900
ctcttggatg ggtacttatg aatgtggcaa tgagacaaga accattcgag agtcgggtct 177960
gtttgcggtt tgccaagcac catgcgcggt tatcctctgt tataagcttt ctccagagcc 178020
agataacgcc gctgtctctg gattgccgaa atatgcttcc cgctacctgg gaaggggcta 178080
tcaactgtac tgcacggtaa tgtgacgtcc tttgcataca tgcagtacat caatgtatta 178140
ctgtagcatc ctgactgttt tagcatagct ttcgcttttgt gtctcctggt gtctcgcttc 178200
agcatgaccc aggtcgcctt ccgttgcgcg atttggttag tacgcgtact ctgtcaggaa 178260
aattgacgca gtggagtagc aaaaatgcaa gcgcgagtga agtgggtcga agggttaact 178320
tttctgggcg aatccgcctc tggtcatcag attttaatgg acggcaactc aggcgataaa 178380
gcaccaagtc cgatggaaat ggtgttgatg gcggcggggg gttgcagtgc catcgatgtg 178440
gtttctatcc tgcaaaaagg gcgtcaggat gtggtcgatt gtgaagtaaa attgacctct 178500
gaacgccgcg aagaggcacc acgcctgttt acgcacatta atctgcattt tatcgtcacc 178560
ggtcgcgacc tgaaagacgc agcggttgcg cgtgcggttg atctctctgc tgagaaatat 178620
tgttcagtgg cgttgatgct ggaaaaagcg gtgaatatta ctcactcgta tgaagtggtt 178680
gccgcgtgat ttaactatcc cgttgtgaag ccggatagta ttttatccgg cgtaatagca 178740
gagttactcg attttcttc cttccatcaa tcgttgcacc agcggcagca taattaattc 178800
cattgccaga cccatttgc cgcccggtac cactaacgta ttgatgtggg aaatgaatga 178860
gccttgcaac atcgccagca gccagggaa atcgatccct tccagattac gaaaatggat 178920
caccacaaag ctttcatcga gcgacggat acctttgcc gcgaacgggt ttgaagtgtc 178980
gacggtggga acgcgctgga agttaagatg ggtgcgggaa aactgcggtg tgatgtagtt 179040
gatatagtct tccattgaac gcactactga gtccatcact gcttctcgtg agtgcccgcg 179100
ctcgctggtg tcgcggatca gtttttgaat ccactcaagg ttaacgatag gcaccacgcc 179160
gaccagtaag tccacatgct gcgcaacgtt atgctgtggc gtgactacgc cgccgtgtaa 179220
accttcataa aacagtacat cagtgggttc cggtaaaggt tgccagggg tgaatgtccc 179280 cggtacctga ttccacgvta cggcttcgtc gtaggtatgc agatatttgc gagatttccc 179340
tttaccgctc tgaccgtatt caatgaaggt ttgttccagc aggccgaagt cgttagcctc 179400
ggggccgaag tagctgatat gccgccggc gtcgcgcgct ttgcggatcg ccatgtccat 179460
ttccgggcgg gtgtaacggt gaaaactgtc gccttccacc tcagctgcat gcagatttaa 179520
ctgcgcgaat attttacgaa acgcgaggct ggtggtggtg gtccccgcgc cgctggatcc 179580
```

```
tgttaccgca atgaccggat gtttggcaga catagtaact ccatgactta gctatcatta   179640
ttatctcgtc cgccgacggt tgcaggttat tcgcgaaact gactgcgcgg cataatattg   179700
accgtttcgt gcagctccga ccataccagc accgcttctc cgcactgtag ctggcgtttg   179760
acgtcggcga ctttctgttc aagtgtacgc tcatgttcac cataatcggt gccttcacgt   179820
aacacaaagc tttcaattaa attttccagc gtttcggggg agaggtcttg ccacggaatc   179880
aacatgattt cgcctccaga tacgttgtta accagtcagg aatgcgtgac tccagccaca   179940
tttgcggatg aagtaatgta ccgccaataa agccaacatg accgccatgt tcagtcagtt   180000
gatactccac ctgcggggggg agactttccg gtttcgggat cacctgatga tccataaacg   180060
gatcgtcttt ggcgtgaata atcagcgtcg gtttggcgat ccggttcagc atcggcatgg   180120
cgctacactg acgataatag tcgatagcgt cggcgtagcc gtgaattctg cggtgatga   180180
gatcgtcaaa ttcacggatg cgacgtaccg attttaactg cgcgagatta atcggcagcg   180240
ttccggggta ggctgccagc ttgcgcgcgg cattggcttt taacaggttc agcaagtaac   180300
gctgataaac gcgggaaaag cccttttcca tatgatagct acaggcttcc agcataaacg   180360
gcgcagagac aatcaccgcc gcatcaaccg ggagatcatt gccttccttt gctagcaaac   180420
aggccagcat attaccgccg agcgaatagc cgacggcagc cgttggcgca tgaccaaatt   180480
cgcgttgcag ccagcgtaaa aaccaactgg cgtcttcggt ttcgcccgaa tggtaaatgc   180540
ggtgcatacg gtttggttca ccgctgcatc cgcgaaaatg catcaccacg cccagccagc   180600
cgcgcttttg cgccgcctca accagaccgt gggcgtaagg gctattgaga ctgccttcca   180660
gcccgtgaaa caccactaaa cgcggtttat gtttcgcctg tgcggggtct tcactccacg   180720
cgagatcgac aaaatcgccg tcgggcaact ccagccgctg ccagtacggg gtgaatttca   180780
cctgacgacg aaacaaacgc ggcagcatag tttgtagatg acaattgcta aagccgcgca   180840
taggggtgaa ttcagcactg ctgctaaatt cattggcagc ggtcgtcgtt atctgcgcca   180900
tcagttgctt tggccttcca gcagcatctg ctcaagctgc tcctgggctt ccagccacgg   180960
catttcgcac tcttccaggc cggatttggc gctggcttgc tgttgcaggc aggcggtcaa   181020
ctccgctttta cggctctggt catacagttc gctgtcgccg agtttctctt ccgcctgcgc   181080
cagttgcgcg ttcagcttct ccatctcttt ttccagacgg gcaatctctt tacgcagcgg   181140
ctgggttgc gcacgcagct ccgcttcccg acgcttctga tctttacgtg cctgggcgct   181200
gttcgcgttc tcttttggcg cttcgtcggt ctggttttcc tgcttttgta cgtcgctcaa   181260
ccactgttga taatcttcca gatcgccgtc gaacggttcg actttacgat cgtgaaccag   181320
gtagagatcg tcagtggtgg aacgcagcaa atgacggtcg tgcgaaacga caaccagcgc   181380
gccttcaaac tcgattaatg cttcggtgag tgcctgacgc atgtcgaggt caaggtggtt   181440
agtcggttcg tcgagcagca gcagattcgg acgctgccag acaattaatg ccagcaccag   181500
gcgggctttt tccccacctg agaagcggcg cgtttcttcg gttactttat cgccctggaa   181560
accaaagccg ccgaggtagt cacgcagttt ttgttccagc cctgcggcg ctaaacgtgc   181620
cagatgttga ataggtgatt cgtcggcgcg caggtattca agttgatgct gggcgaagta   181680
gccgagcttg atcccttcg ccagaccaat ttcaccgctg actggcgcaa gttcaccggc   181740
taacagtttg attaatgtcg atttacccgc gccgttgcgg cctaacagac caatgcgcga   181800
gccgggcacc aggttcagtt taatcgagtc gagaataatg cgatcgccat agcccgcgct   181860
gacttttttcc atcttcagta acggatttgg caggcttttcc ggcgcgcgga agctaaagcg   181920
gaacgggttg tcgacgtgcg cgggggcaat cagctccata cgctcgagca tcttaatgcg   181980
```

```
gctctgggcc tgcttcgctt tggtggcttt ggcacggaaa cggtcgatat aactttgcag   182040
atgcgctacg cgttcctgct ggctttcata catcgcttgt tgctgcgcca gacgggtggc   182100
gcgctgtact tcaaacgaac tgtagttgcc ggtgtactcg aacatgcttt gttgttcgat   182160
atgaataatt ttatcaacga tcggatcgag gaagtcgcgg tcgtgagaga tcaggatcag   182220
cgtgccctga tagctcttca accatttttc cagccagata acggcatcga gatcgaggtg   182280
gttagtcggt tcgtcgagca gcagcaagtc tgaacggcaa atcagcgcct gggcaaggtt   182340
aagacgcata cgccagccac cggagaaatc acttaccggg cgctccagtt gttcattgct   182400
gaaaccgagg ccgtgcagca ggctggcggc acgggagcga atactccatg cgtcaatagc   182460
atccagcttg ccatgaatgg tcgcaatggc gtgcccgtcg ttacgttcgt tggcgtcgtg   182520
tagctgcgct tctagttgac gatattcacg gtcgccgtca atgacatatt ccagcgccgc   182580
ttgcggtaac gccggcgttt cctgattcac ccacgccagt tgccagcttc ccggaaaggt   182640
gtagctgccg ccgtcggcgc tgatttcatt tttcagcaat gccagcaggg tagatttacc   182700
acagccgttt ttacccacca ggccgacttt ctgcccaggg ttgatggtgg cggtggcatt   182760
atccagcagg acgcgcacgc cgcgacgaat ttgtaacgag gagaaaacaa tcataaggcg   182820
ccgtatgttc agactatgtt aacttatcat tatgataatg taatgtatgg gcgagctgcc   182880
gcaccgggcg caatggtagc ccaaaacagc gactatacac aaaaaccata ccgggagggg   182940
gatgatgtct cagccagcga aagttttgct gctgtatgcc catccggaat ctcaggactc   183000
ggtggcaaac cgggtactgc ttaaaccggc cacgcagctc agcaatgtta ccgtgcacga   183060
cctttatgcg cactatcccg atttttttat tgatatcccc cgtgagcagg cattactgcg   183120
cgagcacgag gtgattgtct ttcagcatcc tctttatacc tatagctgcc cggcgctact   183180
gaaagagtgg ctggaccggg tattaagtcg tggttttgcc agcgggccgg gaggaaacca   183240
actggcggga aagtactggc gtagcgtgat taccaccggc gagccggaaa gtgcttaccg   183300
ttatgacgca ttgaatcgct acccgatgag cgatgttctg cgtcccttg aactggcggc    183360 gggcatgtgc cggatgcatt ggttaagtcc catcattatt tactgggcga cacggcaaag   183420
cgcacaggag ctggcgagtc acgccagagc ctacggtgac tggctggcaa atccgctgtc   183480
tccaggaggc cgctgatgga aggttccgat ttttactcg caggagtgct gtttctcttc     183540
gcggcggtgg ctgcggtgcc gctggcatcg cggctgggta ttggcgctgt gttgggatat   183600
ttgctggcag gaattgcaat tggtccatgg gggctggggt ttattagcga cgtcgatgag   183660
atcctccact tttcggaact cggcgtggta ttcctgatgt ttatcatcgg tcttgagttg   183720
aatccctcca aactttggca actgcggcgt tcgattttg gcgtaggcgc ggcacaggtg    183780
ctgttaagcg cggcgttgct ggcgggatta ttgatgctga cggatttcgc ctggcaggcg   183840
gcggttgtcg gtggcattgg ccttgcgatg tcttcaactg caatggcgtt gcaattgatg   183900
cgtgagaaag ggatgaatcg cagcgaatcc gggcagctcg ggtttttcggt tctgctgttt   183960 caggatctgg cggtgatccc ggcactggcg ttagtgccgt tgttggcggg ttcggcagac   184020
gaacatttcg actggatgaa gatcggcatg aaggtgctgg cgtttgtcgg catgctgatt   184080
ggcgggcgct atttactgcg tccggtattc cgttttattg cagcttctgg cgtgcgggaa   184140
gtgttcaccg ccgcgacgct gctgttggtg ttgggttccg cattgtttat ggacgcgctg   184200
gggctgtcga tggcgctcgg tacgttatt gcgggcgtgc tgctggcgga aagtgaatat   184260
cgccatgaac tggaaacggc tatcgatccc ttcaaaggct tgctgctcgg tttgttcttt    184320
```

```
atctctgtcg gcatgtcgct caatctcggg gtgctttata cccatctgtt gtgggtagtg   184380
ataagcgtgg ttgtgctggt ggcggtgaaa attctcgtgt tgtatctgct ggcgcgattg   184440
tatggcgtgc gtagctcaga gcggatgcag tttgctggcg tgttgagtca gggcggtgag   184500
tttgcctttg tcctctttc taccgcttct tcacaacgtt tattccaggg cgaccagatg   184560
gcgctgttgc tggtgacggt gacgctttcc atgatgacca cgccgttgct gatgaagctg   184620
gtggataaat ggctatcccg ccagtttaac ggaccggaag aagaagacga aaaccgtgg   184680 gtcaacgatg ataaaccca ggtcattgtc gtgggcttcg ggcgttttgg tcaggtgatt   184740
ggtcgtttgc tgatggcaaa taaaatgcgc attaccgtgc tggagcggga tatcagcgcc   184800
gttaacctga tgcgtaaata tggctacaaa gtttattacg cgacgccac gcaggtcgat   184860 cttttacgtt ctgcgggtgc agaggccgct gagtctatcg tcattacctg taacgagccg   184920
gaagacacca tgaagctggt ggaaatatgc cagcagcact ttccgcattt gcatattctt   184980
gcgcgagcgc gcggacgtgt ggaagcgcat gagttattac aggcagggt gacgcagttt   185040 tcccgtgaaa cattctccag tgcgttagag ctggggcgca agacgctggt cacgcttggc   185100
atgcatccgc atcaggcaca gcgggcgcaa ctgcattttc gccgcctgga tatgcgaatg   185160
ctgcgggagt taatcccgat gcatgctgat accgtacaaa tttctcgcgc cagggaagcc   185220
cgacgcgaac tggaagagat tttccagcgt gaaatgcaac aagaacgacg ccagctggac   185280
ggctgggatg aatttgagta gagggtaaag atggcaatcc gaaaacgttt tattgcgggc   185340
gcaaaatgcc cggcctgtca ggcgcaggat tcaatggcga tgtggcgcga aaataatatt   185400
gatattgttg aatgtgttaa gtgcggacat cagatgcgag aagcagacaa agaagcccgc   185460
gatcacgttc gcaaagatga gcaagtgatc gggattttc atccggacta gcgatatgcg   185520
ccgagttttt ttaagctagt gagtacacgg ctgcagaatt ccgctacaat ctgcgccact   185580
attcttccca tgctcaggag atatcatgaa agtagcaaaa gacctggtgg tcagcctggc   185640
ctatcaggta cgtacagaag acggtgtgtt ggttgatgag tctccggtga gtgcgccgct   185700
ggactacctg catggtcacg gttccctgat ctctggcctg gaaacggcgc tggaaggtca   185760
tgaagttggc gacaaatttg atgtcgctgt tggcgcgaac gacgcttacg gtcagtacga   185820
cgaaaacctg gtgcaacgtg ttcctaaaga cgtatttatg ggcgttgatg aactgcaggt   185880
aggtatgcgt ttcctggctg aaactgacca gggtccggta ccggttgaaa tcactgcggt   185940
tgaagacgat cacgtcgtgg ttgatggtaa ccacatgctg ccggtcaga acctgaaatt   186000 caacgttgaa gttgtggcga ttcgcgaagc gaccgaagaa gaactggctc atggccacgt   186060
tcacggcgcg cacgatcatc accacgatca cgaccacgac ggttgctgcg gcggtcatgg   186120
ccacgatcac ggtcatgaac acggtggcga aggctgctgt ggcggtaaag gcaacggcgg   186180
ttgtggttgc cactaatacc gaaaaggtga caaaaaagcg gggaatcccc gcttttttta   186240
cgcctcaata atgtggcggt ggcgtttctt cagcctgcga cgcgatgttc gacggctggc   186300
tggcttttaa cttctcggtc agcagacgca gatgatcgcg cagtttcgcc atctccattt   186360
catgagcggt caccgtgacg ttcagttctt caatggtgat ttcctgaaaa gccagtcggc   186420
tctccagctc tgccaggcgt gcttccaatg ataaatcctg catgattcac ctcttttgtc   186480
gaatggtcgc cgcggattct acttaacttt gctgcccgag acagcactca tttcgcggtc   186540
atcgaaacta atttaaacaa aaagagtctg aaaatagatg ataatagggc gtgtctgtat   186600
gtagatttgt tcgacaacgc tttatagtac ccttctgata atagttaacc ctggggtgag   186660
atgccccgat cctggagata tggatgaaat cactgtttaa agtaacgctg ctggcgacca   186720
```

```
caatggccgt tgccctgcat gcaccaatca cttttgctgc tgaagctgca aaacctgcta   186780
caactgctga cagcaaagca gcgttcaaaa atgacgatca gaaatcagct tatgcactgg   186840
gtgcttcgct gggtcgttac atggaaaact ctcttaaaga acaagaaaaa ctgggcatca   186900
aactggataa agatcagctg atcgctggtg ttcaggatgc atttgctgat aagagcaaac   186960
tctccgacca agagatcgaa cagactctgc aagcattcga agctcgcgtg aagtcttctg   187020
ctcaggcgaa gatggaaaaa gacgcggctg ataacgaagc aaaaggtaaa gagtaccgcg   187080
agaaatttgc caaagagaaa ggtgtgaaaa cctcttcaac tggtctggtt tatcaggtag   187140
tagaagccgg taaaggcgaa gcaccgaaag acagcgatac tgttgtagtg aactacaaag   187200
gtacgctgat cgacggtaaa gagttcgaca actcttacac ccgtggtgaa ccgctttctt   187260
tccgtctgga cggtgttatc ccgggttgga cagaaggtct gaagaacatc aagaaaggcg   187320
gtaagatcaa actggttatt ccaccagaac tggcttacgg caaagcgggt gttccgggga   187380
tcccaccgaa ttctaccctg gtgtttgacg tagagctgct ggatgtgaaa ccagcgccga   187440
aggctgatgc aaagccggaa gctgatgcga aagccgcaga ttctgctaaa aataagcat   187500
taagaaccgc cgcctgacca ggcggcggtt tttttattac aggccggata taattagtgc   187560
tggaaagcgg aacctccgct gtattaattt agttacccgc atcattaatg agcctgccct   187620
gaaaagttaa cgacaggctc ctgaaaagga gtgttttttt tcatgtccag gtcgctttta   187680
accaacgaaa ccagtgagtt ggatttactg gatcaacgtc ctttcgacca gaccgatttt   187740
gatattctga aatcctacga agcggtggtg gacgggttag cgatgcttat tggctcccac   187800
tgtgaaatcg ttttgcactc tttgcaggat ctaaaatgtt cagccattcg cattgctaac   187860
ggtgaacata caggccggaa gattggttcg ccaattactg acctggcgct acgtatgctg   187920
cacgatatga cgggagcgga tagcagcgtt tctaaatgct actttactcg cgccaaaagc   187980
ggcgtattaa tgaagtccct gactatcgcg attcgtaacc gcgaacagcg tgtaattggt   188040
ctgctgtgca tcaatatgaa tcttgatgtt cccttctcgc agattatgag cacttttgtg   188100
ccgccagaaa ccccggatgt cggttcaagc gtcaactttg cctcttctgt gaagatctg    188160
gttacccaaa cgctggagtt caccatcgaa gaagtgaatg ccgatcgcaa tgtttctaat   188220
aacgccaaaa atcgtcagat cgtgctgaat ctctacgaga aagggatctt cgatattaaa   188280
gacgcgatca accaggttgc tgaccgcctg aacatctcca aacacactgt ctatctctac   188340
atccgccagt tcaaaagcgg tgatttccag gggcaagata agtaatgcgt tttgccatcg   188400
tggtgaccgg gccagcatac ggtacgcaac aggcgagtag tgcttttcag tttgcgcagg   188460
cgctgatagt agaaggccat gagttaagca gcgtctttt ctatcgggaa ggggtctata    188520
acgctaacca attgacctca ccggcaagtg acgaatttga ccttgtgcgc ggctggcaac   188580
agttgaatgc gcaacatggt gtggcgctga atatctgcgt agcggcagcg ttacgccgcg   188640
gtatcgtcga tgaaactgaa gcaggaaggc tgggctggc ttcgtcaaac cttcagccgg     188700
gatttacctt aagcggactt ggcgcgctgg cggaagcctc gctgacctgt gacagggtgg   188760
tacagttctg atgaaacgaa ttgcgtttgt tttttctact gcacctcatg gtacagctgc   188820
tggtcgggaa ggtttagatg ctttactggc aacttccgca ttaactgacg atctggccgt   188880
cttctttatt gctgatggcg ttttcagct gctgtcagga caaaagcccg atgcagtgct    188940
ggcgcgtgat tacattgcca ctttaaatt gttgggtctg tacgacattg aacagtgctg   189000
ggtttgtgcg gcttcactgc gcgaacgcgg gttagatccg cagacaccct tgttgtcga    189060
```

```
agccacgccg ctcgaagcag atgccttacg ccgcgaactc gccaactacg atgttatttt  189120
gaggttttga ggcgtttatg ctgcacacgt tacatcgttc accctggctg acggattttg  189180
ctgcgctgct gcgtctgctc agtgaaggag acgaactgct attattgcaa gatggcgtaa  189240
ctgccgcagt tgacggtaac cgctaccttg aaagtctgcg taatgcccc attaaggtct  189300 atgccctgaa cgaagacctt attgcccgcg gtttgactgg tcaaatttcg aacgacatca  189360
ttcccattga ctatactgat ttcgtcagac ttacggttaa gcactccagc cagatggcct  189420
ggtgatggcg ggatcgttgt atatttcttg acaccttttc ggcatcgccc taaaattcgg  189480
cgtcctcata ttgtgtgagg acgttttatt acgtgtttac gaagcaaaag ctaaaaccag  189540
gagctattta atggcaacag ttaaccagct ggtacgcaaa ccacgtgctc gcaaagttgc  189600
gaaaagcaac gtgcctgcgc tggaagcatg cccgcaaaaa cgtggcgtat gtactcgtgt  189660
atatactacc actcctaaaa aaccgaactc cgcgctgcgt aaagtatgcc gtgttcgtct  189720
gactaacggt ttcgaagtga cttcctacat cggtggtgaa ggtcacaacc tgcaggagca  189780
ctccgtgatc ctgatccgtg gcggtcgtgt taaagacctc ccgggtgttc gttaccacac  189840
cgtacgtggt gcgcttgact gctccggcgt taaagaccgt aagcaggctc gttccaagta  189900
tggcgtgaag cgtcctaagg cttaatggtt ctccgttaag taaggccaaa cgttttaact  189960
taaatgtcaa actaaactcg tagagttttg acaatcctg aattaacaac ggagtatttc  190020
catgccacgt cgtcgcgtca ttggtcagcg taaaattctg ccggatccga agttcggatc  190080
agaactgctg gctaaatttg taaatatcct gatggtagat ggtaaaaaat ctactgctga  190140
atctatcgta tacagcgcgc tggagaccct ggctcagcgc tctggtaaat ctgaactgga  190200
agcattcgaa gtagctctcg aaaacgtgcg cccgactgta gaagttaagt ctcgccgcgt  190260
tggtggttct acttatcagg taccagttga agtccgtccg gttcgtcgta atgctctggc  190320
aatgcgttgg atcgttgaag ctgctcgtaa acgcggtgat aaatccatgg ctctgcgcct  190380
ggcgaacgaa ctttctgatg ctgcagaaaa caaaggtact gcagttaaga aacgtgaaga  190440
cgttcaccgt atggccgaag ccaacaaggc gttcgcacac taccgttggt aatcccttcg  190500
gagttttagt caccaggcgg gcgcttccag taagcagccc gctttgggct acttaaattg  190560
aacgcctaaa agataaacga ggaaacaaat ggctcgtaca acacccatcg cacgctaccg  190620
taatatcggt atcagtgcgc acatcgacgc cggtaaaacc actactaccg aacgtattct  190680
gttctacacc ggtgtaaacc ataaaatcgg tgaagttcat gacggcgctg caaccatgga  190740
ctggatggag caggagcagg aacgtggtat taccatcact tccgctgcga ctactgcatt  190800
ctggtctggt atggctaagc agtatgagcc gcatcgcatc aacatcatcg acaccccggg  190860
gcacgttgac ttcacaatcg aagtagaacg ttccatgcgt gttctcgatg gtgcggtaat  190920
ggtttactgc gcagttggtg gtgttcagcc gcagtctgaa accgtatggc gtcaggcaaa  190980
caaatataaa gttccgcgca ttgcgttcgt taacaaaatg gaccgcatgg gtgcgaactt  191040
cctgaaagtt gttaaccaga tcaaaacccg tctgggcgcg aacccggttc cgctgcagct  191100
ggcgattggt gctgaagaac atttcaccgg tgttgttgac ctggtgaaaa tgaaagctat  191160
caactggaac gacgctgacc agggcgtaac cttcgaatac gaagatatcc cggcagacat  191220
ggttgaactg gctaacgaat ggcaccagaa cctgatcgaa tccgcagctg aagcttctga  191280
agagctgatg gaaaaatacc tgggtggtga agaactgact gaagcagaaa tcaaaggtgc  191340
tctgcgtcag cgcgttctga acaacgaaat catcctggta acctgtggtt ctgcgttcaa  191400
gaacaaaggt gttcaggcga tgctggatgc ggtaattgat tacctgccat ccccggttga  191460
```

-continued

```
cgtacctgcg atcaacggta tcctggacga cggtaaagac actccggctg aacgtcacgc   191520
aagtgatgac gagccgttct ctgcactggc gttcaaaatc gctaccgacc cgtttgttgg   191580
taacctgacc ttcttccgtg tttactccgg tgtggttaac tctggtgata ccgtactgaa   191640
ctccgtgaaa gctgcacgtg agcgtttcgg tcgtatcgtt cagatgcacg ctaacaaacg   191700
tgaagagatc aaagaagttc gcgcgggcga catcgctgct gctatcggtc tgaaagacgt   191760
aaccactggt gacaccctgt gtgacccgga tgcgccgatc attctggaac gtatggaatt   191820
ccctgagccg gtaatctcca tcgcagttga accgaaaacc aaagctgacc aggaaaaaat   191880
gggtctggct ctgggccgtc tggctaaaga agacccgtct ttccgtgtat ggactgacga   191940
agaatctaac cagaccatca tcgcgggtat gggcgaactg cacctcgaca tcatcgttga   192000
ccgtatgaag cgtgaattca acgttgaagc gaacgtaggc aaaccgcagg ttgcttaccg   192060
tgaaactatc cgccagaaag ttaccgatgt tgaaggtaaa cacgcgaaac agtctggtgg   192120
tcgtggtcag tatggtcatg ttgttatcga catgtacccg ctggagccgg ttcaaacccc   192180
gaaaggctac gagttcatca cgacattaa aggtggtgta atccctggcg aatacatccc   192240
ggccgttgat aaaggtatcc aggaacagct gaaagcaggt ccgctggcag gctacccggt   192300
agtagacatg ggtattcgtc tgcacttcgg ttcttaccat gacgttgact cctctgaact   192360
ggcgtttaaa ctggctgctt ctatcgcctt taaagaaggc tttaagaaag cgaaaccagt   192420
tctgcttgag ccgatcatga aggttgaagt agaaactccg gaagagaaca ccggtgacgt   192480
tatcggtgac ttgagccgtc gtcgtggtat gctcaaaggt caggaatctg aagttactgg   192540
cgttaagatc cacgctgaag taccgctgtc tgaaatgttc ggatacgcaa ctcagctgcg   192600
ttctctgacc aaaggtcgtg catcatacac tatggaattc ctgaagtatg atgaagcgcc   192660
gagtaacgtt gctcaggccg taattgaagc ccgtggtaaa taagcctaag ggttaatacc   192720
aaagtcccgt gctctctcct gaaggggaga gcactatagt aaggaatata gccgtgtcta   192780
aagaaaaatt tgaacgtaca aaaccgcacg ttaacgttgg tactatcggc acgttgacc   192840 acggtaaaac tactctgacc gctgcaatca ccaccgtact ggctaaaacc tacggcggtg   192900
ctgctcgt                                                             192908
```

<210> SEQ ID NO 2
<211> LENGTH: 210
<212> TYPE: PRT
<213> ORGANISM: Escherichia coli

<400> SEQUENCE: 2

```
Met Val Leu Gly Lys Pro Gln Thr Asp Pro Thr Leu Glu Trp Phe Leu
1               5                   10                  15

Ser His Cys His Ile His Lys Tyr Pro Ser Lys Ser Thr Leu Ile His
                20                  25                  30

Gln Gly Glu Lys Ala Glu Thr Leu Tyr Tyr Ile Val Lys Gly Ser Val
            35                  40                  45

Ala Val Leu Ile Lys Asp Glu Glu Gly Lys Glu Met Ile Leu Ser Tyr
        50                  55                  60

Leu Asn Gln Gly Asp Phe Ile Gly Glu Leu Gly Leu Phe Glu Glu Gly
65                  70                  75                  80

Gln Glu Arg Ser Ala Trp Val Arg Ala Lys Thr Ala Cys Glu Val Ala
                85                  90                  95

Glu Ile Ser Tyr Lys Lys Phe Arg Gln Leu Ile Gln Val Asn Pro Asp
            100                 105                 110
```

Ile Leu Met Arg Leu Ser Ala Gln Met Ala Arg Arg Leu Gln Val Thr
            115                 120                 125

Ser Glu Lys Val Gly Asn Leu Ala Phe Leu Asp Val Thr Gly Arg Ile
    130                 135                 140

Ala Gln Thr Leu Leu Asn Leu Ala Lys Gln Pro Asp Ala Met Thr His
145                 150                 155                 160

Pro Asp Gly Met Gln Ile Lys Ile Thr Arg Gln Glu Ile Gly Gln Ile
                165                 170                 175

Val Gly Cys Ser Arg Glu Thr Val Gly Arg Ile Leu Lys Met Leu Glu
            180                 185                 190

Asp Gln Asn Leu Ile Ser Ala His Gly Lys Thr Ile Val Val Tyr Gly
            195                 200                 205

Thr Arg
    210

<210> SEQ ID NO 3
<211> LENGTH: 70
<212> TYPE: DNA
<213> ORGANISM: Artificial Sequence
<220> FEATURE:
<223> OTHER INFORMATION: Primer

<400> SEQUENCE: 3
ggcgttatct ggctctggag aaagcttata acagaggata accgcgcatg tcgagtgtga    60
cggaagatca                                                          70

<210> SEQ ID NO 4
<211> LENGTH: 69
<212> TYPE: DNA
<213> ORGANISM: Artificial Sequence
<220> FEATURE:
<223> OTHER INFORMATION: Primer

<400> SEQUENCE: 4
ctaccaggta acgcgccact ccgacgggat taacgagtgc cgtaaacgac ccttagccat    60
ttgcctgct                                                           69

<210> SEQ ID NO 5
<211> LENGTH: 2830
<212> TYPE: DNA
<213> ORGANISM: Artificial Sequence
<220> FEATURE:
<223> OTHER INFORMATION: mutated gene sequence

<400> SEQUENCE: 5
ggcgttatct ggctctggag aaagcttata acagaggata accgcgcatg tcgagtgtga    60
cggaagatca cttcgcagaa taaataaatc ctggtgtccc tgttgatacc gggaagccct   120
gggccaactt ttggcgaaaa tgagacgttg atcggcacgt aagaggttcc aactttcacc   180
ataatgaaat aagatcacta ccgggcgtat tttttgagtt atcgagattt tcaggagcta   240
aggaagctaa aatggagaaa aaaatcactg gatataccac cgttgatata tcccaatggc   300
atcgtaaaga acattttgag gcatttcagt cagttgctca atgtacctat aaccagaccg   360
ttcagctgga tattacggcc ttttttaaaga ccgtaaagaa aaataagcac aagttttatc   420
cggcctttat tcacattctt gcccgcctga tgaatgctca tccggaattc cgtatggcaa   480
tgaaagacgg tgagctggtg atatgggata gtgttcaccc ttgttacacc gttttccatg   540
agcaaactga aacgttttca tcgctctgga gtgaatacca cgacgatttc cggcagtttc   600

```
tacacatata ttcgcaagat gtggcgtgtt acggtgaaaa cctggcctat ttccctaaag      660
ggtttattga gaatatgttt ttcgtctcag ccaatccctg ggtgagtttc accagttttg      720
atttaaacgt ggccaatatg gacaacttct tcgcccccgt tttcaccatg ggcaaatatt      780
atacgcaagg cgacaaggtg ctgatgccgc tggcgattca ggttcatcat gccgtttgtg      840
atggcttcca tgtcggcaga atgcttaatg aattacaaca gtactgcgat gagtggcagg      900
gcggggcgta attttttaa ggcagttatt ggtgcccta aacgcctggt gctacgcctg       960
aataagtgat aataagcgga tgaatggcag aaattcgaaa gcaaattcga cccggtcgtc     1020
ggttcagggc agggtcgtta aatagccgct agatctaagt aaatcgcgcg ggtttgttac     1080
tgataaagca ggcaagacct aaaatgtgta agggcaaag tgtatacttt ggcgtcaccc      1140
cttacatatt ttaggtcttt ttttattgtg cgtaactaac ttgccatctt caaacaggag     1200
ggctggaaga agcagaccgc taacacagta cataaaaag gagacatgaa cgatgaacat      1260
caaaaagttt gcaaaacaag caacagtatt aacctttact accgcactgc tggcaggagg     1320
cgcaactcaa gcgtttgcga agaaacgaa ccaaaagcca tataaggaaa catacggcat      1380
ttcccatatt acacgccatg atatgctgca aatccctgaa cagcaaaaaa atgaaaaata     1440
tcaagttcct gaattcgatt cgtccacaat taaaaatatc tcttctgcaa aaggcctgga     1500
cgtttgggac agctggccat acaaaacgc tgacggcact gtcgcaaact atcacggcta      1560
ccacatcgtc tttgcattag ccggagatcc taaaaatgcg gatgacacat cgatttacat     1620
gttctatcaa aaagtcggcg aaacttctat tgacagctgg aaaaacgctg gccgcgtctt     1680
taaagacagc gacaaattcg atgcaaatga ttctatccta aaagaccaaa cacaagaatg     1740
gtcaggttca gccacattta catctgacgg aaaaatccgt ttattctaca ctgatttctc     1800
cggtaaacat tacggcaaac aaacactgac aactgcacaa gttaacgtat cagcatcaga     1860
cagctctttg aacatcaacg gtgtagagga ttataaatca atctttgacg gtgacggaaa     1920
aacgtatcaa aatgtacagc agttcatcga tgaaggcaac tacagctcag cgacaaccaa     1980
tacgctgaga gatcctcact acgtagaaga taaaggccac aaatacttag tatttgaagc     2040
aaacactgga actgaagatg gctaccaagg cgaagaatct ttatttaaca aagcatacta     2100
tggcaaaagc acatcattct tccgtcaaga aagtcaaaaa cttctgcaaa gcgataaaaa     2160
acgcacggct gagttagcaa acggcgctct cggtatgatt gagctaaacg atgattacac     2220
actgaaaaaa gtgatgaaac cgctgattgc atctaacaca gtaacagatg aaattgaacg     2280
cgcgaacgtc tttaaaatga acggcaaatg gtacctgttc actgactccc gcggatcaaa     2340
aatgacgatt gacggcatta cgtctaacga tatttacatg cttggttatg tttctaattc     2400
tttaactggc ccatacaagc cgctgaacaa aactggcctt gtgttaaaaa tggatcttga     2460
tcctaacgat gtaaccttta cttactcaca cttcgctgta cctcaagcga aggaaacaa     2520 tgtcgtgatt acaagctata tgacaaacag aggattctac gcagacaaac aatcaacgtt     2580
tgcgccaagc ttcctgctga acatcaaagg caagaaaaca tctgttgtca agacagcat     2640 ccttgaacaa ggacaattaa cagttaacaa ataaaaacgc aaagaaaat gccgatatcc      2700 tattggcatt ttctttttatt tcttatcaac ataaggtga atcccatatg aactatataa      2760
aagcaggcaa atggctaagg gtcgtttacg gcactcgtta atcccgtcgg agtggcgcgt     2820
tacctggtag                                                            2830
```

<210> SEQ ID NO 6

```
<211> LENGTH: 19
<212> TYPE: DNA
<213> ORGANISM: Artificial Sequence
<220> FEATURE:
<223> OTHER INFORMATION: Primer

<400> SEQUENCE: 6
ggcgttatct ggctctgga                                                19

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
gcaatgcggt ccgtcacgtc                                               20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
gacgtgacgg accgcattgc                                               20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ctaccaggta acgcgccact                                               20

<210> SEQ ID NO 10
<211> LENGTH: 633
<212> TYPE: DNA
<213> ORGANISM: Artificial Sequence
<220> FEATURE:
<223> OTHER INFORMATION: mutated gene sequence

<400> SEQUENCE: 10
atggtgcttg gcaaaccgca aacagacccg actctcgaat ggttcttgtc tcattgccac    60
attcataagt acccatccaa gagcacgctt attcaccagg gtgaaaaagc ggaaacgctg   120
tactacatcg ttaaaggctc tgtggcagtg ctgatcaaag acgaagaggg taaagaaatg   180
atcctctcct atctgaatca gggtgatttt attggcgaac tgggcctgtt tgaagagggc   240
caggaacgta gcgcatgggt acgtgcgaaa accgcctgtg aagtggctga aatttcgtac   300
aaaaaatttc gccaattgat tcaggtaaac ccggacattc tgatgcgtct gtctgcacag   360
atggcgcgtc gtctgcaagt cacttcagag aaagtgggca acctggcgtt cctcgacgtg   420
acggaccgca ttgcacagac tctgctgaac ctggcaaaac aaccagatgc tatgactcac   480
ccggacggta tgcaaatcaa aattacccgt caggaaatcg gtcagattgt cggctgttct   540
cgtgaaaccg tgggacgcat tctgaagatg ctggaagatc agaacctgat ctccgcacac   600
ggtaaaacca tcgtcgttta cggcactcgt taa                               633
```

<210> SEQ ID NO 11
<211> LENGTH: 210
<212> TYPE: PRT
<213> ORGANISM: Artificial Sequence
<220> FEATURE:
<223> OTHER INFORMATION: mutated protein
<220> FEATURE:
<221> NAME/KEY: MISC_FEATURE
<222> LOCATION: (142)..(142)
<223> OTHER INFORMATION: wherein Xaa is selected from the group
      consisting of D, P, H, and conservative substitutions thereof

<400> SEQUENCE: 11

Met Val Leu Gly Lys Pro Gln Thr Asp Pro Thr Leu Glu Trp Phe Leu
1               5                   10                  15

Ser His Cys His Ile His Lys Tyr Pro Ser Lys Ser Thr Leu Ile His
                20                  25                  30

Gln Gly Glu Lys Ala Glu Thr Leu Tyr Tyr Ile Val Lys Gly Ser Val
            35                  40                  45

Ala Val Leu Ile Lys Asp Glu Glu Gly Lys Glu Met Ile Leu Ser Tyr
        50                  55                  60

Leu Asn Gln Gly Asp Phe Ile Gly Glu Leu Gly Leu Phe Glu Glu Gly
65                  70                  75                  80

Gln Glu Arg Ser Ala Trp Val Arg Ala Lys Thr Ala Cys Glu Val Ala
                85                  90                  95

Glu Ile Ser Tyr Lys Lys Phe Arg Gln Leu Ile Gln Val Asn Pro Asp
            100                 105                 110

Ile Leu Met Arg Leu Ser Ala Gln Met Ala Arg Arg Leu Gln Val Thr
        115                 120                 125

Ser Glu Lys Val Gly Asn Leu Ala Phe Leu Asp Val Thr Xaa Arg Ile
130                 135                 140

Ala Gln Thr Leu Leu Asn Leu Ala Lys Gln Pro Asp Ala Met Thr His
145                 150                 155                 160

Pro Asp Gly Met Gln Ile Lys Ile Thr Arg Gln Glu Ile Gly Gln Ile
                165                 170                 175

Val Gly Cys Ser Arg Glu Thr Val Gly Arg Ile Leu Lys Met Leu Glu
            180                 185                 190

Asp Gln Asn Leu Ile Ser Ala His Gly Lys Thr Ile Val Val Tyr Gly
        195                 200                 205

Thr Arg
    210

<210> SEQ ID NO 12
<211> LENGTH: 40227
<212> TYPE: DNA
<213> ORGANISM: Escherichia coli

<400> SEQUENCE: 12
gggccgggca gggcgatgtc ggtttcaccg ggaaggacct ttgcaccgag caggggattg    60
accggatggc cggacgtcac tccgccgggg cacaccgaac aggccacgcc ggtgggggca   120
ccaatgcgca ccccggctga accctgaaca atgctaccgc catactgcgt catgtcgccc   180
tgacgcgctg ccggttttcc gctcatctgc tcatccttgt tttatcgggt tatttgtctg   240
cttccaggca aaaccctaca gatttataag aaagccttaa gtgagatatc catcagatag   300
aaacaattag gaaatatttt atatcaccat gataaatatg tgatttattt ggaagtaaca   360
aaccatcaac attttctgcc cttttcccca tcaccaggcc atactgatat ttttcctcgc   420
acaaaggact cggcatgaaa ctcgtcggta gctacaccag cccgtttgta cgcaaacttt   480

| | |
|---|---|
| ctattctgtt gttagaaaag ggcataactt tcgaatttat taatgaactg ccctataacg | 540 |
| cggacaacgg cgtggcgcaa tttaacccgt taggaaaagt gccggtgctg gtgaccgaag | 600 |
| agggcgaatg ttggtttgat tcgccgatca tcgctgaata tattgaatta atgaatgtcg | 660 |
| ctccggcgat gttgccgcgc gatccgctgg agtcgttgcg ggtgcgcaaa attgaggcac | 720 |
| tggcggatgg cattatggat gccgggctgg tatcggtgcg tgaacaggcg cgtccagcgg | 780 |
| cgcagcagtc tgaagatgaa ttgttacgcc agcgggagaa aatcaaccgc agtctggatg | 840 |
| tgctggaagg atatctggtc gatggcacac tcaaaaccga tacggtcaat ctggcgacta | 900 |
| tcgccattgc ctgtgccgtc ggatatctca atttccgccg cgttgcgcca ggttggtgtg | 960 |
| tcgaccgccc acacttagtc aaactggtcg aaaacctgtt tagccgcgaa agttttgctc | 1020 |
| gcaccgaacc gccaaaggct tgatgcgcga tatgtcctcc tgacccatct cacgttacaa | 1080 |
| tccgtggtta tgttaaacgc ccttctccgt gtgagagggc cttgatcagc caggtttcct | 1140 |
| atgacaaccg aaacgcgttc cctctatagt caacttccgg ctattgatcg cttattgcgc | 1200 |
| gatagctcct tcctttcttt gcgtgatact tatggtcaca cccgcgtggt ggaattgttg | 1260 |
| cgtcagatgc tcgacgaagc gcgagaagtg attcgtggca gccagacgct gcctgcgtgg | 1320 |
| tgtgaaaact gggcgcaaga agtcgatgcc cggttgacga agaagcgca gagcgcgctg | 1380 |
| cgtccggtga tcaacctgac gggaaccgtg ctgcatacca accttggacg agctttacag | 1440 |
| gcggaagccg cggtggaagc cgttgcgcag gctatgcgtt cgccagtgac cctcgagtac | 1500 |
| gatctggacg acgccggacg cggacatcgc gatcgggcgc tggcgcaact gctgtgccgt | 1560 |
| attacggggg cggaagatgc ctgtatcgtc aataacaatg cggcggcggt gttattgatg | 1620 |
| ttggcggcca ctgccagcgg gaaagaggtg gtagtatctc gcggcgaatt ggtggagatt | 1680 |
| ggcggcgcgt ttcgtattcc cgatgttatg cgtcaggcag gttgcaccct acacgaagta | 1740 |
| gggaccacca accgcacgca cgcgaatgat tatcgtcagg cggtgaatga aaataccgca | 1800 |
| ctgttgatga aagtacatac cagtaactac agcattcagg ggttcaccaa agcgatagat | 1860 |
| gaagcggaac tggtggcgct cggcaaagag ctggatgttc ccgtagtgac tgatttaggc | 1920 |
| agtggctcgc tggtcgatct tagccagtac ggtttgccga aagagccaat gccgcaggag | 1980 |
| ttgattgcgg cgggcgtcag tctggtgagt ttctccggcg acaagttgtt aggcgggccg | 2040 |
| caggcaggaa ttattgttgg taaaaagag atgatcgccc gcctgcaaag ccacccgctg | 2100 |
| aagcgtgcat acgcgcgga taaaatgacc ctcgcggcgc tggaagccac gttgtgtctt | 2160 |
| tatttacacc ctgaagctct gagtgaaaaa ttaccgaccc tgcgcctgct tacccgcagc | 2220 |
| gcagaggtca ttcaaatcca ggcacaacgt ttacaggctc cccttgccgc acattacggc | 2280 |
| gcggagtttg cggtacaggt tatgccatgt ctttcgcaga ttggcagtgg ttcgctgccg | 2340 |
| gttgatcgcc tgccgagcgc ggcattaacg tttacacccc atgatggacg cggtagccac | 2400 |
| cttgagtcat tagccgcccg ctggcgtgaa ttgccagtgc cggtgattgg tcgtattat | 2460 |
| gacggacgat tgtggctgga tttacgctgc cttgaagatg agcaacggtt tttggagatg | 2520 |
| ttgttgaaat gattattgcg actgccggac acgttgacca cggcaaaaca accttattgc | 2580 |
| aggcgattac tggcgtaaat gctgaccgtc tgccggaaga aaaaaagcgc ggcatgacca | 2640 |
| tcgatctcgg ctatgcctac tggccgcagc cggatggtcg cgtgcctggt tttatcgacg | 2700 |
| tacccggtca tgaaaagttt cttttccaaca tgctggcggg cgttggtggt atcgatcacg | 2760 |
| cgctgttggt ggtggcgtgc gatgacgcg tgatggcgca gacccgtgag catctggcga | 2820 |

```
tttt gcagct gaccggtaac ccgatgctga cagtggcgct gaccaaggcc gatcgcgtgg    2880
acgaagcgcg tgttgatgag gttgaacgcc aggtaaagga ggtgctgcgg gaatacggtt    2940
ttgctgaggc aaaactgttt atcaccgcag caaccgaagg tcggggaatt gatgccctgc    3000
gcgagcatct gcttcagttg ccggaacgcg agcacgccag ccaacatagt ttccgcctcg    3060
ctattgaccg cgcatttacc gtaaaaggtg ccgggctggt cgtcaccggt acggcgttaa    3120
gcggggaagt gaaggtaggc gattcactct ggctgactgg tgtaaataaa ccgatgcgtg    3180
tacgtgcgct gcatgcacaa aaccagccaa cagaaaccgc ccatgccggg cagcgtatcg    3240
cgcttaacat cgcgggtgat gcggaaaaag agcagattaa ccgtggcgac tggctgcttg    3300
ccgatgcgcc gccagagccg ttcacacggg tgattgtcga gcttcaaacc catacgccgc    3360
tgacccagtg gcagccgctg catattcacc acgccgccag ccacgttacg ggacgcgttt    3420
cgctgctgga agataacctt gccgagctgg tgttcgacac gccgctgtgg ctggcggata    3480
acgatcgctt agtgctgcgc gatatctcgg cccgcaacac gctggcgggg gcgcgtgtgg    3540
tgatgcttaa cccgccgcgt cgcggtaaac gtaagccgga atatctgcaa tggctggcgt    3600
ctcttgcacg ggcgcagagc gatgccgatg cgttatctgt tcatctggaa cgcggcgcgg    3660
ttaaccttgc ggatttcgcc tgggcgcgcc agctcaacgg cgaagggatg cgcgaattgc    3720
tgcaacagcc tggctatatt caggctggtt atagcttgtt gaatgcgccg gttgccgctc    3780
gctggcaacg gaaaattctc gacacattag cgacttatca tgagcaacat cgcgatgaac    3840
ctgggcctgg gcgcgaacgt ctgcgacgta tggcgttgcc aatggaagat gaagcgctag    3900
tactgttgct gattgaaaag atgcgcgaaa gcggcgacat cctcagtcat cacgttggc    3960
tgcatctgcc ggatcacaaa gcgggcttca gcgaagagca gcaggccatc tggcaaaaag    4020
cagagccgct gtttggtgac gagccgtggt gggtgcgtga tctggcaaaa gagacgggta    4080
ccgacgagca ggcaatgcgc ctgacgctac gccaggcggc gcagcaagga ataattaccg    4140
cgatcgtcaa agatcgttat taccgtaacg atcggattgt cgaatttgcc aatatgatcc    4200
gcgatctcga tcaggagtgt ggttcaacct gcgcggcgga tttccgcgat cgcttaggcg    4260
taggccgaaa gctggcaatt cagattctgg aatattttga ccgcattggc tttacgcgtc    4320
gtcgtggaaa tgatcatta ttgcgcgacg cattattatt tccggaaaaa taggaaatg    4380
attaattaat tttaaaata aattaataca aatttcttat gattttaaaa aaagcacatt    4440
gtttaatgaa tacaatgtgc ttttattag attaattttg ataatcaata ataatgatca    4500
tgttttcgaa tgaaaatcct cagtaagctg cccaccctt tttacacttt caggagtgtg    4560
ttatggcatc ttcaactttc tttattcctt ctgtgaatgt catcggcgct gattcattga    4620
ctgatgcaat gaatatgatg gcagattatg gatttacccg taccttaatt gtcactgaca    4680
gtatgttaac gaaattaggt atggcgggcg atgtgcaaaa agcactggaa gaacgcaata    4740
tttttagcgt tatttatgat ggcacccaac ctaaccccac cacggaaaac gtcgccgcag    4800
gtttgaaatt acttaaagag aataattgcg atagcgtgat ctccttaggc ggtggttctc    4860
cacacgactg cgcaaaaggt attgcgctgg tggcagccaa tggcggcgat attcgcgatt    4920
acgaaggcgt tgaccgctct gcaaaaccgc agctgccgat gatcgccatc aacaccactg    4980
cgggcacggc ctctgaaatg acccgtttct gcatcatcac tgacgaagcg cgtcatatca    5040
aaatggcgat tgttgataaa catgtcactc cgctgctttc tgtcaatgac tcctctctga    5100
tgattggtat gccgaagtca ctgaccgccg caacgggtat ggatgcctta acgcacgcta    5160
tcgaagcata tgtttctatt gccgccacgc cgatcactga cgcttgtgca ctgaaagccg    5220
```

```
tgaccatgat tgccgaaaac ctgccgttag ccgttgaaga tggcagtaat gcgaaagcgc    5280
gtgaagcaat ggcttatgcc cagttccttg ctggtatggc gttcaataat gcttctctgg    5340
gttatgttca tgcgatggcg caccagctgg gcggtttcta caacctgcca cacggtgtat    5400
gtaacgccgt tttgctgccg catgttcagg tattcaacag caaagtcgcc gccgcacgtc    5460
tgcgtgactg tgccgctgca atgggcgtga acgtgacagg taaaaacgat gcggaaggtg    5520
ctgaagcctg cattaacgcc atccgtgaac tggcgaagaa agtggatatc ccggcaggcc    5580
tacgcgacct gaacgtgaaa gaagaagatt cgcggttct ggcgactaat gccctgaaag    5640
atgcctgtgg ttttactaac ccgatccagg caactcacga agaaattgtg gcgatttatc    5700
gcgcagcgat gtaatcatca tttccacaac ggctggcaaa ttgtcagccg cttttcaac    5760 tatctctgta acccttgccc gtaaattcgt gatagctgtc gtaaagctgt taccgactgg    5820
cgaagatttc gccagtcacg tctacccttg ttatacctca caccgcaagg agacgatcat    5880
gaccaataat cccccttcag cacagattaa gcccggcgag tatggtttcc ccctcaagtt    5940
aaaagcccgc tatgacaact ttattggcgg cgaatgggta gcccctgccg acggcgagta    6000
ttaccagaat ctgacgccgg tgaccgggca gctgctgtgc gaagtggcgt cttcgggcaa    6060
acgagacatc gatctggcgc tggatgctgc gcacaaagtg aaagataaat gggcgcacac    6120
ctcggtgcag gatcgcgcgg cgattctgtt taagattgcc gatcgaatgg aacaaaacct    6180
cgagctgtta gcgacagctg aaacctggga taacggcaaa cccattcgcg aaaccagtgc    6240
tgcggatgta ccgctggcga ttgaccattt ccgctatttc gcctcgtgta ttcgggcgca    6300
ggaaggtggg atcagtgaag ttgatagcga aaccgtggcc tatcatttcc atgaaccgtt    6360
aggcgtggtg gggcagatta tcccgtggaa cttcccgctg ctgatggcga gctggaaaat    6420
ggctcccgcg ctggcggcgg gcaactgtgt ggtgctgaaa cccgcacgtc ttaccccgct    6480
ttctgtactg ctgctaatgg aaattgtcgg tgatttactg ccgccgggcg tggtgaacgt    6540
ggtcaatggc gcaggtgggg aaattggcga atatctggcg acctcgaaac gcatcgccaa    6600
agtggcgttt accggctcaa cggaagtggg ccaacaaatt atgcaatacg caacgcaaaa    6660
cattattccg gtgacgctgg agttgggcgg taagtcgcca aatatcttct ttgctgatgt    6720
gatggatgaa gaagatgcct ttttcgataa agcgctggaa ggctttgcac tgtttgcctt    6780
taaccagggc gaagtttgca cctgtccgag tcgtgcttta gtgcaggaat ctatctacga    6840
acgctttatg gaacgcgcca tccgccgtgt cgaaagcatt cgcagcggta cccgctcga    6900 cagcgtgacg caaatgggcg cgcaggtttc tcacgggcaa ctggaaacca tcctcaacta    6960
cattgatatc ggtaaaaaag agggcgctga cgtgctcaca ggcggggcgg caagctgct    7020 ggaaggtgaa ctgaaagacg ctactacct cgaaccgacg attctgtttg gtcagaacaa    7080
tatgcgggtg ttccaggagg agatttttgg cccggtgctg gcggtgacca ccttcaaaac    7140
gatggaagaa gcgctggagc tggcgaacga tacgcaatat ggcctgggcg cgggcgtctg    7200
gagccgcaac ggtaatctgg cctataagat ggggcgcggc atacaggctg ggcgcgtgtg    7260
gaccaactgc tatcacgctt acccggcaca tgctgcgttt ggtggctaca acaatcagg    7320 tatcggtcgc gaaacccaca agatgatgct ggagcattac cagcaaacca agtgcctgct    7380
ggtgagctac tcggataaac cgttggggct gttctgatat aagaagctgg tcgcattggg    7440
tattcattgc ctgatgcgac gcttacgcgt cttatcatgc ctacgggaac ctgaccgtag    7500
gccggataag gcgtacacgc cgcatccggc ataaacaaag cgcacgttgt tacaatttac    7560
```

```
gttttaaacc tacgtgcgca ataacccaga ctacgccaac agaagtgcgt ttctggggcg    7620
tgttttgtca ggagtttaat ctcgcgtttc gatggtgagc gggcgaacca ggccgtaaat    7680
caccattggt gatccgaggc caatcagcaa taaacggtag ataattgaag gtttaatacg    7740
cttaatctgt actgtggatg ttttactgga gttattcatt agtttggcca atagttccac    7800
tatttcaata tgataaacct cgtcctgttg aaaaaccaga cagcacattt cagaaagtat    7860
ataaaaaaca atatgtcgtt atataaataa ggaaattgca ctgcatcatg gcatttcata    7920
atatgcgtta attgttcttt tttatattct ttgagggaaa tatgttcctg gactattttg    7980
cactgggagt gcttattttt gtatttctgg tgatattcta tgggattatt attttacatg    8040
atattcccta cctgattgct aaaaaacgta atcatcctca tgccgacgcc attcatgttg    8100
ctggttgggt gagtcttttt acgctgcatg ttatctggcc attttgtgg atttgggcca    8160
cgctttaccg cccggagcgg ggatgggaa tgcaaaacca tgactcctcc gttgtgcaac    8220
tacaacagcg tattgccggg ctggagaaac agctcgccga catcaaatcc tcttctgccg    8280
agtaatactt atggatttac tgattatttt gacctatgtg gcttttgcat gggcaatgtt    8340
taagatcttc aaaattcctg taaataaatg gaccattccc acagcggccc tgggtggcat    8400
atttattgtc agtggtttaa ttctgttaat gaactataac catccgtata ccttcaaagc    8460
gcaaaaagcg gttatttcta ttcctgttgt cccacaggtg acaggcgtgg tgatcgaagt    8520
gacggataag aaaaatacgc tgattaaaaa aggtgaggtg ctatttcgac tggacccgac    8580
gcgttatcag gcgcgggtgg atcggctgat ggcggatatc gttaccgcag aacataaaca    8640
gcgggcgttg ggcgcagagt tagatgagat ggcggcgaat actcagcagg caaaggccac    8700
gcgggataaa ttcgctaaag agtatcagcg ttacgcacgc ggcagccagg cgaaagtaaa    8760
cccgttttca gaacgcgata ttgatgtggc gcggcaaaat tatctggcgc aggaagcctc    8820
cgtaaagtca tcggcggcgg aacaaaaaca gatccagagc cagctggata gcctggtgtt    8880
gggtgaacat tctcaaatcg ccagcctgaa agcgcagctc gcggaagcaa aatataacct    8940
tgagcagacg atagtgcgtg cgccgagcga tggttatgtg acccaggtgc tgattcgtcc    9000
gggtacctat gccgcgtcgc tgccgctacg tccggtgatg tgtgtttatac ccgatcagaa    9060
acgacaaatt gtggcgcagt tccgtcagaa ctccttgctg cgactggccc ctggcgacga    9120
tgcggaagtg gtgtttaatg ctctgccagg taaggtattc agcggcaagc tggcagccat    9180
tagtccagct gttcccggcg gagcttatca gtcgaccggc accttacaga cgttaaacac    9240
agcgccgggt tcagatggcg ttatcgcgac cattgaactg gatgagcaca ctgatttgag    9300
cgctttacca gacggtattt acgcccaggt ggcggtctac tctgatcatt tcatccatgt    9360
ctcggtgatg cgcaaagtgc tattacgcat gaccagctgg gtgcattacc tttatctcga    9420
tcattaatct tcgctttccg ccgcttgttc aggccgcagt tgctgcgact gagcaagctg    9480
gtggcgaatt tcacgcagca tttcatccag cacatactgg acccgccagg gctggtattc    9540
ccgtttacgg aagatagcca ccagatccag ccaccattca tacgggtgct gaaagcaggg    9600
caccagcgtg ccgtcttgca gatcgctctg cacacttttg tctggcgcaa acacaatccc    9660
caggtgattt cgtgccagct ccagcgccga ttgcgtgtta tcgcaaacgt aatttccctt    9720
cacgcgataa tcccgcacct ctttactccc ggcgacgttg aagcgccaga tattcgcgtc    9780
atcaatcatc atcgagtcga tcaaaataca ggagtgatgt tcgagttcgt caggacggct    9840
aataggatgt ttctcaagat agcgctggct ggcataagcg gttacggcat attgggtaat    9900
aaaactggca accagcgatt catcttttgg tggagcgtag ctgattaaaa catcacaatc    9960
```

```
atcaggaaat tcgacgcctt cataaaaggc attacgctca agattgcagg tttttagcga    10020
taaggtgata tcaccgatat ctttaatttt atcgattaca tgtttggata aataggtaat    10080
tatgccggtt ggggcgtaga tggtgacccg accacgtttc tcatgcttat aatctgcaat    10140
aaaattatta agctgctcgt ttctgtccag catgtcgttg atgtacggta acagcgcggt    10200
accaaaaggt gtgagcatca gctgccgggt ggttcggtca aagactttta aacccacttt    10260
tgattcaaaa tcagcaagat atttgctgac gttggcctgt gcgatgccaa gtacagtcgc    10320
ggcatggctg atattttcac tggcagcgat taccgagata attttaact cccggtactt     10380 aagttgtaat tttgtcatcg caacagccca attatatata attttatata ttactatata    10440
aatatgaatc ttgcaccgga gaaattgtaa gcattactat gccgactctt ttttatctta    10500
ttttaaaatg gaataccgaa catgttaatt aaccgcaata ttgtggcgtt atttgcgttg    10560
ccttttatgg caagcgcaac tgcttctgaa ttatccattg gtgccggtgc ggcttataat    10620
gaatcgcctt atcgcggtta taatgaaaat acaaaggcaa ttcccctgat tagttatgaa    10680
ggtgattctt tttatgttcg tcagaccacg ttaggtttta ttctgtcgca aagtgaaaaa    10740
aatgaactta gcctgaccgc atcctggatg ccgctggaat ttgaccctgc cgataatgac    10800
gattatgcca tgcaacagct tgataagcgt gatagtacgg ctatggcggg ggttgcctgg    10860
tatcaccacg agcgttgggg aactgtgaaa gcctctgcgg ctgcgacgt tctgataac     10920 agcaacggct gggtggggga gctatcgatt ttccacaaaa tgcagatagg tcgcctgtcg    10980
ctgacacctg cgctgggcgt gctctattat gacgagaatt tcagtgacta ttactatggc    11040
atttcagaga gtgagtcccg tcgtagcggt ctggcaagtt attccgcgca ggatgcctgg    11100
gtgccctatg tcagcctgac ggcaaaaatac ccgataggag agcacgtcgt attgatggcg    11160
agtgcaggat acagcgagct gccggaagag attaccgaca gcccgatgat tgatcgtaat    11220
gagagtttta cctttgtcac cggcgtgagc tggcgttttt aattcaccgg tggatgtcgg    11280
tgcggctggt gctccgtcgt aatgccacaa aggttgttgc tctggattgc tctgttcata    11340 ccgggaaccct ggcgtctgaa tcaggatctt atggctgaac aatcccttgc cttcaaatgt   11400
cgtaaatggc gcatcggcgg gcagcaacag gttatgcagt gactcgacgt tgtcggcctg    11460
ctccatgcaa tacggtttaa tgacgttggc tatttccggc agattttcg caagcacacc     11520 ggtttaacgc cagcagcgtg gaagcggcgt tacagcaagg aacatatcaa ttcgtagtgc    11580
cggggcgatg aagcccggc gtgagggatt actgcccgta ataggcattg gccccatgct    11640
tacgcaggta gtgcttatcc agcagttcgt tttgcatcgt agggagctgc ggcgcaagct    11700
ggcgcgagaa taggcccata taggcgcatt cttcgagtac tacggcgtta tgcacggcat    11760
cggcggcgtt tttaccccat gcgaacgggc catgagaatg caccagcacc gccgggattt    11820
gtgccggact cctgccacgt tcttcgaagg tttcaatgat cacttcgccg gtctgatatt    11880
catattcgcc gttaatctcc tctgcggtca tctgtcgcgt gcaggggatg caccataga     11940 aataatcagc gtgcgtggtg ccccaggcgg ggagatccag cccggcctgc gaccagatgg    12000
tggcgtggcg tgagtgggta tgcacaatgc caccgatttc ggcgtagcga cggtaaagcg    12060
ccagatgcgt tggcgtgtcg gacgagggct ttttgctacc ttccaccacc ttgccgctgg    12120
ctatctcaac caccaccata tcgtcggcgg tcatcacgtc gtactcgacg ccggaaggtt    12180
tgattaccat ccattgccgc gtgtcgtcta ccgcgctgac attgcccag gtgaacgtca    12240 ccagatggtg agcgggaagc gccagattcg ccgccagcac gtcggctttc agttgctcta    12300
```

```
acatataaat ccagcctcct gcatacgcgc ttcaatccag cgccgcgcct gaatgatctc    12360
cagcaccggc tctttggctt tttcggtcca catctcaatc aggaaagaac cgcgatagtt    12420
cagttcatgc agcgttttga agatgccaac gaaatcgacg cagccttcgc caaacggcac    12480
atcacggaac tgtccggggc tttgccggt gactggctgg gtgtctttca ggtggatcgc     12540
ggcgatacgg tcaatgccca gtttcagttc ggcgggaaca tcattgcccc aggcgctgag    12600
gttgccgacg tccgggtaga cggtgaacca cggcgaggcg agcatctcgt cccatttttt    12660
ccatttgctg atggagttca taaacgctgt atccataatc tccaccgcca gcattacttg    12720
tgatgccgcc gcctgttcga ctgcccacgc cagcccttca gcaaaacgtt gccgggtgcc    12780
ttcgtcgtgg tcttcgtaat agacgtcata acctgccagc tggatggtgc gaatgccgag    12840
atcgcgcgcc aggcgaatcg ctttactcat gatttcccgc gcccgttcgc gcactgcctc    12900
gtcacggcta ccaaaaggaa agcgacgatg tgcggacagg cacatcgacg ggatcccaac    12960
acccgtttcg atcatcgcgg caaccagcga agtcctttgt gcggtgctcc agtcaagacg    13020
tgaaagccgt tcgtcggttt catccaccga catttcgaca aaatcaaaac cgcagctttt    13080
tgccagcacc agccgctccg gccaggagag atctttcgcc agcgcctttt cataaatccc    13140
taacggatga ttacgcacgc ttgcctcccc agatagcgtc gatttgcgca tggaaatcgc    13200
cagccacctg cgccggattt gctgagcctg ccagtgctcg cccggcaata aacgctttca    13260
cgcgaatatc tttaaacagc ggcaggtcag caggggtaat cccgccggta atggaaagct    13320
caaggccgat atcggaaagc gccttcatgc gtgccagatc ggcttcgccc cactgttgcc    13380
cgctggcctg tgcatcacga ccgtgatgat aaatcgcctg ccgcacgcca atacgatgcc    13440
agtcgcgggc gtcgtccagc gtccagttac cgaacagctc gatctgaatt tcaccaccgc    13500
agcgttgcgc catcgcgtgg ccttttttcca ccgtcgcgag cggtgcggcg cagatgatgg    13560
tcatccagtt agcgcctgcg ccaaatgcct gttgcgcgag cgtttcacca gcgtcggcga    13620
ccttccagtc ggcaacgatg atttgtcag ggcactgttc gcgcaaggct ttcaccgcgc    13680
caagcccttc gtttaaacag agaatggtgc ccgcttcgac aatatcgacg ctgtcttta    13740 actgcgtcac gtcgcgctgt gcggcttcaa gtgatgagtg gtcgagtgcc agttgcagaa    13800
gtggtcggct cataatatgt gctccttgat gcgggcgtga aagccctgaa gtgcggcaat    13860
gagatgctga tagcgttggt attttttgttg gtaaagctga tgggcggtca tatccggcag    13920
cagggtgcgt accgggtgct gtaagtcacg ttgagcttcg ctgaaatcgc gataaactcc    13980
ggtgccgaca cgggcggcaa gtgccgcgcc aaaacagccg gtttcttcca cctgcggcag    14040
ctcgatacgc agaccgctga cgtccgccag catttgcatc cagacatcgg agtgcgccgg    14100
gccgccagtg acgcgcaggg tgtgcacatc agtaaaacgt tcgcgcatcc ggttgaggtg    14160
ggtcatatgg ctgaacacca ccccttcata aatggcctgc aacaggtgtg cgcgggtgtg    14220
aatggcctgc atcccgtaga aaccgctggt catctcgagt ccggcgttgc tgccgtacag    14280
gaacggcagg aaaaagagat cgccaccggc cttcggcaag ctggcaacgg cctggttgat    14340
ctcatcaaac gagatttctc cccactgtgc ggtaaaccat tcgaggttgc cggaagaggt    14400
ggggctggct tcgtgaacga taaattcacc atcgttaacg tagcgaccat agacatacgg    14460
atgcgcttca ccgtcacgta aaccgcgggt tatgccgctg gtcaccgccc aggtgcccat    14520
caccgcatta agggtaaatt cgtcttcgat cccggcgcag agtgcggtgg aaaccacatc    14580
aaacaggccg ccgacaacgg gcgtacccgc tttcagaccg gtcagtacgg ctgtctgagc    14640
ggtgatctcc ccgcagattt cggcagatcc gacaacaggc ggcagggcgt gattgatttc    14700
```

```
agcaatcccc agccagtcgg tgaggcacgg gtcatattcc ccaagactca tgttgtagag    14760
gttggactcg gaaatattgc tctcttcaca gcctttgacg ccggttaaac accagcgcag    14820
gtagtcgtgc gtcatcatca cgcagccaat ttgcgcgtag cgttccggtt cgtgctcttt    14880
cagccagcgt aacagcgaca ccggatgccc ggtccacaag gtttgtcggg tcaacgggta    14940
gagttttccc gggatgccat cttcctgcca gcgacgaacg atttccatcg cccggcgatc    15000
cgaggacaaa atggcgttac cgagcggctt gttgttttta tccagcaaaa acaagccttt    15060
tccttgtgcg gagataccga taccgacaat tgttccccg ctaacgccgg aatgggtaag    15120
cagttcgcga atgacagcca tgcagcattg ccacagttct gccatatcgc gctctgccca    15180
acctggctgc gggcttaatg cgcacagcgg caggcgctgc acgcctgcct cccggccttc    15240
gcggtcatac agcccggctt tcagccagct accgccacaa tctaacccca gccagtattg    15300
cgtcatggtt tattgcacct catccacggc tttcagtaga tcagcaccct gcggaacatc    15360
ttttacaaac atgtcgcgga cctgagtacc cagtgcgtcg ctaaaggctt tgcggtcgag    15420
atcggtgatg acttccacgc ccgcttcttt catgccgtcg atgattttt gctgatcttc    15480 ggcaaccagt ttgcgctggt agttacccgc ttcctgcgca gatgaaatta gcgcttgctg    15540
gaactccggg cttaagccat caaacttcgc tttgttgatc accaccagaa gcggggaata    15600
ggcgtggtgc gtcagagaaa ggtacttctg cacttcgaaa aattttgctg accagacgac    15660
gttgatcggg tgttcctgag cgtcgatagt gcgggtttcc agcccggtat agacttcggc    15720
aaacggcatc gggatcgggt tagcgccaaa gactttgaat gcggcgatat tcatcgggct    15780
attgttggtg cgaattttca gccctttcag gtcggcgggg gttttaaccg gtgcgcgcga    15840
gttggtgaca tcgcgccagc cgttttccca gtaggccagt acttttagtc ctttaccttc    15900
aagtgaggct ttcagatcat caccgacttt gccgtcgagc gttttatgcg cgtgagcggt    15960
atcgcggaac aggaaaggga catcaagcaa gttcatcact ggtgataacc cggcaaagtt    16020
attcgagccg acatttcca tatcgatggt gccgccacgt acgccgctga tcatcgcctg    16080
cgcgttaccg agggtgctat ccggaaacaa ttttaatttc agctcgcctt tggttctctc    16140
ctgcaataaa tcattgaatt ttttcgccgc aatatgttgc gagtcggttt gtgaggtttc    16200
ataaccgaaa cgtaaagatt gcgccgccag agaagatgtg ctgaatgcag ccaggccagc    16260
aatgaataat gcgtaggtta cagagcgtaa tttcataata ttttccttt aattaatcca    16320 tttcaaaggg aggatgatga gatcgggaat aaaaacaaat acgactaata atgaatataa    16380
aaccaggacg taagggaaaa cgcctctgac tgcatcatcg aatttgagtt ttgccacccc    16440
tgaaataacg ttaagtacat taccgatagg cggtgtaatt aagccgattg agcagttaat    16500
gataaacatg acaccgaaat aaatcggatc gattcctgcc tctttaacta aaggcattaa    16560
taccggggta agaattaata ccgtcggcgt taaatccatg accatgccga caatcaggat    16620
agccaccata atgacgataa acagcagacg cggtgaatcg accaacggtt gcagtaaatc    16680
agaaaccatc atcggcagtt cagcaatggt aatcagccag gcggaaactt gtgccgaggc    16740
caccagaaac ataaccactg aggtggtttt cgccgcgcca atgagtacat gccaaagtgt    16800
ggcgaaggtc atttcacggt aaataactgt ggcgacaaac agcgcataga aagcagcaac    16860
ggccccggct tcggtagggg taaacagacc ggagcgaaac ccgccaataa tgatgactgg    16920
aagaaacagc gcccagatac cggagacaaa agagtgccag atttcctgca tcgttgcttt    16980
ttgctggcgg ggtaaattaa ggcgactggc ctgccaccac caggtaagca tcagcgttgc    17040
```

```
gcccatcatc atgccagggg caatgcccgc cataaacagc ttactgatgg ataatccgct    17100
ggaaacgccg aagataataa acggaatgga aggggggaata attggcgcga taatgccgcc    17160
agaggcaatc agcccccgccg cccggttgac cgggtagttg gcgctgcgca tcatcggcac    17220
cagtagagcg gcaacggcgg cggtatccgc aacggcagaa ccagaaaggc tcgccataat    17280
catagctgcc agcacgccga cgtagcccag cccgcctggt ttatgcccca ccagtttcat    17340
cggcaggtca acaatgcgtt ttgacaagcc gcccgcattc atgatttcac ccgcagcac    17400 aaagaacgga atcgccagca gggagaagct atcggctccg ttcaccagcg tttgtgccat    17460
gatctggaca tcaaacatgt ccagccgaaa cattaacgcc gccccgcaca acaacagtgc    17520
ccaggcaata ggcaaaccga tagcaatacc acccaacaga cagcccagaa aaatcagcac    17580
agccatgatt aagctccttg cggtggcgac gttagagaat tgctacgcgt gatgagttga    17640
tataaatgac gcagttcaaa gaatgcgata acgaggctgg tgggcagaca agcggcatac    17700
atcaggccga tgggtaaacc gaggatcggt gaataatcgc tccagtcctg aattgttttt    17760
agcgttgcgc cccaggccag tgcgccacaa ataaataaga ttaaggaatg ggtaaccaga    17820
gcgactcgtc gttgccatgc gggggagagt ttctccacca gaaaggtgac ctgaacgtgg    17880
gcgttatcca taaaagccac aatcgcgcca ataaatgtta accagacaaa taataacgt    17940 gacaattcat ctacagataa aatgcttgtc tgaaaccat atcttaaaat aatgtttata    18000
aacacaatac aggaaagtac ggcgagatta atcgccagta ttgcttcaag tatttttttc    18060
atagctattc cttgaggcta tgtctgtcat aattcaagtt gcatgtgcag caacctaaat    18120
tattaatata gttagagcaa taacattacc cagtcgttct ggcgtagacg attattcgat    18180
taattcagcg ccgttaatgc gactttaacc acaattttc gtatctcaga ggctgtttgc    18240
aaaatacaac ctggtcggtg aacatcctgc ggaaagaaaa ttgcgtagct gcccggtatc    18300
atttctataa atgattcatg ttcactgtca tgataaaaaa taatatcgcg ctgctctaat    18360
agtgattcgc tgacttattt atttcccgta tcaatagcaa tgccgatttt ctcttcaccc    18420
cacgccagaa actgaatatc gatataccga cgatgcactt ccggacggtt ttccaccgct    18480
tcgcgtgtgg ttaaatcgat aatttgcgca taaatatttt tgccgtcgat ttcgacaacg    18540
cccggctcca gggcgttgaa atcggtagcg cgcagaaaat cgagcgcctt ttcaatggcg    18600
gcgggcaaac ggcacggatt gggctgcgcg atatgtccaa aaatcatgac ttatctcctt    18660
ataacgcctg gattttggcc cacacgctgt catcaacggt aataccgtta cggcggtttt    18720
cggccagcag ggtagtaaat tcgtggccgg gtaagcggat ggcctggttt tcgtcagcgc    18780
gttcagcggt agtaacgtaa tccatgatac gttgcagctt ggcatcgcgg gtgggaccgt    18840
cgataagctt gtccacttca atggcaataa aaatttgtga aatgccgtat tcgtcgctgt    18900
tgtcctgggt gacttcggca accgatgcgc cgtcggaaag gagagtagcg atcatatcca    18960
gcacaatcga catgccagaa cctttccagt agcccatcgg caaaatgcgg cgattcttct    19020
cgataacgcc aggttctttg gtcaaattgc cctcatcatc aaagccacca tcgaccggga    19080
gctgacggcc cgccaggcgg ttaacttcta acatgccgta agagaacatc gacatcgaca    19140
tatcgaccat ggtgatcggc gtggaaggaa tggcgacgat cagcgggtta gtgccaatgc    19200
gacactcttt tgcgccccac ggcggcatta cggcgatgga gttggtccag caaatgccaa    19260
tatagccttt ttccgccgcc tgccagccgt agctgccgcc gcgcatccag tggttggcat    19320
tacgaagtgc caccagacca ataccgtgat cggcagccag ttcaatggcg cgatccatca    19380 tcttttcgc cgtcaggttg ccgatcgaac gctgggcatc ccactgttca attgcgccga    19440
```

-continued

```
ggctggttat acgtttgggt tgggcatcag gaatgatatc gccgttttcc agttgttgaa    19500
tgaaacgagg gaaacgatta acgccgtgag aataaacgcc ggattcggtg gtgcgggcga    19560
acatctctgc acaggcgtca gccgtttcgc tgtcaacgcc gcgtgaaatt aagacccgat    19620
taaaggctgc ttttaactgc tcaaatgtca ctttcatccc aggcttcctt gttttttga    19680
tcgctttttt ggcttaaaat ttcaatatgc gaaacttgat ttcaaatata tcgatcactt    19740
tttaacaaag caatctgatt gatgaatttc aaaagacata aaaatcaagt ggttataaat    19800
tatctgtcga gatcgtgaac tacggcacac tttgcgctac catcaggacg cgacaaaatg    19860
gggaaagaag tgatgggaaa aaagagaac gagatggcgc aggaaaaaga gcgtccagcc     19920
ggaagccaga gtctgtttcg cgggttgatg ctgattgaga ttttgagcaa ctatccaaac    19980
ggttgtccgt tggcgcatct ttcggagctg gctggtttaa ataagagtac cgtccatcgc    20040
ttattgcagg gattacagtc ctgcggctat gtgaccaccg cgcccgccgc agggagttac    20100
cgcctgacta ccaaatttat tgccgtcggg cagaaggcgc tgtcttcgct gaatatcatt    20160
catatcgccg ctccgcatct tgaggcactg aacatcgcca ctggtgaaac cattaacttc    20220
tccagccgcg aagacgatca cgctattttg atttataagc tggaacccac aaccgggatg    20280
ctgcgaaccc gtgcctatat tggccagcat atgccgctct actgttccgc aatgggcaag    20340
atctacatgg cgtttggtca cccggactac gtgaagtcat actgggaaaa ccatcagcat    20400
gagatccagc cgttaacccg caataccatt accgagctgc ccgcgatgtt cgacgaactg    20460
gcgcacattc gtgaaagcgg agcggcgatg gacagagaag aaaacgaact cggcgtctcc    20520
tgtattgctg ttccggtgtt tgatattcat gggcgggtgc cgtacgccgt gtcgatttcg    20580
ctttcgacat cacgtctgaa acaggtggga gagaaaaatc tcctgaaacc actgcgtgaa    20640
accgcgcagg ctatttctaa tgaactggga tttactgtca gggatgaccct gggcgcgatc    20700
acataacgct ttgacaagt gccaaaactt taacatttcc ttcgttggat caaagcagta     20760
gggacgcgct ctctagcact ctgctgtttt agtgcaaagg agtgatcatg aaccggttta    20820
ttattgcgga tgcgacgaaa tgtatccggtt gccgtacctg tgaagtggct tgcgcagtgt   20880
cgcatcagga taatcaggat tgcgctgcgt tgtcaccaga cgagtttatt tcccgtattc    20940
gtgtcattaa agaccacagc tggaccacgg cagtagcctg tcatcagtgt gaagatgcac    21000
cgtgcgcgaa tgtctgccct gttgacgcga taagccgcga acatgggcat attttcgttg    21060
aacaaacacg ttgcattggc tgtaaaagct gtatgctggc ttgcccgttt ggtgcgatgg    21120
aggtcgtttc ttcgcgcaaa aaggcgaggg cgattaagtg cgatctgtgc tggcatcggg    21180
agacggggcc ggcctgtgtt gaagcctgcc cgacaaaggc gttgcagtgc atggatgtcg    21240
agaaagtgca gcggcatcgg ctacggcagc agcctgtttg aaacgttttc cggcgtttct    21300
caacgccgga acagtgcgct ttgtttatgc cagatgcggc gtaaacgcct tatccggcct    21360
acaaattctt ccaaattcaa tatattgcag aaatcatgta ggcctgataa gcgtagcgca    21420
tcaggcaatt tttagtgact ttcagcccag gctctttcta tctcttccgc cagaatcttc    21480
acccccgcct caattttctc cggctctggt acgtagttca tgcgcataca ttgatgcgta    21540
tgcggccacg gtttatccag tcccgggaag aagttgtgcc ccggcaccat cagcacgccg    21600
cgtgctttca ggcgctggta gagttgctcg gtcgtaatgg gcaaatcctt aaaccatagc    21660
cagaggaaaa tggctccttc tggtttatga attaggcagc gatcttccgg taaatagcgg    21720
cgaatgatgg cgatagtttc ctgaacacgc tggtagtaaa acggtttgat gactgtttca    21780
```

```
gacaggcgca gcagatcgtt acgcttaatc atttcacaca tcatcgccgg accaataccg   21840
ccaggtgcca ggctgataat gccgttcata ttggtgatgg cagtgatgat tttttcattg   21900
gcgatgataa tgccgcagcg ggagccaggc agccccagct tggaaagact catgcacagc   21960
acgatattcg gattccatag cgggcgcgct tcactgaaga tgatacccgg aacgggacg    22020 ccataagcgt tatcaatcac cagcggaatg ccgtgttgat tcgccagcgc gtcaagcttc   22080
agcaactctt cgtcagtaat cacattgcct gttggattcg tcggccggga gacgcaaatc   22140
atcccggttt cttcgccaat atgcagatgc tcaaaatcga cgtggtattt aaactggcct   22200
tccggcagca gttcaatatt cggacgcgca gagacaaaca gatcttcttc cagtccggcg   22260
tcagcgtagc caatgtattc cggtgccagc gggaacagca ctttttgac ccgaccatcg    22320 gcacggcgtc cggcaaacag attaaataag tagaaaaacg cgctctggct gccgtttgtt   22380
agtgcaatat tctgtgcttc gatatcccaa cccaacttct cgcgcagcat tccggcaagc   22440
agtgtgagta gctccgtttt cccctgtgga ccgtcgtaat tgcacagtgc atcagtcgct   22500
ttgccacttt ccagcatgtc ggtcagtagc gtctggaagt agtcctgcat ttccgggatc   22560
tgcgccggat taccgccgcc gagcataatc gcgccaggcg tgcgtaaacc gtcgttcaga   22620
tcttccatca gcagcgtaat gccggagtgg cgggtaaatt tgtcaccaaa agggagaat    22680 gtcatagcgg gatatctgtc gaactctgta gcaaggaagg taacaataac gctacatttg   22740
ctggggtgca aatcggtctg ttggagagtg agccggtgctt tatcctgcaa cgctgattag   22800
ggctgacatt ttatcctggt tggcggcttc ccgaggtact gacgaacggg aagccggaaa   22860
agtcactgtt gcccagccca gatgaccagc actttatcgt cgccatgctc acgaacaaag   22920
ccgtagccct gcttcagcga aagtgtcgtt tgtttgcccg cgccaattgc gggatggcgg   22980
gcgcggaact ggctgatttt ctgccagtgc gcgacgttgg cggcagattt accgctaaca   23040
tcctgccagt tcatatccga acgtgtacct tgcagcggat cagaacctgt aggaccgaac   23100
ggacgcgagg attcatcgcc ataaaagatt tgtaccgcgc ctggcgctaa tagtaataac   23160
tctgctgctt tgtcgccccc ttcacggaac agacgggtat catgcgacga gaggtagctc   23220
aacacgttga aaccctgcaa tttctccgcc atttgctgcc aggtcgtatc catctgcgcc   23280
agacaatcga ctgctttcgc cgcctgctcc tgataatcga aattgatcat cgcatcgaag   23340
ccgtggcgat agtagtcact ttgcatcacg ccgtggcccc aggcttcacc ggtcatccag   23400
aaaggtttgt catctaatgc tttgtcgggg ttagcttttt tccattcgcg aagcgcggcg   23460
ctggcttcgg ttttcagttg ctgccaggcg ggcaactcaa catgtttggc ggtatcgacc   23520 cgaaaccat caatcccata gtcgcggacc cactgactta accagtgggt taagtaatcg    23580
cgaggtgtaa agccttcgat gactttagcg tgagtatccg ttttgttttt atagaacacc   23640
ggcagaccag aagcggtagt tgattcggtt ttgatatccg gcaaaaggc cagcgacata    23700 gtgagatcgt cgaatccagg attgtcgtaa tcgccgatat ccgttctgat ccagtttttt   23760
ccccaccatt tatcccagcc tgttttgtcg ctgaaattaa tgtaatcgtt aaagctatgc   23820
caggtttgcc cggcggcagg tttccagtcg ctccagcgtt cacccagcgt ttttttcacc   23880
tcgtcaccag aaagatataa cgcgccaaac tgatactcct gcatatccgc cagcgtggca   23940
tagccggtgt ggttcatcac gacatcaaag agaatacgaa taccgcgctg atgtgcgcta   24000
tcaaccagcg tccgtagatc ggcttcgttg cccatattgg catcaagatt cgtccagtcc   24060
tgtgtgtaat aaccgtggta ggcataatgc gggaaatcgc cttttgtacc gccgccgacc   24120
cagccgtgaa tttgctcaaa tggggcgctt atccataaag cattaacgcc caactgctgg   24180
```

```
aggtaatcca gtttgttggt caggccgcgt aaatcgccgc cgtgaaaagt gccaatttcc   24240
gccataccgt ctttatgacg tccgtaactc tggtcattac tgggatcgcc gttttcgaaa   24300
cgatctgtca gcacaaagta aaccgtggcg ttatgccagt cgaaaggggc aggggcgtca   24360
gtttctgccc gttccagcag gagtaaaccg ttgctggtag cagcggggttg taacgttatt   24420 tgaccgttct tcactatcgc aatttgctgg ctgtaataat cccgtacggc ggctccttcc   24480
gggaaagtgg cgctgacatc cagcgtgagc ggtaatccat cccatttcgg gcattcacgg   24540
accaggtttg ctaccggttc ggcggcgttc tggatggaaa tcatcaatgt tggcgtaccg   24600
gagcgggtgt ctatttgcag cgtatatttg ccgtctctga caatcgcca ttgaggcggc     24660 gtgttgctac aaggttgcag ggaaagcatc tgattgagtt ttatcgcatc tgcaggctgc   24720
cagcactgtt ggtcaaaatt tagcgtgagt ggacgcgtac ctttgggcaa ctgcgcgtgg   24780
ctgacaaatg ttcccgttcc ctgttcgcta aaggcaggga accccggaga agtccagctg   24840
gcggcaacgg cgaagccagg aaggagtgtc agaaaacagg cggcgagttt catggtggat   24900
gagtccttat tgctgcgatt tcagacagtt tgccagcgat aagccagaca aaactcatcc   24960
ctgagcggta agtccacagg atgagaagca agggtgagcg atctcgcgca aaaaacggct   25020
gaattttgcg ataaacccca cattttctgc gatttagcgc caatctgaat cgttaacacg   25080
tgacatagtt tcagatttgg actattcctt ggggtgctct tgacagctat ttttgatatg   25140
atttgagatt caactctcaa atttgtgaaa aatataaggt gttggaatga ttaaatccga   25200
ccaggagacc tgatgatttt gactcccata cgacgatatg gggcgatgat tcttatgtta   25260
ctcactctgg tgttttcgag tgaggtgtta gcgaagacgc acacaacaac agcgagtcaa   25320
aagtcccact taactaaagc tagtaataaa caggtaagca gtaaacaaga gtattctcgc   25380
aatagtgcaa agagtagttc acttcctgat ttgcgaaaat acccttccgg aacaccaagg   25440
aaaaaggcgt ttctccggac cgtaatgcct tacattacca gccaaaatgc agccattact   25500
gcagaacgta actggctgat ttcaaaacag tatcagggcc aatggtcacc tgctgagcgt   25560
gcgcgtctga aagacatcgc caaacgctac aaggtgaaat ggtctggtaa tacgcgaaaa   25620
atcccgtgga ataccttgct tgaacgcgta gacattatcc ctaccagtat ggtggcgacg   25680
atggctgcag cagaaagcgg ttggggaacg tcgaagctgg cgcgcaacaa taacaatctg   25740
ttcggcatga aatgcatgaa aggacgttgt accaatgcgc cgggtaaagt gaaagggtac   25800
tcacagttta gttctgtcaa agaatcggtg agcgcctatg tcactaacct gaatacgcac   25860
ccggcttact cttcgttccg taaatcgcgt gcgcagctgc gtaaagcgga tcaggaagtg   25920
actgccacag cgatgattca caagctgaag ggctactcga ccaaagggaa gagttataat   25980
aactacctgt tcgcaatgta ccaggataac caacggttaa tcgcggcgca tatgtaattg   26040
catttccttg agccttatct gatttgtcgg tcggataagg cttttgctcg catcaggtgg   26100
ctgtgctgag ttccctgatg tgacgccgac aattctcatc atcgctacaa catgacctcg   26160
ctatttacat cgcgatactc ttttggcgtt gtgtcatatg ctttttttaaa aacagagtag   26220 aaatattgca gcgatggata accgcacatt tgcgatatct cattgatcga caaggtggtt   26280
gaaatcagca gactgcgcgc tttctccagc ttctcggcat gaatcatggc atggatggtt   26340
tcacccacct cttctttaaa acgcttctca agattggagc gcgagatccc gaccgcatcc   26400
agtacctgat ccacttttaat ccctttacag gcgtgattac gaatgtaatg catggcctga   26460
ataacggcgg gatcggtcag cgagcgataa tctgttgagc gccgttcaat gacgcgaact   26520
```

```
ggtgggacca aaattcgctg tagcggcatt tcttctttat ctaataatcg atgcaacagt   26580
tttgccgcct gatagcccat ttgccgcgcg ccctgagcga ccgaagaaag ggcgacacgc   26640
gacagatagc gggtcagttc ttcgttatcg atgccaatca cgcataattt ttccggtacg   26700
ggaatatgta gatgttcaca tacttgcaga atatgccgcg ctcgggcgtc agtaacggca   26760
ataatcccgg tttgcggtgg cagcgtttgt agccagtctg ccagccgatt ttgcgcgtgt   26820
tgccagttct ctggcgcggt ttctaacccc tgataaacca ctccgcgata cttttcttca   26880
gcgacaagct gacgaaatgc atattcgcgc tcagtggccc aacgtttgcc gcttgattcc   26940
ggaagaccat aaaaagcaaa gcggttaacg cctttctctt ttaaatgcaa aaatgcgctt   27000
tcaaccagcg catagttatc ggtggcaatg taatgaacgg gtgggtaact ttctgcaagg   27060
tgatacgagc cgccaacccc aacaatgggg acgtcgacat cagccagcgc ttgctcgatc   27120
tgtttgtcgt cgaagtcggc aatgacgcca tctcctaacc agtccttgat tttatcaatg   27180
cgggcgcgga atcttcttc aatgaaaata tcccattccg attgtgacgc ctgtaaatat   27240 tccctacgc cttctactac ctgccggtca taggctttat tggcattgaa cagtaatgtg   27300
atgcggtgac gtttagtaaa catggttctt ttcctgctga atcatgcaaa aactcaaaac   27360
cggtaatacg taaccggctt tgagaaaatt tttatcaaaa tcaagaacgg cgtttggttg   27420
cggagtccat ccatactgcc agcaacagaa tcgcacctt aacgatatac tgccagaagg   27480
tcggtacatc catcatactc atgccgttat ccagtgaagc catgataaat gccccatta   27540 ctgctccggc aacgcttccc actccgccag ccaggctggt gccgccaatc acgcatgctg   27600
caattgcgtc cagttcggcg atatttcccg cagaaggtga accagcgcca agtcgagaac   27660
taaggattaa tccggcgatg gctaccatta atccgttaat cgcgaacacg gcaagtttgg   27720
tgcgttcaac gttaatcccg gagagacgtg ctgcttccag attgccgccg atggcataaa   27780
tgcgtcgtcc aaatgccgtc cgcgttgcca taaacattcc gccgagtaac agcaacgtca   27840
gcagcagaac aggagtggga acgccacggt aatcattcaa cagccagatt gcgcctaata   27900
cgatgatagc ggttaaagcc tggcgaccga ctactgcggt agaggccgga gactgcaaac   27960
ccaaagcctg acggcgcatt cttccgcgcc attgccaacc aacaaaagcc attaagccaa   28020
gcgcgccaat gatgaagcca gtgctggcag gtagatagct ttgcccaatt tgtgacatcg   28080
cggcgctggt gggggaaaca gtcgtgccgt tggtgatgcc aatgagtatg ccgcgaaatg   28140
ccaacatgcc cgcgagggtg acaataaatg aagggacttt gcggtacgcg acccaccatc   28200
cgttccaggc accgagaagc agtcccagaa ccaacgtcac aatgatggta agtggcaaag   28260
gccagcctaa ccagacgtca caaatcgccg cgacgccacc taatagcccc atcattgagc   28320
cgacggaaag gtcgatttca gcagaaatta tgacgaacac cattcctacc gcgaggatgc   28380
cggtaatcgc ggtctggcgt aacaggttgg agacgttacg ggcgcttaag taggcaccat   28440
cggtggtcca ggtaaagaac agcatgattg cgatgatagc tgcaatcatc acgaagacct   28500
gcaaattcag tgatttcagc ccggaaaagc caccggatgt cggtacggcc aatttcactt   28560
cagacggatt gcttttcgac atgatgttcg ctcctcaatg cggcttccat cacctgctcc   28620
tgagtcaggt tatgatttat caggttggct tttagtttcc cttcatgcat caccagtacc   28680
cgatcgctaa ggccgagcac ttcaggtaat tcggaagaga tgacaataac ggcaataccc   28740
tgctggacga gttggttaat taattttag atctcgtatt tcgcgccaat atcgataccc   28800
ctggtaggtt catcaagaat gaggatgcgc gggttaagta acagacagcg agcgaggatc   28860 gcttttgct gattgccgcc gctcaaacgt ccaatagcaa ggtcggggga cgacgtttta   28920
```

```
actttgagtt gctgaattga ttccagaata cattttttgct ctgccgcgtc atcaagctgg   28980
ctaatgccac cggtaaattt attgagtgcg gcgagggtaa tattttttacc aaccgccatt   29040 accggaacga tgccgtcgcg ctttctgtct tcgggtacca tcgcaatccc ctgggcgatg   29100
gcttgctgac agttacgaat atctacctgt ttgccatcaa tataaatttt tccttcccat   29160
tgtccgggcc acacgccaaa caggcactga atggtctcgg tacgtccggc accaacgagt   29220
ccggcaatac ccagtatttc gccacgtttc agggaaaacg agacatcatt aactcgttta   29280
atatgacgat tgaccggatg ccatgccgtc agatgttcaa tacgtaatat ttcatctccg   29340
gtggtatgtg gttcattagg gtaaagcgcg gttaactctc gcccgaccat catggtgata   29400
atatcgtctt cactcattcc ggcagcatca cgcgtaccaa tgtgctgtcc gtcgcgaata   29460
acgcaaatcg tatcggaaat cgctttgact tcgttgagtt tgtgcgaaat ataaatacag   29520
gcgataccgt gctgttgtag atcgcgaata atatccagta aaaccgacgt ttcctgctca   29580
gttaatgagg ctgtcggttc atcgagaatt aacaagcgca cctgtttatt aagtgccttg   29640
gcaatttcaa ccagttgttg ttgcccaagc cctaaatcgc caacgcgggt atcaggtgaa   29700
atggataaac tgacctgtgc gagcagcttc tgacagcgta gcgtcatcag gtcataatcc   29760
ataatgccat tgtgggttat ttcgttaccc aggaagatat tttccagcac ggtcaattct   29820
ttcaccaggg ccaattcctg gtgaatgatg gcgataccttt tgcgttcggt atcgcggatg   29880
tgactcgcct gaatctcttc tcccgcaaaa ataatttcgc cttcgtagga gccatgggga   29940
taaataccac acagcacttt catcagtgtt gatttaccag acccatttttc cccacaaagt   30000 gagacgattt cgccagcatt caaccgcaag cagacgttat caatcgcctt cacactgccg   30060
aaggttttgg taatattctt catttcaagt agataaggca taacgattcc acctaagcca   30120
attcattcac gcggcatgga gagaaatcac gcccccgctc cgcgccgggg cgtaacgctt   30180
acagctcgct ctctttgtgg aatccgtctt taactaccgt gtctttgatg ttgttttttat   30240 tcacatcgat cggtgtcagg aggcgggagg gcacatcttt caggccatta ttcagtgtgg   30300 tatctgctttt tggttcctga ccattgccca actcaacggc aatttctgcg gcagtatttg   30360
ccaacaacgt aataggttta tacaccgtca tagtttgcgt accggcagca atacgttaa   30420 tacctgcgag atccgcatcc tggccggaaa ttgctacttt ccctgataaa ccttgcgcgc   30480
ttaatgcctg aattgcccca cctgcggtgg catcgtttga ggcaactaca gcatcaattt   30540
tgttattatt ggcggttagc gcgttttcca taattttcaa tgcgttttcc ggtaaccagc   30600
catcaaccca ttggtcacca acgactttaa ttttttccgga atcaacgtaa ggttttaaca   30660
ctttcatttg tccggcgcgg aacagcttgg cgttgttatc taccggcgag ccgcccatca   30720
ggaagtaatt accttgcgga acaatatcga ccagggcttt tgcctgcagt tcaccgactt   30780
tttcgttatc gaaagaaata taaaaatcga tatccgcatc gttaatcata cgatcgtaag   30840
ctaatacttt aataccttct tgtttggctt cttttacaac gttacttaat acctgaccgt   30900
tatacggaat aatgacaaga acatcgacac cccggtttat catgttttca atctgcgaca   30960
tttgtgtttc ttcattgcca tttgcagact gtacaaatac tttcgcgccg agagattctg   31020 ccttttttcac aaaaatatct cgatcttttt gccagcgttc aagacggaga tcatcaatcg   31080 ccataccttat tttgacttct ttggcgtgtg ccgcaacgtt ggtaagcaga agtgaggtgc   31140
aaagggtgag tagaatgttc tttatttttca tggtgtaggg ccttctgtag ttagaggaca   31200
gctttaataa gtaacaatca ccgcgataaa cgtaaccaat ttttagcaac taaacagggg   31260
```

-continued

```
aaaacaatta cagatttta tctttcgatt acgattttg gtttatttct tgatttatga    31320
ccgagatctt acttttgttg cgcaattgta cttattgcat ttttctcttc gaggaattac    31380
ccagtttcat cattccattt tattttgcga gcgagcgcac acttgtgaat tatctcaata    31440
gcagtgtgaa ataacataat tgagcaactg aaagggagtg cccaatatta cgacatcatc    31500
catcacccgc ggcattacct gattatggag ttcaatatgc aagcctattt tgaccagctc    31560
gatcgcgttc gttatgaagg ctcaaaatcc tcaaacccgt tagcattccg tcactacaat    31620
cccgacgaac tggtgttggg caagcgtatg gaagagcact tgcgttttgc cgcctgctac    31680
tggcacacat tctgctggaa cggggcggac atgtttggtg tggggcgtt taatcgtccg    31740
tggcagcagc ctggtgaggc actggcgttg gcgaagcgta aagcagatgt cgcatttgag    31800
tttttccaca agttacatgt gccattttat tgcttccacg atgtggatgt ttcccctgag    31860
ggcgcgtcgt taaagagta catcaataat tttgcgcaaa tggttgatgt cctggcaggc    31920
aagcaagaag agagcggcgt gaagctgctg tggggaaccg ctaactgctt tacaaaccct    31980
cgctatggcg cgggtgcggc gacgaaccca gatcctgaag tcttcagttg gcggcaacg    32040
caagttgtta cagcgatgga agcaaccat aaattgggcg gtgaaaacta tgtcctgtgg    32100
ggcggtcgtg aaggttacga aacgctgtta aataccgact gcgtcagga gcgtgaacag    32160
ctgggccgct ttatgcagat ggtggttgag cataaacata aaatcggttt ccagggcacg    32220
ttgcttatcg aaccgaaacc gcaagaaccg accaaacatc aatatgatta cgatgccgcg    32280
acggtctatg gcttcctgaa acagtttggt ctggaaaaag agattaaact gaacattgaa    32340
gctaaccacg cgacgctggc aggtcactct ttccatcatg aaattgccac cgccattgcg    32400
cttggcctgt tcggttctgt cgacgccaac cgtggcgatg cgcaactggg ctgggacacc    32460
gaccagttcc cgaacagtgt ggaagagaat gcgctggtga tgtatgaaat tctcaaagca    32520
ggcggtttca ccaccggtgg tctgaacttc gatgccaaag tacgtcgtca aagtactgat    32580
aaatatgatc tgttttacgg tcatatcggc gcgatggata cgatggcact ggcgctgaaa    32640
attgcagcgc gcatgattga agatggcgag ctggataaac gcatcgcgca gcgttattcc    32700
ggctggaata gcgaattggg ccagcaaatc ctgaaaggcc aaatgtcact ggcagattta    32760
gccaaatatg ctcaggaaca taatttgtct ccggtgcatc agagtggtcg ccaggagcaa    32820
ctggaaaatc tggtaaatca ttatctgttc gacaaataac ggctaactgt gcagtccgtt    32880
ggcccggtta tcggtagcga taccgggcat tttttaagg aacgatcgat atgtatatcg    32940
ggatagatct tggcacctcg ggcgtaaaag ttattttgct caacgagcag gtgaggtgg    33000
ttgcttcgca aacggaaaag ctgaccgttt cgcgcccgca tccactctgg tcggaacaag    33060
acccggaaca gtggtggcag gcaactgatc gcgcaatgaa agctctgggc gatcagcatt    33120
ctctgcagga cgttaaagca ttgggtattg ccggccagat gcatggagca accttactgg    33180
atgctcaaca cgggtattg cgccctgcca ttttgtggaa cgacgggcgc tgtgcgcaag    33240
agtgcacttt gctggaagcg agagttccgc aatcacgagt gattaccggc aacctgatga    33300
tgcccggatt tactgcgcct aaattgctat gggttcagcg gcatgagccg gagatattcc    33360
gtcaaatcga caaagtatta ttaccgaaag attacttgcg tctgcgtatg acggggagt    33420
ttgccagcga tatgtctgac gcagctggca ccatgtggct ggatgtcgca aagcgtgact    33480
ggagtgacgt catgctgcag gcttgcgact tatctcgtga ccagatgccc gcattatatg    33540
aaggcagcga aattactggt gctttgttac ctgaagttgc gaaagcgtgg ggtatggcga    33600
cggtgccagt tgtcgcaggc ggtggcgaca atgcagctgg tgcagttggt gtgggaatgg    33660
```

```
ttgatgctaa tcaggcaatg ttatcgctgg ggacgtcggg ggtctatttt gctgtcagcg   33720
aagggttctt aagcaagcca gaaagcgctg tacacagctt ttgccatgcg ctaccgcagc   33780
gttggcattt aatgtctgta atgctgagtg cagcatcgtg tctggattgg gtcgcgaaat   33840
taaccggcct gtgcaatgtc ccagctttaa tcgctgcagc tcaacaggct gatgaaagtg   33900
ccgagccagt ttggtttctg ccttatcttt ccggcgagcg tacaccacac aataatcccc   33960
aggcgaaggg ggttttcttt ggtttgactc atcaacatgg ccccaatgaa ctggcgcgag   34020
cagtgctgga aggcgtgggt tatgcgctgg cagatggcat ggatgtcgtg catgcctgcg   34080
gcattaaacc gcaaagtgtt acgttgattg gtggcggggc gcgtagtgag tactggcgtc   34140
agatgctggc ggatatcagc ggtcagcagc tcgattaccg tacgggggg gatgtggggc   34200
cagcactggg cgcagcaagg ctggcgcaga ttgcggcgaa tccagagaaa tcgctcattg   34260
agttgttgcc gcagctaccg ttagaacagt cgcatctacc agatgcgcag cgttatgccg   34320
cttatcagcc acgacgtgaa acgttccgtc gcctctatca gcaacttctg ccattaatgg   34380
cgtaaacgtt atccccctgcc tgaccgggtg ggggataatt cacatctata tatctcacta   34440
attaattaat atttagtatg aatttattct gaaaatcatt tgttaatggc atttttcagt   34500
tttgtctttc gttggttact cgtaatgtat cgctggtaga tatggagatc gttatgaaaa   34560
cctcaaaaac tgtggcaaaa ctattatttg ttgtcggggc gctggtttat ctggttgggc   34620
tatggatctc atgcccattg ctaagtggaa aaggctattt tcttggcgtg ttaatgacag   34680
caacttttgg taactatgca tatcttcgcg cagaaaaact cgggcaactg gataattttt   34740
ttacccatat ctgccagtta gttgcgttaa tcactatcgg tctcttgttt atcggtgttt   34800
taaatgcacc tatcaatgct tatgaaatgg tgatctaccc catcgccttt tttgtctgct   34860
tgtttggtca aatgcgtttg tttcgctcgg tatgagcaac ataaagctct tacacattca   34920
ggaatgaaag gaatactgtg atggacaaca aaatatcaac ctattcaccg gcctttagta   34980
ttgtgtcatg gatagctctc gttggtggta tcgttaccta tctgttaggg ctatggaatg   35040
cagagatgca gttaaatgaa aaagggtatt attttgccgt actggtgtta ggactgtttt   35100
ctgctgcgtc ttatcaaaag accgttcggg acaagtatga aggcataccg accacttcca   35160
tttattatat gacctgcctg actgtcttta ttatctctgt tgcattactg atggtaggtc   35220
tgtggaatgc gacattatta ctcagtgaaa aaggttttta tggactggct ttcttcttaa   35280
gcttgtttgg tgcagtagcg gtgcagaaga atattcgtga taccggaata aacccgccaa   35340
aagaaacaca ggttacccag gaagaataca gcgataatt cacgtaagcc cggtcagtcc   35400
aatgtgaacg ggcttttact taactcacta atctgtttct gtcgattcgt tgtaccagca   35460
tagaaagtaa caaactcgct gccaacgtcg cgcaaaagat ccaaataata tccagtattg   35520
gccaattttt aagctcaatt cccgggtgc gcagcgcatg gataatcaag gcgtggaatc   35580
cgtatatacc caatgaatgg cgggagatta gccaagtcc gcgaatggta cgcgtatcca   35640
gcgtgttttt aaccagagtc aatagcgcga ttgcgcagat aaaaaccatc ggcccacagt   35700
aaagatacca ggtatcggca aaatttccgc gccactgcaa ttcatataat gtcccgcgag   35760
agataataaa aaccccgtc gcaaacgcg cggcgctcac ccacgacagt gctttatgct   35820
gtgtgtccat catccctata gcgcggccca acatgccata cagaatgtag taaaaagtat   35880
cgccattgat atataagtta attggcagcc attcaaaacc gtcaatttc tgcggcactg   35940
tgtttgggtt agcgataatg ccaatcacca ccattagcac cagcaacatt tttccgccga   36000
```

-continued

```
cgttcttcac ctgaatcagc ggtgaaacca gataaatcac cgcaatcgcg aagaaaaacc   36060
acaagtggta aaacactggc ttttgcagca ggtttttcag cgctaactcc atattgatgg   36120
aggtaaacag cgcaatgtag agcagtgcga ttgcgctata aaaaatcaga cataagccga   36180
tacgcaagaa atggcgcggc tgggcgctgc gttcgccaaa aaagagatag ccggaaatca   36240
tgaaaaatag cggcacgctg acacgagagg cagaattcag aacattggcg atatcccagg   36300
tgacggggct aacactatga gcattggtca cataccaggt agtggtgtga atcatcacca   36360
ccattaaaca cgctatccct cgcaggttat caatccagta aattttgggc tgcatctgtg   36420
tctctgtatc tggttaaaaa aagtctgacc gataaatcat tcagttggcg cactggaata   36480
atctgagttt tatcactaca gcttatagag cttaaggaa attcgtaaga tatcagccac   36540
tataccgata taaataataa gactcacctg caaaccagac ggtaatttaa tgatgatgaa   36600
cgctttcttt ccggcaatgg cgcttatggt gctagtgggt tgttctacac cgtcacccgt   36660
gcagaaagca caacgggtaa aggttgatcc tctgcgttcg ttgaatatgg aagcgttatg   36720
caaggatcag gcggcaaaac gttataacac cggcgagcaa aaaatcgacg tcaccgcctt   36780
cgaacagttc cagggaagct atgaaatgcg cggttatacc ttccgtaaag agcagtttgt   36840
ctgttctttt gacgcggatg gccatttttt gcatctttcc atgcgttaag ccctgctttt   36900
tcccgtttcg tactgtatat cttccatcca gcgggtatac tgatcccttc ctttaaatcc   36960
acacgtatcc agcacgaaat aatatgcaaa agtttgatac caggaccttc cagggcttga   37020
tcctgacctt acaggattac tgggctcgcc agggctgcac cattgttcaa ccattggaca   37080
tggaagtcgg cgcgggaacc tctcacccaa tgacctgtct gcgcgcgctg gggccagaac   37140
cgatggcggc tgcttatgtt cagccttctc gtcgcccgac cgatggtcgc tacggcgaaa   37200
accccaaccg tttacagcac tactatcagt ttcaggtggt cattaagcca tcgccggaca   37260
atattcagga gctgtacctc ggttctctga aagagctggg catggacccg actattcacg   37320
acatccgttt cgtggaagat aactgggaaa acccgactct gggtgcctgg ggactgggct   37380
gggaagtgtg gctaaacggc atggaagtga cgcagttcac ttacttccag caggttggtg   37440
gtctggagtg taaaccggtt accggcgaga tcacctacgg tctggaacgt ctggccatgt   37500
acattcaggg cgtagacagc gtttacgacc tggtctggag cgacggcccg ctgggtaaaa   37560
ccacctacgg cgacgtgttc catcagaacg aagtggagca gtccacttac aacttcgaat   37620
acgcggatgt ggacttcctg ttcacctgct ttgagcagta cgagaaagaa gcgcagcagc   37680
tgctggcgct ggaaaatccg ctgccgctgc agcctacga gcgtattctg aaagccgccc   37740
acagcttcaa cctgctggat gcgcgtaaag ccatctccgt caccgagcgt cagcgctaca   37800
ttctgcgcat tcgcacctg accaaagcag tggcagaagc atactacgct tcccgtgaag   37860
ccctcggctt cccgatgtgc aacaaagata agtaagaggc ggctatgtct gagaaaactt   37920
ttctggtgga aatcggcact gaagagctgc accaaaagc actgcgcagc ctggctgagt   37980
cctttgctgc gaatttact gcggagctgg ataacgctgg cctcgcacac ggcaccgttc   38040 aatggttttgc tgctccgcgt cgtctggcgc tgaaagtagc taacctggcg gaagcgcaac   38100
cggatcgtga aatcgaaaaa cgcggccgg cgattgccca ggcgttcgac gctgaaggca   38160
aaccgagcaa agcggcagaa ggttgggcgc gtggttgcgg tattaccgtt gaccaggctg   38220
agcgtctgac taccgataaa ggcgaatggc tgctgtatcg cgcccatgtg aagggcgaaa   38280
gcaccgaagc actgctgccg aatatggttg cgacttctct ggcgaaactg ccgatcccga   38340
aactgatgcg ttggggcgca agcgacgtgc acttcgtgcg tccggtgcac accgtgaccc   38400
```

```
tgctgctggg cgacaaagtc attccggcaa ccattctggg cattcagtcc gatcgcgtga    38460
ttcgcggcca ccgctttatg ggcgaaccgg aattcaccat cgacaacgcc gatcagtatc    38520
cggaaattct gcgtgagcgc gggaaagtca tcgccgatta cgaagaacgt aaagcgaaga    38580
ttaaagccga tgccgaagaa gcagcgcgta agattggcgg taacgctgac ttaagcgaaa    38640
gcctgctgga agaagtggct tcgctggtgg agtggccggt cgttctgacc gcaaaattcg    38700
aagagaaatt cctcgcggtg ccggctgaag cgctggttta ccatgaaag gtgaccaga     38760 aatacttccc ggtgtatgcg aacgacggca aactgctgcc gaactttatc ttcgttgcca    38820
acatcgaatc gaaagatccg cagcagatta tctccggtaa cgagaaagtc gttcgtccgc    38880
gtctggcgga tgccgagttc ttcttcaaca ccgaccgtaa aaaacgtctg aagataacc     38940 tgccgcgcct gcaaaccgtg ctgttccagc aacagctggg tacgctgcgt gacaaaactg    39000
accgcatcca ggcgctggct ggctggattg ctgaacagat tggcgctgac gttaaccacg    39060
caacccgtgc gggcctgctg tctaagtgtg acctgatgac caacatggtc ttcgagttca    39120
ccgacaccca gggcgttatg gggatgcact atgcgcgtca cgatggcgaa gcggaagatg    39180
tcgcggtggc gctgaatgag cagtatcagc gcgctttgc cggtgatgac ctgccgtcta    39240
acccggtagc ctgtgcgctg gcgattgctg acaagatgga tactctggcg ggtatcttcg    39300
gtatcggcca gcatccgaaa ggcgacaaag cccgtttgc gctgcgtcgt gccgcacttg    39360
gcgtgctgcg aattatcgtt gagaagaacc tcaaccttga tctgcaaacg ctgaccgaag    39420
aagcggtgcg tctgtatggc gataagctga ctaatgccaa cgtagttgat gatgttatcg    39480
actttatgct cggtcgcttc cgcgcctggt atcaggacga aggttatacc gttgacacca    39540
tccaggcggt actggcgcgt cgtccgactc gtccggctga tttcgatgcc cgtatgaaag    39600
cggtatcgca tttccgtacc ctggatgcag ctgctgcact ggcggcggcg aacaaacgtg    39660
tatctaacat tctggcgaaa tctgacgaag tgctgagcga ccgcgtgaat gcctctaccc    39720
tgaaagagcc ggaagaaatt aaactggcga tgcaggttgt ggtgctacgt gacaagctgg    39780
agccgtactt tgcggaaggt cgttaccagg atgcgctggt cgaactggca gagctgcgtg    39840
agccggttga tgctttcttc gataaagtga tggtcatggt tgatgacaaa gaattgcgtc    39900
tcaaccgtct gaccatgctg gagaaactgc gcgaactgtt cctgcgcgtt gcggatattt    39960
cgctgttgca gtaataacgc cgttattaaa agcctgccca tctggcaggc ttttttatt     40020 atcgctaaat aatacagcaa cctttaataa tcttctgctg aataaagatt atctcatata    40080 ttaatttat gaggttttt taggattata tcaaggagaa gaaacaaact tattaagcta     40140
gaatagccac gggtgcttga gactgtttgt ctcaggtatt caccgaaagg cagacagaga    40200
aaagccccac ctgactataa atcaaag                                        40227
```

<210> SEQ ID NO 13
<211> LENGTH: 392
<212> TYPE: PRT
<213> ORGANISM: Escherichia coli

<400> SEQUENCE: 13

Met Phe Thr Lys Arg His Arg Ile Thr Leu Leu Phe Asn Ala Asn Lys
1               5                   10                  15

Ala Tyr Asp Arg Gln Val Val Glu Gly Val Gly Glu Tyr Leu Gln Ala
            20                  25                  30

Ser Gln Ser Glu Trp Asp Ile Phe Ile Glu Glu Asp Phe Arg Ala Arg
        35                  40                  45

Ile Asp Lys Ile Lys Asp Trp Leu Gly Asp Gly Val Ile Ala Asp Phe
 50                  55                  60

Asp Asp Lys Gln Ile Glu Gln Ala Leu Ala Asp Val Asp Val Pro Ile
 65                  70                  75                  80

Val Gly Val Gly Gly Ser Tyr His Leu Ala Glu Ser Tyr Pro Pro Val
                 85                  90                  95

His Tyr Ile Ala Thr Asp Asn Tyr Ala Leu Val Glu Ser Ala Phe Leu
            100                 105                 110

His Leu Lys Glu Lys Gly Val Asn Arg Phe Ala Phe Tyr Gly Leu Pro
        115                 120                 125

Glu Ser Ser Gly Lys Arg Trp Ala Thr Glu Arg Glu Tyr Ala Phe Arg
130                 135                 140

Gln Leu Val Ala Glu Glu Lys Tyr Arg Gly Val Val Tyr Gln Gly Leu
145                 150                 155                 160

Glu Thr Ala Pro Glu Asn Trp Gln His Ala Gln Asn Arg Leu Ala Asp
                165                 170                 175

Trp Leu Gln Thr Leu Pro Pro Gln Thr Gly Ile Ile Ala Val Thr Asp
            180                 185                 190

Ala Arg Ala Arg His Ile Leu Gln Val Cys Glu His Leu His Ile Pro
        195                 200                 205

Val Pro Glu Lys Leu Cys Val Ile Gly Ile Asp Asn Glu Glu Leu Thr
210                 215                 220

Arg Tyr Leu Ser Arg Val Ala Leu Ser Ser Val Ala Gln Gly Ala Arg
225                 230                 235                 240

Gln Met Gly Tyr Gln Ala Ala Lys Leu Leu His Arg Leu Leu Asp Lys
                245                 250                 255

Glu Glu Met Pro Leu Gln Arg Ile Leu Val Pro Pro Val Arg Val Ile
            260                 265                 270

Glu Arg Arg Ser Thr Asp Tyr Arg Ser Leu Thr Asp Pro Ala Val Ile
        275                 280                 285

Gln Ala Met His Tyr Ile Arg Asn His Ala Cys Lys Gly Ile Lys Val
290                 295                 300

Asp Gln Val Leu Asp Ala Val Gly Ile Ser Arg Ser Asn Leu Glu Lys
305                 310                 315                 320

Arg Phe Lys Glu Glu Val Gly Glu Thr Ile His Ala Met Ile His Ala
                325                 330                 335

Glu Lys Leu Glu Lys Ala Arg Ser Leu Leu Ile Ser Thr Thr Leu Ser
            340                 345                 350

Ile Asn Glu Ile Ser Gln Met Cys Gly Tyr Pro Ser Leu Gln Tyr Phe
        355                 360                 365

Tyr Ser Val Phe Lys Lys Ala Tyr Asp Thr Thr Pro Lys Glu Tyr Arg
370                 375                 380

Asp Val Asn Ser Glu Val Met Leu
385                 390

<210> SEQ ID NO 14
<211> LENGTH: 70
<212> TYPE: DNA
<213> ORGANISM: Artificial Sequence
<220> FEATURE:
<223> OTHER INFORMATION: Primer

<400> SEQUENCE: 14
tctcaaagcc ggttacgtat taccggtttt gagttttttgc atgattcagc tcgagtgtga    60
cggaagatca 70

<210> SEQ ID NO 15
<211> LENGTH: 69
<212> TYPE: DNA
<213> ORGANISM: Artificial Sequence
<220> FEATURE:
<223> OTHER INFORMATION: Primer

<400> SEQUENCE: 15
gataaggctt ttgctcgcat caggtggctg tgctgagttc cctgatgtga ccttagccat     60
ttgcctgct                                                              69

<210> SEQ ID NO 16
<211> LENGTH: 2830
<212> TYPE: DNA
<213> ORGANISM: Artificial Sequence
<220> FEATURE:
<223> OTHER INFORMATION: mutated gene sequence

<400> SEQUENCE: 16
tctcaaagcc ggttacgtat taccggtttt gagttttttgc atgattcagc tcgagtgtga     60
cggaagatca cttcgcagaa taaataaatc ctggtgtccc tgttgatacc gggaagccct    120
gggccaactt ttggcgaaaa tgagacgttg atcggcacgt aagaggttcc aactttcacc    180
ataatgaaat aagatcacta ccgggcgtat tttttgagtt atcgagattt tcaggagcta    240
aggaagctaa aatggagaaa aaaatcactg gatataccac cgttgatata tcccaatggc    300
atcgtaaaga acattttgag gcatttcagt cagttgctca atgtacctat aaccagaccg    360
ttcagctgga tattacggcc ttttttaaaga ccgtaaagaa aaataagcac aagttttatc    420
cggcctttat tcacattctt gcccgcctga tgaatgctca tccggaattc cgtatggcaa    480
tgaaagacgg tgagctggtg atatgggata gtgttcaccc ttgttacacc gttttccatg    540
agcaaactga aacgttttca tcgctctgga gtgaatacca cgacgatttc cggcagtttc    600
tacacatata ttcgcaagat gtggcgtgtt acggtgaaaa cctggcctat ttccctaaag    660
ggtttattga gaatatgttt ttcgtctcag ccaatccctg ggtgagtttc accagttttg    720
atttaaacgt ggccaatatg gacaacttct tcgcccccgt tttcaccatg gcaaatatt    780 atacgcaagg cgacaaggtg ctgatgccgc tggcgattca ggttcatcat gccgtttgtg    840
atggcttcca tgtcggcaga atgcttaatg aattacaaca gtactgcgat gagtggcagg    900
gcggggcgta atttttttaa ggcagttatt ggtgccctta aacgcctggt gctacgcctg    960
aataagtgat aataagcgga tgaatggcag aaattcgaaa gcaaattcga cccggtcgtc   1020
ggttcagggc agggtcgtta aatagccgct agatctaagt aaatcgcgcg gtttgttac    1080 tgataaagca ggcaagacct aaaatgtgta aagggcaaag tgtatacttt ggcgtcaccc   1140
cttacatatt ttaggtcttt ttttattgtg cgtaactaac ttgccatctt caaacaggag   1200
ggctggaaga agcagaccgc taacacagta cataaaaaag gagacatgaa cgatgaacat   1260
caaaaagttt gcaaaacaag caacagtatt aacctttact accgcactgc tggcaggagg   1320
cgcaactcaa gcgtttgcga aagaaacgaa ccaaaagcca tataaggaaa catacggcat   1380
ttcccatatt acacgccatg atatgctgca atccctgaa cagcaaaaaa atgaaaaata    1440
tcaagttcct gaattcgatt cgtccacaat taaaaatatc tcttctgcaa aaggcctgga   1500
cgtttgggac agctggccat tacaaaaacgc tgacggcact gtcgcaaact atcacggcta   1560
ccacatcgtc tttgcattag ccggagatcc taaaaatgcg gatgacacat cgatttacat   1620

-continued

```
gttctatcaa aaagtcggcg aaacttctat tgacagctgg aaaaacgctg gccgcgtctt    1680
taaagacagc gacaaattcg atgcaaatga ttctatccta aaagaccaaa cacaagaatg    1740
gtcaggttca gccacattta catctgacgg aaaaatccgt ttattctaca ctgatttctc    1800
cggtaaacat tacggcaaac aaacactgac aactgcacaa gttaacgtat cagcatcaga    1860
cagctctttg aacatcaacg gtgtagagga ttataaatca atctttgacg gtgacggaaa    1920
aacgtatcaa aatgtacagc agttcatcga tgaaggcaac tacagctcag cgacaaacca    1980
tacgctgaga gatcctcact acgtagaaga taaaggccac aaatacttag tatttgaagc    2040
aaacactgga actgaagatg ctaccaagg cgaagaatct ttatttaaca aagcatacta    2100
tggcaaaagc acatcattct tccgtcaaga aagtcaaaaa cttctgcaaa gcgataaaaa    2160
acgcacggct gagttagcaa acggcgctct cggtatgatt gagctaaacg atgattacac    2220
actgaaaaaa gtgatgaaac cgctgattgc atctaacaca gtaacagatg aaattgaacg    2280
cgcgaacgtc tttaaaatga acggcaaatg gtacctgttc actgactccc gcggatcaaa    2340
aatgacgatt gacggcatta cgtctaacga tatttacatg cttggttatg tttctaattc    2400
tttaactggc ccatacaagc cgctgaacaa aactggcctt gtgttaaaaa tggatcttga    2460
tcctaacgat gtaacctta cttactcaca cttcgctgta cctcaagcga aggaaacaa    2520 tgtcgtgatt acaagctata tgacaaacag aggattctac gcagacaaac aatcaacgtt    2580
tgcgccaagc ttcctgctga acatcaaagg caagaaaaca tctgttgtca agacagcat    2640 ccttgaacaa ggacaattaa cagttaacaa ataaaaacgc aaagaaaat gccgatatcc    2700 tattggcatt ttctttatt tcttatcaac ataaggtga atcccatatg aactatataa    2760
aagcaggcaa atggctaagg tcacatcagg gaactcagca cagccacctg atgcgagcaa    2820
aagccttatc                                                           2830
```

<210> SEQ ID NO 17
<211> LENGTH: 23
<212> TYPE: DNA
<213> ORGANISM: Artificial Sequence
<220> FEATURE:
<223> OTHER INFORMATION: Primer

<400> SEQUENCE: 17
tctcaaagcc ggttacgtat tac                                              23

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
aagcaaagca gttaacgcct                                                  20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
cagcgatgaa taaccgcaca                                                  20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
aaggcgttaa ctgctttgct                                                  20

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
atgtgcggtt attcatcgct g                                                21

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
gataaggctt ttgctcgcat ca                                               22

<210> SEQ ID NO 23
<211> LENGTH: 1179
<212> TYPE: DNA
<213> ORGANISM: Artificial Sequence
<220> FEATURE:
<223> OTHER INFORMATION: mutated gene sequence

<400> SEQUENCE: 23
atgtttacta acgtcaccg catcacatta ctgttcaatg ccaataaagc ctatgaccgg       60
caggtagtag aaggcgtagg ggaatattta caggcgtcac aatcggaatg ggatattttc     120
attgaagaag atttccgcgc ccgcattgat aaaatcaagg actggttagg agatggcgtc     180
attgccgact cgacgacaa acagatcgag caagcgctgg ctgatgtcga cgtccccatt     240
gttggggttg gcggctcgta tcaccttgca gaaagttacc cacccgttca ttacattgcc    300
accgataact atgcgctggt tgaaagcgca tttttgcatt taaaagagaa aggcgttaac    360
tgctttgctt tttatggtct tccggaatca agcggcaaac gttgggccac tgagcgcgaa    420
tatgcatttc gtcagcttgt cgctgaagaa aagtatcgcg gagtggttta tcagggggtta   480 gaaaccgcgc cagagaactg gcaacacgcg caaaatcggc tggcagactg gctacaaacg    540
ctgccaccgc aaaccgggat tattgccgtt actgacgccc gagcgcggca tattctgcaa    600
gtatgtgaac atctacatat tcccgtaccg gaaaaattat gcgtgattgg catcgataac    660
gaagaactga cccgctatct gtcgcgtgtc gcccttttctt cggtcgctca gggcgcgcgg    720
caaatgggct atcaggcggc aaaactgttg catcgattat tagataaaga agaaatgccg     780
ctacagcgaa ttttggtccc accagttcgc gtcattgaac ggcgctcaac agattatcgc    840
tcgctgaccg atcccgccgt tattcaggcc atgcattaca ttcgtaatca cgcctgtaaa    900
gggattaaag tggatcaggt actggatgcg gtcgggatct cgcgctccaa tcttgagaag    960
cgttttaaag aagaggtggg tgaaaccatc catgccatga ttcatgccga aagctggag   1020

| | |
|---|---|
| aaagcgcgca gtctgctgat ttcaaccacc ttgtcgatca atgagatatc gcaaatgtgc | 1080 |
| ggttatccat cgctgcaata tttctactct gttttaaaa aagcatatga cacaacgcca | 1140 |
| aaagagtatc gcgatgtaaa tagcgaggtc atgttgtag | 1179 |

<210> SEQ ID NO 24
<211> LENGTH: 1179
<212> TYPE: DNA
<213> ORGANISM: Artificial Sequence
<220> FEATURE:
<223> OTHER INFORMATION: mutated gene sequence

<400> SEQUENCE: 24

| | |
|---|---|
| atgtttacta aacgtcaccg catcacatta ctgttcaatg ccaataaagc ctatgaccgg | 60 |
| caggtagtag aaggcgtagg ggaatattta caggcgtcac aatcggaatg ggatattttc | 120 |
| attgaagaag atttccgcgc ccgcattgat aaaatcaagg actggttagg agatggcgtc | 180 |
| attgccgact tcgacgacaa acagatcgag caagcgctgg ctgatgtcga cgtccccatt | 240 |
| gttggggttg gcggctcgta tcaccttgca gaaagttacc cacccgttca ttacattgcc | 300 |
| accgataact atgcgctggt tgaaagcgca tttttgcatt taaaagagaa aggcgttaac | 360 |
| cgctttgctt tttatggtct tccggaatca agcggcaaac gttgggccac tgagcgcgaa | 420 |
| tatgcatttc gtcagcttgt cgctgaagaa agtatcgcg gagtggttta tcaggggtta | 480 |
| gaaaccgcgc cagagaactg gcaacacgcg caaaatcggc tggcagactg gctacaaacg | 540 |
| ctgccaccgc aaaccgggat tattgccgtt actgacgccc gagcgcggca tattctgcaa | 600 |
| gtatgtgaac atctacatat tcccgtaccg gaaaaattat gcgtgattgg catcgataac | 660 |
| gaagaactga cccgctatct gtcgcgtgtc gccctttctt cggtcgctca gggcgcgcgg | 720 |
| caaatgggct atcaggcggc aaaactgttg catcgattat tagataaaga agaaatgccg | 780 |
| ctacagcgaa ttttggtccc accagttcgc gtcattgaac ggcgctcaac agattatcgc | 840 |
| tcgctgaccg atcccgccgt tattcaggcc atgcattaca ttcgtaatca cgcctgtaaa | 900 |
| gggattaaag tggatcaggt actggatgcg gtcgggatct cgcgctccaa tcttgagaag | 960 |
| cgttttaaag aagaggtggg tgaaaccatc catgccatga ttcatgccga aagctggag | 1020 |
| aaagcgcgca gtctgctgat ttcaaccacc ttgtcgatca atgagatatc gcaaatgtgc | 1080 |
| ggttattcat cgctgcaata tttctactct gttttaaaa aagcatatga cacaacgcca | 1140 |
| aaagagtatc gcgatgtaaa tagcgaggtc atgttgtag | 1179 |

<210> SEQ ID NO 25
<211> LENGTH: 1179
<212> TYPE: DNA
<213> ORGANISM: Artificial Sequence
<220> FEATURE:
<223> OTHER INFORMATION: mutated gene sequence

<400> SEQUENCE: 25

| | |
|---|---|
| atgtttacta aacgtcaccg catcacatta ctgttcaatg ccaataaagc ctatgaccgg | 60 |
| caggtagtag aaggcgtagg ggaatattta caggcgtcac aatcggaatg ggatattttc | 120 |
| attgaagaag atttccgcgc ccgcattgat aaaatcaagg actggttagg agatggcgtc | 180 |
| attgccgact tcgacgacaa acagatcgag caagcgctgg ctgatgtcga cgtccccatt | 240 |
| gttggggttg gcggctcgta tcaccttgca gaaagttacc cacccgttca ttacattgcc | 300 |
| accgataact atgcgctggt tgaaagcgca tttttgcatt taaaagagaa aggcgttaac | 360 |

```
tgctttgctt tttatggtct tccggaatca agcggcaaac gttgggccac tgagcgcgaa    420
tatgcatttc gtcagcttgt cgctgaagaa aagtatcgcg gagtggttta tcagggggtta   480
gaaccgcgc cagagaactg gcaacacgcg caaaatcggc tggcagactg gctacaaacg    540
ctgccaccgc aaaccgggat tattgccgtt actgacgccc gagcgcggca tattctgcaa    600
gtatgtgaac atctacatat tcccgtaccg gaaaaattat gcgtgattgg catcgataac    660
gaagaactga cccgctatct gtcgcgtgtc gccctttctt cggtcgctca gggcgcgcgg    720
caaatgggct atcaggcggc aaaactgttg catcgattat tagataaaga agaaatgccg    780
ctacagcgaa ttttggtccc accagttcgc gtcattgaac ggcgctcaac agattatcgc    840
tcgctgaccg atcccgccgt tattcaggcc atgcattaca ttcgtaatca cgcctgtaaa    900
gggattaaag tggatcaggt actggatgcg gtcgggatct cgcgctccaa tcttgagaag    960
cgttttaaag aagaggtggg tgaaaccatc catgccatga ttcatgccga aagctggag    1020
aaagcgcgca gtctgctgat ttcaaccacc ttgtcgatca atgagatatc gcaaatgtgc   1080
ggttattcat cgctgcaata tttctactct gtttttaaaa aagcatatga cacaacgcca   1140
aaagagtatc gcgatgtaaa tagcgaggtc atgttgtag                         1179
```

<210> SEQ ID NO 26
<211> LENGTH: 392
<212> TYPE: PRT
<213> ORGANISM: Artificial Sequence
<220> FEATURE:
<223> OTHER INFORMATION: mutated protein
<220> FEATURE:
<221> NAME/KEY: MISC_FEATURE
<222> LOCATION: (121)..(121)
<223> OTHER INFORMATION: wherein Xaa is selected from the group
      consisting of C, S, G, V, P, and conservative substitutions
      thereof <400> SEQUENCE: 26

Met Phe Thr Lys Arg His Arg Ile Thr Leu Leu Phe Asn Ala Asn Lys
1               5                   10                  15

Ala Tyr Asp Arg Gln Val Val Glu Gly Val Gly Glu Tyr Leu Gln Ala
            20                  25                  30

Ser Gln Ser Glu Trp Asp Ile Phe Ile Glu Glu Asp Phe Arg Ala Arg
        35                  40                  45

Ile Asp Lys Ile Lys Asp Trp Leu Gly Asp Gly Val Ile Ala Asp Phe
    50                  55                  60

Asp Asp Lys Gln Ile Glu Gln Ala Leu Ala Asp Val Asp Val Pro Ile
65                  70                  75                  80

Val Gly Val Gly Gly Ser Tyr His Leu Ala Glu Ser Tyr Pro Pro Val
                85                  90                  95

His Tyr Ile Ala Thr Asp Asn Tyr Ala Leu Val Glu Ser Ala Phe Leu
            100                 105                 110

His Leu Lys Glu Lys Gly Val Asn Xaa Phe Ala Phe Tyr Gly Leu Pro
        115                 120                 125

Glu Ser Ser Gly Lys Arg Trp Ala Thr Glu Arg Glu Tyr Ala Phe Arg
    130                 135                 140

Gln Leu Val Ala Glu Glu Lys Tyr Arg Gly Val Val Tyr Gln Gly Leu
145                 150                 155                 160

Glu Thr Ala Pro Glu Asn Trp Gln His Ala Gln Asn Arg Leu Ala Asp
                165                 170                 175

Trp Leu Gln Thr Leu Pro Pro Gln Thr Gly Ile Ile Ala Val Thr Asp
            180                 185                 190

```
Ala Arg Ala Arg His Ile Leu Gln Val Cys Glu His Leu His Ile Pro
            195                 200                 205

Val Pro Glu Lys Leu Cys Val Ile Gly Ile Asp Asn Glu Glu Leu Thr
        210                 215                 220

Arg Tyr Leu Ser Arg Val Ala Leu Ser Ser Val Ala Gln Gly Ala Arg
225                 230                 235                 240

Gln Met Gly Tyr Gln Ala Ala Lys Leu Leu His Arg Leu Leu Asp Lys
            245                 250                 255

Glu Glu Met Pro Leu Gln Arg Ile Leu Val Pro Val Arg Val Ile
        260                 265                 270

Glu Arg Arg Ser Thr Asp Tyr Arg Ser Leu Thr Asp Pro Ala Val Ile
        275                 280                 285

Gln Ala Met His Tyr Ile Arg Asn His Ala Cys Lys Gly Ile Lys Val
        290                 295                 300

Asp Gln Val Leu Asp Ala Val Gly Ile Ser Arg Ser Asn Leu Glu Lys
305                 310                 315                 320

Arg Phe Lys Glu Glu Val Gly Glu Thr Ile His Ala Met Ile His Ala
            325                 330                 335

Glu Lys Leu Glu Lys Ala Arg Ser Leu Leu Ile Ser Thr Thr Leu Ser
            340                 345                 350

Ile Asn Glu Ile Ser Gln Met Cys Gly Tyr Pro Ser Leu Gln Tyr Phe
            355                 360                 365

Tyr Ser Val Phe Lys Lys Ala Tyr Asp Thr Thr Pro Lys Glu Tyr Arg
            370                 375                 380

Asp Val Asn Ser Glu Val Met Leu
385                 390

<210> SEQ ID NO 27
<211> LENGTH: 392
<212> TYPE: PRT
<213> ORGANISM: Artificial Sequence
<220> FEATURE:
<223> OTHER INFORMATION: mutated protein
<220> FEATURE:
<221> NAME/KEY: MISC_FEATURE
<222> LOCATION: (363)..(363)
<223> OTHER INFORMATION: wherein Xaa is selected from the group
      consisting of S, K, R, and conservative substitutions thereof

<400> SEQUENCE: 27

Met Phe Thr Lys Arg His Arg Ile Thr Leu Leu Phe Asn Ala Asn Lys
1               5                   10                  15

Ala Tyr Asp Arg Gln Val Val Glu Gly Val Gly Glu Tyr Leu Gln Ala
            20                  25                  30

Ser Gln Ser Glu Trp Asp Ile Phe Ile Glu Glu Asp Phe Arg Ala Arg
        35                  40                  45

Ile Asp Lys Ile Lys Asp Trp Leu Gly Asp Gly Val Ile Ala Asp Phe
50                  55                  60

Asp Asp Lys Gln Ile Glu Gln Ala Leu Ala Asp Val Asp Val Pro Ile
65                  70                  75                  80

Val Gly Val Gly Gly Ser Tyr His Leu Ala Glu Ser Tyr Pro Pro Val
            85                  90                  95

His Tyr Ile Ala Thr Asp Asn Tyr Ala Leu Val Glu Ser Ala Phe Leu
            100                 105                 110

His Leu Lys Glu Lys Gly Val Asn Arg Phe Ala Phe Tyr Gly Leu Pro
        115                 120                 125
```

```
Glu Ser Ser Gly Lys Arg Trp Ala Thr Glu Arg Glu Tyr Ala Phe Arg
            130                 135                 140

Gln Leu Val Ala Glu Glu Lys Tyr Arg Gly Val Val Tyr Gln Gly Leu
145                 150                 155                 160

Glu Thr Ala Pro Glu Asn Trp Gln His Ala Gln Asn Arg Leu Ala Asp
                165                 170                 175

Trp Leu Gln Thr Leu Pro Pro Gln Thr Gly Ile Ile Ala Val Thr Asp
            180                 185                 190

Ala Arg Ala Arg His Ile Leu Gln Val Cys Glu His Leu His Ile Pro
        195                 200                 205

Val Pro Glu Lys Leu Cys Val Ile Gly Ile Asp Asn Glu Glu Leu Thr
210                 215                 220

Arg Tyr Leu Ser Arg Val Ala Leu Ser Ser Val Ala Gln Gly Ala Arg
225                 230                 235                 240

Gln Met Gly Tyr Gln Ala Ala Lys Leu Leu His Arg Leu Leu Asp Lys
                245                 250                 255

Glu Glu Met Pro Leu Gln Arg Ile Leu Val Pro Pro Val Arg Val Ile
            260                 265                 270

Glu Arg Arg Ser Thr Asp Tyr Arg Ser Leu Thr Asp Pro Ala Val Ile
        275                 280                 285

Gln Ala Met His Tyr Ile Arg Asn His Ala Cys Lys Gly Ile Lys Val
290                 295                 300

Asp Gln Val Leu Asp Ala Val Gly Ile Ser Arg Ser Asn Leu Glu Lys
305                 310                 315                 320

Arg Phe Lys Glu Glu Val Gly Glu Thr Ile His Ala Met Ile His Ala
                325                 330                 335

Glu Lys Leu Glu Lys Ala Arg Ser Leu Leu Ile Ser Thr Thr Leu Ser
            340                 345                 350

Ile Asn Glu Ile Ser Gln Met Cys Gly Tyr Xaa Ser Leu Gln Tyr Phe
        355                 360                 365

Tyr Ser Val Phe Lys Lys Ala Tyr Asp Thr Thr Pro Lys Glu Tyr Arg
    370                 375                 380

Asp Val Asn Ser Glu Val Met Leu
385                 390

<210> SEQ ID NO 28
<211> LENGTH: 392
<212> TYPE: PRT
<213> ORGANISM: Artificial Sequence
<220> FEATURE:
<223> OTHER INFORMATION: mutated protein
<220> FEATURE:
<221> NAME/KEY: MISC_FEATURE
<222> LOCATION: (121)..(121)
<223> OTHER INFORMATION: wherein Xaa is selected from the group
      consisting of C, S, G, V, P, and conservative substitutions
      thereof
<220> FEATURE:
<221> NAME/KEY: MISC_FEATURE
<222> LOCATION: (363)..(363)
<223> OTHER INFORMATION: wherein Xaa is selected from the group
      consisting of S, K, R, and conservative substitutions thereof

<400> SEQUENCE: 28

Met Phe Thr Lys Arg His Arg Ile Thr Leu Leu Phe Asn Ala Asn Lys
1               5                   10                  15

Ala Tyr Asp Arg Gln Val Val Glu Gly Val Gly Glu Tyr Leu Gln Ala
            20                  25                  30

Ser Gln Ser Glu Trp Asp Ile Phe Ile Glu Glu Asp Phe Arg Ala Arg
```

```
                            35                  40                  45
Ile Asp Lys Ile Lys Asp Trp Leu Gly Asp Gly Val Ile Ala Asp Phe
         50                      55                      60

Asp Asp Lys Gln Ile Glu Gln Ala Leu Ala Asp Val Asp Val Pro Ile
 65                      70                      75              80

Val Gly Val Gly Gly Ser Tyr His Leu Ala Glu Ser Tyr Pro Pro Val
                     85                  90                  95

His Tyr Ile Ala Thr Asp Asn Tyr Ala Leu Val Glu Ser Ala Phe Leu
             100                     105                 110

His Leu Lys Glu Lys Gly Val Asn Xaa Phe Ala Phe Tyr Gly Leu Pro
             115                     120                 125

Glu Ser Ser Gly Lys Arg Trp Ala Thr Glu Arg Glu Tyr Ala Phe Arg
             130                     135                 140

Gln Leu Val Ala Glu Glu Lys Tyr Arg Gly Val Val Tyr Gln Gly Leu
145                     150                     155             160

Glu Thr Ala Pro Glu Asn Trp Gln His Ala Gln Asn Arg Leu Ala Asp
                    165                 170                 175

Trp Leu Gln Thr Leu Pro Pro Gln Thr Gly Ile Ile Ala Val Thr Asp
            180                     185                 190

Ala Arg Ala Arg His Ile Leu Gln Val Cys Glu His Leu His Ile Pro
            195                     200                 205

Val Pro Glu Lys Leu Cys Val Ile Gly Ile Asp Asn Glu Glu Leu Thr
    210                     215                 220

Arg Tyr Leu Ser Arg Val Ala Leu Ser Ser Val Ala Gln Gly Ala Arg
225                     230                     235             240

Gln Met Gly Tyr Gln Ala Ala Lys Leu Leu His Arg Leu Leu Asp Lys
                    245                 250                 255

Glu Glu Met Pro Leu Gln Arg Ile Leu Val Pro Pro Val Arg Val Ile
                260                     265                 270

Glu Arg Arg Ser Thr Asp Tyr Arg Ser Leu Thr Asp Pro Ala Val Ile
                275                     280                 285

Gln Ala Met His Tyr Ile Arg Asn His Ala Cys Lys Gly Ile Lys Val
            290                     295                 300

Asp Gln Val Leu Asp Ala Val Gly Ile Ser Arg Ser Asn Leu Glu Lys
305                     310                     315             320

Arg Phe Lys Glu Val Gly Glu Thr Ile His Ala Met Ile His Ala
                    325                 330                 335

Glu Lys Leu Glu Lys Ala Arg Ser Leu Leu Ile Ser Thr Thr Leu Ser
                340                     345                 350

Ile Asn Glu Ile Ser Gln Met Cys Gly Tyr Xaa Ser Leu Gln Tyr Phe
            355                     360                 365

Tyr Ser Val Phe Lys Lys Ala Tyr Asp Thr Thr Pro Lys Glu Tyr Arg
    370                     375                 380

Asp Val Asn Ser Glu Val Met Leu
385                     390
```

MODIFIED MICROORGANISMS FOR CHEMICAL PRODUCTION

RELATED APPLICATION DATA

This application claims priority to and the benefit of U.S. Provisional Application No. 62/175,127 filed Jun. 12, 2015, the contents of which are hereby incorporated by reference in their entirety.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 338,639 byte ASCII (text) file named "Seq_List" created on May 31, 2016.

FIELD OF THE INVENTION

The present invention relates to the bio-based chemical production from woody biomass using recombinant industrial microbes such as *Escherichia coli*.

BACKGROUND OF THE INVENTION

Our transportation fuels and many chemical products including solvents, fertilizers, pesticides, and plastics are derived from petroleum. This dependence on petroleum has probably the biggest impact on our unsustainable way of living. Atmospheric $CO_2$ is at the highest recorded level and it is predicted to further increase in the foreseeable future. Emerging serious environmental issues caused by an accelerated global climate change and ocean acidification are unavoidable if we keep using petroleum at the current rate. In addition, petroleum reservoirs in general and in particular with cheap mining access are going to decline. To ensure the future advancement of human society, there is an ever-increasing demand for renewable biofuels and bioenergy products as an alternative to fossil fuels and petroleum.

Production of cost-competitive fuels and chemicals by microbial fermentation using renewable feedstock is a desirable alternative. Plant biomass especially agricultural residues, such as corn stover and sugarcane bagasse, represents an important feedstock as they are renewable and they do not compete with food production. Sugar content in many types of agricultural residues is about 60-70% of the dry weight, which is comparable to corn. However, utilization of sugars from plant biomass in a cost-effective manner remains a challenge. Unlike starch, woody biomass (both cellulosic and lignocellulosic biomass), including plant biomass, is naturally resistant to deconstruction. Crystalline fibers of cellulose are encased in a covalently linked mesh of lignin and hemicellulose. D-glucose is the subunit of cellulose and xylose is the main component of hemicellulose (20-40% of biomass dry weight). While glucose can be metabolized very efficiently by many common industrial hosts, such as baker's yeast, industrial microbes have either no native xylose catabolism pathway or very low efficient pathways. Furthermore, the presence of glucose prevents the consumption of other sugars like xylose in microbes, a well-described phenomenon called catabolite repression.

Accordingly, there is a need for improving the derivation of cost-competitive fuels and chemicals from woody biomass using industrial microbes. In particular, mechanisms to counteract the wild type industrial microbes' natural inhibition of efficient metabolism using woody biomass as feedstock are needed.

BRIEF SUMMARY OF THE INVENTION

The invention is directed to a recombinant bacterium, wherein the recombinant bacterium produces a mutated XylR protein and/or a mutated CRP protein.

In some embodiments, the mutation XylR protein has a mutation in at least one of residues 121 or 363. For example, the mutated XylR protein has an amino acid sequence selected from the group consisting of SEQ ID NOs:26-28, wherein $X_2$ is selected from the group consisting of C, S, G, V, P and conservative substitutions thereof, $X_3$ is selected from the group consisting of S, K, R, and conservative substitutions thereof, $X_4$ is selected from the group consisting of C, S, G, V, P, and conservative substitutions thereof, and $X_5$ is selected from the group consisting of S, K, R, and conservative substitutions thereof. In some embodiments, the recombinant bacterium expresses a XylR protein is encoded by a nucleic acid sequence set forth in SEQ ID NO:23. In another embodiment, the recombinant bacterium expresses a XylR protein encoded by a nucleic acid sequence set forth in SEQ ID NO:24. In yet another embodiment, the recombinant bacterium expresses a XylR protein encoded by a nucleic acid sequence set forth in SEQ ID NO:25.

In some embodiments, the mutated CRP protein has an amino acid sequence set forth in SEQ ID NO:11, wherein $X_1$ is selected from the group consisting of D, P, H, and conservative substitutions thereof. For example, the CRP protein is encoded by a nucleic acid sequence set forth in SEQ ID NO:10.

The recombinant bacterium may be a member of the Enterobacteriaceae family, for example, from the genera *Escherichia*, *Erwinia*, *Providencia*, or *Serratia*. In some embodiments, the recombinant bacterium may be *Acinetobacter* species, *Achromobacter delmarvae*, *Achromobacter viscosus*, *Achromobacter lacticum*, *Actinomadura madurae*, *Actinomyces violaceochromogenes*, *Aeromonas salmonicida*, *Agrobacterium tumefaciens*, *Agrobacterium radiobacter*, *Alcaligenes faecalis*, *Arthrobacter citreus*, *Arthrobacter tumescens*, *Arthrobacter paraffineus*, *Arthrobacter hydrocarboglutamicus*, *Arthrobacter oxydans*, *Aureobacterium saperdae*, *Azotobacter indicus*, *Bacillus licheniformis*, *Bacillus subtilis*, *Bacillus amyloliquifaciens*, *Bacillus subtilis*, *Bacillus licheniformis*, *Bacillus amyloliqyefaciens*, *Bacillus coagulans*, *Bacillus pumilus*, *Bacillus circulans*, *Bacillus thiaminolyticus*, *Brevibacterium ammoniagenes*, *divaricatum*, *Brevibacterium lactofermentum*, *Brevibacterium flavum*, *Brevibacterium globosum*, *Brevibacterium fuscum*, *Brevibacterium ketoglutamicum*, *Brevibacterium helcolum*, *Brevibacterium pusillum*, *Brevibacterium testaceum*, *Brevibacterium roseum*, *Brevibacterium immariophilium*, *Brevibacterium linens*, *Brevibacterium protopharmiae*, *Clostridium acetobutylicium*, *Corynebacterium acetophilum*, *Corynebacterium glutamicum*, *Corynebacterium callunae*, *Corynebacterium acetoacidophilum*, *Corynebacterium acetoglutamicum*, *Enterobacter aerogenes*, *Erwinia amylovora*, *Erwinia carotovora*, *Erwinia herbicola*, *Erwinia chrysanthemi*, *Escherichia coli*, *Escherichia freundii*, *Flavobacterium peregrinum*, *Flavobacterium fucatum*, *Flavobacterium aurantinum*, *Flavobacterium rhenanum*, *Flavobacterium sew anense*, *Flavobacterium breve*, *Flavobacterium meningosepticum*, *Gluconobacter oxydans*, *Gluconobacter asaii*, *Kitasatosporia parulosa*, *Microbacte-* rium ammoniaphilum, Micrococcus sp. CCM825, Morganella morganii, Nocardia opaca, Nocardia rugosa, Planococcus eucinatus, Pleomorphomonas oryzae, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Pseudomonas syringae, Rhodococcus erythropolis, Rhodococcus rhodochrous, Rhodococcus sp. ATCC 15592, Rhodococcus sp. ATCC 19070, Salmonella typhimurium, Salmonella schottmulleri, Serratia marcescens, Sporosarcina ureae, Staphylococcus aureus, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Vibrio metschnikovii, Vibrio tyrogenes, Xanthomonas campestris, and Xanthomonas citri. The recombinant bacterium may also be a non-ruminant bacteria. In some aspects, the recombinant bacterium is a member of the Enterobacteriaceae family, for example from a member of the *Escherichia* genus, *Envinia* genus, *Providencia* genus, and *Serratia* genus.

The invention also encompasses isolated nucleic acids sequences that encode a mutated CRP protein or a XylR protein. In some embodiments, the isolated nucleic acid sequence encodes a CRP protein having an amino acid sequence set forth in SEQ ID NO:11, wherein $X_1$ is selected from the group consisting of D, P, H, and conservative substitutions thereof. The isolated nucleic acid sequence may have a sequence set forth in SEQ ID NO:10. In other embodiments, the isolated nucleic acid sequence that encodes a XylR protein having an amino acid sequence selected from the group consisting of SEQ ID NOs:26-28, wherein $X_2$ is selected from the group consisting of C, S, G, V, P and conservative substitutions thereof, $X_3$ is selected from the group consisting of S, K, R, and conservative substitutions thereof, $X_4$ is selected from the group consisting of C, S, G, V, P, and conservative substitutions thereof, and $X_5$ is selected from the group consisting of S, K, R, and conservative substitutions thereof. The isolated nucleic acid sequence may have a sequence selected from the group consisting of SEQ ID NO:23, SEQ ID NO:24, and SEQ ID NO:25.

Methods for increasing xylose utilization in microbes and for improved chemical production from woody biomass are also included. The methods for increasing xylose utilization comprises mutating the microbial genomes of the microbes to produce at least one protein selected from the group consisting of: a CRP protein with a point mutation substituting glycine-142, a XylR protein with a point mutation substituting arginine-121, a XylR protein with a point mutation substituting proline-182, and a XylR protein with a point mutation substituting proline-363. The methods for improved chemical production from woody biomass comprise culturing the recombinant bacterium of the invention with woody biomass. In some embodiments, the methods for improved chemical production from woody biomass are methods for improved organic acid production from woody biomass.

BRIEF DESCRIPTION OF THE DRAWINGS

FIG. 7 depicts the fermentation performance of a lactate producer with xylR SNPs. TG114 is an industrial lactate producer with wild-type xylR and strain LN23 is the genetically modified TG114 with the wild-type xylR chromosomally replaced by xylR SNPs R121C and P363S. The only difference between these two strains is the point mutations in xylR. Fermentation experiments were performed three times, and both strains fermented glucose-xylose mixtures (50 g/L for each) for 96 hours under the same condition. Panel A shows extracellular sugar concentrations. Panel B shows cell density (OD550). Panel C shows the product D-lactate concentrations.

FIG. 8 depicts the conservation of residues at the indicated position for Proteobacteria. The bold black letter represents wild-type residues in *E. coli* and the letter "S" indicates this SNP was also identified beneficial for xylose utilization. Some organisms with the same SNP as identified in this invention as listed an example.

DETAILED DESCRIPTION OF THE INVENTION

Figure 1:
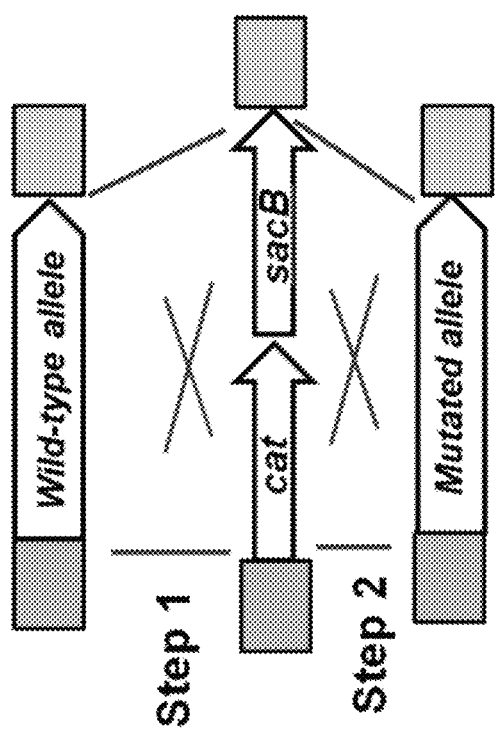
FIG. 1 depicts a schematic of the two-step integration method for homologous recombination of a target gene using the cat-sacB cassette. The gray boxes indicate the adjacent regions of the target gene, which function as homologous regions for recombination.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the invention. It will be understood, however, by those skilled in the relevant arts, that the present invention may be practiced without these specific details. It should be noted that there are many different and alternative configurations, devices and technologies to which the disclosed inventions may be applied. The full scope of the inventions is not limited to the examples that are described below.

The singular forms "a," "an," and "the" include plural referents unless the context clearly dictates otherwise. Thus, for example, reference to "a step" includes reference to one or more of such steps.

The terms "culture medium" and "growth medium" as used herein refer to an aqueous or agar-based medium designed to support the growth of microorganisms.

The term "industrial microbe" as used herein refers to microorganisms that are used in industry to manufacture food or products in large quantities. Industrial microorganisms may be prokaryotic, archae, or eukaryotic cells. Suitable prokaryotic microorganisms include, but are not limited to, any of a variety of gram-positive, gram-negative, or gram-variable bacteria. Examples of prokaryotic microorganisms include, but are not limited to, cells belonging to the genera: *Acinetobacter, Agrobacterium, Alicyclobacillus, Anabaena, Ameicystis, Arthrobacter, Azobacter, acillus, Brevibacterium, Chroinatium, Clostridium, Corynebacterium, Enterobacter, Erwinia, Evcherichia, Lactobacillus, Lactoeoecus, Mesorhizobium, Methylobacterium, Microbacterium, Phormiditim, Phormidium, Pleomorphomonas, Pseudomonas, Rhodobacter, Rhodopseudomoilas, Rhociaspirilium, Rhodococcus, Salmonella, Shigella, Staphlococcus, Sirepromyces, Synnecoccus, Xantaomonas,* and *Zytimmonas.* Suitable archae microorganisms include, but are not limited to, cells belonging to the genera: *Aeropyrum, Archaegiobus, Halobacierium, Methanococcus, Alethanobacterium Pyrococcus, Sulfolobus,* and *Mennopiasma.* In some embodiments, industrial microbes refer to non-ruminant bacterial cells or members of the Enterobacteriaceae family, for example, from the genera *Escherichia, Erwinia, Photorhabdus, Providencia,* or *Serratia.* The industrial microbes may also be Alteromonadaceae or Pseudomonadaceae. Specific species of industrial microbes contemplated in the invention include *Acinetobacter* species, *Achromobacter delmarvae, Achromobacter viscosus, Achromobacter lacticum, Actinomadura madurae, Actinomyces violaceochromogenes, Aeromonas salmonicida, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Bacillus licheniformis, Bacillus subtilis, Bacillus amyloliquifaciens, Bacillus subtilis, Bacillus licheniformis, Bacillus amyloliqyefaciens, Bacillus coagulans, Bacillus pumilus, Bacillus circulans, Bacillus thiaminolyticus, Brevibacterium ammoniagenes, divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Clostridium acetobutylicium, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, E. mallotivora, Escherichia coli, Escherichia freundii, Flavobacterium peregrinum, Flavobacterium fucatum, Flavobacterium aurantinum, Flavobacterium rhenanum, Flavobacterium sewanense, Flavobacterium breve, Flavobacterium meningosepticum, Gluconobacter oxydans, Gluconobacter asaii, Kitasatosporia parulosa, Microbacterium ammoniaphilum, Micrococcus sp.* CCM825, *Morganella morganii, Nocardia opaca, Nocardia rugosa, Planococcus eucinatus, Pleomorphomonas oryzae, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosterone, Pseudomonas aeruginosa, Pseudomonas syringae, Rhodococcus erythropolis, Rhodococcus rhodochrous, Rhodococcus* sp. ATCC 15592, *Rhodococcus* sp. ATCC 19070, *Salmonella typhimurium, Salmonella schottmulleri, Serratia marcescens, Sporosarcina ureae, Staphylococcus aureus, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Vibrio metschnikovii, Vibrio tyrogenes, Xanthomonas campestris,* and *Xanthomonas citri.* Various strains the microbe may be used. For example, with regard to *E. coli,* exemplary strains include *E. coli* B, *E. coli* C, and *E. coli* W.

As used herein, "transform" and "transformation" refer to the transfer of a nucleic acid molecule into a host organism. Preferably, the nucleic acid molecule is integrated into the genome of the host organism. Host organisms containing the transformed nucleic acid fragments are referred to as "transgenic" or "recombinant" or "transformed" or "transformant" organisms.

The terms "plasmid" and "vector" refer to an extra chromosomal element often carrying genes that are not part of the central metabolism of the cell, thus not part of the microbial genome. Usually, plasmids and vectors are in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction that is capable of introducing an expression cassette(s) into a cell.

The term "woody biomass" as used herein refers to cellulosic and lignocellulosic biomass. Accordingly, woody biomass also includes plant biomass, such as corn stover and sugarcane bagasse, in addition to trees and other woody plants. "Woody plants" as used herein refers to any plant that produces wood as its structural tissue.

The replacement of one amino acid with another amino acid at a particular amino acid residue number in a protein sequence is depicted in the format: (single letter abbreviation for the original amino acid)(residue number)(single letter abbreviation for the replacement amino acid). For example, the replacement of arginine with cysteine at amino acid residue 121 of a protein is depicted as R121C.

As used herein, the reference to specific residues of the XylR protein is based on the E. coli XylR protein sequence, which is set forth in SEQ ID NO:11.

As used herein, the term "conservative substitution" refers to a substitution in the amino acid sequence that results in little or no change in the shape and/or other attributes of the protein. In some instances, the substation may be one in which an amino acid residue is replaced with another amino acid residue having a similar side chain. Exemplary conservative substitutions are set out in Tables 1 and 2.

TABLE 1

| Side Chain Characteristic | Amino Acid |
|---|---|
| Aliphatic | |
| Non-polar | G, A, P |
|  | I, L, V |
| Polar, uncharged | C, S, T, M |
|  | N, Q |
| Polar, charged | D, E |
|  | K, R |
| Aromatic | H, F, W, Y |
| Other | N, Q, D, E |
| Non-polar (hydrophobic) | |
| Aliphatic | A, L, I, V, P |
| Aromatic | F, W |
| Sulfur-containing | M |
| Borderline | G |
| Uncharged-polar | |
| Hydroxyl | S, T, Y |
| Amides | N, Q |
| Sulfhydryl | C |
| Borderline | G |
| Positively charged (basic) | K, R, H |
| Negatively charged (acidic) | D, E |

TABLE 2

| Original Residue | Substitutions |
|---|---|
| Alanine (A) | V, L, I |
| Arginine (R) | L, Q, N |
| Asparagine (N) | Q, H, K, R |
| Aspartic Acid (D) | E |
| Cysteine (C) | S |
| Glutamine (Q) | N |
| Glutamic Acid (E) | D |
| Histidine (H) | N, Q, K, R |
| Isoleucine (I) | L, V, M, A, F |
| Leucine (L) | I, V, M, A, F |
| Lysine (K) | R, Q, N |
| Methionine (M) | L, F, I |
| Phenylalanine (F) | L, V, I, A |
| Proline (P) | G |
| Serine (S) | T |
| Threonine (T) | S |
| Tryptophan (W) | Y, F |
| Tyrosine (Y) | W, F, T, S |
| Valine (V) | I, L, M, F, A |

The present invention arises from the discovery that mutations in the xylR gene of industrial microbes can result in increased xylose catabolism and/or utilization, even in the presence of glucose. The crp gene encodes a DNA-binding transcriptional dual regulator. In E. coli strain K12, the crp gene (GenBank: AEDF01000007; SEQ ID NO:1) encodes a protein containing 210 amino acids (NCBI accession No: EFN38624; E. coli K12 b3357) with the sequence set forth in SEQ ID NO:2. The xylR gene encodes a xylose divergent operon transcriptional activator and considered a putative xyl operon. In E. coli strain K12, the xylR gene (GenBank: AEDF01000031; SEQ ID NO:12) encodes a protein containing 392 amino acids (NCBI accession No: EFN36373; E. coli K12 b3569) with the sequence set forth in SEQ ID NO:13. Changing the XylR sequence is an efficient way to enhance xylose catabolism and sugar co-utilization. Additionally, the invention also arises from the discovery of new mutations in crp gene that result in increased xylose catabolism and/or utilization.

The invention is directed to a recombinant industrial microbe comprising at least one mutation in the XylR protein and/or CRP protein. For example, the at least one mutation is selected from the group consisting of: a point mutation at residue 142 of a CRP protein, a point mutation at residue 121 of a XylR protein, a point mutation at residue 182 of a XylR protein, and a point mutation at residue 363 of the XylR protein. The point mutation results in increased xylose utilization in the recombinant industrial microbe compared to its wild type counterpart. The point mutation results in increased xylose utilization in the recombinant industrial microbe compared to its wild type counterpart. In some embodiment, the xylose utilization is increased compared to the wild type counterpart even in the presence of glucose.

The invention is also directed to methods of generating the recombinant bacterium. In preferred embodiments, the mutations in the crp gene or the xylR gene are introduced into the microbial genome of the recombinant bacterium through homologous recombination. Accordingly, the mutated CRP proteins and XylR proteins are expressed from the microbial genome rather than plasmids containing the mutated crp gene or the mutated xylR gene. Thus the expression of mutated crp and xylR genes in the disclosed recombinant bacterium avoids the limitation of plasmids. Introduction of mutations into microbial genomes through homologous recombination is previously known in the art, for example, through a two-step integration method of homologous recombination as shown in FIG. 1. Example 1 presents exemplary methods of generating a CRP protein with a G142D mutation and XylR proteins with a R121C mutation and/or a P363 S mutation.

Mutations in the XylR protein or the CRP protein may be generated in a variety of ways well established in the art. For example, the mutations may be introduced by random mutagenesis, site-directed mutagenesis, or replacement of the wild-type xylR by foreign xylRs with identified useful SNPs. Beneficial SNPs mutations of xylR can be identified by screening the mutated microorganism's xylose utilization. In some embodiments, the recombinant bacterium may comprise multiple mutations in the crp gene and/or the xylR gene. In some aspects, when there are multiple mutations, they might have a synergic effect in xylose utilization than microbes containing only one of the mutations. For example, the recombinant bacterium may comprise a combination of mutations at residue 121 and 363 of the XylR protein. Alternatively, the recombinant bacterium may comprise at least one mutation in both the crp gene and/or the xylR gene, for example so that the recombinant bacterium comprises mutations in residues 121 and 363 of the XylR protein and a mutation in residue 141 of the CRP protein.

The point mutation at residue 142 of the CRP protein may be the substitution of the glycine with aspartic acid (G142D mutation), with proline (G142P mutation), with histidine (G142H mutation), or with a conservative substitution of aspartic acid, proline, or histidine. Accordingly, the recombinant bacterium may comprise a CRP protein having the amino acid sequence set forth in SEQ ID NO:11. In turn, the recombinant bacterium comprises a crp gene having a nucleic acid sequence that encodes the CRP protein having the amino acid sequence set forth in SEQ ID NO:11. For example, the crp gene of the recombinant bacterium has the nucleic acid sequence set forth in SEQ ID NO:10.

The point mutation at residue 121 of the XylR protein may be the substitution of the arginine with cysteine (R121C mutation), with glycine (R121G mutation), with valine (R121V mutation), with proline (R121P mutation), with a conservative substitution of cysteine, glycine, valine, or proline. Accordingly, the recombinant bacterium may comprise a XylR protein having the amino acid sequence set forth in SEQ ID NO:26. In turn, the recombinant bacterium comprises a xylR gene having a nucleic acid sequence that encodes the XylR protein having the amino acid sequence set forth in SEQ ID NO:26. For example, the xylR gene of the recombinant bacterium has the nucleic acid sequence set forth in SEQ ID NO:23.

The point mutation at residue 363 of the XylR protein may be the substitution of the proline with serine (P363S mutation), with lysine (P363K mutation), or with arginine (P363R mutation), or with a conservative substitution of serine, lysine, or arginine. Accordingly, the recombinant bacterium may comprise a XylR protein having the amino acid sequence set forth in SEQ ID NO:27. In turn, the recombinant bacterium comprises a xylR gene having a nucleic acid sequence that encodes the XylR protein having the amino acid sequence set forth in SEQ ID NO:27. For example, the xylR gene of the recombinant bacterium has the nucleic acid sequence set forth in SEQ ID NO:24.

In embodiments where the recombinant bacterium comprises two point mutations in XylR, the recombinant bacterium may comprise a XylR protein having the amino acid sequence set forth in SEQ ID NO:28. Thus the recombinant bacterium comprises a xylR gene having a nucleic acid sequence that encodes the XylR protein having the amino acid sequence set forth in SEQ ID NO:28. For example, the xylR gene of the recombinant bacterium has the nucleic acid sequence set forth in SEQ ID NO:25.

The recombinant bacterium may have at least one mutation in XylR and in CRP. For example, the recombinant bacterium may comprise a XylR protein having the amino acid sequence set forth in one of SEQ ID NOs:26-28 and a CRP protein having the amino acid sequence set forth in SEQ ID NO:11.

Table 3 lists the amino acid sequences of mutated CRP and XylR protein of the invention based on wild type CRP and XylR proteins of *E. coli* strain K12. The mutated residues are in bold.

TABLE 3

Amino acid sequences of wild type CRP and XylR proteins and exemplary amino acid sequences of CRP and XylR proteins mutated for enhanced xylose utilization.

| Identification | Amino Acid Sequence (N-terminus → C-terminus) |
|---|---|
| Wild type CRP (SEQ ID NO: 2) | MVLGKPQTDP TLEWFLSHCH IHKYPSKSTL IHQGEKAETL YYIVKGSVAV LIKDEEGKEM ILSYLNQGDF IGELGLFEEG QERSAWVRAK TACEVAEISY KKFRQLIQVN PDILMRLSAQ MARRLQVTSE KVGNLAFLDV TGRIAQTLLN LAKQPDAMTH PDGMQIKITR QEIGQIVGCS RETVGRILKM LEDQNLISAH GKTIVVYGTR |
| CRP mutated at residue 142 (SEQ ID NO: 11) | MVLGKPQTDP TLEWFLSHCH IHKYPSKSTL IHQGEKAETL YYIVKGSVAV LIKDEEGKEM ILSYLNQGDF IGELGLFEEG QERSAWVRAK TACEVAEISY KKFRQLIQVN PDILMRLSAQ MARRLQVTSE KVGNLAFLDV TX$_1$RIAQTLLN LAKQPDAMTH PDGMQIKITR QEIGQIVGCS RETVGRILKM LEDQNLISAH GKTIVVYGTR wherein X$_1$ is selected from the group consisting of D, P, and H |
| Wild type XylR (SEQ ID NO: 13) | MFTKRHRITL LFNANKAYDR QVVEGVGEYL QASQSEWDIF IEEDFRARID KIKDWLGDGV IADFDDKQIE QALADVDVPI VGVGGSYHLA ESYPPVHYIA TDNYALVESA FLHLKEKGVN RFAFYGLPES SGKRWATERE YAFRQLVAEE KYRGVVYQGL ETAPENWQHA QNRLADWLQT LPPQTGIIAV TDARARHILQ VCEHLHIPVP EKLCVIGIDN EELTRYLSRV ALSSVAQGAR QMGYQAAKLL HRLLDKEEMP LQRILVPPVR VIERRSTDYR SLTDPAVIQA MHYIRNHACK GIKVDQVLDA VGISRSNLEK RFKEEVGETI HAMIHAEKLE KARSLLISTT LSINEISQMC GYPSLQYFYS VFKKAYDTTP KEYRDVNSEV ML |

TABLE 3-continued

Amino acid sequences of wild type CRP and XylR proteins and exemplary amino acid sequences of CRP and XylR proteins mutated for enhanced xylose utilization.

| Identification | Amino Acid Sequence (N-terminus → C-terminus) |
|---|---|
| XylR mutated at residue 121 (SEQ ID NO: 26) | MFTKRHRITL LFNANKAYDR QVVEGVGEYL QASQSEWDIF IEEDFRARID KIKDWLGDGV IADFDDKQIE QALADVDVPI VGVGGSYHLA ESYPPVHYIA TDNYALVESA FLHLKEKGVN X₂FAFYGLPES SGKRWATERE YAFRQLVAEE KYRGVVYQGL ETAPENWQHA QNRLADWLQT LPPQTGIIAV TDARARHILQ VCEHLHIPVP EKLCVIGIDN EELTRYLSRV ALSSVAQGAR QMGYQAAKLL HRLLDKEEMP LQRILVPPVR VIERRSTDYR SLTDPAVIQA MHYIRNHACK GIKVDQVLDA VGISRSNLEK RFKEEVGETI HAMIHAEKLE KARSLLISTT LSINEISQMC GYPSLQYFYS VFKKAYDTTP KEYRDVNSEV ML wherein X₂ is selected from the group consisting of C, S, G, V, and P |
| XylR mutated at residue 363 (SEQ ID NO: 27) | MFTKRHRITL LFNANKAYDR QVVEGVGEYL QASQSEWDIF IEEDFRARID KIKDWLGDGV IADFDDKQIE QALADVDVPI VGVGGSYHLA ESYPPVHYIA TDNYALVESA FLHLKEKGVN RFAFYGLPES SGKRWATERE YAFRQLVAEE KYRGVVYQGL ETAPENWQHA QNRLADWLQT LPPQTGIIAV TDARARHILQ VCEHLHIPVP EKLCVIGIDN EELTRYLSRV ALSSVAQGAR QMGYQAAKLL HRLLDKEEMP LQRILVPPVR VIERRSTDYR SLTDPAVIQA MHYIRNHACK GIKVDQVLDA VGISRSNLEK RFKEEVGETI HAMIHAEKLE KARSLLISTT LSINEISQMC GYX₃SLQYFYS VFKKAYDTTP KEYRDVNSEV ML wherein X₃ is selected from the group consisting of S, K, and R |
| XylR mutated at residues 121 and 363 (SEQ ID NO: 28) | MFTKRHRITL LFNANKAYDR QVVEGVGEYL QASQSEWDIF IEEDFRARID KIKDWLGDGV IADFDDKQIE QALADVDVPI VGVGGSYHLA ESYPPVHYIA TDNYALVESA FLHLKEKGVN X₄FAFYGLPES SGKRWATERE YAFRQLVAEE KYRGVVYQGL ETAPENWQHA QNRLADWLQT LPPQTGIIAV TDARARHILQ VCEHLHIPVP EKLCVIGIDN EELTRYLSRV ALSSVAQGAR QMGYQAAKLL HRLLDKEEMP LQRILVPPVR VIERRSTDYR SLTDPAVIQA MHYIRNHACK GIKVDQVLDA VGISRSNLEK RFKEEVGETI HAMIHAEKLE KARSLLISTT LSINEISQMC GYX₅SLQYFYS VFKKAYDTTP KEYRDVNSEV ML wherein X₄ is selected from the group consisting of C, S, G, V, and P and X₅ is selected from the group consisting of S, K, and R |

In some embodiments where the recombinant bacterium comprises a single point mutation in residue 142 of the CRP protein, the recombinant bacterium may be selected from the group consisting of Acinetobacter species, C. acetobylicum, E. coli or X. campestris. In some embodiments where the recombinant bacterium comprises at least one point mutation in the XylR protein, the recombinant bacteria may be selected from the group consisting of C. acetobylicum, E. coli, P. oryzae, or P. syringae. In some embodiments, the recombinant bacterium may comprise a single point mutation in CRP, a single point mutation in XylR, two point mutations in XylR, or a combination of point mutations in CRP and XylR. In these embodiments, the recombinant bacterium may be C. acetobylicum or E. coli.

The recombinant bacterium may be a microbe other than the aforementioned species so long as the microbe's CRP protein and/or the microbe's XylR protein has a glycine at the residue corresponding to residue 142 of E. coli CRP protein, an arginine at the residue corresponding to residue 121 of the E. coli XylR protein, and/or a proline at the residue corresponding to residue 363 of the E. coli XylR protein. In one example, the microbe's CRP protein sequence must have at least 90%, at least 91%, at least 92%, at least 93%, at least 94%, at least 95%, at least 96%, at least 97%, at least 98%, or at least 99% coverage of SEQ ID NO:2 and also has a glycine at the residue corresponding to residue 142 of SEQ ID NO:2. In another example, the microbe's XylR protein must have least 90%, at least 91%, at least 92%, at least 93%, at least 94%, at least 95%, at least 96%, at least 97%, at least 98%, or at least 99% coverage of SEQ ID NO:13 and also has an arginine at the residue corresponding to residue 121 of SEQ ID NO:13 and/or a proline at the residue corresponding to residue 363 of SEQ ID NO:13. Furthermore, these microbes also have at least 40%, at least 41%, at least 42%, at least 43%, at least 44%, at least 45%, at least 46%, at least 47%, at least 48%, at least 49% or at least 50% sequence identity as SEQ ID NO:2 and/or SEQ ID NO:13.

The invention also encompasses isolated nucleic acids that encode a CRP protein with a point mutation at residue that corresponds to residue 142 of E. coli CRP protein and nucleic acids that encode a XylR protein with a point mutation in the residue that corresponds to residue 121 of E. coli XylR protein, residue 363 of E. coli XylR protein, or both.

In some embodiments, the nucleic acid encodes a CRP protein with the sequence set forth in SEQ ID NO:11, for example the nucleic acid sequence set forth in SEQ ID NO:10. The isolated nucleic acid may also encode a mutated CRP protein, wherein the corresponding wild type CRP protein has a protein sequence with at least 90%, at least 91%, at least 92%, at least 93%, at least 94%, at least 95%, at least 96%, at least 97%, at least 98%, or at least 99% coverage of SEQ ID NO:2 and also has a glycine at the residue corresponding to residue 142 of SEQ ID NO:2. The mutation of the mutated CRP protein comprises substituting the glycine at the residue corresponding to residue 142 of SEQ ID NO:2 with aspartic acid, proline, or histidine.

In other embodiments, the isolated nucleic acid encodes a XylR protein with the sequence set forth in one of SEQ ID NOs:26-28, for example the nucleic acid sequence set forth in one of SEQ ID NOs:23-25. The nucleic acid may also encode a mutated XylR protein, wherein the corresponding wild type XylR protein has a protein sequence with at least 90%, at least 91%, at least 92%, at least 93%, at least 94%, at least 95%, at least 96%, at least 97%, at least 98%, or at least 99% coverage of SEQ ID NO:13 and also has an arginine at the residue corresponding to residue 121 of SEQ ID NO:13 or a proline at the residue corresponding to residue 363 of SEQ ID NO:13. The mutation of the mutated XylR protein comprises substituting the arginine at the residue corresponding to residue 121 of SEQ ID NO:13 is with a cysteine, serine, glycine, valine or proline and/or substituting the proline at the residue corresponding to residue 363 of SEQ ID NO:13 with a serine, lysine, or arginine.

The present invention is further illustrated by the following examples that should not be construed as limiting. The contents of all references, patents, and published patent applications cited throughout this application, as well as the Figures, are incorporated herein by reference in their entirety for all purposes.

EXAMPLES

Example 1. Generation of Point Mutations in CRP and XylR Proteins in Wild Type *E. coli*

The method of generating point mutations in *E. coli* has been previously described, for example in Jantama, K. et al. "Eliminating side products and increasing succinate yields in engineered strains of *Escherichia coli C.*" *Biotechnology and bioengineering* 101, 881-893 (2008). The primary steps comprise transforming an expression plasmid into the desired strain of bacteria, replacing the target gene with the cat-sacB cassette, and replacing the cat-sacB cassette with the mutant allele.

1. Transform pKD46 into the Desired Strain

The desired strain of bacteria was *E. coli* (Migula) Castellani and Chalmers (ATCC® 9637™) obtained from the American Type Culture Collection (ATCC). The bacteria were transformed with the k-red recombinase expression plasmid pKD46 (a temperature sensitive plasmid) using methods well established in the art. The transformed *E. coli* were recovered and incubated at 30° C.

2. Replace the Target Gene with Cat-sacB Cassette

To induce the activity of λ-red recombinase, the transformed *E. coli* were cultured in LB Amp medium with 5% L-arabinose at 30° C. DNA fragments containing the cat-sacB cassette between the adjacent regions of the target gene crp (SEQ ID NO:5) or the target gene xylR (SEQ ID NO:16) were introduced into the transformed *E. coli* by electroporation. Methods of introducing DNA fragments into bacteria by electroporation are well established in the art. Successful integration of the cat-sacB cassette may be detected for resistance to chloramphenicol (cat$^+$) or sensitivity to sucrose (sacB$^s$). Successful integration of the cat-sacB cassette may also be detected by colony PCR, because the successful integration results in larger PCR products.

The DNA fragment containing the adjacent regions of the crp gene with the insertion of cat-sacB cassette was produced using PCR with the primer pairs set forth in SEQ ID NO:3 and SEQ ID NO:4. The PCR produced DNA fragment containing the adjacent regions of the crp gene with the insertion of cat-sacB cassette has a sequence set forth in SEQ ID NO:5. Table 4 summarizes the sequences of the primers and the PCR product. The underline portion of the primers and the depict the adjacent regions of the crp gene.

TABLE 4

Sequences for replacing the crp gene with the cat-sacB cassette.

| Identification | Nucleic Acid Sequence (5' → 3') |
|---|---|
| Forward primer (SEQ ID NO: 3) | <u>GGCGTTATCTGGCTCTGGAGAAAGCTTATAACAGAGGATAACCGCGCATGTC</u>GAGTGTGACGGAAGATCA |
| Reverse primer (SEQ ID NO: 4) | <u>CTACCAGGTAACGCGCCACTCCGACGGGATTAACGAGTGCCGTAAACGACCC</u>TTAGCCATTTGCCTGCT |
| PCR product (SEQ ID NO: 5) | <u>GGCGTTATCTGGCTCTGGAGAAAGCTTATAACAGAGGATAACCGCGCATGTC</u>GAGTGTGACGGAAGATCACTTCGCAGAATAAATAAATCCTGGTGTCCCTGTTGATACCGGGAAGCCCTGGGCCAACTTTTGGCGAAAATGAGACGTTGATCGGCACGTAAGAGGTTCCAACTTTCACCATAATGAAATAAGATCACTACCGGGCGTATTTTTTGAGTTATCGAGATTTTCAGGAGCTAAGGAAGCTAAAATGGAGAAAAAAATCACTGGATATACCACCGTTGATATATCCCAATGGCATCGTAAAGAACATTTTGAGGCATTTCAGTCAGTTGCTCAATGTACCTATAACCAGACCGTTCAGCTGGATATTACGGCCTTTTTAAAGACCGTAAAGAAAAATAAGCACAAGTTTTATCCGGCCTTTATTCACATTCTTGCCCGCCTGATGAATGCTCATCCGGAATTCCGTATGGCAATGAAAGACGGTGAGCTGGTGATATGGGATAGTGTTCACCCTTGTTACACCGTTTTCCATGAGCAAACTGAAACGTTTTCATCGCTCTGGAGTGAATACCACGACGATTTCCGGCAGTTTCTACACATATATTCGCAAGATGTGGCGTGTTACGGTGAAAACCTGGCCTATTTCCCTAAAGGGTTTATTGAGAATATGTTTTTCGTCTCAGCCAATCCCTGGGTGAGTTTCACCAGTTTTGATTTAAACGTGGCCAATATGGACAACTTCTTCGCCCCCGTTTTCACCATGGGCAAATATTATACGCAAGGCGACAAGGTGCTGATGCCGCTGGCGATTCAGGTTCATCATGCCGTTTGTGATGCTTCCATGTCGGCAGAATGCTTAATGAATTACAACAGTACTGCGATGAGTGGCAGGGCGGGCGTAATTTTTTTAAGGCAGTTATTGGTGCCCTTAAACGCCTGGTGCTACGCCTGAATAAGTGATAATAAGCGGATGAATGGCAGAAATTCGAAAGCAAATTCGACCCGGTCGTCGGTTCAGGGCAGGGTCGTTAAATAGCCGCTAGATCTAAGTAAATCGCGCGGGTTTGTTACTGATAAAGCAGGCAAGACCTAAAATGTGTAAAGGGCAAAGTGTATACTTTGGCGTCACCCCTTACATATTTTAGGTCTTTTTTTATTGTGCGTAACTAACTTGCCATCTTCAAACAGGAGGGCTGGAAGAAGCAGACCGCTAACACAGTACATAAAAAAGGAGACATGAACGATGAACATCAAAAAGTTTGCAAAACAAGCAACAGTATTAACCTTTACTACCGCACTGCTGGCAGGAGGCGCAACTCAAGCGTTTGCGAAAGAAACGAACCAAAAGCCATATAAGGAAACATACGGCATTTCCCATATTACACGCCATGATATGCTGCAAATCCCTGAACAGCAAAAAAATGAAAAATATCAAGTTCCTGAATTCGATTCGTCCACAATTAAAAATATCTCTTCTGCAAAAGGCCTGGACGTTTGGGACAGCTGGCCATTACAAAACGCTGACGGCACTGTCGCAAACTATCACGGCTACCACATCGTCTTTGCATTAGCCGGAGATCCTAAAAATGCGGATGACACATCGATTTACATGTTCTATCAAAAAGTCGGCGAAACTTCTATTGACAGCTGGAAAA |

TABLE 4-continued

Sequences for replacing the crp gene with the cat-sacB cassette.

| Identification | Nucleic Acid Sequence (5' → 3') |
|---|---|
| | ACGCTGGCCGCGTCTTTAAAGACAGCGACAAATTCGATGCAAATGATTCTAT
CCTAAAAGACCAAACACAAGAATGGTCAGGTTCAGCCACATTTACATCTGAC
GGAAAAATCCGTTTATTCTACACTGATTTCTCCGGTAAACATTACGGCAAAC
AAACACTGACAACTGCACAAGTTAACGTATCAGCATCAGACAGCTCTTTGAA
CATCAACGGTGTAGAGGATTATAAATCAATCTTTGACGGTGACGGAAAAACG
TATCAAAATGTACAGCAGTTCATCGATGAAGGCAACTACAGCTCAGGCGACA
ACCATACGCTGAGAGATCCTCACTACGTAGAAGATAAAGGCCACAAATACTT
AGTATTTGAAGCAAACACTGGAACTGAAGATGGCTACCAAGGCGAAGAATCT
TTATTTAACAAAGCATACTATGGCAAAAGCACATCATTCTTCCGTCAAGAAA
GTCAAAAACTTCTGCAAAGCGATAAAAAACGCACGGCTGAGTTAGCAAACGG
CGCTCTCGGTATGATTGAGCTAAACGATGATTACACACTGAAAAAAGTGATG
AAACCGCTGATTGCATCTAACACAGTAACAGATGAAATTGAACGCGCGAACG
TCTTTAAAATGAACGGCAAATGGTACCTGTTCACTGACTCCCGCGGATCAAA
AATGACGATTGACGGCATTACGTCTAACGATATTTACATGCTTGGTTATGTT
TCTAATTCTTTAACTGGCCCATACAAGCCGCTGAACAAAACTGGCCTTGTGT
TAAAAATGGATCTTGATCCTAACGATGTAACCTTTACTTACTCACACTTCGC
TGTACCTCAAGCGAAAGGAAACAATGTCGTGATTACAAGCTATATGACAAAC
AGAGGATTCTACGCAGACAAACAATCAACGTTTGCGCCAAGCTTCCTGCTGA
ACATCAAAGGCAAGAAAACATCTGTTGTCAAAGACAGCATCCTTGAACAAGG
ACAATTAACAGTTAACAAATAAAAACGCAAAAGAAAATGCCGATATCCTATT
GGCATTTTCTTTTATTTCTTATCAACATAAAGGTGAATCCCATATGAACTAT
ATAAAAGCAGGCAAATGGCTAAGGGTCGTTTACGGCACTCGTTAATCCCGTC
GGAGTGGCGCGTTACCTGGTAG |

The DNA fragment containing the adjacent regions of the xylR gene with the insertion of cat-sacB cassette was produced using PCR with the primer pairs set forth in SEQ ID NO:14 and SEQ ID NO:15. The PCR produced DNA fragment containing the adjacent regions of the xylR gene with the insertion of cat-sacB cassette has a sequence set forth in SEQ ID NO:5. Table 5 summarizes the sequences of the primers and the PCR product. The underline portion of the primers indicates the adjacent regions of the xylR gene.

TABLE 5

Sequences for replacing the xylR gene with the cat-sacB cassette.

| Identification | Nucleic Acid Sequence (5' → 3') |
|---|---|
| Forward primer (SEQ ID NO: 14) | TCTCAAAGCCGGTTACGTATTACCGGTTTTGAGTTTTTGCATGATTCAGCT
CGAGTGTGACGGAAGATCA |
| Reverse primer (SEQ ID NO: 15) | GATAAGGCTTTTGCTCGCATCAGGTGGCTGTGCTGAGTTCCCTGATGTGAC
CTTAGCCATTTGCCTGCT |
| PCR product (SEQ ID NO: 16) | TCTCAAAGCCGGTTACGTATTACCGGTTTTGAGTTTTTGCATGATTCAGCT
CGAGTGTGACGGAAGATCACTTCGCAGAATAAATAAATCCTGGTGTCCCTG
TTGATACCGGGAAGCCCTGGGCCAACTTTTGGCGAAAATGAGACGTTGATC
GGCACGTAAGAGGTTCAACTTTCACCATAATGAAATAAGATCACTACCGG
GCGTATTTTTTGAGTTATCGAGATTTTCAGGAGCTAAGGAAGCTAAAATGG
AGAAAAAAATCACTGGATATACCACCGTTGATATATCCCAATGGCATCGTA
AAGAACATTTTGAGGCATTTCAGTCAGTTGCTCAATGTACCTATAACCAGA
CCGTTCAGCTGGATATTACGGCCTTTTTAAAGACCGTAAAGAAAAATAAGC
ACAAGTTTTATCCGGCCTTTATTCACATTCTTGCCCGCCTGATGAATGCTC
ATCCGGAATTCCGTATGGCAATGAAAGACGGTGAGCTGGTGATATGGGATA
GTGTTCACCCTTGTTACACCGTTTTCCATGAGCAAACTGAAACGTTTTCAT
CGCTCTGGAGTGAATACCACGACGATTTCCGGCAGTTTCTACACATATATT
CGCAAGATGTGGCGTGTTACGGTGAAAACCTGGCCTATTTCCCTAAAGGGT
TTATTGAGAATATGTTTTTCGTCTCAGCCAATCCCTGGGTGAGTTTCACCA
GTTTTGATTTAAACGTGGCCAATATGGACAACTTCTTCGCCCCCGTTTTCA
CCATGGGCAAATATTATACGCAAGGCGACAAGGTGCTGATGCCGCTGGCGA
TTCAGGTTCATCATGCCGTTTGTGATGGCTTCCATGTCGGCAGAATGCTTA
ATGAATTACAACAGTACTGCGATGAGTGGCAGGGCGGGGCGTAATTTTTTT
AAGGCAGTTATTGGTGCCCTTAAACGCCTGGTGCTACGCCTGAATAAGTGA
TAATAAGCGGATGAATGGCAGAAATTCGAAAGCAAATTCGACCCGGTCGTC
GGTTCAGGGCAGGGTCGTTAAATAGCCGCTAGATCTAAGTAAATCGCGCGG
GTTTGTTACTGATAAAGCAGGCAAGACCTAAAATGTGTAAAGGGCAAAGTG
TATACTTTGGCGTCACCCCTTACATATTTTAGGTCTTTTTTTATTGTGCGT
AACTAACTTGCCATCTTCAAACAGGAGGGCTGGAAGAAGCAGACCGCTAAC
ACAGTACATAAAAAAGGAGACATGAACGATGAACATCAAAAAGTTTGCAAA
ACAAGCAACAGTATTAACCTTTACTACCGCACTGCTGGCAGGAGGCGCAAC
TCAAGCGTTTGCGAAAGAAACGAACCAAAAGCCATATAAGGAAACATACGG
CATTTCCCATATTACACGCCATGATATGCTGCAAATCCCTGAACAGCAAAA
AAATGAAAAATATCAAGTTCCTGAATTCGATTCGTCCACAATTAAAAATAT
CTCTTCTGCAAAAGGCCTGGACGTTTGGGACAGCTGGCCATTACAAAACGC
TGACGGCACTGTCGCAAACTATCACGGCTACCACATCGTCTTTGCATTAGC |

TABLE 5-continued

Sequences for replacing the xylR gene with the cat-sacB cassette.

| Identification | Nucleic Acid Sequence (5' → 3') |
|---|---|
| | CGGAGATCCTAAAAATGCGGATGACACATCGATTTACATGTTCTATCAAAA |
| | AGTCGGCGAAACTTCTATTGACAGCTGGAAAAACGCTGGCCGCGTCTTTAA |
| | AGACAGCGACAAATTCGATGCAAATGATTCTATCCTAAAAGACCAAACACA |
| | AGAATGGTCAGGTTCAGCCACATTTACATCTGACGGAAAAATCCGTTTATT |
| | CTACACTGATTTCTCCGGTAAACATTACGGCAAACAAACACTGACAACTGC |
| | ACAAGTTAACGTATCAGCATCAGACAGCTCTTTGAACATCAACGGTGTAGA |
| | GGATTATAAATCAATCTTTGACGGTGACGGAAAAACGTATCAAATGTACA |
| | GCAGTTCATCGATGAAGGCAACTACAGCTCAGGCGACAACCATACGCTGAG |
| | AGATCCTCACTACGTAGAAGATAAAGGCCACAAATACTTAGTATTTGAAGC |
| | AAACACTGGAACTGAAGATGGCTACCAAGGCGAAGAATCTTTATTTAACAA |
| | AGCATACTATGGCAAAAGCACATCATTCTTCCGTCAAGAAAGTCAAAAACT |
| | TCTGCAAAGCGATAAAAAACGCACGGCTGAGTTAGCAAACGGCGCTCTCGG |
| | TATGATTGAGCTAAACGATGATTACACACTGAAAAAAGTGATGAAACCGCT |
| | GATTGCATCTAACACAGTAACAGATGAAATTGAACGCGCGAACGTCTTTAA |
| | AATGAACGGCAAATGGTACCTGTTCACTGACTCCCGCGGATCAAAAATGAC |
| | GATTGACGGCATTACGTCTAACGATATTTACATGCTTGGTTATGTTTCTAA |
| | TTCTTTAACTGGCCCATACAAGCCGCTGAACAAAACTGGCCTTGTGTTAAA |
| | AATGGATCTTGATCCTAACGATGTAACCTTTACTTACTCACACTTCGCTGT |
| | ACCTCAAGCGAAAGGAAACAATGTCGTGATTACAAGCTATATGACAAACAG |
| | AGGATTCTACGCAGACAAACAATCAACGTTTGCGCCAAGCTTCCTGCTGAA |
| | CATCAAAGGCAAGAAAACATCTGTTGTCAAAGACAGCATCCTTGAACAAGG |
| | ACAATTAACAGTTAACAAATAAAAACGCAAAAGAAAATGCCGATATCCTAT |
| | TGGCATTTTCTTTTATTTCTTATCAACATAAAGGTGAATCCCATATGAACT |
| | ATATAAAAGCAGGCAAATGGCTAAGGTCACATCAGGGAACTCAGCACAGCC |
| | ACCTGATGCGAGCAAAAGCCTTATC |

3. Replace the cat-sacB cassette with mutant allele

*E. coli* clones with the cat-sacB cassette successfully integrated were cultured at 30° C. in LB Amp medium with 5% arabinose to induce the expression of λ-red recombinase from pKD46. DNA fragments containing mutated target gene crp gene (SEQ ID NO:10) or mutated target gene xylR gene (SEQ ID NOs:23-25) were introduced into these strains using electroporation. After a period of recovery by culturing in LB medium with 10% sucrose, individual clones were isolated. Clones with the mutated target genes are sensitive for chloramphenicol (cal). Chloramphenicol sensitive clones were further confirmed with colony PCR and Sanger sequencing. Once the clones are confirmed to have mutated crp gene or mutated xylR gene, the clones are cultured in 39° C. to remove the pKD46 plasmid.

The mutated target genes are produced by overlapping extension PCR using three PCR reactions. Two separate polymerase chain reactions, PCR1 and PCR2, produces two parts of the target gene, wherein the combination of the two PCR products using the forward primer of PCR1 and the reverse primer of PCR2, which involves a third polymerase chain reaction (PCR3), produces a nucleic acid sequence encoding a the gene with a desired mutation. The forward primer of PCR2 is the antisense sequence of the reverse primer of PCR1, and the primer sequences introduce the necessary change in the sequence of the target gene to result in the desired point mutation in the amino acid sequence. Accordingly, PCR1 produces the portion of the target gene from the 5' end to the region of the introduced mutation while PCR2 produces the portion of the target gene from the region of the introduced mutation to the 3' end.

Table 6 lists the PCR primers for the generation of a mutated crp gene that produces the G142D mutation in the CRP protein and the sequence of the PCR3 product. Table 7 lists the PCR primers for the generation of a mutated xylR gene that produces the R121C mutation in the XylR protein and the sequence of the PCR3 product. Table 8 lists the PCR primers for the generation of a mutated xylR gene that produces the P363C mutation in the XylR protein and the sequence of the PCR3 product. The bolded letter represents the substituted nucleic acid to produce the desired point mutation in the protein.

TABLE 6

| Identification | Nucleic Acid Sequence (5' → 3') |
|---|---|
| crp mutagenesis PCR1 and PCR3 forward primer (SEQ ID NO: 6) | GGCGTTATCTGGCTCTGGA |
| crp mutagenesis PCR1 reverse primer (SEQ ID NO: 7) | GCAATGCGGTCCGTCACGTC |
| crp mutagenesis PCR2 forward primer (SEQ ID NO: 8) | GACGTGACGGACCGCATTGC |
| crp mutagenesis PCR2 and PCR3 reverse primer (SEQ ID NO: 9) | CTACCAGGTAACGCGCCACT |

TABLE 6-continued

| Identification | Nucleic Acid Sequence (5' → 3') |
|---|---|
| Sequence of CRP protein with G14D mutation (SEQ ID NO: 10) | ATGGTGCTTGGCAAACCGCAAACAGACCCGACTCTCGAATGGTTCTTGTCT CATTGCCACATTCATAAGTACCCATCCAAGAGCACGCTTATTCACCAGGGT GAAAAAGCGGAAACGCTGTACTACATCGTTAAAGGCTCTGTGGCAGTGCTG ATCAAAGACGAAGAGGGTAAAGAAATGATCCTCTCCTATCTGAATCAGGGT GATTTTATTGGCGAACTGGGCCTGTTTGAAGAGGGCCAGGAACGTAGCGCA TGGGTACGTGCGAAAACCGCCTGTGAAGTGGCTGAAATTTCGTACAAAAAA TTTCGCCAATTGATTCAGGTAAACCCGGACATTCTGATGCGTCTGTCTGCA CAGATGGCGCGTCGTCTGCAAGTCACTTCAGAGAAAGTGGGCAACCTGGCG TTCCTCGACGTGACGGACCGCATTGCACAGACTCTGCTGAACCTGGCAAAA CAACCAGATGCTATGACTCACCCGGACGGTATGCAAATCAAAATTACCCGT CAGGAAATCGGTCAGATTGTCGGCTGTTCTCGTGAAACCGTGGGACGCATT CTGAAGATGCTGGAAGATCAGAACCTGATCTCCGCACACGGTAAAACCATC GTCGTTTACGGCACTCGTTAA |

TABLE 7

| Identification | Nucleic Acid Sequence (5' → 3') |
|---|---|
| xylR mutagenesis PCR1 and PCR3 forward primer (SEQ ID NO: 17) | TCTCAAAGCCGGTTACGTATTAC |
| xylR mutagenesis PCR1 reverse primer (SEQ ID NO: 18) | AAGCAAAGCAGTTAACGCCT |
| xylR mutagenesis PCR2 forward primer (SEQ ID NO: 20) | AAGGCGTTAACTGCTTTGCT |
| xylR mutagenesis PCR2 and PCR3 reverse primer (SEQ ID NO: 22) | GATAAGGCTTTTGCTCGCATCA |
| Sequence of XylR protein with R121C mutation (SEQ ID NO: 23) | ATGTTTACTAAACGTCACCGCATCACATTACTGTTCAATGCCAATAAAGCC TATGACCGGCAGGTAGTAGAAGGCGTAGGGGAATATTTACAGGCGTCACAA TCGGAATGGGATATTTTCATTGAAGAAGATTTCCGCGCCCGCATTGATAAA ATCAAGGACTGGTTAGGAGATGGCGTCATTGCCGACTTCGACGACAAACAG ATCGAGCAAGCGCTGGCTGATGTCGACGTCCCCATTGTTGGGGTTGGCGGC TCGTATCACCTTGCAGAAAGTTACCCACCCGTTCATTACATTGCCACCGAT AACTATGCGCTGGTTAAAGCGCATTTTTGCATTTAAAAGAGAAAGGCGTT AACTGCTTTGCTTTTTATGGTCTTCCGGAATCAAGCGGCAAACGTTGGGCC ACTGAGCGCGAATATGCATTTCGTCAGCTTGTCGCTGAAGAAAAGTATCGC GGAGTGGTTTATCAGGGGTTAGAAACCGCGCCAGAGAACTGGCAACACGCG CAAAATCGGCTGGCAGACTGGCTACAAACGCTGCCACCGCAAACCGGGATT ATTGCCGTTACTGACGCCCGAGCGCGGCATATTCTGCAAGTATGTGAACAT CTACATATTCCCGTACCGGAAAAATTATGCGTGATTGGCATCGATAACGAA GAACTGACCCGCTATCTGTCGCGTGTCGCCCTTTCTTCGGTCGCTCAGGGC GCGCGGCAAATGGGCTATCAGGCGGCAAAACTGTTGCATCGATTATTAGAT AAAGAAGAAATGCCGCTACAGCGAATTTTGGTCCCACCAGTTCGCGTCATT GAACGGCGCTCAACAGATTATCGCTCGCTGACCGATCCCGCCGTTATTCAG GCCATGCATTACATTCGTAATCACGCCTGTAAAGGGATTAAAGTGGATCAG GTACTGGATGCGGTCGGGATCTCGCGCTCCAATCTTGAGAAGCGTTTTAAA GAAGAGGTGGGTGAAACCATCCATGCCATGATTCATGCCGAGAAGCTGGAG AAAGCGCGCAGTCTGCTGATTTCAACCACCTTGTCGATCAATGAGATATCG CAAATGTGCGGTTATCCATCGCTGCAATATTTCTACTCTGTTTTTAAAAAA GCATATGACACAACGCCAAAAGAGTATCGCGATGTAAATAGCGAGGTCATG TTGTAG |

TABLE 8

| Identification | Nucleic Acid Sequence (5' → 3') |
|---|---|
| xylR mutagenesis PCR1 and PCR3 forward primer (SEQ ID NO: 17) | TCTCAAAGCCGGTTACGTATTAC |

TABLE 8-continued

| Identification | Nucleic Acid Sequence (5' → 3') |
|---|---|
| xylR mutagenesis PCR1 reverse primer (SEQ ID NO: 19) | CAGCGATGAATAACCGCACA |
| xylR mutagenesis PCR2 forward primer (SEQ ID NO: 21) | ATGTGCGGTTATTCATCGCTG |
| xylR mutagenesis PCR2 and PCR3 reverse primer (SEQ ID NO: 22) | GATAAGGCTTTTGCTCGCATCA |
| Sequence of XylR protein with G363S mutation (SEQ ID NO: 24) | ATGTTTACTAAACGTCACCGCATCACATTACTGTTCAATGCCAATAAAGCC TATGACCGGCAGGTAGTAGAAGGCGTAGGGGAATATTTACAGGCGTCACAA TCGGAATGGGATATTTTCATTGAAGAAGATTTCCGCGCCCGCATTGATAAA ATCAAGGACTGGTTAGGAGATGGCGTCATTGCCGACTTCGACGACAAACAG ATCGAGCAAGCGCTGGCTGATGTCGACGTCCCCATTGTTGGGGTTGGCGGC TCGTATCACCTTGCAGAAAGTTACCCACCCGTTCATTACATTGCCACCGAT AACTATGCGCTGGTTGAAAGCGCATTTTTGCATTTAAAAGAGAAAGGCGTT AACCGCTTTGCTTTTTATGGTCTTCCGGAATCAAGCGGCAAACGTTGGGCC ACTGAGCGCGAATATGCATTTCGTCAGCTTGTCGCTGAAGAAAAGTATCGC GGAGTGGTTTATCAGGGGTTAGAAACCGCGCCAGAGAACTGGCAACACGCG CAAAATCGGCTGGCAGACTGGCTACAAACGCTGCCACCGCAAACCGGGATT ATTGCCGTTACTGACGCCCGAGCGCGGCATATTCTGCAAGTATGTGAACAT CTACATATTCCCGTACCGGAAAAATTATGCGTGATTGGCATCGATAACGAA GAACTGACCCGCTATCTGTCGCGTGTCGCCCTTTCTTCGGTCGCTCAGGGC GCGCGGCAAATGGGCTATCAGGCGGCAAAACTGTTGCATCGATTATTAGAT AAAGAAGAAATGCCGCTACAGCGAATTTTGGTCCCACCAGTTCGCGTCATT GAACGGCGCTCAACAGATTATCGCTCGCTGACCGATCCCGCCGTTATTCAG GCCATGCATTACATTCGTAATCACGCCTGTAAAGGGATTAAAGTGGATCAG GTACTGGATGCGGTCGGGATCTCGCGCTCCAATCTTGAGAAGCGTTTTAAA GAAGAGGTGGGTGAAACCATCCATGCCATGATTCATGCCGAGAAGCTGGAG AAAGCGCGCAGTCTGCTGATTTCAACCACCTTGTCGATCAATGAGATATCG CAAATGTGCGGTTATTCATCGCTGCAATATTTCTACTCTGTTTTTAAAAAA GCATATGACACAACGCCAAAAGAGTATCGCGATGTAAATAGCGAGGTCATG TTGTAG |

To produce a nucleic acid sequence that encodes a XylR protein containing both the R121C mutation and the P363C mutation, the nucleic acid having the sequence forth at in SEQ ID NO:23 may be used as the DNA template for overlapping PCR extension experiment using the primers listed in Table 6. Alternatively, the nucleic acid having the sequence forth at in SEQ ID NO:24 may be used as the DNA template for overlapping PCR extension experiment using the primers listed in Table 5. The nucleic acid sequence that encodes a XylR protein with both the R121C and P363C mutations has the following sequence:

(SEQ ID NO: 25)
5'-ATGTTTACTAAACGTCACCGCATCACATTACTGTTCAATGCCAATA

AAGCCTATGACCGGCAGGTAGTAGAAGGCGTAGGGGAATATTTACAGGC

GTCACAATCGGAATGGGATATTTTCATTGAAGAAGATTTCCGCGCCCGC

ATTGATAAAATCAAGGACTGGTTAGGAGATGGCGTCATTGCCGACTTCG

ACGACAAACAGATCGAGCAAGCGCTGGCTGATGTCGACGTCCCCATTGT

TGGGGTTGGCGGCTCGTATCACCTTGCAGAAAGTTACCCACCCGTTCAT

TACATTGCCACCGATAACTATGCGCTGGTTGAAAGCGCATTTTTGCATT

TAAAAGAGAAAGGCGTTAACCGCTTTGCTTTTTATGGTCTTCCGGAATC

AAGCGGCAAACGTTGGGCCACTGAGCGCGAATATGCATTTCGTCAGCTT

GTCGCTGAAGAAAAGTATCGCGGAGTGGTTTATCAGGGGTTAGAAACCG

CGCCAGAGAACTGGCAACACGCGCAAAATCGGCTGGCAGACTGGCTACA

AACGCTGCCACCGCAAACCGGGATTATTGCCGTTACTGACGCCCGAGCG

CGGCATATTCTGCAAGTATGTGAACATCTACATATTCCCGTACCGGAAA

AATTATGCGTGATTGGCATCGATAACGAAGAACTGACCCGCTATCTGTC

GCGTGTCGCCCTTTCTTCGGTCGCTCAGGGCGCGCGGCAAATGGGCTAT

CAGGCGGCAAAACTGTTGCATCGATTATTAGATAAAGAAGAAATGCCGC

TACAGCGAATTTTGGTCCCACCAGTTCGCGTCATTGAACGGCGCTCAAC

AGATTATCGCTCGCTGACCGATCCCGCCGTTATTCAGGCCATGCATTAC

ATTCGTAATCACGCCTGTAAAGGGATTAAAGTGGATCAGGTACTGGATG

CGGTCGGGATCTCGCGCTCCAATCTTGAGAAGCGTTTTAAAGAAGAGGT

GGGTGAAACCATCCATGCCATGATTCATGCCGAGAAGCTGGAGAAAGCG

CGCAGTCTGCTGATTTCAACCACCTTGTCGATCAATGAGATATCGCAAA

TGTGCGGTTATTCATCGCTGCAATATTTCTACTCTGTTTTTAAAAAAGC

ATATGACACAACGCCAAAAGAGTATCGCGATGTAAATAGCGAGGTCATG

TTGTAG-3'.

Figure 2:
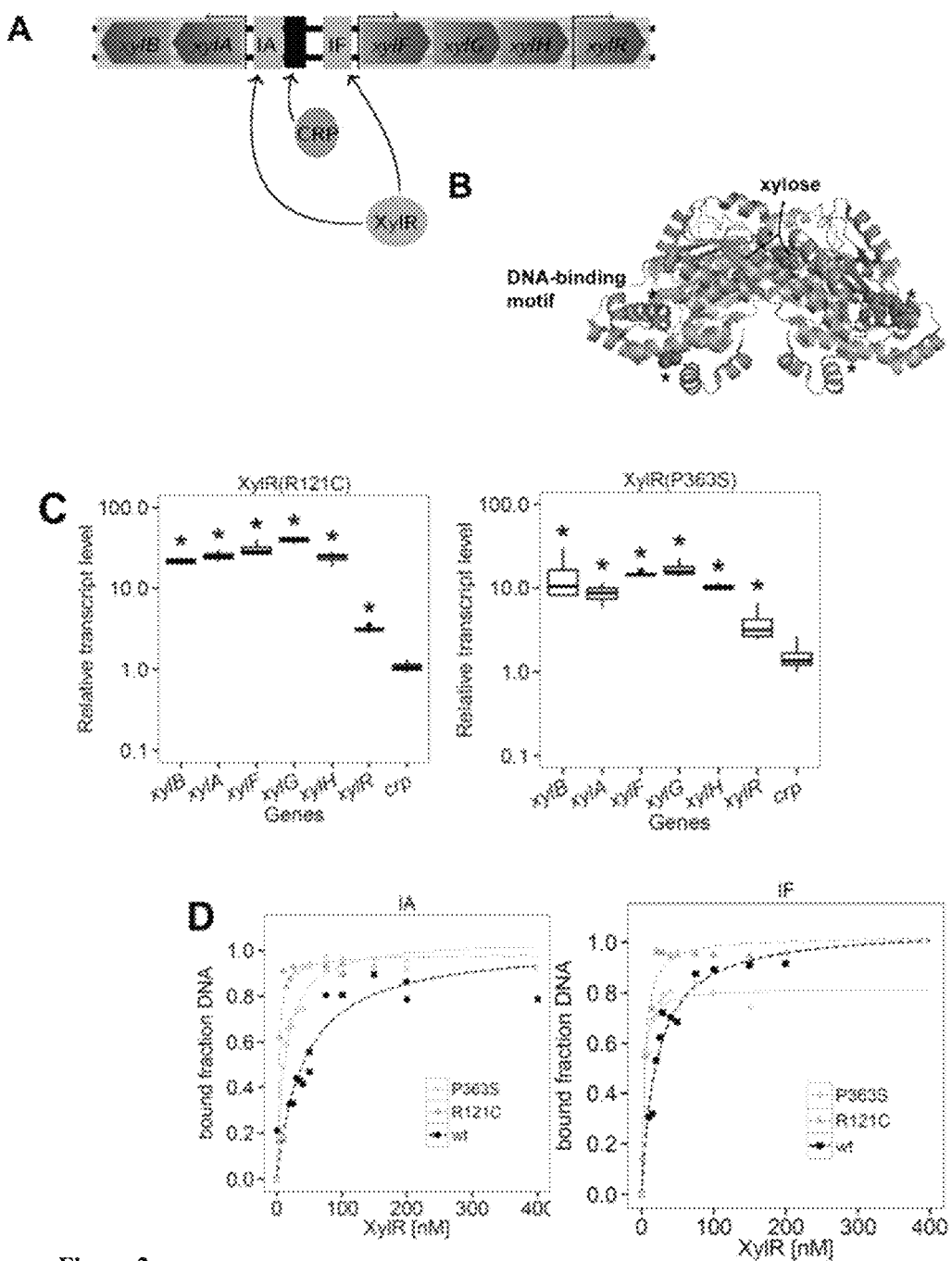
FIG. 2 depicts the molecular mechanism of the enhanced XylR activation by SNP mutations. Panel A is a schematic drawing of the xylFGHR and xylAB operons and transcriptional start points (arrows). Binding sites for the global regulator CRP and XylR are indicated. XylR has two known binding sites indicated with IA and IF. Panel B is a structural model of the dimeric wild-type XylR. The following features are highlighted: xylose (bulbous structure in the center), SNPs (bulbous structure in the outer edges) and DNA binding domain (lighter ribbons in the outer edges near the SNPs). Panel C shows the relative transcript abundance of the indicated genes from the *E. coli* strains with mutated xylR (R121C and P365S) compared to the strain with wild-type xylR using quantitative RT-PCR. Unpaired Student's t-test indicates significance at $p<0.05$ (*). Panel D shows fitted data from the electrophoretic mobility shift assays to determine the binding affinity of different XylR variants with their known binding sites IA and IF, respectively.

Example 2. SNP Mutations Change the Interaction Mode of XylR with its Targeted Promoter DNA The binding affinity and transcriptional activities are increased by a P363C mutation or R121C mutation in the XylR protein (FIG. 2). Dissociation constants derived from FIG. 2D are shown in Table 9.

TABLE 9

| XylR | Site | $K_D$ (nM) |
| --- | --- | --- |
| wt | IA | 38.5 ± 8.4 |
| R121C | IA | 2.7 ± 0.5 |
| P363S | IA | 12.4 ± 2.1 |
| wt | IF | 19.6 ± 3.4 |
| R121C | IF | 4 ± 0.8 |
| P363S | IF | 27 ± 0.6 |

Figure 3:
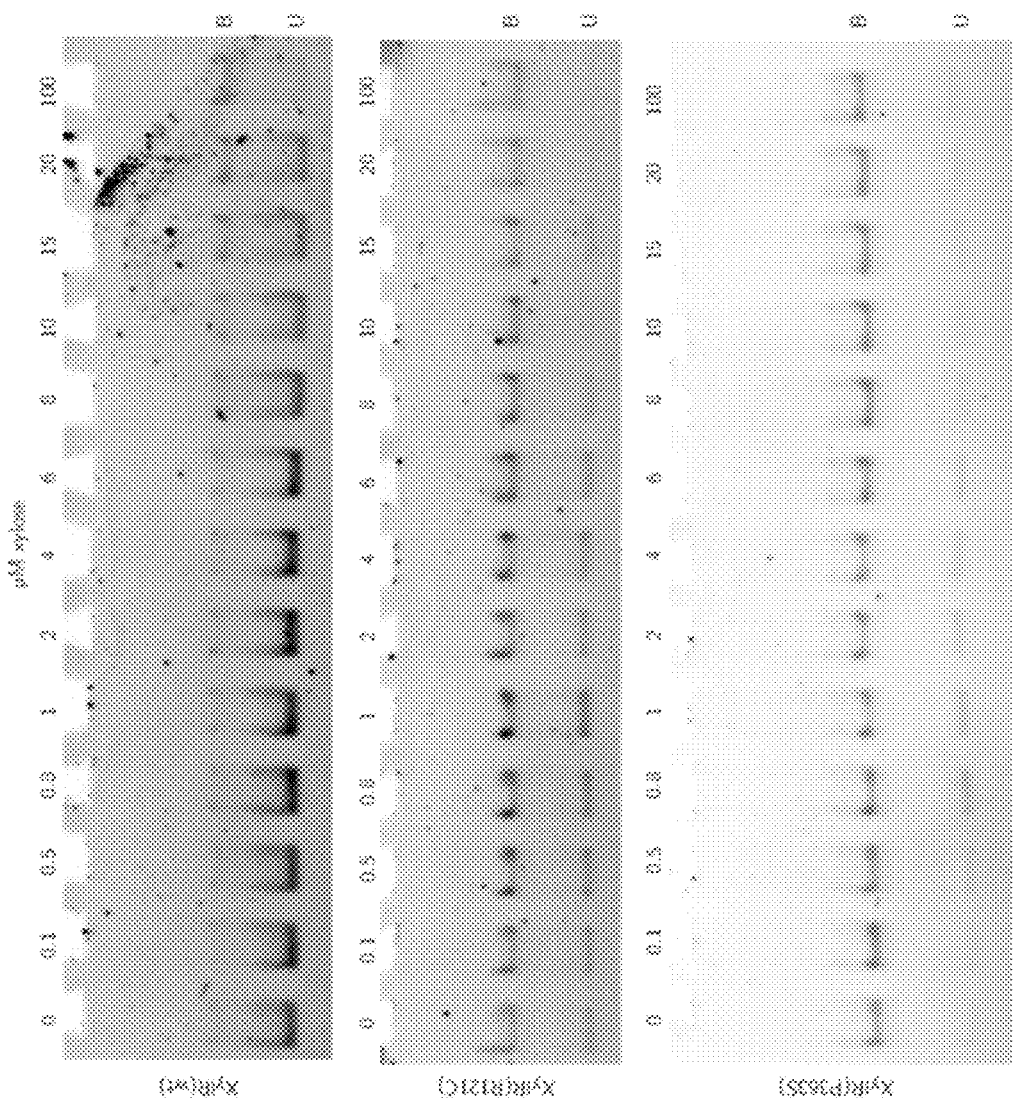
FIG. 3 depicts results of an electrophoretic mobility shift assays for the xylose response of XylR. XylR wild-type (wt) and the SNP variants R121C and P363S were incubated with DNA containing the binding sites with the varying xylose concentrations. B indicates XylR in a DNA-bound form and U indicates a DNA-unbound form.

Example 3. SNP Mutations Change the Interaction Mode of XylR with its Ligand, Xylose For wild-type XylR, increased concentrations of xylose led to the formation of DNA-protein complex (B bands in FIG. 3) and decreased amounts of unbound free XylR proteins (U bands in FIG. 3). SNP mutations induced the formation of DNA-protein complex in the absence of xylose. Therefore, the activator function of XylR is enhanced by these SNP mutations.

Figure 4:
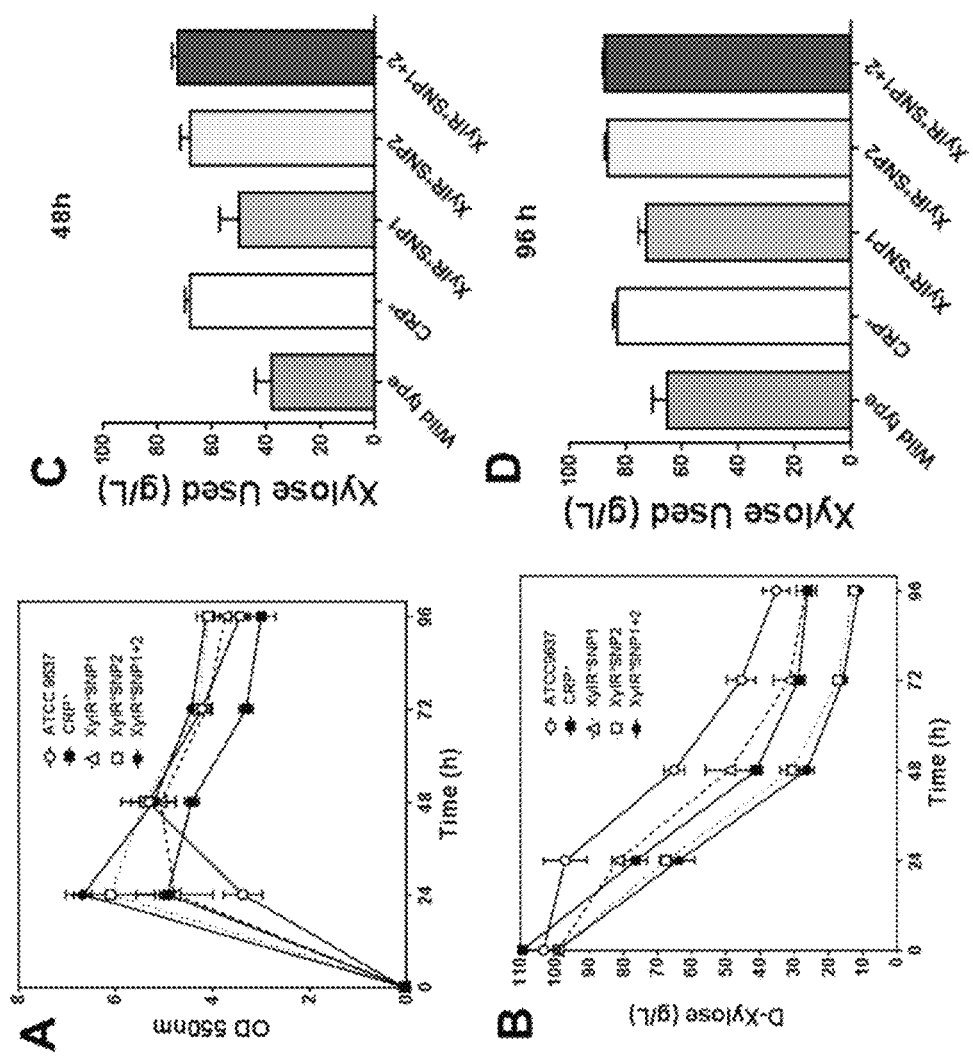
FIG. 4 depicts the effects of point mutations in the crp gene and the xylR gene of *E. coli* (ATCC9637) on the rate of xylose utilization. CRP* is a mutant version of CRP with G142D mutation (glycine to aspartate at residue 142). XylR*SNP1 is a mutant version of XylR with R121C mutation (arginine to cysteine at residue 121). XylR*SNP2 is a mutant version of XylR with P363S mutation (proline to serine at residue 363). XylR*SNP1+2 is a mutant version of XylR with both R121C and P363S mutations. Wild-type *E. coli* and its derived recombinant strains with the indicated mutations were grown in fermentation vessel in mineral salts medium supplemented with 100 g/L xylose. Panel A depicts cell optical densities. Panel B depicts xylose concentrations of the cultures measured every 24 hours. Panels C and D depict the amount of xylose used at 48 hours and 96 hours, respectively, of culturing.

Example 4. Results of Point Mutations in CRP and XylR Proteins in Wild Type E. coli on Sugar Utilization and Metabolism As shown in FIG. 4 the E. coli cells with a CRP protein with the G142D mutation, a XylR protein with the R121C mutation, a XylR protein with the P363C mutation, or a XylR protein with both R121C and P363C mutations all have increased xylose utilization compared to their wild type counterpart. The increased xylose utilization does not come at a significant cost of cell viability. The optical densities of the three cultures of E. coli with mutated XylR proteins have similar cell densities as the culture of wild type E. coli from 48 hours of culture even through 96 hours of culture (FIG. 4 Panel A). Though the optical densities of the culture of E. coli with a mutated CRP protein have lower optical density at 48 hours of culture, its cell density was similar to the wild type culture and cultures containing mutated XylR proteins (FIG. 4 Panel A). Panels B-D of FIG. 4 demonstrates that while all E. coli cultures containing mutations in the CRP protein or the XylR protein have increased xylose utilization after 48 hours of culture, the cultures having a CRP protein with the G142D mutation, a XylR protein with the P363C mutation, and a XylR protein with both the R121C and P363C mutations had the most increase in xylose utilization compared to the wild type counterpart. The increase in xylose utilization in these cultures was sustained even 96 hours after culturing.

Figure 5:
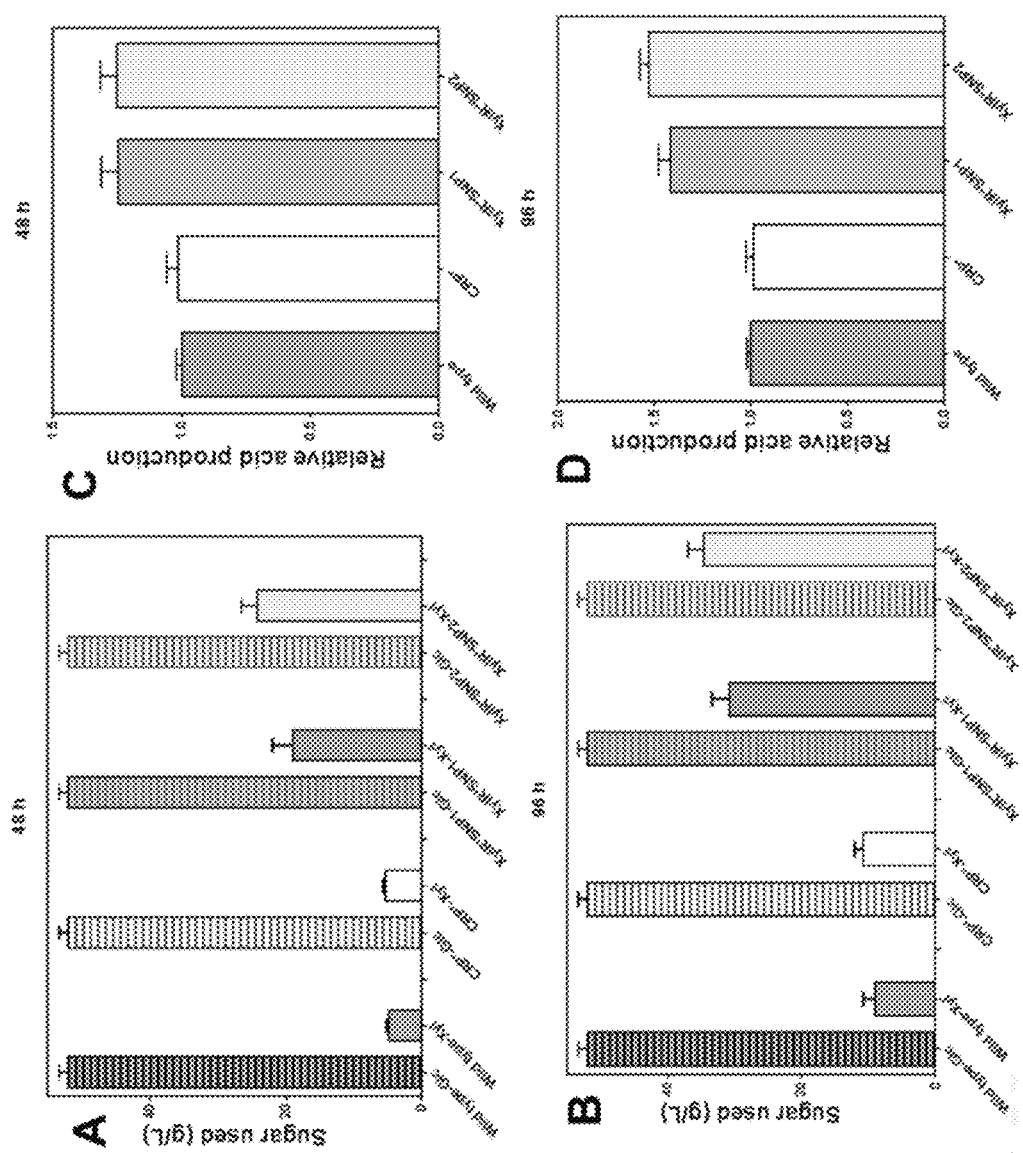
FIG. 5 depicts the effect of point mutations in the crp gene and the xylR gene of *E. coli* (ATCC9637) on the rate of sugar co-utilization and the rate of acid production. CRP* is a mutant version of CRP with G142D mutation (glycine to aspartate at residue 142). XylR*SNP1 is a mutant version of XylR with R121C mutation (arginine to cysteine at residue 121). XylR*SNP2 is a mutant version of XylR with P363S mutation (proline to serine at residue 363). XylR*SNP1+2 is a mutant version of XylR with both R121C and P363S mutations. Wild-type *E. coli* and its derived recombinant strains with the indicated mutations were grown in fermentation vessel in mineral salts medium supplemented with the mixture of 50 g/L glucose and 50 g/L xylose. The used glucose (bars with lines) and xylose (bars without lines) concentrations are measured at 48 hours (Panel A) and 96 hours (Panel B) of culturing. The total acids produced during fermentation were quantified by the amount of base used for titration. Panels C and D depict the amounts of produced acids by recombinant strains relative to that of wild type at 48 hours and 96 hours, respectively, of culturing.

Increase in xylose utilization of E. coli having a XylR protein with the R121C mutation, or a XylR protein with the P363C mutation was sustained even in the presence of glucose without any cost of glucose utilization 48 hours and 96 hours after culturing in mineral salts medium supplemented with the mixture of 50 g/L glucose and 50 g/L xylose (FIG. 5 Panels A and B). Acid production was also increased in these cultures at 48 hours and 96 hours after culturing (FIG. 5 Panels C and D). Thus these mutations resolve decreased xylose utilization from the microbe's natural catabolite repression mechanisms and increase the overall sugar metabolism of these E. coli. However, xylose utilization as not increased for E. coli having a CRP protein with the G142D mutation in the presence of glucose.

The results demonstrate that E. coli strains obtained from culture collections such as ATCC (American Type Culture Collection) can be genetically engineered and subsequently metabolically evolved to obtain a strain with an enhanced ability to produce organic acid in commercially significant amounts.

Example 5. SNP Mutations Enhance Glucose-Xylose Co-Utilization in E. coli

Figure 6:
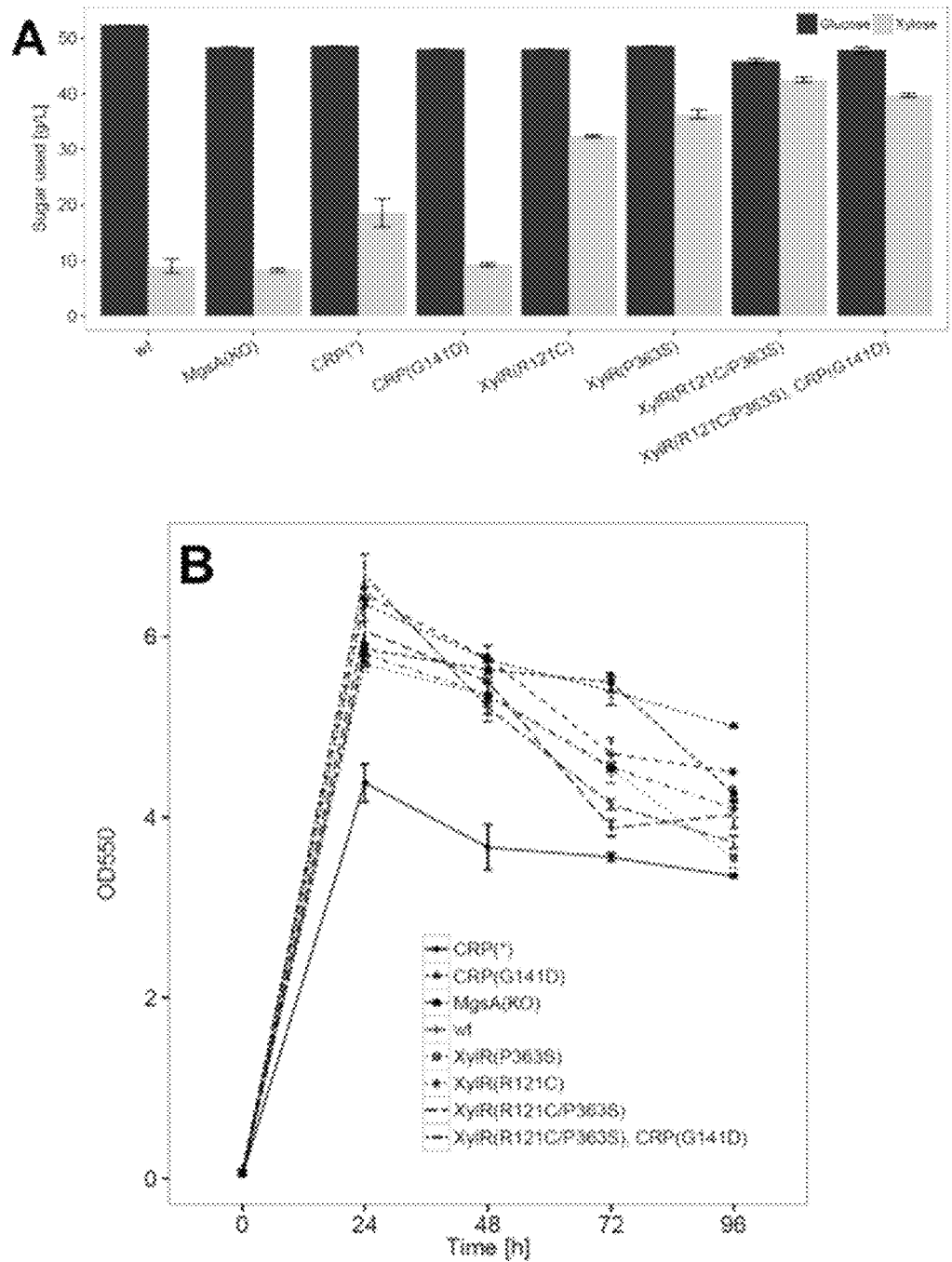
FIG. 6 depicts co-utilization of glucose-xylose mixtures (50 g/L for each) during fermentation of *E. coli* strain ATCC9637 engineered with indicated genotypes: previously reported the mgsA deletion (MgsA(KO)), crp*, crp SNP (CRP G141D), and xylR SNPs of the invention. Panel A compares the sugar utilization of both glucose and xylose after 96 hours of fermentation for all of the engineered *E. coli* strain ATCC9637. Panel B shows the cell density (OD550). Panels C and D show in detail extracellular glucose and xylose concentrations, respectively. In Panels C and D, wt stands for wild-type.
Figure 6:
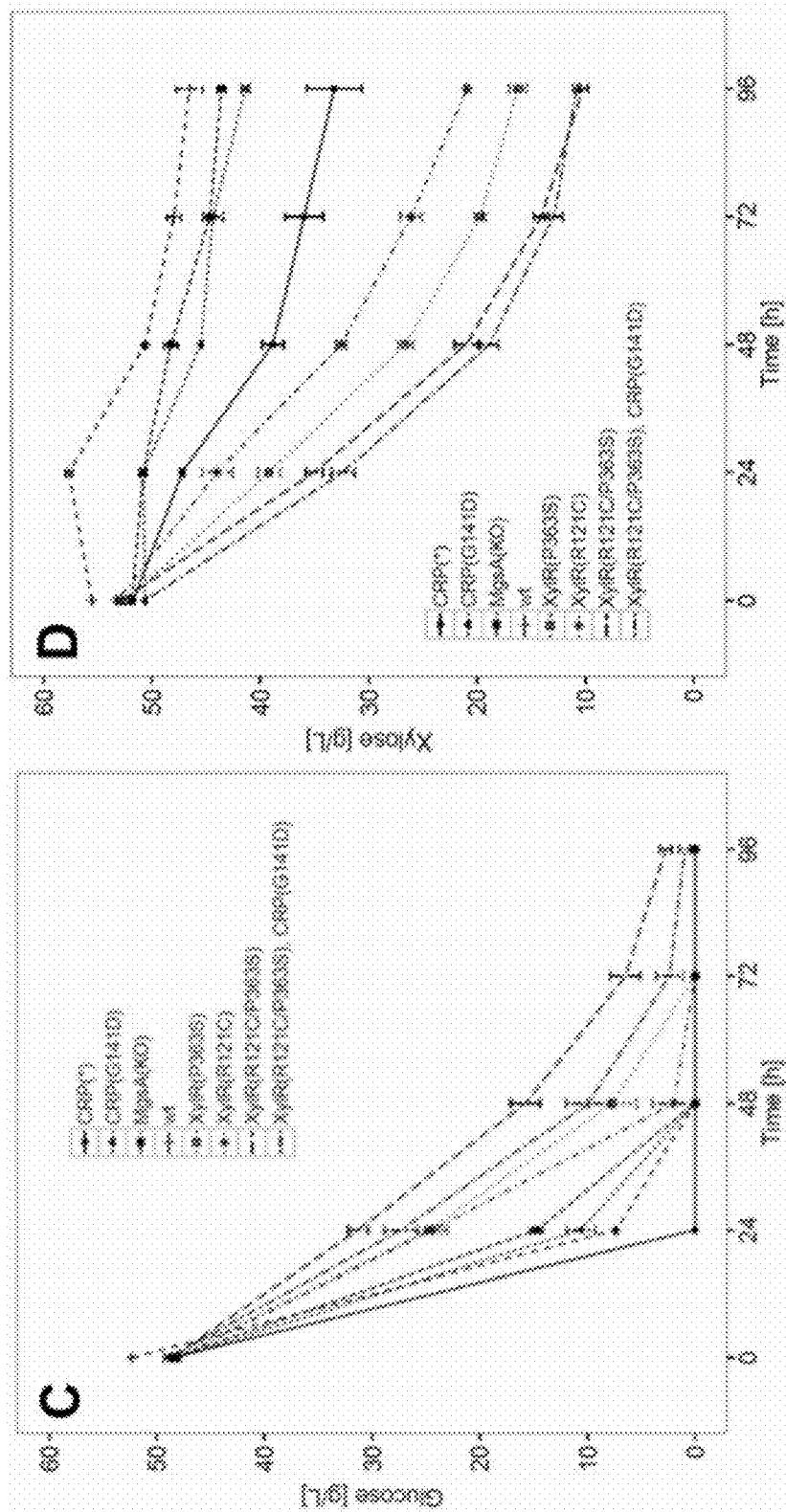

It has been reported that deletion of mgsA gene and mutation in crp* (Crp I112L, T127I, and A144T) led to the improvement of glucose-xylose co-utilization in some E. coli strains. The recombinant bacteria of the application were compared to these previously developed methods in the same background, a wild-type industrial E. coli strain ATCC9637. Recombinant bacteria of the application dramatically outperformed these previous methods (FIG. 6). More than 40 g/L xylose was consumed by the E. coli strains with xylR SNP mutations while the stain with crp* or mgsA deletion only used less than 20 g/L within 96 hours when these strains ferment a sugar mixture (50 g/L glucose and 50 g/L xylose) under the same condition (FIG. 6).

Example 6. Example of Applications to Enhance Fermentative Production Using Industrial Recombinant Bacteria of the Application The E. coli TG114 is an industrial lactate producer with an excellent performance to convert glucose into D-lactate. However, when using glucose-xylose mixtures (each 50 g/L) as its fermentation substrates, it was only able to use less than 10 g/L xylose and 40 g/L xylose was a waste for its lactate fermentation (FIG. 7A). After xylR SNPs (R121C and P363S) were introduced into TG114, the strain LN23 was able to use more than 40 g/L xylose under the same fermentation condition (FIG. 7A). This led to improved cell growth (FIG. 7B) and D-lactate production (FIG. 7C).

Example 7. XylR Variants from Different Species have the SNPs that May Enhance Sugar Co-Utilization The point mutations in xylR (R121C and P363S) led to upregulation of xylose catabolic pathway and rates (FIGS. 2, 6 and 7). By performing multiple sequence alignments and evaluating phylogenetic relationships between homologs of the appropriate transcription factors, we determined their grade of conservation among the Proteobacteria (FIG. 8). Some clusters of the reconstructed phylogenetic trees code for the same or a biochemically similar amino acid as the SNP mutations we identified (FIG. 8). Remarkably, these clusters such as the Pseudomonadaceae family include species which are well known plant commensals or plant pathogens with a lifestyle for xylose degradation. These XylR homologs from different species will probably have similar effect as our identified SNP variants of E. coli XylR.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed:

1. A method for increasing xylose utilization in microbes of the Enterobacteriaceae family, the method comprising mutating the microbial genomes of the microbes to produce a mutated microbe of the Enterobacteriaceae family having a mutated XylR protein, wherein the mutated XylR protein comprises a point mutation substituting the proline at position 363, wherein the amino acid positioning corresponds to the amino acid sequence positioning set forth in SEQ ID NO:13.

2. The method of claim 1, wherein the mutated microbe of the Enterobacteriaceae family further comprises a mutated CRP protein comprising a point mutation substituting the glycine at position 142, wherein the amino acid positioning corresponds to the amino acid sequence positioning set forth in SEQ ID NO:2.

3. The method of claim 2, wherein the mutated XylR protein further comprises a point mutation substituting the arginine at position 121.

4. The method of claim 3, wherein the arginine at position 121 is substituted with a cysteine, a serine, a glycine, a valine, a proline, or a conservative substitution thereof.

5. The method of claim 2, wherein the glycine at position 142 is substituted with an aspartate, a proline, a histidine, or a conservative substitution thereof.

6. The method of claim 2, wherein the mutated CRP protein comprises the amino acid sequence the sequence set forth in SEQ ID NO:11.

7. The method of claim 2, wherein the mutated CRP protein comprises the amino acid sequence the sequence set forth in SEQ ID NO:11 and the mutated XylR protein comprises the amino acid sequence the sequence set forth in SEQ ID NO:27.

8. The method of claim 2, wherein the mutated CRP protein comprises the amino acid sequence the sequence set forth in SEQ ID NO:11 and the mutated XylR protein comprises the amino acid sequence the sequence set forth in SEQ ID NO:28.

9. The method of claim 1, wherein the mutated microbe of the Enterobacteriaceae family is a member of a genus selected from the group consisting of *Escherichia, Erwinia, Providencia,* and *Serratia*.

10. The method of claim 1, wherein the mutated XylR protein further comprises a point mutation substituting the proline at position 182.

11. The method of claim 1, wherein the proline at position at 363 is substituted with a serine, a lysine, an arginine, or a conservative substitution thereof.

12. The method of claim 1, wherein the mutated XylR protein comprises the amino acid sequence the sequence set forth in SEQ ID NO:27.

13. The method of claim 1, wherein the mutated XylR protein comprises the amino acid sequence the sequence set forth in SEQ ID NO:28.

14. The method of claim 1, wherein the mutated XylR protein further comprises a point mutation substituting the arginine at position 121.

15. The method of claim 14, wherein the arginine at position 121 is substituted with a cysteine, a serine, a glycine, a valine, a proline, or a conservative substitution thereof.

16. A method for improved chemical production from woody biomass comprising culturing a recombinant bacterium having increased xylose utilization with woody biomass, wherein the recombinant bacterium having increased xylose utilization expresses a mutated XylR protein;
wherein the mutated XylR protein has the amino acid sequence selected from the group consisting of SEQ ID NO:27 and SEQ ID NO:28, wherein:
Xaa at position 363 in SEQ ID NO:27 is selected from the group consisting of: S, K, R, and conservative substitutions thereof,
Xaa at position 121 in SEQ ID NO:28 is selected from the group consisting of: C, S, G, V, P, and conservative substitutions thereof, and
Xaa at position 363 in SEQ ID NO:28 is selected from the group consisting of: S, K, R, and conservative substitutions thereof.

17. The method of claim 16, wherein the recombinant bacterium having increased xylose utilization further expresses a mutated CRP protein having the amino acid sequence set forth in SEQ ID NO:11, wherein Xaa at position 142 is selected from the group consisting of: D, P, H, and conservative substitutions thereof.

18. The method of claim 16, wherein the mutated XylR protein has the amino acid sequence set forth in SEQ ID NO:27.

19. The method of claim 16, wherein the mutated XylR protein has the amino acid sequence set forth in SEQ ID NO:28.

20. The method of claim 19, wherein the recombinant bacterium having increased xylose utilization further expresses a mutated CRP protein having the amino acid sequence set forth in SEQ ID NO:11, wherein Xaa at position 142 is selected from the group consisting of: D, P, H, and conservative substitutions thereof.

* * * * *